(12) United States Patent
Christensen et al.

(10) Patent No.: US 11,136,590 B2
(45) Date of Patent: Oct. 5, 2021

(54) NUCLEOTIDE SEQUENCES AND POLYPEPTIDES ENCODED THEREBY USEFUL FOR MODIFYING PLANT CHARACTERISTICS

(71) Applicant: CERES, INC., Thousand Oaks, CA (US)

(72) Inventors: Cory Christensen, Zionsville, IN (US); Nestor Apuya, Culver City, CA (US); Kenneth A. Feldmann, Tucson, AZ (US)

(73) Assignee: CERES, INC., Thousand Oaks, CA (US)

( * ) Notice: Subject to any disclaimer, the term of this patent is extended or adjusted under 35 U.S.C. 154(b) by 0 days.

(21) Appl. No.: 16/793,520

(22) Filed: Feb. 18, 2020

(65) Prior Publication Data

US 2020/0239902 A1  Jul. 30, 2020

Related U.S. Application Data

(60) Division of application No. 15/953,264, filed on Apr. 13, 2018, now Pat. No. 10,655,139, which is a continuation of application No. 14/565,186, filed on Dec. 9, 2014, now Pat. No. 9,957,521, which is a division of application No. 13/184,361, filed on Jul. 15, 2011, now Pat. No. 8,962,921, which is a division of application No. 11/140,450, filed on May 27, 2005, now Pat. No. 8,022,273.

(60) Provisional application No. 60/575,253, filed on May 27, 2004.

(51) Int. Cl.
   *C12N 15/82* (2006.01)
   *C07K 14/415* (2006.01)

(52) U.S. Cl.
   CPC ........ *C12N 15/8273* (2013.01); *C07K 14/415* (2013.01); *C12N 15/8242* (2013.01); *C12N 15/8261* (2013.01); *C12N 15/8271* (2013.01); *Y02A 40/146* (2018.01)

(58) Field of Classification Search
   None
   See application file for complete search history.

(56) References Cited

U.S. PATENT DOCUMENTS

2013/0042367 A1 * 2/2013 Nadzan .............. C12N 15/8201
                                                    800/260
2020/0216854 A1   7/2020 Christensen et al.

FOREIGN PATENT DOCUMENTS

| EP | 1033405 A2 | 6/2000 | |
|----|------------|--------|---|
| EP | 1033405 A2 * | 9/2000 | ........... C07K 14/415 |
| WO | 2002/016655 | 2/2002 | |
| WO | 2003/081988 | 10/2003 | |

OTHER PUBLICATIONS

Wells (Biochemistry 29:8509-8517, 1990).*
Guo et al. (PNAS, 101: 9205-9210, 2004).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
U.S. Appl. No. 16/793,481, filed Feb. 18, 2020, Christensen et al.
Kasuga et al. (Nature Biotechnology, vol. 17, pp. 287-291, Mar. 1999).
Thornton et al. (Nature structural Biology, structural genomics supplement, pp. 991-994; Nov. 2000).
Office Action dated Nov. 22, 2011 in Australian Application No. 2005250447.
Office Action dated Mar. 22, 2013 in Canadian Patent Application 2,568,367.
GenBank Accession No. AY084231, dated Jun. 13, 2002.
GenBank Accession No. AY084504, dated Jun. 13, 2002.
GenBank Accession No. AY084803, dated Jun. 13, 2002.
GenBank Accession No. AY085031, dated Jun. 13, 2002.
GenBank Accession No. AY085703, dated Jun. 13, 2002.
GenBank Accession No. AY086590, dated Jun. 13, 2002.
GenBank Accession No. NM_104688, dated Jan. 29, 2002.
GenBank Accession No. NM_106061, dated Jan. 29, 2002.
USPTO: Non-Final Office Action regarding U.S. Appl. No. 16/793,481, dated Mar. 25, 2021.
USPTO: Response to Non-Final Office Action regarding U.S. Appl. No. 16/793,481, filed Apr. 26, 2021.
USPTO: Supplemental Response to Non-Final Office Action regarding U.S. Appl. No. 16/793,481, filed May 3, 2021.
U.S. Appl. No. 17/217,729, filed Mar. 20, 2021, Christensen et al.
USPTOL Notice of Allowance regarding U.S. Appl. No. 16/793,481, dated Jun. 10, 2021.

* cited by examiner

*Primary Examiner* — Vinod Kumar
(74) *Attorney, Agent, or Firm* — Dentons US LLP

(57) ABSTRACT

Isolated polynucleotides and polypeptides encoded thereby are described, together with the use of those products for making transgenic plants with increased tolerance to abiotic stress (e.g., high or low temperature, drought, flood).

11 Claims, No Drawings
Specification includes a Sequence Listing.

SEQUENCE LISTING

<160> NUMBER OF SEQ ID NOS: 262

<210> SEQ ID NO 1
<211> LENGTH: 577
<212> TYPE: DNA
<213> ORGANISM: Arabidopsis thaliana
<220> FEATURE:
<221> NAME/KEY: misc_feature
<223> OTHER INFORMATION: clone11830_inplanta_experimental_L18

<400> SEQUENCE: 1

```
aaacttccta actagataga tcagatctgg atctctctgc accactcatt gccttctcta      60
gaaacatgtc aactttcttg ataaggatac ttcttccttt gcttatcata gcaatgactc     120
ttcctcgacg ttcagaggca gagtcggaac aatggtgcat agcggatgaa caaacgccag     180
acgatgagtt gcaagcagcc ttagactggg cttgcggaaa aggtggagca gactgcagca     240
aaatgcagca ggaaaaccag ccttgcttct tgcctaacac aatcagagat catgcctcct     300
ttgctttcaa cagttactac caaacttata aaaacaaagg tggttcttgt tacttcaaag     360
gagctgccat gatcactgag cttgacccca gccatggttc ttgccagtat gagtataacc     420
cctgattcaa acgacacagc aaagacaaga tacagcaaga tgaaaagcta tgattttgca     480
tttatacgtt ttctctatgt aatgttttca ttccaaagca gtatccatgt actgttctcc     540
cattacactc cagtctgaga taaaaatttc ttcaacg                              577
```

<210> SEQ ID NO 2
<211> LENGTH: 119
<212> TYPE: PRT
<213> ORGANISM: Arabidopsis thaliana
<220> FEATURE:
<221> NAME/KEY: MISC_FEATURE
<223> OTHER INFORMATION: peptide_clone11830_inplanta_experimental_L18

<400> SEQUENCE: 2

Met Ser Thr Phe Leu Ile Arg Ile Leu Leu Pro Leu Leu Ile Ile Ala

```
  1               5                  10                 15
Met Thr Leu Pro Arg Ser Glu Ala Glu Ser Glu Gln Trp Cys Ile
            20                  25                 30
Ala Asp Glu Gln Thr Pro Asp Glu Leu Gln Ala Ala Leu Asp Trp
            35                  40                 45
Ala Cys Gly Lys Gly Gly Ala Asp Cys Ser Lys Met Gln Gln Glu Asn
            50                  55                 60
Gln Pro Cys Phe Leu Pro Asn Thr Ile Arg Asp His Ala Ser Phe Ala
 65                  70                  75                  80
Phe Asn Ser Tyr Tyr Gln Thr Tyr Lys Asn Lys Gly Gly Ser Cys Tyr
                85                  90                  95
Phe Lys Gly Ala Ala Met Ile Thr Glu Leu Asp Pro Ser His Gly Ser
               100                 105                 110
Cys Gln Tyr Glu Tyr Asn Pro
               115
```

<210> SEQ ID NO 3
<211> LENGTH: 118
<212> TYPE: PRT
<213> ORGANISM: Glycine max
<220> FEATURE:
<221> NAME/KEY: MISC_FEATURE
<223> OTHER INFORMATION: CeresClone:1058242

<400> SEQUENCE: 3

```
Met Ala Thr Phe Met Leu Lys Leu Val Leu Pro Leu Leu Phe Leu Phe
 1               5                  10                 15
Met Ile Pro Pro Lys Thr Ala Tyr Ala Glu Phe Glu Gln Trp Cys Val
            20                  25                 30
Ala Asp Glu Gln Thr Thr Glu Ser Glu Leu Gln Ala Ala Leu Asp Trp
            35                  40                 45
Ala Cys Gly Lys Gly Gly Ala Asp Cys Ser Lys Ile Gln Val Asn Gln
            50                  55                 60
Pro Cys Tyr Leu Pro Asn Thr Leu Lys Asp His Ala Ser Tyr Ala Phe
 65                  70                  75                  80
Asn Ser Tyr Tyr Gln Lys Phe Lys His Ser Gly Gly Ser Cys Tyr Phe
                85                  90                  95
Arg Gly Ala Ala Ile Thr Thr Glu Val Asp Pro Ser His Gly Ser Cys
               100                 105                 110
His Tyr Asp Phe Ile Pro
               115
```

<210> SEQ ID NO 4
<211> LENGTH: 123
<212> TYPE: PRT
<213> ORGANISM: Olea europaea
<220> FEATURE:
<221> NAME/KEY: MISC_FEATURE
<223> OTHER INFORMATION: gi[29]465664

<400> SEQUENCE: 4

```
Met Arg Gly Thr Ala Gly Val Pro Asp Gln Pro Val Pro Thr Pro Thr
 1               5                  10                 15
Pro Ser Val Pro Thr Ser Ser Pro Val Pro Lys Pro Thr Gln
            20                  25                 30
Gly Asn Lys Lys Trp Cys Val Pro Lys Ala Glu Ala Thr Asp Ala Gln
            35                  40                 45
Leu Gln Ser Asn Ile Asp Tyr Val Cys Ser Gln Ser Gly Met Asp Cys
```

```
                50                  55                  60
Gly Pro Ile Gln Ala Asn Gly Ala Cys Phe Asn Pro Asn Thr Val Arg
 65                  70                  75                  80

Ala His Ala Ser Tyr Ala Met Asn Ser Trp Tyr Gln Ser Lys Gly Arg
                 85                  90                  95

Asn Asp Phe Asp Cys Asp Phe Ser Gly Thr Gly Ala Ile Thr Ser Ser
            100                 105                 110

Asp Pro Ser Asn Gly Ser Cys Ser Phe Leu Ser
        115                 120

<210> SEQ ID NO 5
<211> LENGTH: 123
<212> TYPE: PRT
<213> ORGANISM: Parthenium argentatum
<220> FEATURE:
<221> NAME/KEY: MISC_FEATURE
<223> OTHER INFORMATION: CeresClone:1602924

<400> SEQUENCE: 5

Met Thr Thr Val Thr Thr Pro His Phe Ile Thr Val Leu Phe Phe Phe
 1               5                  10                  15

Leu Leu Ile Ser Gly Gly Ile Phe Gly His Ala Lys Ala Gln Ala Pro
            20                  25                  30

Gly Gln Gly Thr Trp Cys Val Ala Lys Pro Ala Thr Ser Asp Glu Asp
        35                  40                  45

Leu Gln Asn Asn Ile Asn Tyr Ala Cys Thr Tyr Val Asp Cys Arg Ile
   50                   55                  60

Ile Arg Pro Gly Ser Val Cys Phe Glu Pro Gln Lys Leu Val Asn Arg
 65                  70                  75                  80

Ala Ser Val Ala Met Asn Leu Tyr Tyr Gln Thr Asn Gly Arg Asn Tyr
                 85                  90                  95

Trp Asn Cys Asp Phe Lys Gly Ser Gly Ile Ile Ala Val Thr Asp Pro
            100                 105                 110

Ser Tyr Gly Asp Cys Lys Tyr Ser Tyr Lys Gln
        115                 120

<210> SEQ ID NO 6
<211> LENGTH: 703
<212> TYPE: DNA
<213> ORGANISM: Arabidopsis thaliana
<220> FEATURE:
<221> NAME/KEY: MISC_FEATURE
<223> OTHER INFORMATION: clone35743_inplanta_experimental_L19

<400> SEQUENCE: 6
caataaccac aaacaacaat acacttctct tgacgcctat ctctttctca ccaccaccat      60
taccttcgtc acttctctct tccaagcaat ttaaaccttc aactaatcca gaaatgcaaa    120
tgctaagaaa cttaagcacg aggacgagga gtcgtcgcgg cggatatgag cgtgtaagcg    180
atgattccac cttcagccta cttggagcaa agctaaggag gtcaacgagc gttccatact    240
atgctccatc gataaggctt ggtggagatt ttcctgtgat tttggaaaag cttccacgcc    300
aaaaaccaac taaacagtg gtgacaagca aattaagcca tccaatcttc agtttatttg    360
atggttatcg ccgccgtagc aagaagaaag cgacggccaa accggagttc tctagatacc    420
atgaatacct taagaaagt ggaatgtggg atttgagatc taatagtccg gtcatctact    480
ttaagtagat atatatataa cactatatat gttatgattt gtgttcattt attatattat    540
ttgtgacaat tcttagtgat atgattgatc gatctataag agctatcttc agttttatt    600
```

```
tttctccccc ttgtaaatat ttttttaatt gatctataaa tttaaacaca acgtttttg      660 gtcaacagtc ttgtgttatt ctattgtaaa cacaacgttt acc                       703
```

<210> SEQ ID NO 7
<211> LENGTH: 124
<212> TYPE: PRT
<213> ORGANISM: Arabidopsis thaliana
<220> FEATURE:
<221> NAME/KEY: MISC_FEATURE
<223> OTHER INFORMATION: peptide_clone35743_inplanta_experimental_L19

<400> SEQUENCE: 7

```
Met Gln Met Leu Arg Asn Leu Ser Thr Arg Thr Arg Ser Arg Arg Gly
1               5                   10                  15

Gly Tyr Glu Arg Val Ser Asp Asp Ser Thr Phe Ser Leu Leu Gly Ala
            20                  25                  30

Lys Leu Arg Arg Ser Thr Ser Val Pro Tyr Tyr Ala Pro Ser Ile Arg
        35                  40                  45

Leu Gly Gly Asp Phe Pro Val Ile Leu Glu Lys Leu Pro Arg Gln Lys
    50                  55                  60

Pro Thr Lys Thr Val Val Thr Ser Lys Leu Ser His Pro Ile Phe Ser
65                  70                  75                  80

Leu Phe Asp Gly Tyr Arg Arg Arg Ser Lys Lys Lys Ala Thr Ala Lys
                85                  90                  95

Pro Glu Phe Ser Arg Tyr His Glu Tyr Leu Lys Glu Ser Gly Met Trp
            100                 105                 110

Asp Leu Arg Ser Asn Ser Pro Val Ile Tyr Phe Lys
        115                 120
```

<210> SEQ ID NO 8
<211> LENGTH: 124
<212> TYPE: PRT
<213> ORGANISM: Arabidopsis thaliana
<220> FEATURE:
<221> NAME/KEY: MISC_FEATURE
<223> OTHER INFORMATION: gi[38]603980

<400> SEQUENCE: 8

```
Met Gln Met Leu Arg Asn Leu Ser Thr Arg Thr Arg Ser Arg Arg Gly
1               5                   10                  15

Gly Tyr Glu Arg Val Ser Asp Asp Ser Thr Phe Ser Leu Leu Gly Ala
            20                  25                  30

Lys Leu Arg Arg Ser Thr Ser Val Pro Tyr Tyr Ala Pro Ser Ile Arg
        35                  40                  45

Leu Gly Gly Asp Phe Pro Val Ile Leu Glu Lys Leu Pro Arg Gln Lys
    50                  55                  60

Pro Thr Lys Thr Val Val Thr Ser Lys Leu Ser His Pro Ile Phe Ser
65                  70                  75                  80

Leu Phe Asp Gly Tyr Arg Arg His Asn Lys Lys Lys Ala Thr Ala Lys
                85                  90                  95

Pro Glu Phe Ser Arg Tyr His Glu Tyr Leu Lys Glu Ser Gly Met Trp
            100                 105                 110

Asp Leu Arg Ser Asn Ser Pro Val Ile Tyr Phe Lys
        115                 120
```

<210> SEQ ID NO 9
<211> LENGTH: 118
<212> TYPE: PRT

<213> ORGANISM: Brassica napus
<220> FEATURE:
<221> NAME/KEY: MISC_FEATURE
<223> OTHER INFORMATION: CeresClone:963524

<400> SEQUENCE: 9

```
Met Gln Met Leu Arg Ser Phe Ser Thr Arg Thr Arg Ser Arg Arg Gly
1               5                   10                  15

Gly Tyr Glu Arg Val Ile Asp Asp Ser Thr Phe Ser Leu Leu Gly Ala
            20                  25                  30

Lys Leu Arg Arg Ser Thr Ser Val Pro Tyr Tyr Ala Pro Ser Ile Lys
        35                  40                  45

Leu Gly Ala Gly Gly Val Pro Thr Ile Leu Glu Glu Leu Pro Arg Gln
    50                  55                  60

Lys Ser Lys Lys Val Lys Pro Thr Ser Lys Phe Ser His Pro Ile Phe
65                  70                  75                  80

Ser Phe Leu Tyr Gly Lys Lys Lys Ser Thr Thr Arg Lys Pro Glu
                85                  90                  95

Phe Ser Arg Tyr Leu Glu Tyr Leu Lys Glu Gly Gly Met Trp Asp Ala
                100                 105                 110

Arg Thr Asn Thr Pro Val
        115
```

<210> SEQ ID NO 10
<211> LENGTH: 870
<212> TYPE: DNA
<213> ORGANISM: Arabidopsis thaliana
<220> FEATURE:
<221> NAME/KEY: MISC_FEATURE
<223> OTHER INFORMATION: clone26006_inplanta_experimental_L20

<400> SEQUENCE: 10

```
aaaaagtacg aaaggaaaat atgagtgagg agaagaggaa gcaacacttc gtgctagtac      60
atggtgcgtg ccacggcgca tggtgctggt acaaggttaa gcctcttctc gaggctttgg     120
gccatcgtgt aaccgcctta gacctagctg cttccggtat agacacaacc aggtcaatca     180
ctgacatttc tacatgtgaa caatattctg agccattgat gcagctaatg acttcattgc     240
cgaatgatga aaggttgta ctcgttggtc atagctttgg aggtttgagt ttagccttag      300
ccatggataa gtttcccgat aaaatctctg tctctgtctt cgtgactgca ttcatgcccg     360
acaccaaaca ctcaccatcg ttcgtcgagg aaaagtttgc aagcagcatg acaccagaag     420
gatggatggg ctctgagctc gagacatatg gttcagataa ttccggcttg tctgtgttct     480
tcagcaccga cttcatgaag caccgtctct accaactttc tcctgtggag gatcttgagc     540
ttggattgct tctaaagagg cctagttcat tgtttattaa tgaattatcg aagatggaga     600
actttctga gaagggtat ggatctgttc ctcgagctta cattgtgtgc aaagaggaca       660
acattatctc ggaagaccat caacgatgga tgatccataa ttatccggcg aatttagtga     720
ttgagatgga agagacggat catatgccaa tgttttgcaa acctcaagta ctaagtgacc     780
atctattggc aatcgctgac aatttctctt aaataatatt ttgatgaaaa tgtatttgga     840
gtggatacaa taaaaatgtg ttctaaatgg                                       870
```

<210> SEQ ID NO 11
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: peptide_clone26006_inplanta_experimental_L20

<400> SEQUENCE: 11

```
Met Ser Glu Glu Lys Arg Lys Gln His Phe Val Leu Val His Gly Ala
1               5                   10                  15

Cys His Gly Ala Trp Cys Trp Tyr Lys Val Lys Pro Leu Leu Glu Ala
            20                  25                  30

Leu Gly His Arg Val Thr Ala Leu Asp Leu Ala Ala Ser Gly Ile Asp
        35                  40                  45

Thr Thr Arg Ser Ile Thr Asp Ile Ser Thr Cys Glu Gln Tyr Ser Glu
50                  55                  60

Pro Leu Met Gln Leu Met Thr Ser Leu Pro Asn Asp Glu Lys Val Val
65                  70                  75                  80

Leu Val Gly His Ser Phe Gly Gly Leu Ser Leu Ala Leu Ala Met Asp
            85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Glu Glu Lys Phe Ala Ser
        115                 120                 125

Ser Met Thr Pro Glu Gly Trp Met Gly Ser Glu Leu Glu Thr Tyr Gly
    130                 135                 140

Ser Asp Asn Ser Gly Leu Ser Val Phe Phe Ser Thr Asp Phe Met Lys
145                 150                 155                 160

His Arg Leu Tyr Gln Leu Ser Pro Val Glu Asp Leu Glu Leu Gly Leu
            165                 170                 175

Leu Leu Lys Arg Pro Ser Ser Leu Phe Ile Asn Glu Leu Ser Lys Met
            180                 185                 190

Glu Asn Phe Ser Glu Lys Gly Tyr Gly Ser Val Pro Arg Ala Tyr Ile
        195                 200                 205

Val Cys Lys Glu Asp Asn Ile Ile Ser Glu Asp His Gln Arg Trp Met
210                 215                 220

Ile His Asn Tyr Pro Ala Asn Leu Val Ile Glu Met Glu Glu Thr Asp
225                 230                 235                 240

His Met Pro Met Phe Cys Lys Pro Gln Val Leu Ser Asp His Leu Leu
            245                 250                 255

Ala Ile Ala Asp Asn Phe Ser
            260
```

<210> SEQ ID NO 12
<211> LENGTH: 267
<212> TYPE: PRT
<213> ORGANISM: Citrus sinensis
<220> FEATURE:
<221> NAME/KEY: MISC_FEATURE
<223> OTHER INFORMATION: gi[14]279437

<400> SEQUENCE: 12

```
Met Glu Glu Val Val Gly Met Glu Glu Lys His Phe Val Leu Val His
1               5                   10                  15

Gly Val Asn His Gly Ala Trp Cys Trp Tyr Lys Leu Lys Ala Arg Leu
            20                  25                  30

Val Ala Gly Gly His Arg Val Thr Ala Val Asp Leu Ala Ala Ser Gly
        35                  40                  45

Ile Asn Met Lys Arg Ile Glu Asp Val His Thr Phe His Ala Tyr Ser
50                  55                  60

Glu Pro Leu Met Glu Val Leu Ala Ser Leu Pro Ala Glu Glu Lys Val
```

```
                65                  70                  75                  80
        Ile Leu Val Gly His Ser Leu Gly Gly Val Thr Leu Ala Leu Ala Gly
                            85                  90                  95

Asp Lys Phe Pro His Lys Ile Ser Val Ala Val Phe Val Thr Ala Phe
                        100                 105                 110

Met Pro Asp Thr Thr His Arg Pro Ser Phe Val Leu Glu Gln Tyr Ser
                    115                 120                 125

Glu Lys Met Gly Lys Glu Asp Ser Trp Leu Asp Thr Gln Phe Ser
        130                 135                 140

Gln Cys Asp Ala Ser Asn Pro Ser His Ile Ser Met Leu Phe Gly Arg
        145                 150                 155                 160

Glu Phe Leu Thr Ile Lys Ile Tyr Gln Leu Cys Pro Pro Glu Asp Leu
                        165                 170                 175

Glu Leu Ala Lys Met Leu Val Arg Pro Gly Ser Met Phe Ile Asp Asn
                    180                 185                 190

Leu Ser Lys Glu Ser Lys Phe Ser Asp Glu Gly Tyr Gly Ser Val Lys
                195                 200                 205

Arg Val Tyr Leu Val Cys Glu Glu Asp Ile Gly Leu Pro Lys Gln Phe
        210                 215                 220

Gln His Trp Met Ile Gln Asn Tyr Pro Val Asn Glu Val Met Glu Ile
        225                 230                 235                 240

Lys Gly Gly Asp His Met Ala Met Leu Ser Asp Pro Gln Lys Leu Cys
                        245                 250                 255

Asp Cys Leu Ser Gln Ile Ser Leu Lys Tyr Ala
                    260                 265

<210> SEQ ID NO 13
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: CeresClone:1010900

<400> SEQUENCE: 13

Met Ser Glu Glu Lys Arg Lys Gln His Phe Val Leu Val His Gly Ser
        1               5                   10                  15

Cys His Gly Ala Trp Cys Trp Tyr Lys Val Lys Pro Leu Leu Glu Ala
                        20                  25                  30

Val Gly His Arg Val Thr Ala Val Asp Leu Ala Ala Ser Gly Ile Asp
                    35                  40                  45

Thr Thr Arg Ser Ile Thr Asp Ile Pro Thr Cys Glu Gln Tyr Ser Glu
                50                  55                  60

Pro Leu Thr Lys Leu Leu Thr Ser Leu Pro Asn Asp Glu Lys Val Val
        65                  70                  75                  80

Leu Val Gly His Ser Phe Gly Gly Leu Asn Leu Ala Ile Ala Met Glu
                        85                  90                  95

Lys Phe Pro Glu Lys Ile Ser Val Ala Val Phe Leu Thr Ala Phe Met
                    100                 105                 110

Pro Asp Thr Glu His Ser Pro Ser Phe Val Leu Asp Lys Phe Gly Ser
                115                 120                 125

Asn Met Pro Gln Glu Ala Trp Met Gly Thr Glu Phe Glu Pro Tyr Gly
        130                 135                 140

Ser Asp Asn Ser Gly Leu Ser Met Phe Ser Pro Asp Phe Met Lys
        145                 150                 155                 160
```

```
Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 14
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: gi[20]196998

<400> SEQUENCE: 14

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
    130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255
```

```
Lys Ile Ala Asp Lys Phe Val
            260

<210> SEQ ID NO 15
<211> LENGTH: 263
<212> TYPE: PRT
<213> ORGANISM: Arabidopsis thaliana
<220> FEATURE:
<221> NAME/KEY: MISC_FEATURE
<223> OTHER INFORMATION: gi[27]754457

<400> SEQUENCE: 15

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
    50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Lys Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
    130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
    210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 16
<211> LENGTH: 257
<212> TYPE: PRT
<213> ORGANISM: Hevea brasiliensis
<220> FEATURE:
<221> NAME/KEY: MISC_FEATURE
<223> OTHER INFORMATION: gi[50]513520

<400> SEQUENCE: 16

Met Ala Phe Ala His Phe Val Leu Ile His Thr Ile Cys His Gly Ala
1               5                   10                  15
```

Trp Ile Trp His Lys Leu Lys Pro Leu Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
            100                 105                 110

Cys Pro Ser Tyr Val Val Asp Lys Leu Met Glu Val Phe Pro Asp Trp
        115                 120                 125

Lys Asp Thr Thr Tyr Phe Thr Tyr Thr Lys Asp Gly Lys Glu Ile Thr
130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
        195                 200                 205

Ile Phe Leu Pro Glu Phe Gln Leu Trp Gln Ile Glu Asn Tyr Lys Pro
    210                 215                 220

Asp Lys Val Tyr Lys Val Glu Gly Gly Asp His Leu Leu Gln Leu Thr
225                 230                 235                 240

Lys Thr Lys Glu Ile Ala Glu Ile Leu Gln Glu Val Ala Asp Thr Tyr
                245                 250                 255

Asn

<210> SEQ ID NO 17
<211> LENGTH: 257
<212> TYPE: PRT
<213> ORGANISM: Hevea brasiliensis
<220> FEATURE:
<221> NAME/KEY: MISC_FEATURE
<223> OTHER INFORMATION: gi[64]35646

<400> SEQUENCE: 17

Met Ala Phe Ala His Phe Val Leu Ile His Thr Ile Cys His Gly Ala
1               5                   10                  15

Trp Ile Trp His Lys Leu Lys Pro Leu Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
            100                 105                 110

Cys Pro Ser Tyr Val Val Asp Lys Leu Met Glu Val Phe Pro Asp Trp
            115                 120                 125

Lys Asp Thr Thr Tyr Phe Thr Tyr Thr Lys Asp Gly Lys Glu Ile Thr
130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
                180                 185                 190

Gly Tyr Gly Ser Ile Lys Lys Ile Tyr Val Trp Thr Asp Gln Asp Glu
                195                 200                 205

Ile Phe Leu Pro Glu Phe Gln Leu Trp Gln Ile Glu Asn Tyr Lys Pro
            210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn

<210> SEQ ID NO 18
<211> LENGTH: 258
<212> TYPE: PRT
<213> ORGANISM: Manihot esculenta
<220> FEATURE:
<221> NAME/KEY: MISC_FEATURE
<223> OTHER INFORMATION: gi[27]80225

<400> SEQUENCE: 18

Met Ala Val Val Asp Phe Val Leu Ile His Thr Ile Cys His Gly Ala
1               5                   10                  15

Trp Ile Trp Tyr Lys Leu Lys Pro Val Leu Glu Ala Ala Gly His Lys
            20                  25                  30

Val Thr Ala Leu Asp Leu Ala Ala Ser Gly Val Asp Pro Arg Gln Ile
        35                  40                  45

Glu Gln Ile Asn Ser Phe Asp Glu Tyr Ser Glu Pro Leu Leu Thr Phe
    50                  55                  60

Met Glu Ser Leu Pro Gln Gly Glu Lys Val Ile Leu Val Gly Glu Ser
65                  70                  75                  80

Cys Gly Gly Leu Asn Ile Ala Ile Ala Ala Asp Lys Tyr Pro Glu Lys
                85                  90                  95

Ile Ala Ala Ala Val Phe Gln Asn Ser Leu Leu Pro Asp Thr Lys His
                100                 105                 110

Lys Pro Ser Tyr Val Val Asp Lys Leu Met Glu Val Phe Pro Asp Trp
            115                 120                 125

Lys Asp Thr Glu Tyr Phe Glu Phe Ser Asn Ser Asn Gly Glu Thr Ile
130                 135                 140

Thr Gly Met Val Leu Gly Leu Lys Leu Met Arg Glu Asn Leu Tyr Thr
145                 150                 155                 160

Ile Cys Pro Pro Glu Asp Tyr Glu Leu Ala Lys Met Leu Thr Arg Arg
                165                 170                 175

Gly Ser Leu Phe Gln Ser Ile Leu Ala Gln Arg Glu Lys Phe Thr Glu
                180                 185                 190

Lys Gly Tyr Gly Ser Ile Lys Lys Ile Tyr Val Trp Thr Gly Asp Asp
                195                 200                 205

-continued

```
Lys Ile Phe Leu Pro Glu Phe Gln Leu Trp Gln Ile Glu Asn Tyr Lys
        210                 215                 220

Pro Asp Leu Val Phe Arg Val Met Gly Gly Asp His Lys Leu Gln Leu
225                 230                 235                 240

Thr Lys Thr Asn Glu Ile Ala Gly Ile Leu Gln Lys Val Ala Asp Ile
                245                 250                 255

Tyr Ala
```

<210> SEQ ID NO 19
<211> LENGTH: 258
<212> TYPE: PRT
<213> ORGANISM: Catharanthus roseus
<220> FEATURE:
<221> NAME/KEY: MISC_FEATURE
<223> OTHER INFORMATION: gi[53]830670

<400> SEQUENCE: 19

```
Met Glu Val Met Lys His Phe Val Thr Val His Gly Val Gly His Gly
1               5                   10                  15

Ala Trp Val Tyr Tyr Lys Leu Lys Pro Arg Ile Glu Ala Ala Gly His
            20                  25                  30

Arg Cys Thr Ala Val Asn Leu Ala Ala Ser Gly Ile Asn Glu Lys Lys
        35                  40                  45

Leu Glu Glu Val Arg Ser Ser Ile Asp Tyr Ala Ala Pro Leu Leu Glu
50                  55                  60

Val Leu Asp Ser Val Pro Glu Asn Gly Lys Val Ile Leu Val Gly His
65                  70                  75                  80

Ser Gly Gly Gly Met Thr Ala Ala Val Gly Met Glu Lys Phe Pro Asn
                85                  90                  95

Lys Ile Ser Leu Ala Val Phe Leu Asn Ala Ile Met Pro Asp Thr Glu
            100                 105                 110

Asn Arg Pro Ser Tyr Val Leu Glu Glu Tyr Thr Ala Lys Thr Pro Pro
        115                 120                 125

Glu Ala Trp Lys Asp Cys Gln Phe Ser Ala Tyr Gly Asp Pro Pro Ile
130                 135                 140

Thr Ser Leu Val Cys Gly Pro Glu Phe Ile Ser Ser Thr Leu Tyr His
145                 150                 155                 160

Leu Ser Pro Ile Glu Asp His Ala Leu Gly Lys Ile Leu Val Arg Pro
                165                 170                 175

Gly Ser Leu Phe Ile Glu Asp Leu Leu Lys Ala Glu Lys Phe Thr Glu
            180                 185                 190

Glu Gly Phe Gly Ser Val Pro Arg Val Tyr Val Ile Ala Ala Glu Asp
        195                 200                 205

Lys Thr Ile Pro Pro Glu Phe Gln Arg Trp Met Ile Glu Asn Asn Pro
210                 215                 220

Val Lys Glu Val Lys Glu Ile Lys Gly Ala Asp His Met Pro Met Phe
225                 230                 235                 240

Ser Lys Pro Asp Glu Leu Ser Gln Cys Leu Leu Asp Ile Ala Lys Lys
                245                 250                 255

His Ala
```

<210> SEQ ID NO 20
<211> LENGTH: 264
<212> TYPE: PRT
<213> ORGANISM: Rauvolfia serpentina
<220> FEATURE:

```
<221> NAME/KEY: MISC_FEATURE
<223> OTHER INFORMATION: gi[66]51393

<400> SEQUENCE: 20

Met His Ser Ala Ala Asn Ala Lys Gln Gln Lys His Phe Val Leu Val
1               5                   10                  15

His Gly Gly Cys Leu Gly Ala Trp Ile Trp Tyr Lys Leu Lys Pro Leu
            20                  25                  30

Leu Glu Ser Ala Gly His Lys Val Thr Ala Val Asp Leu Ser Ala Ala
        35                  40                  45

Gly Ile Asn Pro Arg Arg Leu Asp Glu Ile His Thr Phe Arg Asp Tyr
    50                  55                  60

Ser Glu Pro Leu Met Glu Val Met Ala Ser Ile Pro Pro Asp Glu Lys
65                  70                  75                  80

Val Val Leu Leu Gly His Ser Phe Gly Gly Met Ser Leu Gly Leu Ala
                85                  90                  95

Met Glu Thr Tyr Pro Glu Lys Ile Ser Val Ala Val Phe Met Ser Ala
            100                 105                 110

Met Met Pro Asp Pro Asn His Ser Leu Thr Tyr Pro Phe Glu Lys Tyr
        115                 120                 125

Asn Glu Lys Cys Pro Ala Asp Met Met Leu Asp Ser Gln Phe Ser Thr
    130                 135                 140

Tyr Gly Asn Pro Glu Asn Pro Gly Met Ser Met Ile Leu Gly Pro Gln
145                 150                 155                 160

Phe Met Ala Leu Lys Met Phe Gln Asn Cys Ser Val Glu Asp Leu Glu
                165                 170                 175

Leu Ala Lys Met Leu Thr Arg Pro Gly Ser Leu Phe Phe Gln Asp Leu
            180                 185                 190

Ala Lys Ala Lys Lys Phe Ser Thr Glu Arg Tyr Gly Ser Val Lys Arg
        195                 200                 205

Ala Tyr Ile Phe Cys Asn Glu Asp Lys Ser Phe Pro Val Glu Phe Gln
    210                 215                 220

Lys Trp Phe Val Glu Ser Val Gly Ala Asp Lys Val Lys Glu Ile Lys
225                 230                 235                 240

Glu Ala Asp His Met Gly Met Leu Ser Gln Pro Arg Glu Val Cys Lys
                245                 250                 255

Cys Leu Leu Asp Ile Ser Asp Ser
            260

<210> SEQ ID NO 21
<211> LENGTH: 262
<212> TYPE: PRT
<213> ORGANISM: Lycopersicon esculentum
<220> FEATURE:
<221> NAME/KEY: MISC_FEATURE
<223> OTHER INFORMATION: gi[41]814856

<400> SEQUENCE: 21

Met Glu Lys Gly Asp Lys Asn His Phe Val Leu Val His Gly Ala Cys
1               5                   10                  15

His Gly Ala Trp Cys Trp Tyr Lys Val Val Thr Ile Leu Arg Ser Glu
            20                  25                  30

Gly His Lys Val Ser Val Leu Asp Met Ala Ala Ser Gly Ile Asn Pro
        35                  40                  45

Lys His Val Asp Asp Leu Asn Ser Met Ala Asp Tyr Asn Glu Pro Leu
    50                  55                  60
```

```
Met Glu Phe Met Asn Ser Leu Pro Gln Leu Glu Arg Val Val Leu Val
 65                  70                  75                  80

Gly His Ser Met Gly Gly Ile Asn Ile Ser Leu Ala Met Glu Lys Phe
                 85                  90                  95

Pro Gln Lys Ile Val Ala Val Phe Val Thr Ala Phe Met Pro Gly
            100                 105                 110

Pro Asp Leu Asn Leu Val Ala Leu Gly Gln Gln Tyr Asn Gln Gln Val
            115                 120                 125

Glu Ser His Met Asp Thr Glu Phe Val Tyr Asn Asn Gly Gln Asp Lys
            130                 135                 140

Ala Pro Thr Ser Leu Val Leu Gly Pro Glu Val Leu Ala Thr Asn Phe
145                 150                 155                 160

Tyr Gln Leu Ser Pro Pro Glu Asp Leu Thr Leu Ala Thr Tyr Leu Val
                165                 170                 175

Arg Pro Val Pro Leu Phe Asp Glu Ser Ile Leu Leu Ala Asn Thr Thr
                180                 185                 190

Leu Ser Lys Glu Lys Tyr Gly Ser Val His Arg Val Tyr Val Val Cys
            195                 200                 205

Asp Lys Asp Asn Val Leu Lys Glu Gln Gln Phe Gln Lys Trp Leu Ile
210                 215                 220

Asn Asn Asn Pro Pro Asp Glu Val Gln Ile Ile His Asn Ala Asp His
225                 230                 235                 240

Met Val Met Phe Ser Lys Pro Arg Asp Leu Ser Ser Cys Leu Val Met
                245                 250                 255

Ile Ser Gln Lys Tyr Tyr
            260

<210> SEQ ID NO 22
<211> LENGTH: 260
<212> TYPE: PRT
<213> ORGANISM: Nicotiana tabacum
<220> FEATURE:
<221> NAME/KEY: MISC_FEATURE
<223> OTHER INFORMATION: gi[40]549303

<400> SEQUENCE: 22

Met Lys Glu Gly Lys His Phe Val Leu Val His Gly Ala Cys His Gly
 1               5                  10                  15

Gly Trp Ser Trp Tyr Lys Leu Lys Pro Leu Leu Glu Ala Ala Gly His
                20                  25                  30

Lys Val Thr Ala Leu Asp Leu Ala Ala Ser Gly Thr Asp Leu Arg Lys
            35                  40                  45

Ile Glu Glu Leu Arg Thr Leu Tyr Asp Tyr Thr Leu Pro Leu Met Glu
 50                  55                  60

Leu Met Glu Ser Leu Ser Ala Asp Glu Lys Val Ile Leu Val Gly His
 65                  70                  75                  80

Ser Leu Gly Gly Met Asn Leu Gly Leu Ala Met Glu Lys Tyr Pro Gln
                 85                  90                  95

Lys Ile Tyr Ala Ala Val Phe Leu Ala Ala Phe Met Pro Asp Ser Val
            100                 105                 110

His Asn Ser Ser Phe Val Leu Glu Gln Tyr Asn Glu Arg Thr Pro Ala
            115                 120                 125

Glu Asn Trp Leu Asp Thr Gln Phe Leu Pro Tyr Gly Ser Pro Glu Glu
            130                 135                 140

Pro Leu Thr Ser Met Phe Phe Gly Pro Lys Phe Leu Ala His Lys Leu
145                 150                 155                 160
```

Tyr Gln Leu Cys Ser Pro Glu Asp Leu Ala Leu Ala Ser Ser Leu Val
                165                 170                 175

Arg Pro Ser Ser Leu Phe Met Glu Asp Leu Ser Lys Ala Lys Tyr Phe
            180                 185                 190

Thr Asp Glu Arg Phe Gly Ser Val Lys Arg Val Tyr Ile Val Cys Thr
        195                 200                 205

Glu Asp Lys Gly Ile Pro Glu Glu Phe Gln Arg Trp Gln Ile Asp Asn
    210                 215                 220

Ile Gly Val Thr Glu Ala Ile Glu Ile Lys Gly Ala Asp His Met Ala
225                 230                 235                 240

Met Leu Cys Glu Pro Gln Lys Leu Cys Ala Ser Leu Leu Glu Ile Ala
                245                 250                 255

His Lys Tyr Asn
            260

<210> SEQ ID NO 23
<211> LENGTH: 262
<212> TYPE: PRT
<213> ORGANISM: Solanum tuberosum
<220> FEATURE:
<221> NAME/KEY: MISC_FEATURE
<223> OTHER INFORMATION: gi[56]392765

<400> SEQUENCE: 23

Met Glu Lys Gly Asn Lys Asn His Phe Val Leu Val His Gly Ala Cys
1               5                   10                  15

His Gly Ala Trp Cys Trp Tyr Lys Val Val Thr Ile Leu Arg Ser Glu
            20                  25                  30

Gly His Lys Val Ser Val Leu Asp Met Ala Ala Ser Gly Ile Asn Pro
        35                  40                  45

Lys His Val Glu Asp Leu Asn Ser Met Ala Asp Tyr Asn Glu Pro Leu
    50                  55                  60

Met Glu Phe Met Asn Ser Leu Pro Gln Gln Glu Arg Val Val Leu Val
65                  70                  75                  80

Gly His Ser Met Gly Gly Ile Asn Ile Ser Leu Ala Met Glu Lys Phe
                85                  90                  95

Pro His Lys Ile Ala Val Ala Val Phe Val Ser Ala Ser Met Pro Gly
            100                 105                 110

Pro Asp Leu Asn Leu Val Ala Val Thr Gln Gln Tyr Ser Gln Gln Val
        115                 120                 125

Glu Thr Pro Met Asp Thr Glu Phe Val Tyr Asn Asn Gly Leu Asp Lys
    130                 135                 140

Gly Pro Thr Ser Val Val Leu Gly Pro Lys Val Leu Ala Thr Ile Tyr
145                 150                 155                 160

Tyr Gln Phe Ser Pro Pro Glu Asp Leu Thr Leu Ala Thr Tyr Leu Val
                165                 170                 175

Arg Pro Val Pro Leu Phe Asp Glu Ser Val Leu Leu Thr Asn Thr Thr
            180                 185                 190

Leu Ser Lys Glu Lys Tyr Gly Ser Val His Arg Val Tyr Val Val Cys
        195                 200                 205

Asp Lys Asp Lys Val Leu Lys Glu Glu Gln Phe Gln Arg Trp Leu Ile
    210                 215                 220

Lys Asn Asn Pro Pro Asn Glu Val Gln Met Ile His Asp Ala Gly His
225                 230                 235                 240

Met Val Met Phe Ser Lys Pro Arg Glu Leu Cys Ser Cys Leu Val Met

```
                245                 250                 255
Ile Ser Gln Lys Tyr His
            260

<210> SEQ ID NO 24
<211> LENGTH: 266
<212> TYPE: PRT
<213> ORGANISM: Triticum aestivum
<220> FEATURE:
<221> NAME/KEY: MISC_FEATURE
<223> OTHER INFORMATION: CeresClone:644331

<400> SEQUENCE: 24

Met Glu Ala Cys Ala Gly Gln Ala Ser Ser Ala His Ile Val Leu Val
1               5                   10                  15

His Gly Ala Cys Leu Gly Gly Trp Ser Trp Phe Lys Val Ala Thr Arg
            20                  25                  30

Leu Arg Ser Ala Gly His Arg Val Ser Thr Pro Asp Leu Ala Ala Ser
        35                  40                  45

Gly Val Asp Pro Arg Pro Leu Arg Glu Val Pro Thr Phe Arg Asp Tyr
    50                  55                  60

Thr Lys Pro Leu Leu Asp Leu Glu Ser Leu Pro Ser Gly Glu Lys
65                  70                  75                  80

Val Val Leu Val Gly His Ser Leu Gly Gly Val Asn Val Ala Leu Ala
                85                  90                  95

Cys Glu Leu Phe Pro Glu Lys Ile Ala Ala Val Phe Val Ala Ala
            100                 105                 110

Phe Met Pro Asp His Arg Ser Pro Pro Ser Tyr Val Leu Glu Lys Phe
        115                 120                 125

Val Glu Gly Arg Thr Leu Asp Trp Met Asp Thr Glu Phe Lys Pro Gln
    130                 135                 140

Asp Pro Glu Gly Lys Leu Pro Thr Ser Met Leu Phe Gly Pro Leu Val
145                 150                 155                 160

Thr Arg Ala Lys Phe Phe Gln Leu Cys Ser Pro Glu Asp Leu Thr Leu
                165                 170                 175

Gly Arg Ser Leu Met Arg Val Asn Ser Met Phe Val Asp Asp Leu Arg
            180                 185                 190

Leu Gln Pro Pro His Thr Glu Ala Arg Tyr Gly Ser Val Arg Lys Ala
        195                 200                 205

Tyr Val Val Phe Lys Asp Asp His Ala Ile Val Glu Gln Phe Gln Arg
    210                 215                 220

Trp Met Val His Asn Tyr Pro Val Asp Glu Val Met Glu Ile Asp Gly
225                 230                 235                 240

Ala Asp His Met Ala Leu Leu Ser Thr Pro Thr Glu Leu Ala Arg Cys
                245                 250                 255

Leu Ala Asp Ile Ala Val Lys Tyr Ala Ala
            260                 265

<210> SEQ ID NO 25
<211> LENGTH: 265
<212> TYPE: PRT
<213> ORGANISM: Triticum aestivum
<220> FEATURE:
<221> NAME/KEY: MISC_FEATURE
<223> OTHER INFORMATION: CeresClone:936068

<400> SEQUENCE: 25

Met Glu Gly Ser Ser Ser Gly Lys His Phe Ile Leu Ile His Gly Leu
```

```
                1               5                   10                  15
            Cys His Gly Ala Trp Cys Trp Tyr Lys Leu Val Pro Met Leu Arg Ala
                            20                  25                  30

Ala Gly His Arg Val Thr Ala Leu Asp Met Ala Ala Ser Gly Ala His
                        35                  40                  45

Pro Ala Arg Met Asp Glu Val Pro Ser Phe Glu Asp Tyr Ser Trp Pro
                    50                  55                  60

Leu Leu Asp Ala Val Ala Ala Pro Ala Gly Glu Arg Leu Val Leu
            65                  70                  75                  80

Val Gly His Ser Leu Gly Gly Leu Asn Ile Ala Leu Ala Met Glu Arg
                            85                  90                  95

Phe Pro Arg Lys Val Ala Ala Val Phe Leu Ala Ala Cys Met Pro
                            100                 105                 110

Cys Val Gly Arg His Met Gly Ala Thr Thr Glu Glu Ile Met Arg Arg
                            115                 120                 125

Ile Lys Pro Asp Phe Phe Met Asp Met Lys Arg Met Val Leu Asn Thr
                    130                 135                 140

Ser Gln Gly Pro Arg Pro Ala Leu Val Phe Gly Pro Lys Ile Leu Ala
            145                 150                 155                 160

Ala Lys Leu Tyr Asp Arg Ser Ser Gly Glu Asp Gln Thr Leu Ala Thr
                            165                 170                 175

Met Leu Val Arg Pro Gly Cys Gln Phe Leu Asp Asp Pro Thr Met Lys
                        180                 185                 190

Asp Glu Ala Leu Leu Thr Glu Ala Lys Tyr Gly Ser Val Lys Lys Val
                        195                 200                 205

Tyr Val Val Ala Met Ala Asp Ala Ser Asn Ser Glu Glu Met Gln Arg
                    210                 215                 220

Trp Met Val Asp Met Ser Pro Gly Thr Glu Ala Glu Ile Ala Gly
            225                 230                 235                 240

Ala Asp His Met Ala Met Cys Ser Lys Pro Arg Glu Leu Cys Asp Val
                            245                 250                 255

Leu Leu Arg Ile Ala Asp Lys Tyr Glu
                            260                 265

<210> SEQ ID NO 26
<211> LENGTH: 268
<212> TYPE: PRT
<213> ORGANISM: Oryza sativa subsp. japonica
<220> FEATURE:
<221> NAME/KEY: MISC_FEATURE
<223> OTHER INFORMATION: gi[34]907176

<400> SEQUENCE: 26

Met Glu Ile Ser Ser Ser Lys Lys His Phe Ile Leu Val His Gly
            1               5                   10                  15

Leu Cys His Gly Ala Trp Cys Trp Tyr Arg Val Val Ala Ala Leu Arg
                            20                  25                  30

Ala Ala Gly His Arg Ala Thr Ala Leu Asp Met Ala Ala Ser Gly Ala
                        35                  40                  45

His Pro Ala Arg Val Asp Glu Val Gly Thr Phe Glu Glu Tyr Ser Arg
                    50                  55                  60

Pro Leu Leu Asp Ala Val Ala Ala Ala Ala Pro Gly Glu Arg Leu
            65                  70                  75                  80

Val Leu Val Gly His Ser His Gly Gly Leu Ser Val Ala Leu Ala Met
                            85                  90                  95
```

```
Glu Arg Phe Pro Asp Lys Val Ala Ala Val Phe Val Ala Ala
            100                 105                 110

Met Pro Cys Val Gly Lys His Met Gly Val Pro Thr Glu Glu Phe Met
        115                 120                 125

Arg Arg Thr Ala Pro Glu Gly Leu Leu Met Asp Cys Glu Met Val Ala
    130                 135                 140

Ile Asn Asn Ser Gln Gly Ser Gly Val Ala Ile Asn Leu Gly Pro Thr
145                 150                 155                 160

Phe Leu Ala Gln Lys Tyr Tyr Gln Gln Ser Pro Ala Glu Asp Leu Ala
                165                 170                 175

Leu Ala Lys Met Leu Val Arg Pro Gly Asn Gln Phe Met Asp Asp Pro
            180                 185                 190

Val Met Lys Asp Glu Ser Leu Leu Thr Asn Gly Asn Tyr Gly Ser Val
        195                 200                 205

Lys Lys Val Tyr Val Ile Ala Lys Ala Asp Ser Ser Thr Glu Glu
    210                 215                 220

Met Gln Arg Trp Met Val Ala Met Ser Pro Gly Thr Asp Val Glu Glu
225                 230                 235                 240

Ile Ala Gly Ala Asp His Ala Val Met Asn Ser Lys Pro Arg Glu Leu
                245                 250                 255

Cys Asp Ile Leu Ile Lys Ile Ala Asn Lys Tyr Glu
            260                 265

<210> SEQ ID NO 27
<211> LENGTH: 262
<212> TYPE: PRT
<213> ORGANISM: Oryza sativa (japonica cultivar-group)
<220> FEATURE:
<221> NAME/KEY: MISC_FEATURE
<223> OTHER INFORMATION: gi[57]899620

<400> SEQUENCE: 27

Met Glu Gly Ser Ser Ser Ser Lys His Phe Ile Leu Val His Gly
1               5                   10                  15

Leu Cys His Gly Ala Trp Cys Trp Tyr Lys Val Val Thr Met Leu Arg
            20                  25                  30

Ser Glu Gly His Arg Val Thr Ala Leu Asp Leu Ala Ala Ser Gly Val
        35                  40                  45

His Pro Ala Arg Val Asp Glu Val His Ser Phe Glu Glu Tyr Ser Gln
    50                  55                  60

Pro Leu Leu Asp Ala Val Ala Glu Ala Pro Ala Gly Glu Arg Leu Ile
65                  70                  75                  80

Leu Val Gly His Ser Phe Gly Gly Leu Ser Ile Ala Leu Ala Met Glu
                85                  90                  95

Arg Phe Pro Glu Lys Ile Ala Val Ala Val Phe Val Ala Ala Ala Val
            100                 105                 110

Pro Cys Val Gly Lys Arg Ile Ile Pro Glu Leu Ile Arg Glu Lys Ala
        115                 120                 125

Pro Lys Asp Met Leu Leu Asp Ser Lys Met Ile Pro Ile Asn Asn Lys
    130                 135                 140

Gln Gly Pro Gly Thr Ala Ile Leu Leu Gly Pro Asn Phe Leu Ala Glu
145                 150                 155                 160

Lys Gly Tyr Pro Leu Ser Pro Ala Glu Asp Leu Thr Leu Ala Lys Leu
                165                 170                 175

Leu Val Arg Pro Thr Ser Gln Phe Val Asp Asp Pro Thr Met Lys Asp
            180                 185                 190
```

```
Asp Arg Leu Leu Thr Ser Ala Asn Tyr Gly Ser Val Lys Arg Val Cys
        195                 200                 205

Leu Met Ala Met Glu Asp Asp Leu Lys Glu Val His Arg Tyr Met Ile
210                 215                 220

Thr Leu Ser Pro Gly Val Glu Val Glu Ile Ala Gly Ala Asp His
225             230                 235                 240

Ala Val Met Cys Ser Arg Pro Arg Glu Leu Ser Asp Leu Leu Ala Lys
                245                 250                 255

Ile Gly Ser Lys Tyr Asp
            260

<210> SEQ ID NO 28
<211> LENGTH: 265
<212> TYPE: PRT
<213> ORGANISM: Capsella rubella
<220> FEATURE:
<221> NAME/KEY: MISC_FEATURE
<223> OTHER INFORMATION: gi[15]866583

<400> SEQUENCE: 28

Met Gly Gly Asp Gly Gly Ala Glu Gln Pro Val Ile His Phe Val Phe
1               5                   10                  15

Val His Gly Ala Ser His Gly Ala Trp Cys Trp Tyr Lys Leu Thr Ser
            20                  25                  30

Leu Leu Glu Thr Ala Gly Phe Lys Thr Thr Ser Val Asp Leu Thr Gly
        35                  40                  45

Ala Gly Ile Ser Val Thr Asp Ser Asn Thr Val Leu Glu Ser Asp Gln
    50                  55                  60

Tyr Asn Arg Pro Leu Phe Ser Leu Leu Ser Asp Leu Pro Pro Ser His
65                  70                  75                  80

Lys Val Ile Leu Val Gly His Ser Ile Gly Gly Ser Val Thr Asp
                85                  90                  95

Ala Leu Cys Arg Phe Thr Asp Lys Ile Ser Met Ala Ile Tyr Leu Ala
            100                 105                 110

Ala Ser Met Val Lys Pro Gly Ser Val Pro Ser Pro His Val Ser Asp
        115                 120                 125

Met His Ala Asp Ala Arg Glu Glu Asn Ile Trp Glu Tyr Thr Tyr Gly
    130                 135                 140

Glu Gly Thr Asp Lys Pro Pro Thr Gly Val Ile Met Lys Gln Glu Phe
145                 150                 155                 160

Leu Arg Gln Tyr Tyr Tyr Ser Gln Ser Pro Leu Glu Asp Val Ser Leu
                165                 170                 175

Ala Thr Lys Leu Leu Arg Pro Ala Pro Met Arg Ala Phe Gln Asp Leu
            180                 185                 190

Asp Lys Ser Pro Pro Asn Pro Glu Val Glu Lys Val Pro Arg Val Tyr
        195                 200                 205

Ile Lys Thr Gly Lys Asp Asn Leu Phe Ser Ser Val Arg Gln Asp Leu
    210                 215                 220

Leu Val Lys Asn Trp Pro Pro Ser Gln Phe Tyr Val Leu Glu Glu Ser
225                 230                 235                 240

Asp His Ser Ala Phe Phe Ser Val Pro Thr Thr Leu Phe Val Tyr Leu
                245                 250                 255

Leu Arg Ala Val Ser Phe Leu His Lys
            260                 265
```

```
<210> SEQ ID NO 29
<211> LENGTH: 265
<212> TYPE: PRT
<213> ORGANISM: Lycopersicon hirsutum f. glabratum
<220> FEATURE:
<221> NAME/KEY: MISC_FEATURE
<223> OTHER INFORMATION: gi[56]393011
<220> FEATURE:
<221> NAME/KEY: misc_feature
<222> LOCATION: (46)..(46)
<223> OTHER INFORMATION: Xaa can be any naturally occurring amino acid

<400> SEQUENCE: 29

Met Glu Lys Ser Met Ser Pro Phe Val Lys His Phe Val Leu Val
1               5                   10                  15

His Thr Ala Phe His Gly Ala Trp Cys Trp Tyr Lys Ile Val Ala Leu
            20                  25                  30

Met Arg Ser Ser Gly His Asn Val Thr Ala Leu Asp Leu Xaa Ala Ser
        35                  40                  45

Gly Ile Asn Pro Lys Gln Ala Leu Gln Ile Pro Asn Phe Ser Asp Tyr
    50                  55                  60

Leu Ser Pro Leu Met Glu Phe Met Ala Ser Leu Pro Ala Asn Glu Lys
65                  70                  75                  80

Ile Ile Leu Val Gly His Ala Leu Gly Gly Leu Ala Ile Ser Lys Ala
                85                  90                  95

Met Glu Thr Phe Pro Glu Lys Ile Ser Val Ala Val Phe Leu Ser Gly
            100                 105                 110

Leu Met Pro Gly Pro Asn Ile Asp Ala Thr Thr Val Cys Thr Lys Ala
        115                 120                 125

Gly Ser Ala Val Leu Gly Gln Leu Asp Asn Cys Val Thr Tyr Glu Asn
    130                 135                 140

Gly Pro Thr Asn Pro Pro Thr Thr Leu Ile Ala Gly Pro Lys Phe Leu
145                 150                 155                 160

Ala Thr Asn Val Tyr His Leu Ser Pro Ile Glu Asp Leu Ala Leu Ala
                165                 170                 175

Thr Ala Leu Val Arg Pro Leu Tyr Leu Tyr Leu Ala Glu Asp Ile Ser
            180                 185                 190

Lys Glu Val Val Leu Ser Ser Lys Arg Tyr Gly Ser Val Lys Arg Val
        195                 200                 205

Phe Ile Val Ala Thr Glu Asn Asp Ala Leu Lys Lys Glu Phe Leu Lys
    210                 215                 220

Leu Met Ile Glu Lys Asn Pro Pro Asp Glu Val Lys Glu Ile Glu Gly
225                 230                 235                 240

Ser Asp His Val Thr Met Met Ser Lys Pro Gln Gln Leu Phe Thr Thr
                245                 250                 255

Leu Leu Ser Ile Ala Asn Lys Tyr Lys
            260                 265

<210> SEQ ID NO 30
<211> LENGTH: 412
<212> TYPE: DNA
<213> ORGANISM: Arabidopsis thaliana
<220> FEATURE:
<221> NAME/KEY: MISC_FEATURE
<223> OTHER INFORMATION: clone34419_inplanta_experimental_L21

<400> SEQUENCE: 30
aacaacgcca caatcatggc tttgttctta tctcctaaaa ccatcactct tctcttcttc    60
tccctctccc tcgcactcta ctgcagcatc gatcctttcc acactgcgcc atttccgatt   120
```

```
tccccaatttt cgtctctcac gaagttatct ctccacgtcc cgacgaagtt ccatgggaga      180
gagattcaca aaattcactt cagaaatcaa agattctgtt ttttaaccaa atccaaggtc      240
cagagagcgt cgcctttgat tctctcggac gtggtccgta cacggcgttg ctgatggtag      300
ggttttgttt tgggatggag agaaatggat tgatttcgct tatacttcga gtaatcgatc      360
ggagatttgt gatccgaagt ataagcgaaa tcaatccatt tctctccatc cc              412
```

<210> SEQ ID NO 31
<211> LENGTH: 92
<212> TYPE: PRT
<213> ORGANISM: Arabidopsis thaliana
<220> FEATURE:
<221> NAME/KEY: MISC_FEATURE
<223> OTHER INFORMATION: peptide_clone34419_inplanta_experimental_L21

<400> SEQUENCE: 31

```
Met Ala Leu Phe Leu Ser Pro Lys Thr Ile Thr Leu Leu Phe Phe Ser
1               5                   10                  15

Leu Ser Leu Ala Leu Tyr Cys Ser Ile Asp Pro Phe His Thr Ala Pro
            20                  25                  30

Phe Pro Ile Ser Pro Ile Ser Ser Leu Thr Lys Leu Ser Leu His Val
        35                  40                  45

Pro Thr Lys Phe His Gly Arg Glu Ile His Lys Ile His Phe Arg Asn
    50                  55                  60

Gln Arg Phe Cys Phe Leu Thr Lys Ser Lys Val Gln Arg Ala Ser Pro
65                  70                  75                  80

Leu Ile Leu Ser Asp Val Val Arg Thr Arg Arg Cys
                85                  90
```

<210> SEQ ID NO 32
<211> LENGTH: 1776
<212> TYPE: DNA
<213> ORGANISM: Arabidopsis thaliana
<220> FEATURE:
<221> NAME/KEY: MISC_FEATURE
<223> OTHER INFORMATION: cDNA12659859_inplanta_experimental_L22

<400> SEQUENCE: 32

```
gagcagaaga acttacttat agaaaaaaat gggaatttca aaaccactcc ttctattttc      60
gattttagtc ctctattttt cactctacac cattacacca acttcttcat tagcctccct     120
ccaagatcaa ttcatcaact gtgtccaaag aaacacacat gtttacttcc cacttgagaa     180
aacgttcttt gctcctacaa aaaatgtctc tatgttcagc caagttcttg aatcgacggc     240
tcaaaatctc cggttcttga aaaaatccat gcctaaaccg ggattcatat tcagccctat     300
tcacgagtct cacgtacaag cttccatcat ttgttccaag aaactccgaa tgcatctccg     360
tgtcagaagc ggcggtcacg actacgaagg cttgtcttat gtctctcaga tcgataaacc     420
gtttatattg atggatctgt caaagatgag acaggtcaac attaatattc aagcaacag      480 tgcttgggtt caatctggtg ccactgttgg tgaactttat tacaggattg cggagaagag     540
caaagtccat gggttcccgg cgggtttgtg ctcgagctta gcataggag gacacataac      600 aggcggtgcg tacggttcca tgatgcgaaa atatggtcta ggtgcagaca atgttctaga     660
cgcaaagatt gttgatgcca acggtaaatt actcgataga gccgcgatgg gtgaggatac     720 atttgggct attagaggag gcgctggagg gagttttggg ataattctag catggaagat     780
caagcttgtt cctgttccta agaccgtgac cgtctttacc gtcaccaaaa cgttacaaca     840
```

```
agacgtgggt aacaagatta tctcaaagtg gcaaagagtt gcggacaagc ttgttgaaga    900
gctattcatc agagtgctct tcaacgtagc tggaaccggt gggaacaaga ctgtgacgac    960
gtcgtacaat gctctgtttc ttggcgggaa aggaacgctg atgaacgtta tgaagaagag   1020
tttcccgag ctagggctaa catttaaaga ttgtatcgaa atgagctggc ttgaatccat    1080
tgcttacatt tctggattcc cgacccacac gcctactaat gttttgcttc aagggaagtc   1140
tccgttccca aaggtcagct tcaaagccaa atcggatttc gtgaaaaccc cgattcccga   1200
atccgggctt caagggatct tcaagaagct acttaaagaa gatattccat tgatgatatg   1260
gaatccttac ggaggaatga tggcgaaaat ccccgaatcc caaatccctt ttccgcatcg   1320
aaaaggagtc ctcttcaagg ttcagtacgt aacaagttgg ctagacagtg acaagagacc   1380
gagcagacac atcaactgga tcagagatct ctatagttac atgacgcctt atgtctcaag   1440
taacccacga gaagcttacg tgaactaccg tgatttagac ctgggaagga acacgaaaga   1500
cgtgaaaaca tgcatcaaac aagctcaagt ctggggagct aactacttca aaaacaattt   1560
caacagattg atgatgatta aagcaaaggt tgatccagaa aacttcttta gacacgagca   1620
gagcattcca cctatgatgt aacgaggtca atcaaataag aataaattag aagaaaatca   1680
gataatggtt cttctgtatt tcggaaaaat gttattctag ctatgcttgt agtagtacta   1740
tgtttcacct aaaattcgat atgttgcttc ttagta                             1776
```

```
<210> SEQ ID NO 33
<211> LENGTH: 537
<212> TYPE: PRT
<213> ORGANISM: Arabidopsis thaliana
<220> FEATURE:
<221> NAME/KEY: MISC_FEATURE
<223> OTHER INFORMATION: peptide_cDNA12659859_inplanta_experimental_L22

<400> SEQUENCE: 33

Met Gly Ile Ser Lys Pro Leu Leu Phe Ser Ile Leu Val Leu Tyr
 1               5                  10                  15

Phe Ser Leu Tyr Thr Ile Thr Pro Thr Ser Ser Leu Ala Ser Leu Gln
            20                  25                  30

Asp Gln Phe Ile Asn Cys Val Gln Arg Asn Thr His Val Tyr Phe Pro
        35                  40                  45

Leu Glu Lys Thr Phe Phe Ala Pro Thr Lys Asn Val Ser Met Phe Ser
    50                  55                  60

Gln Val Leu Glu Ser Thr Ala Gln Asn Leu Arg Phe Leu Lys Lys Ser
65                  70                  75                  80

Met Pro Lys Pro Gly Phe Ile Phe Ser Pro Ile His Glu Ser His Val
                85                  90                  95

Gln Ala Ser Ile Ile Cys Ser Lys Lys Leu Arg Met His Leu Arg Val
            100                 105                 110

Arg Ser Gly Gly His Asp Tyr Glu Gly Leu Ser Tyr Val Ser Gln Ile
        115                 120                 125

Asp Lys Pro Phe Ile Leu Met Asp Leu Ser Lys Met Arg Gln Val Asn
    130                 135                 140

Ile Asn Ile Gln Asp Asn Ser Ala Trp Val Gln Ser Gly Ala Thr Val
145                 150                 155                 160

Gly Glu Leu Tyr Tyr Arg Ile Ala Glu Lys Ser Lys Val His Gly Phe
                165                 170                 175

Pro Ala Gly Leu Cys Ser Ser Leu Gly Ile Gly Gly His Ile Thr Gly
            180                 185                 190
```

Gly Ala Tyr Gly Ser Met Met Arg Lys Tyr Gly Leu Gly Ala Asp Asn
            195                 200                 205

Val Leu Asp Ala Lys Ile Val Asp Ala Asn Gly Lys Leu Leu Asp Arg
    210                 215                 220

Ala Ala Met Gly Glu Asp Thr Phe Trp Ala Ile Arg Gly Gly Ala Gly
225                 230                 235                 240

Gly Ser Phe Gly Ile Ile Leu Ala Trp Lys Ile Lys Leu Val Pro Val
                245                 250                 255

Pro Lys Thr Val Thr Val Phe Thr Val Thr Lys Thr Leu Gln Gln Asp
            260                 265                 270

Val Gly Asn Lys Ile Ile Ser Lys Trp Gln Arg Val Ala Asp Lys Leu
        275                 280                 285

Val Glu Glu Leu Phe Ile Arg Val Leu Phe Asn Val Ala Gly Thr Gly
    290                 295                 300

Gly Asn Lys Thr Val Thr Thr Ser Tyr Asn Ala Leu Phe Leu Gly Gly
305                 310                 315                 320

Lys Gly Thr Leu Met Asn Val Met Lys Lys Ser Phe Pro Glu Leu Gly
                325                 330                 335

Leu Thr Phe Lys Asp Cys Ile Glu Met Ser Trp Leu Glu Ser Ile Ala
            340                 345                 350

Tyr Ile Ser Gly Phe Pro Thr His Thr Pro Thr Asn Val Leu Leu Gln
        355                 360                 365

Gly Lys Ser Pro Phe Pro Lys Val Ser Phe Lys Ala Lys Ser Asp Phe
    370                 375                 380

Val Lys Thr Pro Ile Pro Glu Ser Gly Leu Gln Gly Ile Phe Lys Lys
385                 390                 395                 400

Leu Leu Lys Glu Asp Ile Pro Leu Met Ile Trp Asn Pro Tyr Gly Gly
                405                 410                 415

Met Met Ala Lys Ile Pro Glu Ser Gln Ile Pro Phe Pro His Arg Lys
            420                 425                 430

Gly Val Leu Phe Lys Val Gln Tyr Val Thr Ser Trp Leu Asp Ser Asp
        435                 440                 445

Lys Arg Pro Ser Arg His Ile Asn Trp Ile Arg Asp Leu Tyr Ser Tyr
    450                 455                 460

Met Thr Pro Tyr Val Ser Ser Asn Pro Arg Glu Ala Tyr Val Asn Tyr
465                 470                 475                 480

Arg Asp Leu Asp Leu Gly Arg Asn Thr Lys Asp Val Lys Thr Cys Ile
                485                 490                 495

Lys Gln Ala Gln Val Trp Gly Ala Asn Tyr Phe Lys Asn Asn Phe Asn
            500                 505                 510

Arg Leu Met Met Ile Lys Ala Lys Val Asp Pro Glu Asn Phe Phe Arg
        515                 520                 525

His Glu Gln Ser Ile Pro Pro Met Met
    530                 535

<210> SEQ ID NO 34
<211> LENGTH: 543
<212> TYPE: PRT
<213> ORGANISM: Glycine max
<220> FEATURE:
<221> NAME/KEY: MISC_FEATURE
<223> OTHER INFORMATION: CeresClone:522974

<400> SEQUENCE: 34

Asn Thr Arg Glu Ser Arg Asn Gln Arg Thr Met Lys Ser Leu Arg Ser
1               5                   10                  15

```
Ile Leu Ala Thr Phe Val Leu Leu Ser Ile Ser Leu Thr Ile Ser
             20                  25                  30

Leu Pro Ile Glu Glu Ala Phe Asn His Cys Leu Thr Gln His Ser Gln
             35                  40                  45

Thr Pro Asn Gln Phe Pro Ser Ser Ile Tyr Tyr Thr Asn Gly Ser
 50                  55                  60

Phe Thr Ser Ile Leu Glu Ser Thr Ala Gln Asn Leu Arg Tyr Leu Leu
 65                  70                  75                  80

Pro Ser Val Pro Lys Pro Asp Phe Ile Phe Thr Pro Leu Asp Asp Ser
                 85                  90                  95

Gln Val Gln Ala Ala Val Val Cys Ala Lys Lys Leu Gly Ile His Met
             100                 105                 110

Arg Val Arg Ser Gly Gly His Asp Tyr Glu Gly Leu Ser Tyr Val Ser
             115                 120                 125

Leu Ile Glu Lys Pro Phe Met Ile Leu Asp Leu Ala Lys Leu Arg Ala
 130                 135                 140

Val Asn Val Asp Ile Ala Arg Asn Thr Ala Trp Ile Gln Ala Gly Ala
145                 150                 155                 160

Thr Ile Gly Glu Val Tyr Tyr Arg Ile Ser Glu Lys Ser Ala Val His
                 165                 170                 175

Gly Phe Pro Ala Gly Leu Cys Thr Thr Leu Gly Ile Gly Gly His Ile
             180                 185                 190

Thr Gly Gly Ala Tyr Gly Ser Met Met Arg Lys Tyr Gly Leu Gly Ala
             195                 200                 205

Asp Asn Val Leu Asp Ala Arg Ile Val Asp Ala Asn Gly Lys Val Leu
             210                 215                 220

Asp Arg Lys Ala Met Gly Glu Asp Leu Phe Trp Ala Ile Arg Gly Gly
225                 230                 235                 240

Gly Gly Gly Ser Phe Gly Val Ile Leu Trp Trp Lys Ile Lys Leu Val
                 245                 250                 255

Pro Val Pro Gln Thr Val Thr Val Phe Thr Val Thr Lys Thr Leu Glu
             260                 265                 270

Gln Gly Gly Ser Lys Leu Leu His Arg Trp Gln Gln Val Ala Pro His
             275                 280                 285

Ile Asp Glu Asn Leu Phe Ile Arg Val Ile Gln Pro Gly Asn Gly
 290                 295                 300

Thr Val Pro Gly Lys Arg Thr Val Thr Thr Ser Tyr Asn Ala Leu Phe
305                 310                 315                 320

Leu Gly Gly Ala Asn Arg Leu Leu Gln Val Met Lys His Gly Phe Pro
                 325                 330                 335

Glu Leu Gly Leu Thr Arg Lys Asp Cys Val Glu Thr Ser Trp Ile Glu
             340                 345                 350

Ser Val Leu Tyr Ile Ala Gly Tyr Pro Asp Gly Thr Ala Pro Glu Val
             355                 360                 365

Leu Leu Gln Gly Lys Ser Thr Thr Lys Ala Tyr Phe Lys Ala Lys Ser
 370                 375                 380

Asp Phe Val Arg Glu Val Ile Thr Glu Lys Ser Leu Asn Ala Leu Trp
385                 390                 395                 400

Lys Ile Phe Leu Gln Asp Asp Gly Pro Leu Met Ile Trp Asn Pro Tyr
                 405                 410                 415

Gly Gly Lys Met Ser Arg Ile Ala Glu Ser Ala Thr Pro Phe Pro His
             420                 425                 430
```

```
Arg Lys Gly Val Leu Tyr Lys Ile Gln His Val Thr Gly Trp Leu Asp
            435                 440                 445

Gly Glu Lys Ser Met Ala Lys His Met Asn Trp Met Arg Lys Phe Tyr
450                 455                 460

Phe Tyr Met Ala Pro Tyr Val Ser Lys Tyr Pro Arg Glu Thr Tyr Val
465                 470                 475                 480

Asn Tyr Arg Asp Leu Asp Ile Gly Met Asn Gln Lys Asn Asn Thr Ser
                485                 490                 495

Leu Leu Lys Ala Ser Ser Trp Gly Tyr Arg Tyr Phe Lys Gly Asn Phe
            500                 505                 510

Asn Arg Leu Val Lys Val Lys Thr Lys Val Asp Pro Ser Asn Phe Phe
            515                 520                 525

Arg His Glu Gln Ser Ile Pro Leu Leu Pro Thr Gly Lys Lys Glu
            530                 535                 540

<210> SEQ ID NO 35
<211> LENGTH: 538
<212> TYPE: PRT
<213> ORGANISM: Glycine max
<220> FEATURE:
<221> NAME/KEY: MISC_FEATURE
<223> OTHER INFORMATION: CeresClone:561310

<400> SEQUENCE: 35

Thr Glu Thr Arg Glu Ile Ile Val Asn Met Glu Leu Ser Tyr Cys Ala
1               5                   10                  15

Val Phe Leu Ile Leu Leu Ile Pro Ile Ser Arg Ala Asp Ala Thr Ser
            20                  25                  30

Val Glu Lys Gln Phe Lys Glu Cys Leu Leu Thr Gln Leu Asp Gly Asn
        35                  40                  45

Ser Glu His Ile Glu Lys Ile Thr Phe Thr Ser Ser Thr Leu Tyr
    50                  55                  60

Pro Gln Val Trp Asp Ser Leu Ala Gln Asn Pro Arg Trp Val Asn Ile
65                  70                  75                  80

Ser Ser Arg Lys Pro Leu Met Ile Leu Thr Pro Phe His Glu Ser Glu
                85                  90                  95

Ile Gln Ala Ala Ile Leu Cys Ser Lys Glu Leu Lys Leu Gln Leu Arg
            100                 105                 110

Val Arg Ser Gly Gly His Asp Tyr Glu Gly Leu Ser Tyr Leu Ser Asp
        115                 120                 125

Val Pro Phe Val Met Val Asp Leu Ile Asn Ile Arg Ser Ile Glu Ile
    130                 135                 140

Asn Leu Ala Asp Glu Thr Ala Trp Val Gln Ala Gly Ala Ser Ile Gly
145                 150                 155                 160

Glu Leu Tyr Tyr Lys Ile Ser Lys Ala Ser Lys Val His Gly Phe Pro
                165                 170                 175

Ala Gly Thr Cys Pro Ser Val Gly Ile Gly Gly His Ile Ser Gly Gly
            180                 185                 190

Gly Gln Gly Leu Met Leu Arg Lys His Gly Leu Ala Ala Asp Asn Val
        195                 200                 205

Val Asp Ala Tyr Leu Ile Asp Ala Asn Gly Lys Ile His Asp Arg Lys
    210                 215                 220

Ser Met Gly Glu Asp Val Phe Trp Ala Ile Arg Gly Gly Asp Ala Ser
225                 230                 235                 240

Ser Phe Gly Val Ile Leu Ala Trp Lys Ile Lys Leu Val Arg Val Pro
                245                 250                 255
```

```
Pro Ile Val Thr Gly Phe Asn Val Pro Arg Thr Pro Glu Glu Gly Val
            260                 265                 270

Thr Asp Leu Ile His Arg Trp Gln Tyr Ile Ala His Asp Leu His Glu
            275                 280                 285

Asp Leu Val Ile Arg Val Ile Ala Gln Ile Ser Gly His Asp Lys Ser
            290                 295                 300

Lys Lys Phe Arg Ala Thr Phe Asn Ser Ile Phe Leu Gly Gly Val Asp
305                 310                 315                 320

Arg Leu Ile Pro Leu Met Asn Glu Ser Phe Pro Glu Leu Gly Leu Gln
                325                 330                 335

Ala Lys Asp Cys Thr Glu Met Ser Trp Ile Gln Ser Val Met Phe Ile
                340                 345                 350

Ala Gly Tyr Asn Ile Glu Asp Pro Leu Glu Leu Leu Asn Arg Thr
                355                 360                 365

Thr Met Phe Lys Arg Ser Phe Lys Ala Lys Ser Asp Phe Phe Lys Glu
    370                 375                 380

Pro Val Pro Lys Ser Gly Leu Glu Gly Ala Trp Lys Leu Leu Leu Glu
385                 390                 395                 400

Glu Glu Ile Ala Phe Leu Ile Met Glu Pro Tyr Gly Gly Arg Met Asn
                405                 410                 415

Glu Ile Ser Glu Ser Glu Ile Pro Phe Pro His Arg Lys Gly Asn Leu
                420                 425                 430

Tyr Asn Leu Gln Tyr Leu Val Asn Trp Glu Val Asn Ser Asp Glu Ala
                435                 440                 445

Ser Arg Arg His Leu Gln Trp Ala Lys Met Val Tyr Lys Tyr Met Thr
    450                 455                 460

Pro Tyr Val Ser Lys Ser Pro Arg Ala Ala Tyr Phe Asn Tyr Lys Asp
465                 470                 475                 480

Leu Asp Leu Gly Lys Asn Lys Leu Asp Ser Thr Ser Tyr Ser Glu Ala
                485                 490                 495

Ser Val Trp Gly Lys Lys Tyr Phe Lys Gly Asn Phe Arg Arg Leu Ala
                500                 505                 510

Gln Ile Lys Thr Lys Phe Asp Pro Leu Asn Phe Phe Arg Asn Glu Gln
    515                 520                 525

Ser Ile Pro Leu Leu Asn Ser His His Ser
    530                 535

<210> SEQ ID NO 36
<211> LENGTH: 535
<212> TYPE: PRT
<213> ORGANISM: Vigna unguiculata
<220> FEATURE:
<221> NAME/KEY: MISC_FEATURE
<223> OTHER INFORMATION: gi[13]161397

<400> SEQUENCE: 36

Met Lys Thr Leu Ser Cys Tyr Tyr Thr Phe Ala Thr Val Ile Ala Leu
1               5                   10                  15

Leu Phe Ser Phe Thr Pro Ser Ser Ala Asp Thr His Glu Asn Phe Leu
                20                  25                  30

Gln Cys Leu Tyr Ser Tyr Pro His Asn Thr Asn Ser Ile Ser Ser Val
            35                  40                  45

Leu Tyr Thr Gln Thr Asn Ser Ser Tyr Phe Ser Val Leu Asp Ala Thr
    50                  55                  60

Met Gln Asn Leu Arg Phe Ser Asp Ser Arg Lys Pro Leu Val Ile Val
```

-continued

```
            65                  70                  75                  80
Thr Pro Gln Val Val Ser His Ile Gln Ala Thr Ile Lys Cys Ser Gln
                    85                  90                  95
Arg His Gly Leu Gln Ile Arg Thr Arg Ser Gly Gly His Asp Tyr Glu
                100                 105                 110
Gly Leu Ser Tyr Val Ala Arg Val Pro Phe Val Ile Leu Asp Leu Leu
                115                 120                 125
Asn Phe Arg Glu Ile Lys Val Asp Val Glu Asn Arg Thr Ala Trp Val
            130                 135                 140
Gln Val Gly Ala Thr Leu Gly Glu Leu Tyr Tyr Thr Ile Ser Gln Ala
145                 150                 155                 160
Ser Lys Thr Leu Gly Phe Pro Ala Gly Val Cys Tyr Ser Val Gly Ala
                165                 170                 175
Gly Gly His Ile Ser Gly Gly Tyr Gly Phe Leu Met Arg Lys Tyr
                180                 185                 190
Gly Leu Ala Ala Asp Asn Val Ile Asp Ala His Ile Ile Asp Val Asn
                195                 200                 205
Gly Asn Leu Leu Asp Arg Lys Ala Met Gly Glu Asp Leu Phe Trp Ala
            210                 215                 220
Ile Arg Gly Gly Gly Ala Ser Phe Gly Val Ile Val Ser Trp Lys
225                 230                 235                 240
Ile Lys Leu Val Pro Val Pro Ser Thr Val Thr Val Phe Asn Val Glu
                245                 250                 255
Arg Ile Leu Glu Glu Asn Ala Thr Glu Ile Ile Glu Lys Trp Gln Leu
                260                 265                 270
Val Ala Asn Lys Leu Asp Glu Arg Ile Phe Leu Arg Met Asp Leu Ala
            275                 280                 285
Arg Ala Asn Ser Ser Gln His Gly Lys Leu Ala Leu Gln Ala Asn Phe
            290                 295                 300
Val Ala Met Phe Gln Gly Gly Val Glu Glu Leu Ile Pro Leu Met Gln
305                 310                 315                 320
Lys Asn Phe Pro Glu Leu Gly Leu Lys Arg Lys Asp Cys Thr Glu Thr
                325                 330                 335
Ser Trp Ile Gly Ser Ala Val Phe Thr Asn Gly Ala Leu Ile Gly Ser
                340                 345                 350
Ser Gly His Glu Ala Pro Glu Val Leu Leu Asn Arg Thr Gln Ile Arg
                355                 360                 365
Ser Gly Lys Tyr Lys Gly Lys Ser Asp Tyr Val Arg Lys Pro Ile Pro
            370                 375                 380
Val Asp Gly Leu Arg Gly Leu Trp Arg Trp Leu Asn Asp Asp Lys Val
385                 390                 395                 400
Gln Tyr Ser Gln Leu Gln Phe Ala Pro Tyr Gly Gly Lys Met Asp Asn
                405                 410                 415
Ile Ser Glu Ser Glu Ile Pro Phe Ala His Arg Ser Gly Tyr Ile Phe
                420                 425                 430
His Ile His Tyr Val Val Trp Gln Glu Glu Gly Asp Glu Ala Thr
            435                 440                 445
Gln Arg His Val Asn Trp Ile Arg Arg Leu Tyr Lys Tyr Met Glu Pro
            450                 455                 460
Tyr Val Ser Asn Ser Pro Arg Ala Ala Tyr Val Asn Tyr Arg Asp Leu
465                 470                 475                 480
Asp Ile Gly Val Asn Asn Asn Gly Tyr Thr Ser Tyr His Gln Ala Ser
                485                 490                 495
```

```
Ile Trp Gly Leu Lys Tyr Phe Ser Asn Asn Phe Lys Arg Leu Ala Thr
            500                 505                 510

Val Lys Thr Lys Val Asp Pro His Asn Phe Phe Arg Asn Glu Gln Ser
            515                 520                 525

Ile Pro Thr Leu Ser Lys Glu
            530                 535

<210> SEQ ID NO 37
<211> LENGTH: 538
<212> TYPE: PRT
<213> ORGANISM: Helianthus annuus
<220> FEATURE:
<221> NAME/KEY: MISC_FEATURE
<223> OTHER INFORMATION: gi[18]652400

<400> SEQUENCE: 37

Met Ala Asn Ile Thr Ser Ser Phe Asn Met Gln Thr Ser Ile Leu Thr
1               5                   10                  15

Leu Leu Leu Leu Leu Ser Thr Gln Ser Ser Ala Thr Ser Arg Ser
            20                  25                  30

Ile Thr Asp Arg Phe Ile Gln Cys Leu His Asp Arg Ala Asp Pro Ser
            35                  40                  45

Phe Pro Ile Thr Gly Glu Val Tyr Thr Pro Gly Asn Ser Ser Phe Pro
    50                  55                  60

Thr Val Leu Gln Asn Tyr Ile Arg Asn Leu Arg Phe Asn Glu Thr Thr
65                  70                  75                  80

Thr Pro Lys Pro Phe Leu Ile Ile Thr Ala Glu His Val Ser His Ile
            85                  90                  95

Gln Ala Ala Val Val Cys Gly Lys Gln Asn Arg Leu Leu Leu Lys Thr
            100                 105                 110

Arg Ser Gly Gly His Asp Tyr Glu Gly Leu Ser Tyr Leu Thr Asn Thr
            115                 120                 125

Asn Gln Pro Phe Phe Ile Val Asp Met Phe Asn Leu Arg Ser Ile Asn
        130                 135                 140

Val Asp Ile Glu Gln Glu Thr Ala Trp Val Gln Ala Gly Ala Thr Leu
145                 150                 155                 160

Gly Glu Val Tyr Tyr Arg Ile Ala Glu Lys Ser Asn Lys His Gly Phe
                165                 170                 175

Pro Ala Gly Val Cys Pro Thr Val Gly Val Gly His Phe Ser Gly
            180                 185                 190

Gly Gly Tyr Gly Asn Leu Met Arg Lys Tyr Gly Leu Ser Val Asp Asn
            195                 200                 205

Ile Val Asp Ala Gln Ile Ile Asp Val Asn Gly Lys Leu Leu Asp Arg
        210                 215                 220

Lys Ser Met Gly Glu Asp Leu Phe Trp Ala Ile Thr Gly Gly Gly Gly
225                 230                 235                 240

Val Ser Phe Gly Val Val Leu Ala Tyr Lys Ile Lys Leu Val Arg Val
                245                 250                 255

Pro Glu Val Val Thr Val Phe Thr Ile Glu Arg Arg Glu Glu Gln Asn
            260                 265                 270

Leu Ser Thr Ile Ala Glu Arg Trp Val Gln Val Ala Asp Lys Leu Asp
            275                 280                 285

Arg Asp Leu Phe Leu Arg Met Thr Phe Ser Val Ile Asn Asp Thr Asn
        290                 295                 300

Gly Gly Lys Thr Val Arg Ala Ile Phe Pro Thr Leu Tyr Leu Gly Asn
```

```
305                 310                 315                 320
Ser Arg Asn Leu Val Thr Leu Leu Asn Lys Asp Phe Pro Glu Leu Gly
                325                 330                 335

Leu Gln Glu Ser Asp Cys Thr Glu Met Ser Trp Val Glu Ser Val Leu
                340                 345                 350

Tyr Tyr Thr Gly Phe Pro Ser Gly Thr Pro Thr Thr Ala Leu Leu Ser
                355                 360                 365

Arg Thr Pro Gln Arg Leu Asn Pro Phe Lys Ile Lys Ser Asp Tyr Val
370                 375                 380

Gln Asn Pro Ile Ser Lys Arg Gln Phe Glu Phe Ile Phe Glu Arg Met
385                 390                 395                 400

Lys Glu Leu Glu Asn Gln Met Leu Ala Phe Asn Pro Tyr Gly Gly Arg
                405                 410                 415

Met Ser Glu Ile Ser Glu Phe Ala Lys Pro Phe Pro His Arg Ser Gly
                420                 425                 430

Asn Ile Ala Lys Ile Gln Tyr Glu Val Asn Trp Glu Asp Leu Ser Asp
                435                 440                 445

Glu Ala Glu Asn Arg Tyr Leu Asn Phe Thr Arg Leu Met Tyr Asp Tyr
                450                 455                 460

Met Thr Pro Phe Val Ser Lys Asn Pro Arg Glu Ala Phe Leu Asn Tyr
465                 470                 475                 480

Arg Asp Leu Asp Ile Gly Ile Asn Ser His Gly Arg Asn Ala Tyr Thr
                485                 490                 495

Glu Gly Met Val Tyr Gly His Lys Tyr Phe Lys Glu Thr Asn Tyr Lys
                500                 505                 510

Arg Leu Val Ser Val Lys Thr Lys Val Asp Pro Asp Asn Phe Phe Arg
                515                 520                 525

Asn Glu Gln Ser Ile Pro Thr Leu Ser Ser
                530                 535

<210> SEQ ID NO 38
<211> LENGTH: 522
<212> TYPE: PRT
<213> ORGANISM: Cynodon dactylon
<220> FEATURE:
<221> NAME/KEY: MISC_FEATURE
<223> OTHER INFORMATION: gi[41]393750

<400> SEQUENCE: 38

Met Ala Arg Ser Arg Ala Phe Ala Phe Ala Leu Leu Ile Cys Ala Val
1               5                   10                  15

Ala Ala Ser Cys His Val Ala Leu Ser Ala Pro Pro Tyr Ala Lys
                20                  25                  30

Gln Val Glu Arg Asp Phe Leu Thr Cys Leu Thr Lys Asp Ile Pro Pro
                35                  40                  45

Arg Gln Leu Tyr Ala Lys Ser Ser Pro Ala Tyr Ala Ser Val Trp Ser
50                  55                  60

Ser Thr Val Arg Asn Ile Lys Phe Leu Ser Asp Lys Thr Val Lys Pro
65                  70                  75                  80

Leu Tyr Ile Ile Thr Pro Thr Asn Ala Ser His Ile Gln Ala Ala Val
                85                  90                  95

Val Cys Gly Arg Arg His Gly Met Arg Ile Arg Val Arg Ser Gly Gly
                100                 105                 110

His Asp Tyr Glu Gly Leu Ser Tyr Arg Ser Glu Lys Pro Glu Pro Phe
                115                 120                 125
```

Ala Val Val Asp Met Asn Lys Met Arg Ala Val Ser Ile Asp Gly Lys
130                 135                 140

Ala Ala Thr Ala Trp Val Asp Ser Gly Ala Gln Leu Gly Asp Leu Tyr
145                 150                 155                 160

Tyr Gly Ile Ala Lys Ala Ser Pro Lys Leu Gly Phe Pro Ala Gly Val
                165                 170                 175

Cys Thr Thr Ile Gly Val Gly His Phe Ser Gly Gly Gly Phe Gly
                180                 185                 190

Met Leu Leu Arg Lys Tyr Gly Thr Ala Ala Asp Asn Val Ile Asp Ala
                195                 200                 205

Lys Val Val Asp Ala Gln Gly Arg Leu Leu Asp Arg Lys Ala Met Gly
210                 215                 220

Glu Asp His Phe Trp Ala Ile Arg Gly Gly Gly Glu Ser Phe Gly
225                 230                 235                 240

Ile Val Ala Ser Trp Gln Val Lys Leu Leu Pro Val Pro Pro Lys Val
                245                 250                 255

Thr Val Phe Gln Val His Lys Gly Ile Lys Glu Gly Ala Ile Asp Leu
                260                 265                 270

Val Thr Lys Trp Gln Thr Val Ala Pro Ala Leu Pro Asp Asp Leu Met
        275                 280                 285

Ile Arg Ile Met Ala Met Gly Gln Gly Ala Met Phe Glu Ala Leu Tyr
        290                 295                 300

Leu Gly Thr Cys Lys Asp Leu Val Leu Leu Met Thr Ala Arg Phe Pro
305                 310                 315                 320

Glu Leu Gly Met Asn Ala Thr His Cys Lys Glu Met Thr Trp Ile Glu
                325                 330                 335

Ser Val Pro Tyr Ile Pro Met Gly Pro Lys Gly Thr Val Arg Asp Leu
                340                 345                 350

Leu Asn Arg Thr Ser Asn Ile Lys Ala Phe Gly Lys Tyr Lys Ser Asp
        355                 360                 365

Tyr Val Leu Glu Pro Ile Pro Lys Ser Asp Trp Glu Lys Ile Phe Thr
        370                 375                 380

Trp Leu Val Lys Pro Gly Ala Gly Val Met Ile Met Asp Pro Tyr Gly
385                 390                 395                 400

Gly Gly Ile Ala Ser Val Pro Glu Ser Ala Thr Pro Phe Pro Arg Arg
                405                 410                 415

Ser Gly Val Leu Phe Asn Ile Gln Tyr Val Val Tyr Trp Phe Gly Glu
                420                 425                 430

Gly Ala Ala Ala Leu Pro Thr Gln Trp Thr Arg Asp Ile Tyr Asp Phe
        435                 440                 445

Met Thr Pro Tyr Val Ser Lys Asn Pro Arg Gln Ala Tyr Val Asn Tyr
        450                 455                 460

Arg Asp Leu Asp Leu Gly Val Asn Gln Val Val Gly Asn Val Ser Thr
465                 470                 475                 480

Tyr Ala Ser Gly Lys Val Trp Gly Glu Lys Tyr Phe Lys Gly Asn Phe
                485                 490                 495

Glu Arg Leu Ala Arg Thr Lys Gly Lys Ile Asp Pro Glu Asp Tyr Phe
                500                 505                 510

Arg Asn Glu Gln Ser Ile Pro Pro Leu Leu
                515                 520

<210> SEQ ID NO 39
<211> LENGTH: 540
<212> TYPE: PRT

<213> ORGANISM: Lactuca sativa
<220> FEATURE:
<221> NAME/KEY: MISC_FEATURE
<223> OTHER INFORMATION: gi[18]652398

<400> SEQUENCE: 39

```
Met Ala Ile Thr Tyr Ser Phe Asn Phe Lys Ser Tyr Ile Phe Pro Leu
 1               5                  10                  15

Leu Leu Val Leu Leu Ser Thr His Ser Ser Ala Thr Ser Thr Ser Ile
             20                  25                  30

Ile Asp Arg Phe Thr Gln Cys Leu Asn Asn Arg Ala Asp Pro Ser Phe
         35                  40                  45

Pro Leu Ser Gly Gln Leu Tyr Thr Pro Asp Asn Ser Ser Phe Pro Ser
     50                  55                  60

Val Leu Gln Ala Tyr Ile Arg Asn Leu Arg Phe Asn Glu Ser Thr Thr
 65                  70                  75                  80

Pro Lys Pro Ile Leu Ile Ile Thr Ala Leu His Pro Ser His Ile Gln
                 85                  90                  95

Ala Ala Val Val Cys Ala Lys Thr His Arg Leu Leu Met Lys Thr Arg
            100                 105                 110

Ser Gly Gly His Asp Tyr Glu Gly Leu Ser Tyr Val Thr Asn Ser Asn
        115                 120                 125

Gln Pro Phe Phe Val Val Asp Met Phe Asn Leu Arg Ser Ile Asn Val
    130                 135                 140

Ser Ile Glu Asp Glu Thr Ala Trp Val Gln Ala Gly Ala Thr Leu Gly
145                 150                 155                 160

Glu Val Tyr Tyr Arg Ile Ala Glu Lys Ser Asn Ser His Ala Phe Pro
                165                 170                 175

Ala Gly Val Cys Pro Thr Val Gly Val Gly Gly His Phe Ser Gly Gly
            180                 185                 190

Gly Tyr Gly Asn Leu Met Gly Lys Tyr Gly Leu Ser Val Asp Asn Ile
        195                 200                 205

Val Asp Ala Gln Leu Ile Asp Val Asn Gly Lys Leu Leu Asn Arg Lys
    210                 215                 220

Ser Met Gly Glu Asp Leu Phe Trp Ala Ile Thr Gly Gly Gly Gly Val
225                 230                 235                 240

Ser Phe Gly Val Val Val Ala Tyr Lys Ile Lys Leu Val Arg Val Pro
                245                 250                 255

Thr Thr Val Thr Val Phe Asn Val Gln Arg Thr Ser Glu Gln Asn Leu
            260                 265                 270

Ser Thr Ile Ala His Arg Trp Ile Gln Val Ala Asp Lys Leu Asp Asn
        275                 280                 285

Asp Leu Phe Leu Arg Met Thr Phe Asn Val Ile Asn Asn Thr Asn Gly
    290                 295                 300

Glu Lys Thr Ile Arg Gly Leu Phe Pro Thr Leu Tyr Leu Gly Asn Ser
305                 310                 315                 320

Thr Ala Leu Val Ala Leu Leu Asn Lys Asp Phe Pro Glu Leu Gly Val
                325                 330                 335

Glu Ile Ser Asp Cys Ile Glu Met Ser Trp Ile Glu Ser Val Leu Phe
            340                 345                 350

Tyr Thr Asn Phe Pro Ile Gly Thr Pro Thr Thr Ala Leu Leu Ser Arg
        355                 360                 365

Thr Pro Gln Arg Leu Asn Pro Phe Lys Ile Lys Ser Asp Tyr Val Lys
    370                 375                 380
```

-continued

```
Asn Thr Ile Ser Lys Gln Gly Phe Glu Ser Ile Phe Glu Arg Met Lys
385                 390                 395                 400

Glu Leu Glu Asn Gln Met Leu Ala Phe Asn Pro Tyr Gly Gly Arg Met
            405                 410                 415

Ser Glu Ile Ser Glu Phe Ala Lys Pro Phe Pro His Arg Ser Gly Asn
        420                 425                 430

Ile Ala Lys Ile Gln Tyr Glu Val Asn Trp Asp Glu Leu Gly Val Glu
    435                 440                 445

Ala Ala Asn Arg Tyr Leu Asn Phe Thr Arg Val Met Tyr Asp Tyr Met
450                 455                 460

Thr Pro Phe Val Ser Lys Asn Pro Arg Glu Ala Phe Leu Asn Tyr Arg
465                 470                 475                 480

Asp Leu Asp Ile Gly Val Asn Ser His Gly Lys Asn Ala Tyr Gly Glu
                485                 490                 495

Gly Met Val Tyr Gly His Lys Tyr Phe Lys Glu Thr Asn Tyr Lys Arg
            500                 505                 510

Leu Thr Met Val Lys Thr Arg Val Asp Pro Ser Asn Phe Phe Arg Asn
        515                 520                 525

Glu Gln Ser Ile Pro Thr Leu Ser Ser Ser Trp Lys
    530                 535                 540

<210> SEQ ID NO 40
<211> LENGTH: 545
<212> TYPE: PRT
<213> ORGANISM: Cannabis sativa
<220> FEATURE:
<221> NAME/KEY: MISC_FEATURE
<223> OTHER INFORMATION: gi[26]005814

<400> SEQUENCE: 40

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205
```

```
Leu Val Asn Val Asp Gly Lys Val Leu Asp Arg Lys Ser Met Gly Glu
            210                 215                 220
Asp Leu Phe Trp Ala Ile Arg Gly Gly Gly Glu Asn Phe Gly Ile
225                 230                 235                 240
Ile Ala Ala Trp Lys Ile Lys Leu Val Ala Val Pro Ser Lys Ser Thr
                245                 250                 255
Ile Phe Ser Val Lys Lys Asn Met Glu Ile His Gly Leu Val Lys Leu
                260                 265                 270
Phe Asn Lys Trp Gln Asn Ile Ala Tyr Lys Tyr Asp Lys Asp Leu Val
            275                 280                 285
Leu Met Thr His Phe Ile Thr Lys Asn Ile Thr Asp Asn His Gly Lys
290                 295                 300
Asn Lys Thr Thr Val His Gly Tyr Phe Ser Ser Ile Phe His Gly Gly
305                 310                 315                 320
Val Asp Ser Leu Val Asp Leu Met Asn Lys Ser Phe Pro Glu Leu Gly
                325                 330                 335
Ile Lys Lys Thr Asp Cys Lys Glu Phe Ser Trp Ile Asp Thr Thr Ile
                340                 345                 350
Phe Tyr Ser Gly Val Val Asn Phe Asn Thr Ala Asn Phe Lys Lys Glu
            355                 360                 365
Ile Leu Leu Asp Arg Ser Ala Gly Lys Lys Thr Ala Phe Ser Ile Lys
370                 375                 380
Leu Asp Tyr Val Lys Lys Pro Ile Pro Glu Thr Ala Met Val Lys Ile
385                 390                 395                 400
Leu Glu Lys Leu Tyr Glu Glu Asp Val Gly Ala Gly Met Tyr Val Leu
                405                 410                 415
Tyr Pro Tyr Gly Gly Ile Met Glu Glu Ile Ser Glu Ser Ala Ile Pro
            420                 425                 430
Phe Pro His Arg Ala Gly Ile Met Tyr Glu Leu Trp Tyr Thr Ala Ser
            435                 440                 445
Trp Glu Lys Gln Glu Asp Asn Glu Lys His Ile Asn Trp Val Arg Ser
            450                 455                 460
Val Tyr Asn Phe Thr Thr Pro Tyr Val Ser Gln Asn Pro Arg Leu Ala
465                 470                 475                 480
Tyr Leu Asn Tyr Arg Asp Leu Asp Leu Gly Lys Thr Asn His Ala Ser
                485                 490                 495
Pro Asn Asn Tyr Thr Gln Ala Arg Ile Trp Gly Glu Lys Tyr Phe Gly
            500                 505                 510
Lys Asn Phe Asn Arg Leu Val Lys Val Lys Thr Lys Val Asp Pro Asn
            515                 520                 525
Asn Phe Phe Arg Asn Glu Gln Ser Ile Pro Leu Pro Pro His His
530                 535                 540
His
545

<210> SEQ ID NO 41
<211> LENGTH: 535
<212> TYPE: PRT
<213> ORGANISM: Oryza sativa subsp. japonica
<220> FEATURE:
<221> NAME/KEY: MISC_FEATURE
<223> OTHER INFORMATION: gi[53]792953

<400> SEQUENCE: 41

Met Ser Thr Thr Pro Thr Ala Ala Ser Arg Arg Leu Val Leu Ile Leu
```

-continued

```
1               5                   10                  15
Cys Thr Leu Ala Ile Ser Cys Ser Ser Gly Ile Ala Gly Phe Ala Ala
                20                  25                  30
Gly Asp Asp Ala Phe Ile Arg Cys Leu Ala Ala Ala Val Pro
        35                  40                  45
Pro Arg Leu Val His Thr Pro Gly Ser Ala Ser Tyr Ala Pro Thr Leu
        50                  55                  60
Val Ser Ser Ile Arg Asn Leu Arg Phe Val Thr Pro Gly Thr Pro Arg
 65                 70                  75                  80
Pro Leu Ala Ile Val Ala Ala Ala Glu Ala Gly His Ala Gln Ala Ala
                85                  90                  95
Val Arg Cys Gly Arg Arg His Gly Val Arg Val Arg Ala Arg Ser Gly
                100                 105                 110
Gly His Asp Tyr Glu Gly Leu Ser Tyr Leu Ser Leu Asp Arg Arg Glu
                115                 120                 125
Arg Phe Ala Val Leu Asp Leu Ala Ala Leu Arg Asp Val Arg Val Asp
        130                 135                 140
Ala Asp Arg Ala Glu Ala Trp Val Gly Ser Gly Ala Thr Leu Gly Glu
145                 150                 155                 160
Leu Tyr Tyr Ala Val Gly Ala Ala Ser Arg Thr Leu Ala Phe Pro Ala
                    165                 170                 175
Gly Val Cys Pro Thr Val Gly Val Gly Gly His Ile Ser Gly Gly Gly
                180                 185                 190
Phe Gly Thr Leu Met Arg Arg Tyr Gly Leu Ala Ala Asp Asn Val Leu
                195                 200                 205
Asp Ala Val Leu Val Asp Ala Asp Gly Arg Leu Leu Asn Arg Thr Thr
        210                 215                 220
Met Gly Glu Gly Leu Phe Trp Ala Ile Arg Gly Gly Gly Gly Glu Ser
225                 230                 235                 240
Phe Gly Val Val Leu Ser Trp Lys Leu Arg Leu Val Arg Val Pro Glu
                    245                 250                 255
Thr Val Thr Val Phe Thr Ile Arg Arg Pro Arg Asn Gln Ser Ala Thr
                260                 265                 270
Asp Leu Ile Thr Lys Trp Gln Glu Ile Ser Pro Ser Leu Pro Arg Asp
            275                 280                 285
Val Ile Leu Arg Val Val Gln Ser Gln His Ala Gln Phe Glu Ser
        290                 295                 300
Leu Phe Leu Gly Arg Cys Arg Arg Leu Ala Arg Leu Met Arg Ala Arg
305                 310                 315                 320
Phe Pro Glu Leu Gly Met Thr Gln Ser Asp Cys Glu Glu Ile Thr Trp
                325                 330                 335
Ile Gln Ser Thr Val Tyr Phe Ala Phe Tyr Ser Ser Lys Pro Leu
                340                 345                 350
Glu Leu Leu Leu Asp Arg Gly Thr Glu Pro Asp Arg Tyr Phe Lys Ala
            355                 360                 365
Lys Ser Asp Tyr Val Gln Glu Pro Ile Pro Arg His Ala Trp Glu Ser
        370                 375                 380
Thr Trp Pro Trp Leu Glu Glu His Asp Ala Gly Leu Leu Ile Leu Asp
385                 390                 395                 400
Pro Tyr Gly Gly Glu Met Ala Arg Val Ser Pro Ala Ala Thr Pro Phe
                405                 410                 415
Pro His Arg Lys Gly Asn Leu Tyr Asn Leu Gln Tyr Tyr Ser Phe Trp
                420                 425                 430
```

```
Phe Glu His Gly Ala Glu Thr Leu Glu Arg His Leu Ser Trp Val Arg
        435                 440                 445

Gly Leu Tyr Gly Glu Met Glu Pro Tyr Val Ser Lys Asn Pro Arg Thr
    450                 455                 460

Gly Tyr Val Asn Tyr Arg Asp Met Asp Leu Gly Arg Asn Glu Ile Glu
465                 470                 475                 480

Gly Asn Val Thr Ser Tyr Thr Lys Gly Lys Val Trp Gly Glu Lys Tyr
                485                 490                 495

Phe Arg Gly Asn Phe Glu Arg Leu Ala Ala Val Lys Ala Met Val Asp
            500                 505                 510

Pro Asp Asp Phe Phe Arg Asn Glu Gln Ser Ile Pro Pro Leu Pro Ala
        515                 520                 525

Ala Lys Gly Trp Ser Ser Ile
    530                 535

<210> SEQ ID NO 42
<211> LENGTH: 542
<212> TYPE: PRT
<213> ORGANISM: Helianthus annuus
<220> FEATURE:
<221> NAME/KEY: MISC_FEATURE
<223> OTHER INFORMATION: gi[20]563190

<400> SEQUENCE: 42

Met Asn Asn Ser Arg Ser Val Phe Leu Leu Val Leu Ala Leu Ser Phe
1               5                   10                  15

Cys Val Ser Phe Gly Ala Leu Ser Ser Ile Phe Asp Val Thr Ser Thr
            20                  25                  30

Ser Glu Asp Phe Ile Thr Cys Leu Gln Ser Asn Ser Asn Asn Val Thr
        35                  40                  45

Thr Ile Ser Gln Leu Val Phe Thr Pro Ala Asn Thr Ser Tyr Ile Pro
    50                  55                  60

Ile Trp Gln Ala Ala Asp Pro Ile Arg Phe Asn Lys Ser Tyr Ile
65                  70                  75                  80

Pro Lys Pro Ser Val Ile Val Thr Pro Thr Asp Glu Thr Gln Ile Gln
            85                  90                  95

Thr Ala Leu Leu Cys Ala Lys Lys His Gly Tyr Glu Phe Arg Ile Arg
        100                 105                 110

Asp Gly Gly His Asp Phe Glu Gly Asn Ser Tyr Thr Ala Asn Ala Pro
    115                 120                 125

Phe Val Met Leu Asp Leu Val Asn Met Arg Ala Ile Glu Ile Asn Val
130                 135                 140

Glu Asn Arg Thr Ala Leu Val Gln Gly Gly Ala Leu Leu Gly Glu Leu
145                 150                 155                 160

Tyr Tyr Thr Ile Ser Gln Lys Thr Asp Thr Leu Tyr Phe Pro Ala Gly
            165                 170                 175

Ile Trp Ala Gly Val Gly Val Ser Gly Phe Leu Ser Gly Gly Gly Tyr
        180                 185                 190

Gly Asn Leu Leu Arg Lys Tyr Gly Leu Gly Ala Asp Asn Val Leu Asp
    195                 200                 205

Ile Arg Phe Met Asp Val Asn Gly Asn Ile Leu Asp Arg Lys Ser Met
210                 215                 220

Gly Glu Asp Leu Phe Trp Ala Leu Arg Gly Gly Gly Ala Ser Ser Phe
225                 230                 235                 240

Gly Ile Val Leu Gln Trp Lys Leu Asn Leu Val Pro Val Pro Glu Arg
```

```
          245                 250                 255
Val Thr Leu Phe Ser Val Ser Tyr Thr Leu Glu Gln Gly Ala Thr Asp
        260                 265                 270

Ile Phe His Lys Tyr Gln Tyr Val Leu Pro Lys Phe Asp Arg Asp Leu
        275                 280                 285

Leu Ile Arg Val Gln Leu Asn Thr Glu Tyr Ile Gly Asn Thr Thr Gln
        290                 295                 300

Lys Thr Val Arg Ile Leu Phe His Gly Ile Tyr Gln Gly Asn Ile Asp
305                 310                 315                 320

Thr Leu Leu Pro Leu Leu Asn Gln Ser Phe Pro Glu Leu Asn Val Thr
                325                 330                 335

Arg Glu Val Cys Gln Glu Val Arg Met Val Gln Thr Thr Leu Glu Phe
                340                 345                 350

Gly Gly Phe Asn Ile Ser Thr Pro Thr Ser Val Leu Ala Asn Arg Ser
                355                 360                 365

Ala Ile Pro Lys Leu Ser Phe Lys Gly Lys Ser Asp Tyr Val Arg Thr
            370                 375                 380

Pro Ile Pro Arg Ser Gly Leu Arg Lys Leu Trp Arg Lys Met Phe Glu
385                 390                 395                 400

Asn Asp Asn Ser Gln Thr Leu Phe Met Tyr Thr Phe Gly Gly Lys Met
                405                 410                 415

Glu Glu Tyr Ser Asp Thr Ala Ile Pro Tyr Pro His Arg Ala Gly Val
                420                 425                 430

Leu Tyr Gln Val Phe Lys Arg Val Asp Phe Val Asp Gln Pro Ser Asp
            435                 440                 445

Lys Thr Leu Ile Ser Leu Arg Arg Leu Ala Trp Leu Arg Ser Phe Asp
450                 455                 460

Lys Thr Leu Glu Pro Tyr Val Thr Ser Asn Pro Arg Glu Ala Tyr Met
465                 470                 475                 480

Asn Tyr Asn Asp Leu Asp Leu Gly Phe Asp Ser Ala Ala Tyr Glu Glu
                485                 490                 495

Ala Ser Glu Trp Gly Glu Arg Tyr Trp Lys Arg Glu Asn Phe Lys Lys
                500                 505                 510

Leu Ile Arg Ile Lys Ala Lys Val Asp Pro Glu Asn Phe Phe Arg His
            515                 520                 525

Pro Gln Ser Ile Pro Val Phe Ser Arg Pro Leu Ser Asp Met
        530                 535                 540

<210> SEQ ID NO 43
<211> LENGTH: 1174
<212> TYPE: DNA
<213> ORGANISM: Arabidopsis thaliana
<220> FEATURE:
<221> NAME/KEY: MISC_FEATURE
<223> OTHER INFORMATION: cDNA12723147_L23

<400> SEQUENCE: 43
agtggctact gagtaaagct tgggccacc gagagaaacc attttctgag agcacacttt    60
cgttgacttc tctttaacca atgtctttaa ccacagtccc tacgctcgcc atcagatccg   120
gaccatccgg tcatcactcg atgccggttc ttggttttgg aaccgccgct ctccgctac    180 cggaaccaac gatgctgaaa gagacggtga ttgaggctat taagcttggt tatcgccatt   240
tcgacacctc tccaaggtac caaacggagg agccgatcgg cgaagcttta gcggaggcgg   300
tttcactcgg cttagttcga tctcgatctg aattctttgt cactaccaaa ctttggtgtg   360
```

-continued

```
ctgatgctca tggtggtctc gtcgtaccgg cgatcaaacg gagtttgaaa aaccttaaac    420
tggactatct tgatctttat ataattcatt ggccggttag ctcgaaacct ggtaaataca    480
agtttcctat tgatgaagat gattttatgc caatggattt cgaagtagtg tggtctgaaa    540
tggaggagtg tcagagactt gggctcgcaa aatgcatagg agtaagcaat ttttcatgta    600
agaagcttca acacatactc tctatcgcga caatcccgcc tagcgtcaat caagttgaga    660
tgagtccaat atggcaacaa agaaagctaa gggagctttg tagatcgaac gacattgttg    720
tcacagcgta ctcggtgttg ggatctagag gagcttttttg gggaactccc aaaattatgg    780
aatctgatgt tctcaaagaa atagcagaag caaaggaaaa aacagtggcc caggtgagta    840
tgagatgggc ttatgaacaa ggagtgagca tggtagtgaa gagctttacc aaagagagat    900
tagaagagaa tctaaagata tttgattggt ctttgacaga ggatgagaca cagagaattt    960
caactgagat tcctcagttc agaaacgtcc acggagaggt ttatacctct aagaaaggtc   1020
ccatcaaatc tgtcgccgag atgtgggacg gggagatctg atcactttgt gtgaaaatag   1080
cctattgaaa acggcacaat tatcattcgt cacaatgatt ttcttgtcat tctctctaat   1140
aatgaaataa tgaataatga ataaggacta tctc                              1174
```

<210> SEQ ID NO 44
<211> LENGTH: 326
<212> TYPE: PRT
<213> ORGANISM: Arabidopsis thaliana
<220> FEATURE:
<221> NAME/KEY: MISC_FEATURE
<223> OTHER INFORMATION: peptide_cDNA12723147_L23

<400> SEQUENCE: 44

```
Met Ser Leu Thr Thr Val Pro Thr Leu Ala Ile Arg Ser Gly Pro Ser
1               5                   10                  15

Gly His His Ser Met Pro Val Leu Gly Phe Gly Thr Ala Ala Ser Pro
                20                  25                  30

Leu Pro Glu Pro Thr Met Leu Lys Glu Thr Val Ile Glu Ala Ile Lys
            35                  40                  45

Leu Gly Tyr Arg His Phe Asp Thr Ser Pro Arg Tyr Gln Thr Glu Glu
        50                  55                  60

Pro Ile Gly Glu Ala Leu Ala Glu Ala Val Ser Leu Gly Leu Val Arg
65                  70                  75                  80

Ser Arg Ser Glu Phe Phe Val Thr Thr Lys Leu Trp Cys Ala Asp Ala
                85                  90                  95

His Gly Gly Leu Val Val Pro Ala Ile Lys Arg Ser Leu Lys Asn Leu
            100                 105                 110

Lys Leu Asp Tyr Leu Asp Leu Tyr Ile Ile His Trp Pro Val Ser Ser
        115                 120                 125

Lys Pro Gly Lys Tyr Lys Phe Pro Ile Asp Glu Asp Phe Met Pro
    130                 135                 140

Met Asp Phe Glu Val Val Trp Ser Glu Met Glu Glu Cys Gln Arg Leu
145                 150                 155                 160

Gly Leu Ala Lys Cys Ile Gly Val Ser Asn Phe Ser Cys Lys Lys Leu
                165                 170                 175

Gln His Ile Leu Ser Ile Ala Thr Ile Pro Pro Ser Val Asn Gln Val
            180                 185                 190

Glu Met Ser Pro Ile Trp Gln Gln Arg Lys Leu Arg Glu Leu Cys Arg
        195                 200                 205

Ser Asn Asp Ile Val Val Thr Ala Tyr Ser Val Leu Gly Ser Arg Gly
```

-continued

```
            210                 215                 220
Ala Phe Trp Gly Thr Pro Lys Ile Met Glu Ser Asp Val Leu Lys Glu
225                 230                 235                 240

Ile Ala Glu Ala Lys Glu Lys Thr Val Ala Gln Val Ser Met Arg Trp
            245                 250                 255

Ala Tyr Glu Gln Gly Val Ser Met Val Val Lys Ser Phe Thr Lys Glu
            260                 265                 270

Arg Leu Glu Glu Asn Leu Lys Ile Phe Asp Trp Ser Leu Thr Glu Asp
            275                 280                 285

Glu Thr Gln Arg Ile Ser Thr Glu Ile Pro Gln Phe Arg Asn Val His
            290                 295                 300

Gly Glu Val Tyr Thr Ser Lys Lys Gly Pro Ile Lys Ser Val Ala Glu
305                 310                 315                 320

Met Trp Asp Gly Glu Ile
                325

<210> SEQ ID NO 45
<211> LENGTH: 321
<212> TYPE: PRT
<213> ORGANISM: Papaver somniferum
<220> FEATURE:
<221> NAME/KEY: MISC_FEATURE
<223> OTHER INFORMATION: gi[64]78216

<400> SEQUENCE: 45

Met Glu Ile Gly Gly Val Pro Val Val Thr Leu Ser Ser Gly Arg Gly
1               5                   10                  15

Met Pro Ile Leu Gly Met Gly Thr Ala Glu Asn Asn Leu Gln Gly Ser
            20                  25                  30

Glu Arg Val Lys Leu Ala Ile Leu Lys Ala Ile Glu Val Gly Tyr Arg
            35                  40                  45

His Phe Asp Thr Ala Phe Val Tyr Gln Thr Glu Gly Ser Leu Gly Glu
            50                  55                  60

Ala Val Ala Glu Ala Leu Gln Asn Gly Leu Ile Lys Ser Arg Asp Glu
65                  70                  75                  80

Leu Phe Ile Thr Ser Lys Leu Trp Cys Ala Asp Ala Tyr Pro Asp His
            85                  90                  95

Val Leu Pro Ala Leu Gln Asn Ser Leu Arg Asn Leu Lys Leu Glu Tyr
            100                 105                 110

Leu Asp Leu Tyr Leu Ile His Trp Pro Val Ser Leu Lys Pro Gly Lys
            115                 120                 125

Phe Val His Pro Ile Pro Lys Asp Glu Ile Phe Pro Ile Asp Tyr Lys
            130                 135                 140

Ser Val Trp Ala Ala Met Glu Lys Cys Gln Met Leu Gly Leu Thr Lys
145                 150                 155                 160

Ser Ile Gly Val Ser Asn Phe Ser Cys Lys Lys Leu His Tyr Leu Met
            165                 170                 175

Ala Thr Ala Asn Ile Pro Pro Ala Val Asn Gln Val Glu Met Asn Pro
            180                 185                 190

Ile Trp Gln Gln Gln Lys Leu Arg Asp Tyr Cys Lys Thr Asn Asn Ile
            195                 200                 205

Met Val Thr Ala Tyr Ser Pro Leu Gly Ala Lys Gly Thr Met Trp Gly
            210                 215                 220

Ser Ser Gly Val Met Asp Ser Glu Val Leu Asn Gln Ile Ser Gln Val
225                 230                 235                 240
```

```
Arg Gly Lys Ser Val Ala Gln Val Ser Leu Arg Trp Val Tyr Glu Gln
                245                 250                 255

Gly Ala Ser Leu Leu Val Lys Ser Phe Asn Glu Glu Arg Met Lys Glu
            260                 265                 270

Asn Leu Lys Ile Phe Asp Trp Glu Leu Ser Pro Glu Asp Leu Lys Asn
            275                 280                 285

Ile Ser Glu Leu Pro Gln Arg Arg Val Ser Thr Gly Asp Pro Phe Val
290                 295                 300

Ser Ile Asn Gly Pro Phe Lys Ser Val Glu Glu Leu Trp Asp Asp Glu
305                 310                 315                 320

Val

<210> SEQ ID NO 46
<211> LENGTH: 327
<212> TYPE: PRT
<213> ORGANISM: Arabidopsis thaliana
<220> FEATURE:
<221> NAME/KEY: MISC_FEATURE
<223> OTHER INFORMATION: gi[50]80825

<400> SEQUENCE: 46

Met Val Ala Ser Gly His Glu Val Val Thr Leu Thr Phe Pro Ile Gly
1               5                   10                  15

Ser Val His His Leu Met Pro Val Leu Ala Leu Gly Thr Ala Ala Ser
                20                  25                  30

Pro Pro Pro Glu Pro Ile Val Leu Lys Arg Thr Val Leu Glu Ala Ile
            35                  40                  45

Lys Leu Gly Tyr Arg His Phe Asp Thr Ser Pro Arg Tyr Gln Thr Glu
50                  55                  60

Glu Pro Leu Gly Glu Ala Leu Ala Glu Ala Val Ser Leu Gly Leu Ile
65                  70                  75                  80

Gln Ser Arg Ser Glu Leu Phe Val Thr Ser Lys Leu Trp Cys Ala Asp
                85                  90                  95

Ala His Gly Gly Leu Val Val Pro Ala Ile Gln Arg Ser Leu Glu Thr
            100                 105                 110

Leu Lys Leu Asp Tyr Leu Asp Leu Tyr Leu Ile His Trp Pro Val Ser
            115                 120                 125

Ser Lys Pro Gly Lys Tyr Lys Phe Pro Ile Glu Glu Asp Asp Phe Leu
130                 135                 140

Pro Met Asp Tyr Glu Thr Val Trp Ser Glu Met Glu Glu Cys Gln Arg
145                 150                 155                 160

Leu Gly Val Ala Lys Cys Ile Gly Val Ser Asn Phe Ser Cys Lys Lys
                165                 170                 175

Leu Gln His Ile Leu Ser Ile Ala Lys Ile Pro Pro Ser Val Asn Gln
            180                 185                 190

Val Glu Met Ser Pro Val Trp Gln Gln Arg Lys Leu Arg Glu Leu Cys
            195                 200                 205

Lys Ser Lys Gly Ile Val Val Thr Ala Tyr Ser Val Leu Gly Ser Arg
210                 215                 220

Gly Ala Phe Trp Gly Thr His Lys Ile Met Glu Ser Asp Val Leu Lys
225                 230                 235                 240

Glu Ile Ala Glu Ala Lys Gly Lys Thr Val Ala Gln Val Ser Met Arg
                245                 250                 255

Trp Ala Tyr Glu Glu Gly Val Ser Met Val Val Lys Ser Phe Arg Lys
            260                 265                 270
```

Asp Arg Leu Glu Glu Asn Leu Lys Ile Phe Asp Trp Ser Leu Thr Glu
            275                 280                 285

Glu Glu Lys Gln Arg Ile Ser Thr Glu Ile Ser Gln Ser Arg Ile Val
            290                 295                 300

Asp Gly Glu Val Tyr Ile Ser Glu Lys Gly Pro Ile Lys Ser Val Thr
305                 310                 315                 320

Glu Met Trp Asp Gly Glu Ile
            325

<210> SEQ ID NO 47
<211> LENGTH: 320
<212> TYPE: PRT
<213> ORGANISM: Arabidopsis thaliana
<220> FEATURE:
<221> NAME/KEY: MISC_FEATURE
<223> OTHER INFORMATION: gi[15]218958

<400> SEQUENCE: 47

Met Ser Ala Leu Thr Phe Pro Ile Gly Ser Val His His Leu Met Pro
1               5                   10                  15

Val Leu Ala Leu Gly Thr Ala Ala Ser Pro Pro Glu Pro Ile Val
            20                  25                  30

Leu Lys Arg Thr Val Leu Glu Ala Ile Lys Leu Gly Tyr Arg His Phe
            35                  40                  45

Asp Thr Ser Pro Arg Tyr Gln Thr Glu Pro Leu Gly Glu Ala Leu
50                  55                  60

Ala Glu Ala Val Ser Leu Gly Leu Ile Gln Ser Arg Ser Glu Leu Phe
65                  70                  75                  80

Val Thr Ser Lys Leu Trp Cys Ala Asp Ala His Gly Leu Val Val
            85                  90                  95

Pro Ala Ile Gln Arg Ser Leu Glu Thr Leu Lys Leu Asp Tyr Leu Asp
            100                 105                 110

Leu Tyr Leu Ile His Trp Pro Val Ser Ser Lys Pro Gly Lys Tyr Lys
            115                 120                 125

Phe Pro Ile Glu Glu Asp Asp Phe Leu Pro Met Asp Tyr Glu Thr Val
            130                 135                 140

Trp Ser Glu Met Glu Glu Cys Gln Arg Leu Gly Val Ala Lys Cys Ile
145                 150                 155                 160

Gly Val Ser Asn Phe Ser Cys Lys Lys Leu Gln His Ile Leu Ser Ile
            165                 170                 175

Ala Lys Ile Pro Pro Ser Val Asn Gln Val Glu Met Ser Pro Val Trp
            180                 185                 190

Gln Gln Arg Lys Leu Arg Glu Leu Cys Lys Ser Lys Gly Ile Val Val
            195                 200                 205

Thr Ala Tyr Ser Val Leu Gly Ser Arg Gly Ala Phe Trp Gly Thr His
            210                 215                 220

Lys Ile Met Glu Ser Asp Val Leu Lys Glu Ile Ala Glu Ala Lys Gly
225                 230                 235                 240

Lys Thr Val Ala Gln Val Ser Met Arg Trp Ala Tyr Glu Glu Gly Val
            245                 250                 255

Ser Met Val Val Lys Ser Phe Arg Lys Asp Arg Leu Glu Glu Asn Leu
            260                 265                 270

Lys Ile Phe Asp Trp Ser Leu Thr Glu Glu Lys Gln Arg Ile Ser
            275                 280                 285

Thr Glu Ile Ser Gln Ser Arg Ile Val Asp Gly Glu Val Tyr Ile Ser
            290                 295                 300

```
Glu Lys Gly Pro Ile Lys Ser Val Thr Glu Met Trp Asp Gly Glu Ile
305                 310                 315                 320

<210> SEQ ID NO 48
<211> LENGTH: 323
<212> TYPE: PRT
<213> ORGANISM: Fragaria x ananassa
<220> FEATURE:
<221> NAME/KEY: MISC_FEATURE
<223> OTHER INFORMATION: gi[53]988164

<400> SEQUENCE: 48

Met Thr Ala Thr Gln Ile Pro Glu Val Val Leu Glu Ser Ser Asn Gly
1               5                   10                  15

Arg Arg Thr Met Pro Val Leu Gly Phe Gly Thr Ala Ser Asn Asn Leu
            20                  25                  30

Gln Pro Glu Val Leu Ile Glu Ala Val Leu Glu Ala Ile Lys Leu Gly
        35                  40                  45

Tyr Arg His Phe Asp Thr Ala Ser Ile Tyr Gly Ser Glu Gln Thr Leu
    50                  55                  60

Gly Val Ala Ile Ala Gln Ala Leu Lys Leu Gly Leu Val Ala Ser Arg
65                  70                  75                  80

Asp Glu Leu Phe Ile Thr Ser Lys Leu Trp Pro Asn Asp Gly His Pro
                85                  90                  95

Asn Leu Val Ile Pro Ala Leu Lys Lys Ser Leu Gln Asn Leu Glu Leu
            100                 105                 110

Glu Tyr Leu Asp Leu Tyr Leu Ile His Trp Pro Ile Ser Ala Lys Pro
        115                 120                 125

Gly Lys Leu Ser His Ala Leu Glu Glu Lys Asp Gln Met Pro Met Asp
    130                 135                 140

Phe Lys Gly Val Trp Ala Asp Met Glu Glu Ala Gln Arg Leu Gly Leu
145                 150                 155                 160

Thr Lys Ser Ile Gly Ile Ser Asn Phe Ser Thr Lys Lys Thr Gln Asn
                165                 170                 175

Leu Leu Ser Phe Ala Thr Ile Pro Pro Ser Val Asn Gln Val Glu Met
            180                 185                 190

Ser Pro Phe Trp Gln Gln Lys Lys Leu Arg Asp Phe Cys Lys Ala Ser
        195                 200                 205

Gly Ile Val Val Thr Ala Phe Ser Pro Leu Gly Ala Ile Gly Thr Ser
    210                 215                 220

Trp Gly Thr Asn His Val Leu Glu Ser Lys Val Leu Asn Glu Ile Ala
225                 230                 235                 240

Glu Ala His Gly Lys Thr Val Ala Gln Val Cys Ile Arg Trp Val Tyr
                245                 250                 255

Gln Val Gly Ala Thr Leu Ala Val Lys Ser Tyr Asn Lys Glu Arg Leu
            260                 265                 270

Lys Gln Asn Val Gln Val Phe Asp Trp Glu Leu Thr Glu Glu Asp Leu
        275                 280                 285

Glu Lys Ile Asn Gln Ile Pro Gln Arg Lys Met Met Pro Arg Glu Glu
    290                 295                 300

Leu Val Thr Ala Thr Gly Pro Tyr Lys Ser Leu Asp Asp Leu Trp Asp
305                 310                 315                 320

Gly Glu Tyr

<210> SEQ ID NO 49
```

<211> LENGTH: 319
<212> TYPE: PRT
<213> ORGANISM: Fragaria x ananassa
<220> FEATURE:
<221> NAME/KEY: MISC_FEATURE
<223> OTHER INFORMATION: gi[27]92295

<400> SEQUENCE: 49

```
Met Ala Lys Val Pro Ser Val Thr Leu Ser Ser Cys Gly Asp Asp Ile
1               5                   10                  15

Gln Thr Met Pro Val Ile Gly Met Gly Thr Ser Ser Tyr Pro Arg Ala
            20                  25                  30

Asp Pro Glu Thr Ala Lys Ala Ala Ile Leu Glu Ala Ile Arg Ala Gly
        35                  40                  45

Tyr Arg His Phe Asp Thr Ala Ala Ala Tyr Gly Ser Glu Lys Asp Leu
50                  55                  60

Gly Glu Ala Ile Ala Glu Ala Leu Arg Leu Gln Leu Ile Lys Ser Arg
65                  70                  75                  80

Asp Glu Leu Phe Ile Thr Thr Lys Leu Trp Ala Ser Phe Ala Glu Lys
                85                  90                  95

Asp Leu Val Leu Pro Ser Ile Lys Ala Ser Leu Ser Asn Leu Gln Val
            100                 105                 110

Glu Tyr Ile Asp Met Tyr Ile Ile His Trp Pro Phe Lys Leu Gly Lys
        115                 120                 125

Glu Val Arg Thr Met Pro Val Glu Arg Asp Leu Val Gln Pro Leu Asp
130                 135                 140

Ile Lys Ser Val Trp Glu Ala Met Glu Glu Cys Lys Lys Leu Gly Leu
145                 150                 155                 160

Ala Arg Gly Ile Gly Val Ser Asn Phe Thr Ser Ser Met Leu Glu Glu
                165                 170                 175

Leu Leu Ser Phe Ala Glu Ile Pro Pro Ala Val Asn Gln Leu Glu Met
            180                 185                 190

Asn Pro Ala Trp Gln Leu Lys Lys Leu Arg Asp Phe Cys Lys Ala Lys
        195                 200                 205

Gly Ile His Val Thr Ala Tyr Ser Pro Leu Gly Ala Ala Arg Thr Lys
210                 215                 220

Trp Gly Asp Asp Arg Val Leu Gly Ser Asp Ile Ile Glu Glu Ile Ala
225                 230                 235                 240

Gln Ala Lys Gly Lys Ser Thr Ala Gln Ile Ser Leu Arg Trp Val Tyr
                245                 250                 255

Glu Gln Gly Val Ser Ile Val Thr Lys Ser Tyr Asn Lys Glu Arg Met
            260                 265                 270

Arg Gln Asn Leu Asp Ile Phe Asp Phe Cys Leu Thr Glu Glu Glu Leu
        275                 280                 285

Glu Lys Met Ser His Leu Pro Gln Arg Lys Gly Val Thr Phe Ala Ser
290                 295                 300

Ile Leu Gly Pro His Asp Ile Val Leu Glu Val Asp Glu Glu Leu
305                 310                 315
```

<210> SEQ ID NO 50
<211> LENGTH: 319
<212> TYPE: PRT
<213> ORGANISM: Fragaria x ananassa
<220> FEATURE:
<221> NAME/KEY: MISC_FEATURE
<223> OTHER INFORMATION: gi[50]380153

<400> SEQUENCE: 50

```
Met Ala Lys Val Pro Ser Val Thr Leu Ser Ser Cys Gly Asp Asp Ile
1               5                   10                  15

Gln Thr Met Pro Val Ile Gly Met Gly Thr Ser Ser Tyr Pro Arg Ala
            20                  25                  30

Asp Pro Glu Thr Ala Lys Ala Ala Ile Leu Glu Ala Ile Arg Ala Gly
        35                  40                  45

Tyr Arg His Phe Asp Thr Ala Ala Ala Tyr Gly Ser Glu Lys Asp Leu
50                  55                  60

Gly Glu Ala Ile Ala Glu Ala Leu Arg Leu Gln Leu Ile Lys Ser Arg
65                  70                  75                  80

Asp Glu Leu Phe Ile Thr Thr Lys Leu Trp Ala Ser Phe Ala Glu Lys
                85                  90                  95

Asp Leu Val Leu Pro Ser Ile Lys Ala Ser Leu Ser Asn Leu Gln Val
            100                 105                 110

Glu Tyr Ile Asp Met Tyr Ile Ile His Trp Pro Phe Lys Leu Gly Lys
        115                 120                 125

Glu Val Arg Thr Met Pro Val Glu Arg Asp Leu Val Gln Pro Leu Asp
130                 135                 140

Ile Lys Ser Val Trp Glu Ala Met Glu Glu Cys Lys Lys Leu Gly Leu
145                 150                 155                 160

Ala Arg Gly Ile Gly Val Ser Asn Phe Thr Ser Ser Met Leu Glu Glu
                165                 170                 175

Leu Leu Ser Phe Ala Glu Ile Pro Pro Ala Val Asn Gln Leu Glu Met
            180                 185                 190

Asn Pro Ala Trp Gln Leu Lys Lys Leu Arg Asp Phe Cys Lys Ala Lys
        195                 200                 205

Gly Ile His Val Thr Ala Tyr Ser Pro Leu Gly Ala Ala Arg Thr Lys
210                 215                 220

Trp Gly Asp Asp Arg Val Leu Gly Ser Asp Ile Ile Glu Glu Ile Ala
225                 230                 235                 240

Gln Ala Lys Gly Lys Ser Thr Ala Gln Ile Ser Leu Arg Trp Val Tyr
                245                 250                 255

Glu Gln Gly Val Ser Ile Val Thr Lys Ser Tyr Asn Lys Glu Arg Met
            260                 265                 270

Arg Gln Asn Leu Asp Ile Phe Asp Phe Cys Leu Thr Glu Glu Glu Leu
        275                 280                 285

Glu Lys Met Ser His Leu Pro Gln Arg Lys Gly Val Thr Phe Ala Ser
290                 295                 300

Ile Leu Gly Pro His Asp Ile Val Leu Lys Val Asp Glu Glu Leu
305                 310                 315

<210> SEQ ID NO 51
<211> LENGTH: 314
<212> TYPE: PRT
<213> ORGANISM: Glycine max
<220> FEATURE:
<221> NAME/KEY: MISC_FEATURE
<223> OTHER INFORMATION: CeresClone:1074583

<400> SEQUENCE: 51

Met Gly Ala Gly Asp Lys Thr Ala Gly Met Pro Arg Ile Gly Met
1               5                   10                  15

Gly Thr Ala Val Gln Gly Pro Lys Pro Asp Pro Ile Arg Arg Ala Val
            20                  25                  30

Leu Arg Ala Ile Glu Val Gly Tyr Arg His Phe Asp Thr Ala Ala His
```

```
            35                  40                  45
Tyr Glu Thr Glu Ala Pro Ile Gly Glu Ala Ala Glu Ala Val Arg
 50                  55                  60

Ser Gly Ala Val Ala Ser Arg Asp Asp Leu Phe Ile Thr Ser Lys Leu
 65                  70                  75                  80

Trp Cys Ser Asp Ala His Arg Asp Arg Val Pro Ala Leu Arg Gln
                 85                  90                  95

Thr Leu Arg Asn Leu Gln Met Glu Tyr Val Asp Leu Tyr Leu Val His
                100                 105                 110

Trp Pro Val Ser Met Lys Pro Gly Arg Phe Lys Ala Pro Phe Thr Ala
                115                 120                 125

Glu Asp Phe Val Pro Phe Asp Met Arg Ala Val Trp Glu Ala Met Glu
130                 135                 140

Glu Cys His Arg Leu Gly Leu Ala Lys Ala Ile Gly Val Ala Asn Phe
145                 150                 155                 160

Ser Cys Lys Lys Leu Glu Thr Leu Leu Ser Phe Ala Thr Ile Pro Pro
                165                 170                 175

Thr Val Asn Gln Val Glu Val Asn Pro Val Trp Gln Gln Arg Lys Leu
                180                 185                 190

Arg Glu Phe Cys Arg Gly Lys Gly Ile Gln Leu Cys Ala Tyr Ser Pro
                195                 200                 205

Leu Gly Ala Lys Gly Thr His Trp Gly Ser Asp Ala Val Met Asp Ala
                210                 215                 220

Gly Val Leu Gln Glu Ile Ala Ala Ser Arg Gly Lys Ser Val Ala Gln
225                 230                 235                 240

Val Cys Leu Arg Trp Val Tyr Glu Gln Gly Asp Cys Leu Ile Val Lys
                245                 250                 255

Ser Phe Asp Glu Ala Arg Met Arg Glu Asn Leu Asp Val Asp Gly Trp
                260                 265                 270

Glu Leu Thr Glu Glu His Arg Arg Ile Ala Glu Ile Pro Gln Arg
                275                 280                 285

Lys Ile Asn Leu Gly Lys Arg Tyr Val Ser Glu His Gly Pro Tyr Lys
                290                 295                 300

Ser Leu Glu Glu Leu Trp Asp Gly Glu Ile
305                 310

<210> SEQ ID NO 52
<211> LENGTH: 315
<212> TYPE: PRT
<213> ORGANISM: Glycine max
<220> FEATURE:
<221> NAME/KEY: MISC_FEATURE
<223> OTHER INFORMATION: gi[18]728

<400> SEQUENCE: 52

Met Ala Ala Ala Ile Glu Ile Pro Thr Ile Val Phe Pro Asn Ser Ser
 1                   5                  10                  15

Ala Gln Gln Arg Met Pro Val Val Gly Met Gly Ser Ala Pro Asp Phe
                 20                  25                  30

Thr Cys Lys Lys Asp Thr Lys Glu Ala Ile Ile Glu Ala Val Lys Gln
                 35                  40                  45

Gly Tyr Arg His Phe Asp Thr Ala Ala Ala Tyr Gly Ser Glu Gln Ala
                 50                  55                  60

Leu Gly Glu Ala Leu Lys Glu Ala Ile His Leu Gly Leu Val Ser Arg
 65                  70                  75                  80
```

```
Gln Asp Leu Phe Val Thr Ser Lys Leu Trp Val Thr Glu Asn His Pro
             85                  90                  95

His Leu Val Leu Pro Ala Leu Arg Lys Ser Leu Lys Thr Leu Gln Leu
            100                 105                 110

Glu Tyr Leu Asp Leu Tyr Leu Ile His Trp Pro Leu Ser Ser Gln Pro
            115                 120                 125

Gly Lys Phe Ser Phe Pro Ile Glu Val Glu Asp Leu Leu Pro Phe Asp
            130                 135                 140

Val Lys Gly Val Trp Glu Ser Met Glu Glu Cys Gln Lys Leu Gly Leu
145                 150                 155                 160

Thr Lys Ala Ile Gly Val Ser Asn Phe Ser Val Lys Lys Leu Gln Asn
                165                 170                 175

Leu Leu Ser Val Ala Thr Ile Arg Pro Val Val Asp Gln Val Glu Met
            180                 185                 190

Asn Leu Ala Trp Gln Gln Lys Lys Leu Arg Glu Phe Cys Lys Glu Asn
            195                 200                 205

Gly Ile Ile Val Thr Ala Phe Ser Pro Leu Arg Lys Gly Ala Ser Arg
            210                 215                 220

Gly Pro Asn Glu Val Met Glu Asn Asp Val Leu Lys Glu Ile Ala Glu
225                 230                 235                 240

Ala His Gly Lys Ser Ile Ala Gln Val Ser Leu Arg Trp Leu Tyr Glu
                245                 250                 255

Gln Gly Val Thr Phe Val Pro Lys Ser Tyr Asp Lys Glu Arg Met Asn
            260                 265                 270

Gln Asn Leu His Ile Phe Asp Trp Ala Leu Thr Glu Gln Asp His His
            275                 280                 285

Lys Ile Ser Gln Ile Ser Gln Ser Arg Leu Ile Ser Gly Pro Thr Lys
            290                 295                 300

Pro Gln Leu Ala Asp Leu Trp Asp Asp Gln Ile
305                 310                 315

<210> SEQ ID NO 53
<211> LENGTH: 320
<212> TYPE: PRT
<213> ORGANISM: Glycine max
<220> FEATURE:
<221> NAME/KEY: MISC_FEATURE
<223> OTHER INFORMATION: CeresClone:473625

<400> SEQUENCE: 53

Met Glu Ala Lys Lys Ile Pro Glu Val Ile Leu Asn Ser Gly Lys Lys
1               5                  10                  15

Met Pro Val Ile Gly Leu Gly Thr Ala Ser Ile Pro Leu Pro Ser His
            20                  25                  30

Glu Ala Leu Thr Ser Ile Leu Ile Asp Ala Phe Glu Val Gly Tyr Arg
            35                  40                  45

His Phe Asp Thr Ala Ser Leu Tyr Glu Ser Glu Glu Ser Leu Gly Lys
            50                  55                  60

Ala Val Ala Lys Ala Leu Glu Leu Gly Leu Ile Asn Ser Arg Glu Glu
65                  70                  75                  80

Leu Phe Ile Thr Ser Lys Leu Trp Ser Thr Asp Ala His Pro Asp Leu
                85                  90                  95

Val Val Pro Ala Leu Lys Thr Ser Leu Gln Lys Leu Gly Leu Glu Tyr
            100                 105                 110

Val Asp Leu Tyr Leu Ile His Trp Pro Val Arg Leu Lys Pro Glu Ala
            115                 120                 125
```

Lys Gly Tyr His Asn Ile Leu Lys Glu Asn Val Leu Pro Ser Phe Asp
            130                 135                 140

Met Lys Gly Ile Trp Glu Ala Met Glu Glu Cys Tyr Arg Leu Gly Leu
145                 150                 155                 160

Ala Lys Ser Ile Gly Val Ser Asn Phe Gly Ile Lys Lys Leu Ser Gln
                165                 170                 175

Leu Leu Glu Asn Ala Thr Ile Pro Pro Ala Val Asn Gln Val Glu Met
            180                 185                 190

Ser Pro Thr Trp Gln Gln Gly Lys Leu Lys Glu Phe Cys Lys Gln Lys
        195                 200                 205

Gly Ile His Val Ser Ala Trp Ser Pro Leu Gly Ala Tyr Lys Ser Ala
210                 215                 220

Gln Gly Thr Asn Ala Val Met Glu Ser Pro Ile Leu Lys Glu Ile Ala
225                 230                 235                 240

Cys Glu Arg Gln Lys Ser Met Ala Gln Ile Ala Leu Arg Trp Ile Tyr
                245                 250                 255

Glu Gln Gly Ala Ile Ala Ile Val Lys Ser Phe Asn Lys Glu Arg Met
            260                 265                 270

Lys Gln Asn Leu Asp Ile Phe Asp Trp Glu Leu Ser Gln Glu Ser
        275                 280                 285

Gln Lys Phe Ser Gln Ile Pro Gln Arg Arg Met Tyr Arg Gly Ile Thr
290                 295                 300

Phe Val Ser Glu Asn Gly Pro Tyr Lys Thr Leu Glu Glu Leu Trp Asp
305                 310                 315                 320

<210> SEQ ID NO 54
<211> LENGTH: 322
<212> TYPE: PRT
<213> ORGANISM: Glycine max
<220> FEATURE:
<221> NAME/KEY: MISC_FEATURE
<223> OTHER INFORMATION: CeresClone:474019
<220> FEATURE:
<221> NAME/KEY: misc_feature
<222> LOCATION: (274)..(274)
<223> OTHER INFORMATION: Xaa can be any naturally occurring amino acid

<400> SEQUENCE: 54

Met Ala Gly Lys Lys Ile Pro Asp Val Leu Leu Asn Ser Gly His Lys
1               5                   10                  15

Met Pro Val Ile Gly Met Gly Thr Ser Val Glu Asn Arg Pro Ser Asn
            20                  25                  30

Glu Thr Leu Ala Ser Ile Tyr Val Gly Ala Ile Glu Val Gly Tyr Arg
        35                  40                  45

His Phe Asp Thr Ala Ala Val Tyr Gly Thr Glu Ala Ile Gly Leu
    50                  55                  60

Ala Val Ala Lys Ala Ile Asp Lys Gly Leu Ile Lys Ser Arg Asp Glu
65                  70                  75                  80

Val Phe Ile Thr Ser Lys Pro Trp Asn Thr Asp Ala His Arg Asp Leu
                85                  90                  95

Ile Val Pro Ala Leu Lys Thr Thr Leu Lys Lys Leu Gly Thr Glu Tyr
            100                 105                 110

Val Asp Leu Tyr Leu Ile His Trp Pro Val Arg Leu Arg His Asp Leu
        115                 120                 125

Glu Asn Pro Thr Val Phe Thr Lys Glu Asp Val Leu Pro Phe Asp Ile
    130                 135                 140

```
Glu Gly Thr Trp Lys Ala Met Glu Glu Cys Tyr Lys Leu Gly Ile Ala
145                 150                 155                 160

Lys Ser Ile Gly Ile Cys Asn Tyr Gly Ile Lys Leu Thr Lys Leu
            165                 170                 175

Leu Glu Ile Ala Thr Ile Pro Pro Ala Val Asn Gln Val Glu Met Asn
                180                 185                 190

Pro Ser Trp Gln Gln Gly Lys Leu Arg Glu Phe Cys Lys Gln Lys Gly
        195                 200                 205

Ile His Val Ser Ala Trp Ser Ala Leu Gly Ala Tyr Lys Ile Phe Trp
        210                 215                 220

Gly Ser Gly Ala Val Met Glu Asn Pro Ile Leu Gln Asp Ile Ala Lys
225                 230                 235                 240

Ala Lys Gly Lys Thr Ile Ala Gln Val Ala Leu Arg Trp Val Tyr Gln
                245                 250                 255

Gln Gly Ser Ser Ala Met Ala Lys Ser Thr Asn Ser Glu Arg Met Lys
                260                 265                 270

Gln Xaa Leu Asp Ile Phe Asp Phe Val Leu Ser Glu Glu Asp Leu Glu
        275                 280                 285

Arg Ile Ser Gln Val Pro Gln Arg Arg Gln Tyr Thr Gly Asp Ile Trp
        290                 295                 300

Leu Ser Glu Asn Gly Ser Cys Lys Thr Leu Glu Glu Leu Trp Asp Gly
305                 310                 315                 320

Asp Val

<210> SEQ ID NO 55
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi[56]3536

<400> SEQUENCE: 55

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
                20                  25                  30

Cys Lys Lys Asp Thr Lys Asp Ala Ile Ile Glu Ala Ile Lys Gln Gly
            35                  40                  45

Tyr Arg His Phe Asp Thr Ala Ala Tyr Gly Ser Glu Gln Ala Leu
        50                  55                  60

Gly Glu Ala Leu Lys Glu Ala Ile Glu Leu Gly Leu Val Thr Arg Asp
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
                100                 105                 110

Tyr Leu Asp Leu Tyr Leu Ile His Trp Pro Leu Ser Ser Gln Pro Gly
            115                 120                 125

Lys Phe Ser Phe Pro Ile Asp Val Ala Asp Leu Leu Pro Phe Asp Val
        130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175
```

```
Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala His Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Arg Ile Phe Asp Trp Ser Leu Thr Lys Glu Asp His Glu Lys
        275                 280                 285

Ile Ala Gln Ile Lys Gln Asn Arg Leu Ile Pro Gly Pro Thr Lys Pro
    290                 295                 300

Gly Leu Asn Asp Leu Tyr Asp Asp
305                 310

<210> SEQ ID NO 56
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi[53]7298

<400> SEQUENCE: 56

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Glu
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala Asn Gly
        195                 200                 205

Ile Val Leu Thr Ala Phe Ser Pro Leu Arg Lys Gly Ala Ser Arg Gly
    210                 215                 220
```

```
Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
            245                 250                 255

Gly Val Thr Phe Val Pro Lys Ser Tyr Asp Lys Glu Arg Met Asn Gln
        260                 265                 270

Asn Leu Cys Ile Phe Asp Trp Ser Leu Thr Lys Glu Asp His Glu Lys
    275                 280                 285

Ile Asp Gln Ile Lys Gln Asn Arg Leu Ile Pro Gly Pro Thr Lys Pro
290                 295                 300

Gly Leu Asn Asp Leu Tyr Asp Asp
305                 310

<210> SEQ ID NO 57
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi[56]3538

<400> SEQUENCE: 57

Met Asp Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Glu
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala Asn Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
```

```
                260                 265                 270
Asn Leu Cys Ile Phe Asp Trp Ser Leu Thr Lys Glu Asp His Glu Lys
            275                 280                 285

Ile Asp Gln Ile Lys Gln Asn Arg Leu Ile Pro Gly Pro Thr Lys Pro
290                 295                 300

Gly Leu Asn Asp Leu Tyr Asp Asp
305                 310

<210> SEQ ID NO 58
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi[56]3540

<400> SEQUENCE: 58

Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Asp
65                  70                  75                  80

Glu Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Thr Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala His Gly
        195                 200                 205

Ile Val Leu Thr Ala Phe Ser Pro Leu Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Arg Ile Phe Asp Trp Ser Leu Thr Lys Glu Asp His Glu Lys
        275                 280                 285

Ile Asp Gln Ile Lys Gln Asn Arg Leu Ile Pro Gly Pro Thr Lys Pro
    290                 295                 300
```

```
Gly Leu Asn Asp Leu Tyr Asp Asp
305                 310
```

<210> SEQ ID NO 59
<211> LENGTH: 312
<212> TYPE: PRT
<213> ORGANISM: Medicago sativa
<220> FEATURE:
<221> NAME/KEY: MISC_FEATURE
<223> OTHER INFORMATION: gi[53]7296

<400> SEQUENCE: 59

```
Met Gly Ser Val Glu Ile Pro Thr Lys Val Leu Thr Asn Thr Ser Ser
1               5                   10                  15

Gln Leu Lys Met Pro Val Val Gly Met Gly Ser Ala Pro Asp Phe Thr
            20                  25                  30

Cys Lys Lys Asp Thr Lys Asp Ala Ile Ile Glu Ala Ile Lys Gln Gly
        35                  40                  45

Tyr Arg His Phe Asp Thr Ala Ala Ala Tyr Gly Ser Glu Gln Ala Leu
    50                  55                  60

Gly Glu Ala Leu Lys Glu Ala Ile Glu Leu Gly Leu Val Thr Arg Asp
65                  70                  75                  80

Asp Leu Phe Val Thr Ser Lys Leu Trp Val Thr Glu Asn His Pro His
                85                  90                  95

Leu Val Ile Pro Ala Leu Gln Lys Ser Leu Lys Thr Leu Gln Leu Asp
            100                 105                 110

Tyr Leu Asp Leu Tyr Leu Ile His Trp Pro Leu Ser Ser Gln Pro Gly
        115                 120                 125

Lys Phe Ser Phe Pro Ile Asp Val Ala Asp Leu Leu Pro Phe Asp Val
    130                 135                 140

Lys Gly Val Trp Glu Ser Met Glu Glu Ser Leu Lys Leu Gly Leu Thr
145                 150                 155                 160

Lys Ala Ile Gly Val Ser Asn Phe Ser Val Lys Lys Leu Glu Asn Leu
                165                 170                 175

Leu Ser Val Ala Thr Val Leu Pro Ala Val Asn Gln Val Glu Met Asn
            180                 185                 190

Leu Ala Trp Gln Gln Lys Lys Leu Arg Glu Phe Cys Asn Ala His Gly
        195                 200                 205

Ile Val Leu Thr Ala Phe Ser Pro Val Arg Lys Gly Ala Ser Arg Gly
    210                 215                 220

Pro Asn Glu Val Met Glu Asn Asp Met Leu Lys Glu Ile Ala Asp Ala
225                 230                 235                 240

His Gly Lys Ser Val Ala Gln Ile Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Arg Ile Phe Asp Trp Ser Leu Thr Lys Glu Asp His Glu Lys
        275                 280                 285

Ile Ala Gln Ile Lys Gln Asn Arg Leu Ile Pro Gly Pro Thr Lys Pro
    290                 295                 300

Gly Leu Asn Asp Leu Tyr Asp Asp
305                 310
```

<210> SEQ ID NO 60
<211> LENGTH: 314
<212> TYPE: PRT
<213> ORGANISM: Pueraria lobata

```
<220> FEATURE:
<221> NAME/KEY: MISC_FEATURE
<223> OTHER INFORMATION: gi[20]147510

<400> SEQUENCE: 60

Met Ala Ala Ile Glu Ile Pro Thr Ile Val Phe Pro Asn Ser Phe Ala
1               5                   10                  15

Gln His Arg Val Pro Val Val Glu Met Gly Ser Ala Pro Asp Phe Thr
            20                  25                  30

Cys Lys Lys Asp Thr Lys Glu Ala Ile Glu Ala Val Lys Gln Gly
        35                  40                  45

Tyr Arg His Phe Asp Thr Ala Ala Tyr Gly Ser Glu Gln Ala Leu
    50                  55                  60

Gly Glu Ala Leu Lys Glu Ala Val Asp Leu Gly Leu Val Ser Arg Gln
65                  70                  75                  80

Asp Leu Phe Val Thr Ser Lys Leu Trp Val Thr Asp Asn His Pro His
                85                  90                  95

Leu Val Val Ser Ala Leu Arg Lys Ser Leu Lys Thr Leu Gln Leu Glu
            100                 105                 110

Tyr Leu Asp Leu Tyr Leu Ile His Trp Pro Leu Ser Ser Gln Pro Gly
        115                 120                 125

Lys Phe Ser Phe Pro Ile Glu Val Glu Asp Leu Leu Pro Phe Asp Val
    130                 135                 140

Lys Gly Val Trp Glu Ala Met Gln Glu Cys Gln Lys Leu Gly Leu Thr
145                 150                 155                 160

Lys Ala Ile Gly Val Ser Asn Phe Ser Val Lys Leu Gln Asn Leu
                165                 170                 175

Leu Ser Val Ala Thr Ile Arg Pro Val Val Asn Gln Val Glu Met Asn
            180                 185                 190

Leu Ala Trp Gln Gln Lys Lys Leu Arg Glu Phe Cys Lys Glu Asn Gly
        195                 200                 205

Ile Val Ile Thr Ala Phe Ser Pro Leu Arg Lys Gly Ala Ser Arg Gly
    210                 215                 220

Pro Asn Glu Val Met Glu Asn Asp Val Leu Lys Glu Ile Ala Asp Ala
225                 230                 235                 240

His Gly Lys Ser Ile Ala Gln Val Ser Leu Arg Trp Leu Tyr Glu Gln
                245                 250                 255

Gly Val Thr Phe Val Pro Lys Ser Tyr Asp Lys Glu Arg Met Asn Gln
            260                 265                 270

Asn Leu Gln Ile Phe Asp Trp Ala Leu Thr Gln Glu Asp His His Lys
        275                 280                 285

Ile Ser Gln Ile Ser Gln Ser Arg Leu Ile Ser Gly Pro Thr Lys Pro
    290                 295                 300

Gln Leu Ser Asp Leu Trp Asp Asp Glu Ile
305                 310

<210> SEQ ID NO 61
<211> LENGTH: 322
<212> TYPE: PRT
<213> ORGANISM: Sesbania rostrata
<220> FEATURE:
<221> NAME/KEY: MISC_FEATURE
<223> OTHER INFORMATION: gi[27]92155

<400> SEQUENCE: 61

Met Ala Glu Lys Lys Ile Pro Glu Val Leu Leu Asn Ser Gly His Lys
1               5                   10                  15
```

Met Pro Val Ile Gly Met Gly Thr Ser Val Glu Ser Arg Pro Ser Asn
            20                  25                  30

Asp Val Leu Ala Ser Ile Phe Val Asp Ala Ile Gln Val Gly Tyr Arg
            35                  40                  45

His Phe Asp Ser Ala Ser Val Tyr Gly Thr Glu Glu Ala Ile Gly Met
 50                  55                  60

Ala Val Ser Lys Ala Ile Glu Gln Gly Leu Ile Lys Ser Arg Asp Glu
 65                  70                  75                  80

Val Phe Ile Thr Ser Lys Pro Trp Asn Thr Asp Ala His His Asp Leu
                85                  90                  95

Ile Val Pro Ala Leu Lys Thr Thr Leu Lys Lys Leu Gly Met Glu Tyr
            100                 105                 110

Val Asp Leu Tyr Leu Ile His Trp Pro Val Arg Leu Arg His Asp Leu
            115                 120                 125

Glu Asn Pro Val Ile Phe Ser Lys Glu Asp Leu Leu Pro Phe Asp Ile
130                 135                 140

Glu Gly Thr Trp Lys Ala Met Glu Glu Cys Tyr Arg Leu Gly Leu Ala
145                 150                 155                 160

Lys Ser Ile Gly Ile Cys Asn Tyr Gly Thr Lys Leu Thr Lys Leu
                165                 170                 175

Leu Glu Ile Ala Thr Ile Pro Pro Ala Val Asn Gln Val Glu Met Asn
            180                 185                 190

Pro Ser Trp Gln Gln Gly Asn Leu Arg Glu Phe Cys Lys Gln Lys Gly
            195                 200                 205

Ile His Val Ser Ala Trp Ser Pro Leu Gly Ala Tyr Lys Ile Phe Trp
210                 215                 220

Gly Ser Gly Ala Val Met Glu Asn Gln Ile Leu Gln Asp Ile Ala Thr
225                 230                 235                 240

Ala Lys Gly Lys Thr Ile Ala Gln Val Ala Leu Arg Trp Val Tyr Gln
                245                 250                 255

Gln Gly Ser Ser Ala Met Ala Lys Ser Phe Asn Lys Glu Arg Met Lys
            260                 265                 270

Gln Asn Leu Glu Ile Phe Asp Phe Glu Leu Ser Glu Glu Leu Glu
            275                 280                 285

Lys Ile Lys Gln Ile Pro Gln Arg Arg Gln Tyr Thr Gly Asp Met Trp
            290                 295                 300

Leu Ser Glu Asn Gly Ser Cys Lys Thr Leu Glu Glu Leu Trp Asp Gly
305                 310                 315                 320

Asp Val

<210> SEQ ID NO 62
<211> LENGTH: 315
<212> TYPE: PRT
<213> ORGANISM: Digitalis purpurea
<220> FEATURE:
<221> NAME/KEY: MISC_FEATURE
<223> OTHER INFORMATION: gi[13]160397

<400> SEQUENCE: 62

Met Ala Glu Glu Ile Arg Phe Phe Lys Leu Asn Thr Gly Ala Lys Ile
 1               5                  10                  15

Pro Ser Val Gly Leu Gly Thr Trp Gln Ser Ser Pro Gly Asp Ala Ala
            20                  25                  30

Gln Ala Val Glu Val Ala Ile Lys Cys Gly Tyr Arg His Ile Asp Gly
            35                  40                  45

Ala Arg Leu Tyr Glu Asn Glu Lys Glu Ile Gly Val Val Leu Lys Lys
            50                  55                  60

Leu Phe Asp Asp Gly Val Val Lys Arg Glu Asp Leu Phe Ile Thr Ser
 65                  70                  75                  80

Lys Leu Trp Ser Thr Asp His Ala Pro Glu Asp Val Pro Val Ala Leu
                85                  90                  95

Asp Lys Thr Leu Glu Asp Leu Gln Leu Asp Tyr Ile Asp Leu Tyr Leu
                100                 105                 110

Ile His Trp Pro Val Arg Leu Lys Lys Gly Ser Val Gly Leu Asp Pro
            115                 120                 125

Glu Asn Phe Ile Pro Thr Asp Ile Pro Gly Thr Trp Lys Ala Met Glu
130                 135                 140

Ala Leu Tyr Asp Ser Gly Lys Ala Arg Ala Ile Gly Val Ser Asn Phe
145                 150                 155                 160

Thr Leu Lys Lys Leu Ser Asp Leu Leu Asp Val Ala Arg Ile Pro Pro
                165                 170                 175

Ala Val Asn Gln Val Gly Cys His Pro Ser Cys Ala Gln Thr Lys Leu
            180                 185                 190

Arg Ala Phe Cys Lys Ser Lys Gly Val His Leu Ser Gly Tyr Ser Pro
            195                 200                 205

Leu Gly Ser Pro Gly Thr Pro Trp Val Lys His Asp Val Leu Glu Asn
210                 215                 220

Pro Ile Leu Val Asp Val Ala Glu Lys Leu Gly Lys Thr Pro Ala Gln
225                 230                 235                 240

Val Ala Ile Arg Trp Gly Leu Gln Met Gly His Ser Val Leu Pro Lys
                245                 250                 255

Ser Val His Glu Ser Arg Ile Lys Glu Asn Ile Asp Val Phe Ser Trp
            260                 265                 270

Cys Ile Pro Asp Asp Leu Phe Ala Lys Phe Ser Glu Ile Glu Gln Val
            275                 280                 285

Ser Pro Gly Lys Pro Glu Phe Pro Val His Pro Glu Ile Ser Gln Tyr
290                 295                 300

Lys Thr Val Glu Glu Met Trp Asp Gly Gly Ile
305                 310                 315

<210> SEQ ID NO 63
<211> LENGTH: 315
<212> TYPE: PRT
<213> ORGANISM: Digitalis purpurea
<220> FEATURE:
<221> NAME/KEY: MISC_FEATURE
<223> OTHER INFORMATION: gi[13]160399

<400> SEQUENCE: 63

Met Ala Glu Glu Ile Arg Phe Phe Glu Leu Asn Thr Gly Ala Lys Ile
 1               5                  10                  15

Pro Ser Val Gly Leu Gly Thr Trp Gln Ser Ser Pro Gly Asp Ala Ala
            20                  25                  30

Gln Ala Val Glu Val Ala Ile Lys Cys Gly Tyr Arg His Ile Asp Gly
            35                  40                  45

Ala Arg Leu Tyr Glu Asn Glu Lys Glu Ile Gly Val Val Leu Lys Lys
            50                  55                  60

Leu Phe Asp Asp Gly Val Val Lys Arg Glu Asp Leu Phe Ile Thr Ser
 65                  70                  75                  80

Lys Leu Trp Ser Thr Asp His Ala Pro Glu Asp Val Pro Val Ala Leu

```
                85                  90                  95
Asp Lys Thr Leu Glu Asp Leu Gln Leu Asp Tyr Ile Asp Leu Tyr Leu
            100                 105                 110

Ile His Trp Pro Val Arg Leu Lys Lys Gly Ser Val Gly Leu Asp Pro
        115                 120                 125

Glu Asn Phe Val Pro Thr Asp Ile Pro Gly Thr Trp Lys Ala Met Glu
    130                 135                 140

Ala Leu Tyr Asp Ser Gly Lys Ala Arg Ala Ile Gly Val Ser Asn Phe
145                 150                 155                 160

Thr Leu Lys Lys Leu Ser Asp Leu Leu Asp Val Ala Arg Ile Pro Pro
                165                 170                 175

Ala Val Asn Gln Val Gly Cys His Pro Ser Cys Ala Gln Thr Lys Leu
            180                 185                 190

Arg Ala Phe Cys Lys Ser Lys Gly Ile His Leu Ser Gly Tyr Ser Pro
        195                 200                 205

Leu Gly Ser Pro Gly Thr Pro Trp Val Lys His Asp Val Leu Glu Asn
    210                 215                 220

Pro Ile Leu Val Asp Val Ala Glu Lys Leu Gly Lys Thr Pro Ala Gln
225                 230                 235                 240

Val Ala Leu Arg Trp Gly Leu Gln Met Gly His Ser Val Leu Pro Lys
                245                 250                 255

Ser Val His Glu Ser Arg Ile Lys Glu Asn Ile Asp Val Phe Ser Trp
            260                 265                 270

Cys Ile Pro Asp Val Leu Phe Ala Lys Phe Ser Glu Ile Glu Gln Val
        275                 280                 285

Ser Pro Gly Lys Pro Glu Phe Pro Val His Pro Glu Ile Ser Gln Tyr
    290                 295                 300

Lys Thr Val Glu Glu Met Trp Asp Gly Gly Ile
305                 310                 315

<210> SEQ ID NO 64
<211> LENGTH: 319
<212> TYPE: PRT
<213> ORGANISM: Avena fatua
<220> FEATURE:
<221> NAME/KEY: MISC_FEATURE
<223> OTHER INFORMATION: gi[11]55213

<400> SEQUENCE: 64

Met Ala Ser Ala Lys Ala Met Gly Gln Gly Glu Gln Asp Arg Phe Val
1               5                   10                  15

Leu Lys Ser Gly His Ala Ile Pro Ala Val Gly Leu Gly Thr Trp Arg
            20                  25                  30

Ala Gly Ser Asp Thr Ala His Ser Val Gln Thr Ala Ile Thr Glu Ala
        35                  40                  45

Gly Tyr Arg His Val Asp Thr Ala Ala Gln Tyr Gly Ile Glu Lys Glu
    50                  55                  60

Val Asp Lys Gly Leu Lys Ala Ala Met Glu Ala Gly Ile Asp Arg Lys
65                  70                  75                  80

Asp Leu Phe Val Thr Ser Lys Ile Trp Arg Thr Asn Leu Ala Pro Glu
                85                  90                  95

Arg Ala Arg Pro Ala Leu Glu Asn Thr Leu Lys Asp Leu Gln Leu Asp
            100                 105                 110

Tyr Ile Asp Leu Tyr Leu Ile His Trp Pro Phe Arg Leu Lys Asp Gly
        115                 120                 125
```

Ala His Gln Pro Pro Glu Ala Gly Glu Val Leu Glu Phe Asp Met Glu
        130                 135                 140

Gly Val Trp Lys Glu Met Glu Lys Leu Val Lys Asp Gly Leu Val Lys
145                 150                 155                 160

Asp Ile Asp Val Cys Asn Phe Thr Val Thr Lys Leu Asn Arg Leu Leu
                165                 170                 175

Arg Ser Ala Asn Ile Pro Pro Ala Val Cys Gln Met Glu Met His Pro
            180                 185                 190

Gly Trp Lys Asn Asp Lys Ile Phe Glu Ala Cys Lys Lys His Gly Ile
        195                 200                 205

His Val Thr Ala Tyr Ser Pro Leu Gly Ser Ser Glu Lys Asn Leu Val
    210                 215                 220

His Asp Pro Val Val Glu Lys Val Ala Asn Lys Leu Asn Lys Thr Pro
225                 230                 235                 240

Gly Gln Val Leu Ile Lys Trp Ala Leu Gln Arg Gly Thr Ser Val Ile
                245                 250                 255

Pro Lys Ser Ser Lys Asp Glu Arg Ile Lys Glu Asn Ile Gln Ala Phe
            260                 265                 270

Gly Trp Glu Ile Pro Glu Asp Asp Phe Gln Val Leu Cys Ser Ile Lys
        275                 280                 285

Asp Glu Lys Arg Val Leu Thr Gly Glu Glu Leu Phe Val Asn Lys Thr
    290                 295                 300

His Gly Pro Tyr Lys Ser Ala Ser Glu Val Trp Asp His Glu Asn
305                 310                 315

<210> SEQ ID NO 65
<211> LENGTH: 320
<212> TYPE: PRT
<213> ORGANISM: Hordeum vulgare
<220> FEATURE:
<221> NAME/KEY: MISC_FEATURE
<223> OTHER INFORMATION: gi[72]8592

<400> SEQUENCE: 65

Met Ala Ser Ala Lys Ala Thr Met Gly Gln Gly Glu Gln Asp His Phe
1               5                   10                  15

Val Leu Lys Ser Gly His Ala Met Pro Ala Val Gly Leu Gly Thr Trp
                20                  25                  30

Arg Ala Gly Ser Asp Thr Ala His Ser Val Arg Thr Ala Ile Thr Glu
            35                  40                  45

Ala Gly Tyr Arg His Val Asp Thr Ala Ala Glu Tyr Gly Val Glu Lys
        50                  55                  60

Glu Val Gly Lys Gly Leu Lys Ala Ala Met Glu Ala Gly Ile Asp Arg
65                  70                  75                  80

Lys Asp Leu Phe Val Thr Ser Lys Ile Trp Cys Thr Asn Leu Ala Pro
                85                  90                  95

Glu Arg Val Arg Pro Ala Leu Glu Asn Thr Leu Lys Asp Leu Gln Leu
            100                 105                 110

Asp Tyr Ile Asp Leu Tyr His Ile His Trp Pro Phe Arg Leu Lys Asp
        115                 120                 125

Gly Ala His Met Pro Pro Glu Ala Gly Glu Val Leu Glu Phe Asp Met
    130                 135                 140

Glu Gly Val Trp Lys Glu Met Glu Asn Leu Val Lys Asp Gly Leu Val
145                 150                 155                 160

Lys Asp Ile Gly Val Cys Asn Tyr Thr Val Thr Lys Leu Asn Arg Leu
                165                 170                 175

```
Leu Arg Ser Ala Lys Ile Pro Pro Ala Val Cys Gln Met Glu Met His
            180                 185                 190

Pro Gly Trp Lys Asn Asp Lys Ile Phe Glu Ala Cys Lys Lys His Gly
            195                 200                 205

Ile His Ile Thr Ala Tyr Ser Pro Leu Gly Ser Ser Glu Lys Asn Leu
            210                 215                 220

Ala His Asp Pro Val Val Glu Lys Val Ala Asn Lys Leu Asn Lys Thr
225                 230                 235                 240

Pro Gly Gln Val Leu Ile Lys Trp Ala Leu Gln Arg Gly Thr Ser Val
                245                 250                 255

Ile Pro Lys Ser Ser Lys Asp Glu Arg Ile Lys Glu Asn Ile Gln Val
                260                 265                 270

Phe Gly Trp Glu Ile Pro Glu Glu Asp Phe Lys Val Leu Cys Ser Ile
            275                 280                 285

Lys Asp Glu Lys Arg Val Leu Thr Gly Glu Glu Leu Phe Val Asn Lys
290                 295                 300

Thr His Gly Pro Tyr Arg Ser Ala Arg Asp Val Trp Asp His Glu Asn
305                 310                 315                 320

<210> SEQ ID NO 66
<211> LENGTH: 321
<212> TYPE: PRT
<213> ORGANISM: Oryza sativa subsp. japonica
<220> FEATURE:
<221> NAME/KEY: MISC_FEATURE
<223> OTHER INFORMATION: gi[31]429855

<400> SEQUENCE: 66

Met Ala Thr Ile Pro Glu Val Pro Ala Ser Glu Leu Ile Gln Thr Met
1               5                   10                  15

Pro Arg Val Gly Met Gly Thr Ala Ala Phe Pro Phe Thr Ser Ser Glu
            20                  25                  30

Asp Thr Thr Ala Ala Met Leu Arg Ala Ile Glu Leu Gly Tyr Arg His
            35                  40                  45

Phe Asp Thr Ala Arg Ile Tyr Ala Thr Glu Gly Cys Val Gly Glu Ala
        50                  55                  60

Val Ala Glu Ala Val Arg Arg Gly Leu Ile Ala Ser Arg Ala Asp Val
65                  70                  75                  80

Phe Val Thr Ser Lys Ile Trp Cys Ser Asp Leu His Ala Gly Arg Val
                85                  90                  95

Val Pro Ala Ala Arg Glu Thr Leu Arg Asn Leu Gly Met Asp Tyr Val
            100                 105                 110

Asp Leu Leu Leu Val His Trp Pro Val Ser Leu Thr Pro Gly Asn Tyr
            115                 120                 125

Asp Phe Pro Phe Pro Lys Glu Val Ile Leu Pro Ser Phe Asp Met Glu
        130                 135                 140

Gly Val Trp Arg Gly Met Glu Glu Cys His Arg Leu Gly Leu Ala Arg
145                 150                 155                 160

Ala Ile Gly Val Ser Asn Phe Ser Ala Lys Lys Leu Glu Gln Leu Leu
                165                 170                 175

Ser Leu Ala Ala Val Arg Pro Ala Val Asn Gln Val Glu Val Asn Pro
            180                 185                 190

Met Trp Gln Gln Arg Thr Leu Arg Glu Val Cys Arg Arg Glu Gly Val
            195                 200                 205

Gln Leu Cys Gly Tyr Ser Pro Leu Gly Ala Lys Gly Thr Pro Trp Gly
```

```
            210                 215                 220
Ser Ala Val Met Asp Ser Gly Val Leu Gln Glu Ile Ala Gly Ala
225                 230                 235                 240

Lys Gly Lys Thr Leu Ala Gln Ile Cys Leu Arg Trp Leu Tyr Glu Gln
                245                 250                 255

Gly Asp Val Leu Leu Val Lys Thr Tyr Asn Glu Lys Arg Met Lys Glu
                260                 265                 270

Asn Leu Asp Ile Phe Asn Trp Glu Leu Thr Asp Glu Glu Arg Glu Arg
            275                 280                 285

Ile Ser Gln Leu Pro Gln Leu Arg Gly Leu Pro Gly Leu Glu Phe Ile
        290                 295                 300

Ser Asp His Gly Pro Tyr Lys Ser Val Glu Asp Leu Trp Asp Gly Asp
305                 310                 315                 320

Val

<210> SEQ ID NO 67
<211> LENGTH: 322
<212> TYPE: PRT
<213> ORGANISM: Oryza sativa subsp. japonica
<220> FEATURE:
<221> NAME/KEY: MISC_FEATURE
<223> OTHER INFORMATION: gi[31]429856

<400> SEQUENCE: 67

Met Ala Met Ala Thr Ile Pro Glu Val Pro Ala Ser Ala Leu Leu Pro
1               5                   10                  15

Thr Met Pro Arg Ile Gly Met Gly Thr Ala Ala Phe Pro Phe Thr Ser
                20                  25                  30

Ser Glu Glu Thr Thr Ala Ala Leu Leu Arg Ala Ile Glu Leu Gly Tyr
            35                  40                  45

Arg His Phe Asp Thr Ala Arg Leu Tyr Ala Thr Glu Gly Cys Val Ser
        50                  55                  60

Glu Ala Val Ala Glu Ala Val Arg Arg Gly Leu Val Ala Ser Arg Ala
65                  70                  75                  80

Asp Val Phe Val Thr Ser Lys Leu Trp Cys Ser Asp Leu His Ala Gly
                85                  90                  95

Arg Val Val Pro Ala Ala Arg Glu Thr Leu Arg Asn Leu Gly Met Asp
            100                 105                 110

Tyr Val Asp Leu Leu Leu Val His Trp Pro Ala Thr Val Ala Pro Gly
        115                 120                 125

Ser Tyr Asp Phe Pro Phe Pro Lys Glu Glu Met Ala Pro Ala Phe Asp
130                 135                 140

Met Glu Gly Val Trp Arg Gly Met Glu Glu Cys His Arg Leu Gly Leu
145                 150                 155                 160

Ala Arg Ala Ile Gly Val Ser Asn Phe Ser Ala Lys Lys Leu Glu Gln
                165                 170                 175

Leu Leu Ser Phe Ala Val Val Arg Pro Ala Ala Asn Gln Val Glu Met
            180                 185                 190

Asn Pro Met Trp Gln Gln Arg Thr Leu Arg Glu Val Cys Arg Arg Glu
        195                 200                 205

Gly Val Gln Leu Cys Gly Tyr Ser Pro Leu Gly Ala Lys Gly Thr Pro
    210                 215                 220

Trp Gly Ser Ala Ala Val Met Asp Ser Gly Val Leu His Asp Ile Ala
225                 230                 235                 240

Gln Thr Lys Gly Lys Thr Leu Ala Gln Ile Cys Leu Arg Trp Met Tyr
                245                 250                 255
```

```
                   245                 250                 255
Glu Gln Gly Asp Val Leu Leu Val Lys Thr Tyr Asn Glu Asn Arg Met
            260                 265                 270

Lys Glu Asn Leu Asp Ile Phe Asp Trp Glu Leu Thr Glu Glu Glu Arg
            275                 280                 285

Asp Lys Ile Ser Lys Leu Pro Gln Gln Arg Gly Leu Thr Gly Met Gln
            290                 295                 300

Phe Val Cys Asp Asn Gly Pro Tyr Lys Cys Val Glu Asp Leu Trp Asp
305                 310                 315                 320

Gly Ala

<210> SEQ ID NO 68
<211> LENGTH: 314
<212> TYPE: PRT
<213> ORGANISM: Triticum aestivum
<220> FEATURE:
<221> NAME/KEY: MISC_FEATURE
<223> OTHER INFORMATION: CeresClone:677995

<400> SEQUENCE: 68

Met Gly Ala Gly Asp Lys Thr Ala Ala Gly Met Pro Arg Ile Gly Met
1               5                   10                  15

Gly Thr Ala Val Gln Gly Pro Lys Pro Asp Pro Ile Arg Arg Ala Val
            20                  25                  30

Leu Arg Ala Ile Glu Val Gly Tyr Arg His Phe Asp Thr Ala Ala His
            35                  40                  45

Tyr Glu Thr Glu Ala Pro Ile Gly Glu Ala Ala Glu Ala Val Arg
        50                  55                  60

Ser Gly Ala Val Ala Ser Arg Asp Asp Leu Phe Ile Thr Ser Lys Leu
65              70                  75                  80

Trp Cys Ser Asp Ala His Arg Asp Arg Val Val Pro Ala Leu Arg Gln
                85                  90                  95

Thr Leu Arg Asn Leu Gln Met Glu Tyr Val Asp Leu Tyr Leu Val His
            100                 105                 110

Trp Pro Val Ser Met Lys Pro Gly Arg Phe Lys Ala Pro Phe Thr Ala
            115                 120                 125

Glu Asp Phe Val Pro Phe Asp Met Arg Ala Val Trp Glu Ala Met Glu
    130                 135                 140

Glu Cys His Arg Leu Gly Leu Ala Lys Ala Ile Gly Val Ala Asn Phe
145                 150                 155                 160

Ser Cys Lys Lys Leu Glu Thr Leu Leu Ser Phe Ala Thr Ile Pro Pro
                165                 170                 175

Thr Val Asn Gln Val Glu Val Asn Pro Val Trp Gln Gln Arg Lys Leu
            180                 185                 190

Arg Glu Phe Cys Arg Gly Lys Gly Ile Gln Leu Cys Thr Tyr Ser Pro
        195                 200                 205

Leu Gly Ala Lys Gly Thr His Trp Gly Ser Asp Ala Val Met Asp Ala
    210                 215                 220

Gly Val Leu Gln Glu Ile Ala Ala Ser Arg Gly Lys Ser Val Ala Gln
225                 230                 235                 240

Val Cys Leu Arg Trp Val Tyr Glu Gln Gly Asp Cys Leu Ile Val Lys
                245                 250                 255

Ser Phe Asp Glu Ala Arg Met Arg Glu Asn Leu Asp Val Asp Gly Trp
            260                 265                 270

Glu Leu Thr Glu Glu Glu His Arg Arg Ile Ala Glu Ile Pro Gln Arg
```

```
                275                 280                 285
Lys Ile Asn Leu Gly Lys Arg Tyr Val Ser Glu His Gly Pro Tyr Lys
            290                 295                 300

Ser Leu Glu Glu Leu Trp Asp Gly Glu Ile
305                 310

<210> SEQ ID NO 69
<211> LENGTH: 329
<212> TYPE: PRT
<213> ORGANISM: Zea mays
<220> FEATURE:
<221> NAME/KEY: MISC_FEATURE
<223> OTHER INFORMATION: CeresClone:290117

<400> SEQUENCE: 69

Met Ala Ser Ala Gly Thr Thr Ala Val Val Pro Glu Val Ala Leu Arg
1               5                   10                  15

Ser Gly Asn Ala Arg Thr Ala Met Pro Met Val Gly Met Gly Thr Ala
            20                  25                  30

Ser Phe Pro Leu Val His Glu Ala Val Lys Asp Ala Val Leu Ser Ala
        35                  40                  45

Ile Glu Val Gly Phe Arg His Phe Asp Thr Ala Ser Met Tyr Gly Thr
50                  55                  60

Glu Lys Pro Leu Gly Asp Ala Val Ala Glu Ala Leu Arg Arg Gly Thr
65                  70                  75                  80

Leu Arg Ser Arg Glu Asp Leu Phe Val Thr Ser Lys Leu Trp Cys Ser
                85                  90                  95

Gln Asn His Pro Asp Leu Val Leu Pro Ser Leu Arg Glu Thr Leu Lys
            100                 105                 110

Asn Leu Gln Met Glu Tyr Val Asp Leu Tyr Leu Ile His Trp Pro Val
        115                 120                 125

Cys Leu Lys Pro Gly Pro Pro Glu Leu Pro Thr Arg Lys Glu Asn Ala
130                 135                 140

Val Pro Leu Asp Leu Ala Gly Val Trp Arg Ala Met Glu Glu Cys Gln
145                 150                 155                 160

Arg Leu Gly Leu Ala Lys Ala Ile Gly Val Ser Asn Phe Thr Thr Arg
                165                 170                 175

His Leu Asp Gly Val Leu Ala Val Ala Thr Val Pro Pro Ala Val Asn
            180                 185                 190

Gln Val Glu Leu Asn Pro Ala Trp Gln Gln Arg Thr Leu Arg Ala Tyr
        195                 200                 205

Cys Ala Asp Arg Gly Ile His Val Ala Ala Tyr Ser Pro Leu Gly Gly
210                 215                 220

Gln Asn Trp Asp Gly Gln Gly Ser Ala Val Leu Asp Ser Glu Val Leu
225                 230                 235                 240

Ala Ala Ile Ala Lys Ala Arg Gly Lys Thr Val Ala Gln Val Ala Leu
                245                 250                 255

Arg Trp Ile His Glu Gln Gly Val Thr Cys Ile Val Lys Ser Tyr Ser
            260                 265                 270

Lys Glu Arg Leu Arg Gln Asn Leu Gly Ile Phe Asp Trp Glu Leu Thr
        275                 280                 285

Asp Glu Glu Arg Leu Lys Ile Ser Gln Ile Pro Gln Arg Lys Val Val
290                 295                 300

Gln Thr Ser Ser Leu Phe Ser Gln Glu Gly Glu Phe Thr Ala Val Asp
305                 310                 315                 320
```

```
Pro Ala Glu Leu Asn Ile Leu Glu Glu
            325

<210> SEQ ID NO 70
<211> LENGTH: 320
<212> TYPE: PRT
<213> ORGANISM: Bromus inermis
<220> FEATURE:
<221> NAME/KEY: MISC_FEATURE
<223> OTHER INFORMATION: gi[54]3632

<400> SEQUENCE: 70

Met Ala Ser Ala Lys Ala Met Met Gly Gln Glu Arg Gln Asp His Phe
1               5                   10                  15

Val Leu Lys Ser Gly His Ala Ile Pro Ala Val Gly Leu Gly Thr Trp
                20                  25                  30

Arg Ala Gly Ser Asp Thr Ala His Ser Val Gln Thr Ala Ile Thr Glu
            35                  40                  45

Ala Gly Tyr Arg His Val Asp Thr Ala Ala Glu Tyr Gly Val Glu Lys
        50                  55                  60

Glu Val Gly Lys Gly Leu Lys Ala Ala Met Glu Ala Gly Ile Asp Arg
65              70                  75                  80

Lys Asp Leu Phe Val Thr Ser Lys Leu Trp Cys Thr Asp Leu Val Pro
                85                  90                  95

Asp Arg Val Arg Pro Ala Leu Glu Lys Thr Leu Lys Asp Leu Gln Leu
            100                 105                 110

Asp Tyr Leu Asp Leu Tyr Leu Ile His Trp Pro Phe Arg Leu Lys Asp
        115                 120                 125

Gly Ala His Lys Pro Pro Glu Ala Gly Glu Val Leu Glu Phe Asp Met
130                 135                 140

Glu Gly Val Trp Lys Glu Met Glu Asn Leu Val Lys Asp Gly Leu Val
145                 150                 155                 160

Lys Asp Ile Gly Val Cys Asn Tyr Thr Val Thr Lys Leu Asn Arg Leu
                165                 170                 175

Leu Gln Ser Ala Lys Ile Ala Pro Ala Val Cys Gln Met Glu Met His
            180                 185                 190

Pro Gly Trp Lys Asn Asp Lys Ile Leu Glu Ala Cys Lys Lys His Gly
        195                 200                 205

Ile His Ala Thr Ala Tyr Ser Pro Leu Cys Ser Ser Glu Lys Asn Leu
210                 215                 220

Ala His Asp Pro Val Val Glu Lys Val Ala Asn Lys Leu Asn Lys Thr
225                 230                 235                 240

Pro Gly Gln Val Leu Ile Lys Trp Ala Leu Gln Arg Gly Thr Ile Val
                245                 250                 255

Ile Pro Lys Ser Ser Lys Asp Glu Arg Ile Lys Glu Asn Ile Gln Val
            260                 265                 270

Phe Gly Trp Glu Ile Pro Glu Glu Asp Phe Gln Val Leu Cys Ser Ile
        275                 280                 285

Lys Asp Glu Lys Arg Val Leu Thr Gly Glu Glu Leu Phe Val Asn Lys
290                 295                 300

Thr His Gly Pro Tyr Lys Ser Ala Ser Glu Val Trp Asp Asn Glu Asn
305                 310                 315                 320

<210> SEQ ID NO 71
<211> LENGTH: 321
<212> TYPE: PRT
<213> ORGANISM: Hydrangea macrophylla
```

```
<220> FEATURE:
<221> NAME/KEY: MISC_FEATURE
<223> OTHER INFORMATION: gi[40]781601

<400> SEQUENCE: 71

Met Ala Phe Thr Ile Pro Glu Val Pro Leu Ser Ser Gly Gly Arg Lys
1               5                   10                  15

Met Pro Val Leu Gly Leu Gly Thr Ala Ala Asp Pro Val Asp Pro
            20                  25                  30

Glu Thr Val Arg Lys Ala Val Thr Glu Ala Leu Lys Leu Gly Tyr Arg
            35                  40                  45

His Phe Asp Thr Ala Ala Leu Tyr Asn Ser Glu Gln Pro Leu Gly Asp
        50                  55                  60

Ala Ile Ala Glu Ala Leu Gly Glu Gly Leu Ile Lys Ser Arg Asp Glu
65                  70                  75                  80

Leu Phe Ile Thr Ser Lys Leu Trp Cys Ser Asp Ala His Arg Glu Asn
                85                  90                  95

Val Glu Pro Ala Leu Gln Lys Thr Leu Lys Asn Leu Lys Leu Glu Tyr
            100                 105                 110

Ile Asp Met Tyr Leu Ile His Trp Pro Val Ser Ser Lys Pro Gly Asn
            115                 120                 125

Tyr Glu Tyr Pro Ile Lys Lys Glu Asp Phe Leu Gln Met Asp Tyr Lys
            130                 135                 140

Ser Val Trp Glu Ala Met Glu Glu Cys Gln Lys Leu Gly Leu Thr Lys
145                 150                 155                 160

Ala Ile Gly Val Ser Asn Phe Ser Cys Lys Lys Leu Ser Asp Val Leu
                165                 170                 175

Ala Asn Ala Lys Val Pro Pro Ala Val Asn Gln Val Glu Val Asn Pro
            180                 185                 190

Cys Trp Gln Gln Lys Gln Leu Thr Glu Phe Cys Lys Ser Asn Gly Ile
            195                 200                 205

Leu Val Val Ala Tyr Ala Ala Leu Gly Ala Val Gly Thr Phe Tyr Gly
            210                 215                 220

Thr Asn Arg Val Met Gly Ser Glu Val Leu Asn Glu Ile Ala Arg Ile
225                 230                 235                 240

Arg Gly Asn Thr Val Ala Gln Val Cys Leu Arg Trp Ala Tyr Glu Gln
                245                 250                 255

Gly Ile Gly Val Leu Val Lys Ser Phe Asn Lys Glu Arg Met Glu Gln
            260                 265                 270

Asn Leu Gln Ile Phe Asn Trp Thr Leu Ser Asp Glu Ser Lys Lys
            275                 280                 285

Ile Ser Glu Ile Pro Gln Gly Arg Ala Cys Leu Gly Thr Asp Tyr Thr
            290                 295                 300

Ser Val His Gly Pro Phe Lys Thr Ile Glu Glu Leu Trp Asp Gly Glu
305                 310                 315                 320

Phe

<210> SEQ ID NO 72
<211> LENGTH: 321
<212> TYPE: PRT
<213> ORGANISM: Oryza sativa subsp. japonica
<220> FEATURE:
<221> NAME/KEY: MISC_FEATURE
<223> OTHER INFORMATION: gi[50]920555

<400> SEQUENCE: 72
```

Met Ser Asp Gly Gly Ala Gly Ala Lys Gly Ala Gly Phe Gly Met Pro
1               5                   10                  15

Arg Val Gly Met Gly Thr Ala Val Gln Gly Pro Arg Pro Glu Pro Ile
            20                  25                  30

Arg Arg Ala Val Leu Lys Ala Ile Glu Ala Gly Tyr Arg His Phe Asp
        35                  40                  45

Thr Ala Ala His Tyr Glu Thr Glu Ala Pro Ile Gly Glu Ala Ala Ala
    50                  55                  60

Glu Ala Val Arg Ser Gly Ala Ile Ala Ser Arg Ala Asp Leu Phe Ile
65                  70                  75                  80

Thr Ser Lys Leu Trp Cys Ser Asp Ala His Arg Asp Arg Val Leu Pro
            85                  90                  95

Ala Leu Arg Gln Thr Leu Trp Asn Leu Gln Met Glu Tyr Val Asp Leu
            100                 105                 110

Tyr Leu Val His Trp Pro Val Ser Met Lys Pro Gly Arg Tyr Lys Ala
            115                 120                 125

Pro Phe Thr Ala Asp Asp Phe Val Pro Phe Asp Met Arg Ala Val Trp
    130                 135                 140

Glu Ala Met Glu Glu Cys His Arg Leu Gly Leu Ala Lys Ala Ile Gly
145                 150                 155                 160

Val Cys Asn Phe Ser Cys Lys Lys Leu Asp Thr Leu Leu Ser Phe Ala
                165                 170                 175

Thr Ile Pro Pro Ala Val Asn Gln Val Glu Val Asn Pro Val Trp Gln
            180                 185                 190

Gln Arg Lys Leu Arg Glu Leu Cys Arg Glu Lys Gly Val Gln Ile Cys
            195                 200                 205

Ala Tyr Ser Pro Leu Gly Ala Ser Gly Thr His Trp Gly Ser Asp Ser
    210                 215                 220

Val Met Ala Ser Ala Val Leu Arg Asp Ile Ala Gln Ser Lys Gly Lys
225                 230                 235                 240

Thr Val Ala Gln Ala Arg His Val Cys Leu Arg Trp Val Tyr Glu Gln
                245                 250                 255

Gly Asp Cys Leu Ile Val Lys Ser Phe Asp Glu Ala Arg Met Arg Glu
            260                 265                 270

Asn Leu Asp Ile Val Gly Trp Glu Leu Thr Glu Glu Glu Arg Gln Arg
            275                 280                 285

Ile Ala Gly Ile Pro Gln Arg Lys Ile Asn Arg Ala Leu Arg Phe Val
    290                 295                 300

Ser Asp His Gly Pro Tyr Lys Ser Leu Asp Asp Leu Trp Asp Gly Glu
305                 310                 315                 320

Ile

<210> SEQ ID NO 73
<211> LENGTH: 323
<212> TYPE: PRT
<213> ORGANISM: Oryza sativa subsp. japonica
<220> FEATURE:
<221> NAME/KEY: MISC_FEATURE
<223> OTHER INFORMATION: gi[50]900440

<400> SEQUENCE: 73

Met Ala Ala Val Pro Glu Val Ala Leu Arg His Gly Ala Gly Arg Pro
1               5                   10                  15

Met Pro Ala Val Gly Val Gly Thr Ala Asp Ser Ala Ala Thr Ser Pro
            20                  25                  30

```
Glu Thr Lys Arg Gly Ala Ala Leu Ala Ala Leu Glu Val Gly Phe Arg
            35                  40                  45

His Phe Asp Thr Ala Ala Leu Tyr Gly Thr Glu Ala Pro Leu Gly Glu
 50                  55                  60

Ala Ile Ala Glu Ala Thr Arg Arg Gly Leu Val Ala Ser Arg Glu Glu
 65                  70                  75                  80

Val Phe Val Thr Thr Lys Leu Trp Cys Thr Gln Cys His Pro Gly Leu
                 85                  90                  95

Val Leu Pro Ser Leu Arg Glu Ser Leu Arg Asn Leu Gln Met Glu Tyr
            100                 105                 110

Val Asp Leu Tyr Leu Val His Trp Pro Ile Ser Val Lys Pro Gly Pro
            115                 120                 125

Pro Met Leu Pro Val Lys Arg Glu Asp Ala Val Pro Phe Asp Phe Glu
            130                 135                 140

Gly Val Trp Arg Ala Met Glu Glu Cys His Arg Leu Gly Leu Ala Lys
145                 150                 155                 160

Ala Ile Gly Val Ser Asn Phe Thr Thr Lys His Leu Asp Lys Leu Leu
                165                 170                 175

Ala Val Ala Thr Ile Pro Pro Ala Val Asn Gln Val Glu Met Asn Pro
            180                 185                 190

Val Trp Gln Gln Arg Thr Val Arg Glu Tyr Cys Ala Ala Lys Gly Ile
            195                 200                 205

Arg Val Ala Ala Tyr Ser Pro Leu Gly Gly Gln Asn Trp Ile Gly Glu
            210                 215                 220

Gly Asn Asp Val Met Glu Ser Pro Val Leu Ala Asp Ile Ala Arg Ala
225                 230                 235                 240

Arg Gly Lys Ser Ile Ala Gln Val Ser Leu Arg Trp Ile His Glu Gln
                245                 250                 255

Gly Val Thr Pro Ile Pro Lys Ser Tyr Asn Lys Glu Arg Leu Lys Gln
            260                 265                 270

Asn Leu Glu Ile Phe Asp Trp Glu Leu Thr Lys Glu Asp Arg Leu Lys
            275                 280                 285

Ile Ser Gln Ile Pro Gln Lys Lys Ile Val Thr Ala Ala Arg Met Phe
290                 295                 300

Ser Pro Asp Gly Glu Phe Ala Ser Val Asp Leu Ser Asp Met Glu Ile
305                 310                 315                 320

Val Glu Glu

<210> SEQ ID NO 74
<211> LENGTH: 323
<212> TYPE: PRT
<213> ORGANISM: Oryza sativa subsp. japonica
<220> FEATURE:
<221> NAME/KEY: MISC_FEATURE
<223> OTHER INFORMATION: gi[50]900438

<400> SEQUENCE: 74

Met Ala Val Val Val Pro Glu Ala Val Leu Arg His Gly Asp Ala Arg
 1               5                  10                  15

Pro Met Pro Ala Val Gly Met Gly Val Ala Glu Tyr Pro Ser Thr Pro
                 20                  25                  30

Glu Arg Thr Arg Asp Ala Val Leu Ala Ala Leu Glu Ala Gly Phe Arg
            35                  40                  45

His Phe Asp Thr Ala Ser Leu Tyr Arg Thr Glu Ala Pro Leu Gly Glu
 50                  55                  60
```

```
Ala Ile Ala Glu Ala Thr Arg Arg Gly Leu Leu Ala Ser Arg Glu Glu
 65                  70                  75                  80

Ala Phe Val Thr Thr Lys Leu Trp Cys Thr Gln Cys His Pro Asp Leu
                 85                  90                  95

Val Leu Pro Ser Leu Arg Glu Ser Leu Arg Asn Leu Gln Met Glu Tyr
            100                 105                 110

Val Asp Leu Tyr Leu Ile His Leu Pro Ile Ser Val Lys Pro Gly Pro
        115                 120                 125

Met Val Phe Pro Val Lys Lys Glu Asp Val Val Pro Phe Asp Phe Gly
    130                 135                 140

Gly Val Trp Arg Ala Met Glu Glu Cys His Arg Leu Gly Leu Ala Lys
145                 150                 155                 160

Ala Ile Gly Val Ser Asn Phe Thr Thr Lys His Ile Asp Lys Leu Leu
                165                 170                 175

Ala Val Ala Thr Ile Leu Pro Ala Val Asn Gln Val Glu Met Asn Pro
            180                 185                 190

Thr Trp Gln Gln Arg Thr Val Arg Glu Tyr Cys Asp Ala Lys Gly Ile
        195                 200                 205

Arg Val Thr Ala Tyr Ser Pro Leu Gly Gly Gln Asn Trp Gly Gly Ser
    210                 215                 220

Ala Asn Tyr Val Met Glu Ser Ser Val Leu Thr Glu Ile Ala Arg Ala
225                 230                 235                 240

Arg Gly Lys Ser Ile Ala Gln Val Ser Leu Arg Trp Ile Tyr Glu Gln
                245                 250                 255

Gly Val Thr Pro Ile Ala Lys Ser Tyr Arg Lys Glu Arg Leu Lys Glu
            260                 265                 270

Asn Leu Glu Ile Phe Asp Trp Glu Leu Thr Asp Glu Asp Arg Leu Lys
        275                 280                 285

Ile Ser Gln Ile Pro Gln Arg Lys Arg Val Thr Ala Ala Ser Leu Phe
    290                 295                 300

Ser Pro Asp Gly Glu Phe Thr Ser Val Asp Leu Pro Asp Ile Glu Ile
305                 310                 315                 320

Val Glu Glu

<210> SEQ ID NO 75
<211> LENGTH: 316
<212> TYPE: PRT
<213> ORGANISM: Glycyrrhiza glabra
<220> FEATURE:
<221> NAME/KEY: MISC_FEATURE
<223> OTHER INFORMATION: gi[15]14979

<400> SEQUENCE: 75

Met Ala Ala Ala Ile Glu Ile Pro Thr Lys Val Leu Pro Asn Ser
1               5                   10                  15

Thr Cys Glu Leu Arg Val Pro Val Ile Gly Met Gly Ser Ala Pro Asp
            20                  25                  30

Phe Thr Cys Lys Lys Asp Thr Lys Glu Ala Ile Ile Glu Ala Ile Lys
        35                  40                  45

Gln Gly Tyr Arg His Phe Asp Thr Ala Ala Tyr Gly Ser Glu Thr
    50                  55                  60

Ala Leu Gly Glu Ala Leu Lys Glu Ala Arg Asp Leu Gly Leu Val Thr
 65                 70                  75                  80

Arg Glu Asp Leu Phe Val Thr Ser Lys Leu Trp Val Thr Glu Asn His
                85                  90                  95
```

Pro His Leu Val Val Pro Ala Leu Arg Lys Ser Leu Glu Thr Leu Gln
            100                 105                 110

Leu Glu Tyr Leu Asp Leu Tyr Leu Ile His Trp Pro Leu Ser Ser Gln
        115                 120                 125

Pro Gly Lys Phe Ser Phe Pro Ile Gln Ala Glu Asp Leu Leu Pro Phe
    130                 135                 140

Asp Val Lys Gly Val Trp Glu Ser Met Glu Glu Ser Leu Lys Leu Gly
145                 150                 155                 160

Leu Thr Lys Ala Ile Gly Val Ser Asn Phe Ser Val Lys Lys Leu Gln
                165                 170                 175

Asn Leu Leu Ser Val Ala Thr Ile Arg Pro Ala Val Asn Gln Val Glu
            180                 185                 190

Met Asn Leu Ala Trp Gln Gln Lys Leu Arg Glu Phe Cys Asn Ala
        195                 200                 205

Asn Gly Ile Val Leu Thr Ala Phe Ser Pro Leu Arg Lys Gly Ala Ser
    210                 215                 220

Arg Gly Pro Asn Glu Val Met Glu Asn Asp Met Leu Lys Gly Ile Ala
225                 230                 235                 240

Glu Ala His Gly Lys Ser Ile Ala Gln Val Ser Leu Arg Trp Leu Tyr
                245                 250                 255

Glu Gln Gly Val Thr Phe Val Ala Lys Ser Tyr Asp Lys Glu Arg Met
            260                 265                 270

Asn Gln Asn Leu Gln Ile Phe Asp Trp Glu Leu Thr Thr Glu Asp His
        275                 280                 285

Gln Lys Ile Asp Gln Ile Lys Gln Asn Arg Leu Ile Pro Gly Pro Thr
    290                 295                 300

Lys Pro Gln Leu Asn Asp Leu Trp Asp Asp Glu Ile
305                 310                 315

<210> SEQ ID NO 76
<211> LENGTH: 315
<212> TYPE: PRT
<213> ORGANISM: Glycyrrhiza glabra
<220> FEATURE:
<221> NAME/KEY: MISC_FEATURE
<223> OTHER INFORMATION: gi[15]14981

<400> SEQUENCE: 76

Met Ala Ala Ile Glu Ile Pro Thr Lys Val Leu Pro Asn Ser Thr
1               5                   10                  15

Cys Glu Leu Arg Val Pro Val Ile Gly Met Gly Ser Ala Pro Asp Phe
            20                  25                  30

Thr Cys Lys Lys Asp Thr Lys Glu Ala Ile Ile Glu Ala Ile Lys Gln
        35                  40                  45

Gly Tyr Arg His Phe Asp Thr Ala Ala Ala Tyr Gly Ser Glu Thr Ala
    50                  55                  60

Leu Gly Glu Ala Leu Lys Glu Ala Arg Asp Leu Gly Leu Val Thr Arg
65                  70                  75                  80

Glu Asp Leu Phe Val Thr Ser Lys Leu Trp Val Thr Glu Asn His Pro
                85                  90                  95

His Leu Val Val Pro Ala Leu Arg Lys Ser Leu Glu Thr Leu Gln Leu
            100                 105                 110

Glu Tyr Leu Asp Leu Tyr Leu Ile His Trp Pro Leu Ser Ser Gln Pro
        115                 120                 125

Gly Lys Phe Ser Phe Pro Ile Gln Ala Glu Asp Leu Leu Pro Phe Asp
    130                 135                 140

Val Lys Gly Val Trp Glu Ser Met Glu Ser Leu Lys Leu Gly Leu
145                 150                 155                 160

Thr Lys Ala Ile Gly Val Ser Asn Phe Ser Val Lys Lys Leu Gln Asn
                165                 170                 175

Leu Leu Ser Val Ala Thr Ile Arg Pro Ala Val Asn Gln Val Glu Met
            180                 185                 190

Asn Leu Ala Trp Gln Gln Lys Lys Leu Arg Glu Phe Cys Asn Ala Asn
        195                 200                 205

Gly Ile Val Leu Thr Ala Phe Ser Pro Leu Arg Lys Gly Ala Ser Arg
    210                 215                 220

Gly Pro Asn Glu Val Met Glu Asn Asp Met Leu Lys Gly Ile Ala Glu
225                 230                 235                 240

Ala His Gly Lys Ser Ile Ala Gln Val Ser Leu Arg Trp Leu Tyr Glu
                245                 250                 255

Gln Gly Val Thr Phe Val Ala Lys Ser Tyr Asp Lys Glu Arg Met Asn
            260                 265                 270

Gln Asn Leu Gln Ile Phe Asp Trp Glu Leu Thr Thr Glu Asp His Gln
        275                 280                 285

Lys Ile Asp Gln Ile Lys Gln Asn Arg Leu Ile Pro Gly Pro Thr Lys
    290                 295                 300

Pro Gln Leu Asn Asp Leu Trp Asp Asp Glu Ile
305                 310                 315

<210> SEQ ID NO 77
<211> LENGTH: 1133
<212> TYPE: DNA
<213> ORGANISM: Arabidopsis thaliana
<220> FEATURE:
<221> NAME/KEY: MISC_FEATURE
<223> OTHER INFORMATION: clone125039_inplanta_experimental_L24

<400> SEQUENCE: 77 aagttttga tttcagagtc caccgttgag cctgttcaat taaatcgttg aatctcgcgg    60
tgcgttttac tttgattctt tcgaattttt tttatatgga tgttccgcg atggcgagat    120 gtgtgggaag gtgctacgtt tcgccggcgt tcggtgagtc tgaatcgcac cggttatcgg    180
agcggcggtt tctgaaattg tctagctcca cgaattcgga tcccgccggt agtaaaagtt    240
tgaagcttcg cgggaaaatt catcggagaa tgagctactt ccgtccgatc atggcaaaag    300
atgaatccat tcatcgcgg tccggtgaaa cgaagcaaat caatggaaag caaaagaaca    360
ttgtctggca tgattgtccc gttactaaat ccgacaggca agaattaatt aagcataagg    420
gatgtgtgat ttggattact ggcttaagtg gttcaggtaa agtagtctg gcatgtgctc    480 ttagtcgagc tttgcacaat cgtggaaagc tttcgtatat acttgatggt gacaatgttc    540
gacatggttt aaacagcgat cttagtttcg aagcagatga tcgagctgaa acattcgaa    600 gagttggtga agtggctaaa ctgtttgcag attctgtat tatctgtatt gcaagtttaa    660
tatctcctta ccggatagaa cgagctgcct gccgtgcatt attaccacaa ggagatttca    720
ttgaggtatt tatggatgtg ccactccatg tttgtgaagc tagagatcca aagggcttat    780
acaaacgtgc acgcgctggt aaaatcaaag gttttacagg agtagatgat ccatatgaag    840
cgcctttgga ttgcgagatt gtaatacaaa acagtagaga caagggcctt tcttcttcat    900
cttcatcttc atcttcacct tcatcttcgt cttcttctct gtgtgaaatg gcagatattg    960
ttgtgtcgta cttggaccaa aatggatacc tgaagaaaca ctccacaaaa tcacgtgatt    1020

```
gtatgtaaat gtaatattaa tatcattgtt gtaacgtttc ttaaacctat tttacctatg    1080
gacgattaaa ttgtgaaaac ataaatgtaa ttcacaatct gcaaagagtt ggc           1133
```

<210> SEQ ID NO 78
<211> LENGTH: 310
<212> TYPE: PRT
<213> ORGANISM: Arabidopsis thaliana
<220> FEATURE:
<221> NAME/KEY: MISC_FEATURE
<223> OTHER INFORMATION: peptide_clone125039_inplanta_experimental_L24

<400> SEQUENCE: 78

```
Met Asp Val Ala Ala Met Ala Arg Cys Val Gly Arg Cys Tyr Val Ser
1               5                   10                  15

Pro Ala Phe Gly Glu Ser Glu Ser His Arg Leu Ser Glu Arg Arg Phe
            20                  25                  30

Leu Lys Leu Ser Ser Ser Thr Asn Ser Asp Pro Ala Gly Ser Lys Ser
        35                  40                  45

Leu Lys Leu Arg Gly Lys Ile His Arg Arg Met Ser Tyr Phe Arg Pro
    50                  55                  60

Ile Met Ala Lys Asp Glu Ser Ile Ser Ser Arg Ser Gly Glu Thr Lys
65                  70                  75                  80

Gln Ile Asn Gly Lys Gln Lys Asn Ile Val Trp His Asp Cys Pro Val
                85                  90                  95

Thr Lys Ser Asp Arg Gln Glu Leu Ile Lys His Lys Gly Cys Val Ile
            100                 105                 110

Trp Ile Thr Gly Leu Ser Gly Ser Gly Lys Ser Ser Leu Ala Cys Ala
        115                 120                 125

Leu Ser Arg Ala Leu His Asn Arg Gly Lys Leu Ser Tyr Ile Leu Asp
    130                 135                 140

Gly Asp Asn Val Arg His Gly Leu Asn Ser Asp Leu Ser Phe Glu Ala
145                 150                 155                 160

Asp Asp Arg Ala Glu Asn Ile Arg Arg Val Gly Glu Val Ala Lys Leu
                165                 170                 175

Phe Ala Asp Ser Gly Ile Ile Cys Ile Ala Ser Leu Ile Ser Pro Tyr
            180                 185                 190

Arg Ile Glu Arg Ala Ala Cys Arg Ala Leu Leu Pro Gln Gly Asp Phe
        195                 200                 205

Ile Glu Val Phe Met Asp Val Pro Leu His Val Cys Glu Ala Arg Asp
    210                 215                 220

Pro Lys Gly Leu Tyr Lys Arg Ala Arg Ala Gly Lys Ile Lys Gly Phe
225                 230                 235                 240

Thr Gly Val Asp Asp Pro Tyr Glu Ala Pro Leu Asp Cys Glu Ile Val
                245                 250                 255

Ile Gln Asn Ser Arg Asp Lys Gly Leu Ser Ser Ser Ser Ser Ser Ser
            260                 265                 270

Ser Ser Pro Ser Ser Ser Ser Leu Cys Glu Met Ala Asp Ile
        275                 280                 285

Val Val Ser Tyr Leu Asp Gln Asn Gly Tyr Leu Lys Lys His Ser Thr
    290                 295                 300

Lys Ser Arg Asp Cys Met
305                 310
```

<210> SEQ ID NO 79
<211> LENGTH: 271
<212> TYPE: PRT

<213> ORGANISM: Enteromorpha intestinalis
<220> FEATURE:
<221> NAME/KEY: MISC_FEATURE
<223> OTHER INFORMATION: gi[33]29471

<400> SEQUENCE: 79

Met Leu Arg Ala Ile Ala Gln Arg Ala Arg Gly Ser Ala Leu Gln Cys
1               5                   10                  15

Ala Ala Pro Gly Thr Glu Trp Ala Ser Cys Val Arg Gly Ser Ser Gly
            20                  25                  30

Phe Thr Ala Tyr Asp Val Gly Glu Ser Thr Asn Ile Lys Trp His Glu
        35                  40                  45

Thr Met Val Ser Arg Gly Asp Lys Glu Arg Leu Leu Asn Gln Arg Gly
    50                  55                  60

Cys Val Leu Trp Phe Thr Gly Leu Ser Gly Ser Gly Lys Ser Thr Val
65                  70                  75                  80

Ala Cys Thr Leu Glu His Ala Leu Asn Ala Arg Gly Lys Met Thr Ala
                85                  90                  95

Leu Leu Asp Gly Asp Asn Val Arg His Gly Leu Asn Ser Asn Leu Thr
            100                 105                 110

Phe Thr Ala Glu Asp Arg Thr Glu His Pro His Arg Arg Ser Glu
        115                 120                 125

Gln Ala Leu Cys Arg Arg Trp Arg Pro Pro Leu Arg Glu Leu His Leu
    130                 135                 140

Arg Pro Ile Ala Pro Thr Arg Pro Val Arg Glu Arg Cys Ala Gly Asp
145                 150                 155                 160

Phe Val Glu Cys Tyr Met Lys Ile Pro Ile Glu Leu Cys Glu Gln Arg
                165                 170                 175

Asp Pro Lys Gly Leu Tyr Lys Lys Ala Arg Ala Gly Leu Met Lys Gly
            180                 185                 190

Phe Thr Gly Ile Asp Asp Pro Tyr Glu Glu Pro Leu Glu Pro Glu Leu
        195                 200                 205

Thr Ile Thr Val Arg Glu Glu Gly Ser Asp Met Asn Ser Pro Glu Ala
    210                 215                 220

Met Ala Lys Gln Ile Phe Asp Tyr Leu Glu Ala Lys Gly Phe Leu Lys
225                 230                 235                 240

Gly Pro Ala Val Ala Ser Ser Gly Gly Ser Cys Ala Arg Val Ala Arg
                245                 250                 255

Trp Gly Gly His Gly Arg Arg Gly Arg Gln Arg Leu Ala Trp
            260                 265                 270

<210> SEQ ID NO 80
<211> LENGTH: 290
<212> TYPE: PRT
<213> ORGANISM: Arabidopsis thaliana
<220> FEATURE:
<221> NAME/KEY: MISC_FEATURE
<223> OTHER INFORMATION: gi[97]57873

<400> SEQUENCE: 80

Met Ala Arg Cys Val Gly Arg Cys Tyr Val Ser Pro Ala Phe Gly Glu
1               5                   10                  15

Ser Glu Ser His Arg Leu Ser Glu Arg Phe Leu Lys Leu Ser Ser
            20                  25                  30

Ser Thr Asn Ser Asp Pro Ala Gly Ser Lys Ser Leu Lys Leu Arg Gly
            35                  40                  45

Lys Ile His Arg Arg Met Ser Tyr Phe Arg Pro Ile Met Ala Lys Asp

```
            50                  55                  60
Glu Ser Ile Ser Ser Arg Ser Gly Glu Thr Lys Gln Ile Asn Gly Lys
 65                  70                  75                  80

Gln Lys Asn Ile Val Trp His Asp Cys Pro Val Thr Lys Ser Asp Arg
                 85                  90                  95

Gln Glu Leu Ile Lys Gln Lys Gly Cys Val Ile Trp Ile Thr Gly Leu
            100                 105                 110

Ser Gly Ser Gly Lys Ser Ser Leu Ala Cys Ala Leu Ser Arg Ala Leu
            115                 120                 125

His Asn Arg Gly Lys Leu Ser Tyr Ile Leu Asp Gly Asp Asn Val Arg
            130                 135                 140

His Gly Leu Asn Ser Asp Leu Ser Phe Glu Ala Asp Arg Ala Glu
145                 150                 155                 160

Asn Ile Arg Arg Val Gly Glu Val Ala Lys Leu Phe Ala Asp Ser Gly
                165                 170                 175

Ile Ile Cys Ile Ala Ser Leu Ile Ser Pro Tyr Arg Ile Glu Arg Ala
            180                 185                 190

Ala Cys Arg Ala Leu Leu Pro Gln Gly Asp Phe Ile Glu Val Phe Met
            195                 200                 205

Asp Val Pro Leu His Val Cys Glu Ala Arg Asp Pro Lys Gly Leu Tyr
210                 215                 220

Lys Arg Ala Arg Ala Gly Lys Ile Lys Gly Phe Thr Gly Val Asp Asp
225                 230                 235                 240

Pro Tyr Glu Ala Pro Leu Asp Cys Glu Val His Ile Ile Ser Asn Phe
                245                 250                 255

Ser Ser Ser Ser Ser Leu Cys Glu Met Ala Asp Ile Val Val Ser Tyr
            260                 265                 270

Leu Asp Gln Asn Gly Tyr Leu Lys Lys His Ser Thr Lys Ser Arg Asn
            275                 280                 285

Cys Met
    290

<210> SEQ ID NO 81
<211> LENGTH: 312
<212> TYPE: PRT
<213> ORGANISM: Catharanthus roseus
<220> FEATURE:
<221> NAME/KEY: MISC_FEATURE
<223> OTHER INFORMATION: gi[28]32300

<400> SEQUENCE: 81

Met Ile Gly Ser Val Lys Arg Pro Val Val Ser Cys Val Leu Pro Glu
  1               5                  10                  15

Phe Asp Phe Thr Glu Ser Thr Gly Leu Gly Lys Lys Ser Ser Val
                 20                  25                  30

Lys Leu Pro Val Asn Phe Gly Ala Phe Gly Ser Gly Gly Glu Val
             35                  40                  45

Lys Leu Gly Phe Leu Ala Pro Ile Lys Ala Thr Glu Gly Ser Lys Thr
            50                  55                  60

Ser Ser Phe Gln Val Asn Gly Lys Val Asp Asn Phe Arg His Leu Gln
 65                  70                  75                  80

Pro Ser Asp Cys Asn Ser Asn Ser Asp Ser Ser Leu Asn Asn Cys Asn
                 85                  90                  95

Gly Phe Pro Gly Lys Lys Ile Leu Gln Thr Thr Val Gly Asn Ser
            100                 105                 110
```

```
Thr Asn Ile Leu Trp His Lys Cys Ala Val Glu Lys Ser Glu Arg Gln
            115                 120                 125

Glu Pro Leu Gln Gln Arg Gly Cys Val Ile Trp Ile Thr Gly Leu Ser
        130                 135                 140

Gly Ser Gly Lys Ser Thr Leu Ala Cys Ala Leu Ser Arg Gly Leu His
145                 150                 155                 160

Ala Lys Gly Lys Leu Thr Tyr Ile Leu Asp Gly Asp Asn Val Arg His
                165                 170                 175

Gly Leu Asn Ser Asp Leu Ser Phe Lys Ala Glu Asp Arg Ala Glu Asn
            180                 185                 190

Ile Arg Arg Ile Gly Glu Val Ala Lys Leu Phe Ala Asp Ala Gly Val
        195                 200                 205

Ile Cys Ile Ala Ser Leu Ile Ser Pro Tyr Arg Lys Pro Pro Asp Ala
    210                 215                 220

Cys Arg Ser Leu Leu Pro Glu Gly Asp Phe Ile Glu Val Phe Met Asp
225                 230                 235                 240

Val Pro Leu Lys Val Cys Glu Ala Arg Asp Pro Lys Gly Leu Tyr Lys
                245                 250                 255

Leu Ala Arg Ala Gly Lys Ile Lys Gly Phe Thr Gly Ile Asp Asp Pro
            260                 265                 270

Tyr Glu Pro Pro Leu Lys Ser Glu Ile Val Leu His Gln Lys Leu Gly
        275                 280                 285

Met Cys Asp Ser Pro Cys Asp Leu Ala Asp Ile Val Ile Ser Tyr Leu
    290                 295                 300

Glu Glu Asn Gly Tyr Leu Lys Ala
305                 310

<210> SEQ ID NO 82
<211> LENGTH: 275
<212> TYPE: PRT
<213> ORGANISM: Zea mays
<220> FEATURE:
<221> NAME/KEY: MISC_FEATURE
<223> OTHER INFORMATION: CeresClone:300011

<400> SEQUENCE: 82

Met Leu Ala Arg Ala Pro Pro Arg Pro Cys Ser Ser Gly Val Cys
1               5                   10                  15

Ile Ala Arg Ala His Pro Arg Ala Ala Ala Val Ala Ala Arg Pro Gly
                20                  25                  30

Thr Thr Arg Thr Thr Thr Thr Val Ala Ala Ala Ala Glu Ala Ala
            35                  40                  45

Ser Asn Gly Ser Ala Ala Ala Val Ala Gly Ile Ser Ser Ser Ser
    50                  55                  60

Ser Ala Leu Val Thr Ser Thr Val Gly Lys Ser Thr Asn Ile Leu Trp
65                  70                  75                  80

His Glu Cys Ala Ile Gly Gln Lys Glu Arg Gln Gly Leu Leu Asn Gln
                85                  90                  95

Lys Gly Cys Val Val Trp Ile Thr Gly Leu Ser Gly Ser Gly Lys Ser
            100                 105                 110

Thr Leu Ala Cys Ala Leu Ser Arg Glu Leu His Gly Arg Gly His Leu
        115                 120                 125

Thr Tyr Val Leu Asp Gly Asp Asn Leu Arg His Gly Leu Asn Arg Asp
    130                 135                 140

Leu Ser Phe Gly Ala Glu Asp Arg Ala Glu Asn Ile Arg Arg Val Gly
145                 150                 155                 160
```

Glu Val Ala Lys Leu Phe Ala Asp Ala Gly Leu Val Cys Ile Ala Ser
            165                 170                 175

Leu Ile Ser Pro Tyr Arg Ser Asp Arg Ser Ala Cys Arg Asp Leu Leu
            180                 185                 190

Pro Lys His Ser Phe Ile Glu Val Phe Leu Asp Val Pro Leu Gln Val
            195                 200                 205

Cys Glu Ala Arg Asp Pro Lys Gly Leu Tyr Lys Leu Ala Arg Ala Gly
210                 215                 220

Lys Ile Lys Gly Phe Thr Gly Ile Asp Asp Pro Tyr Glu Pro Pro Ser
225                 230                 235                 240

Asp Cys Glu Ile Val Ile Gln Cys Lys Val Gly Asp Cys Pro Ser Pro
            245                 250                 255

Glu Ser Met Ala Gly His Val Val Ser Tyr Leu Glu Thr Asn Gly Phe
            260                 265                 270

Leu Gln Asp
            275

<210> SEQ ID NO 83
<211> LENGTH: 345
<212> TYPE: PRT
<213> ORGANISM: Oryza sativa subsp. japonica
<220> FEATURE:
<221> NAME/KEY: MISC_FEATURE
<223> OTHER INFORMATION: gi[50]938537

<400> SEQUENCE: 83

Met Glu Ala Ser Leu Pro Phe His His His Pro Ala Ala Ser Ser
1               5                   10                  15

Thr Ala Ala His His Ala Ala Arg Leu Thr Pro Pro Pro Pro Arg
            20                  25                  30

Asp Pro Arg Ala Thr Ala Arg Trp Val Pro Ala Ala Ala Pro Val
            35                  40                  45

Arg Ser Arg Ser Pro Ala Asn Leu Gly Leu Pro His Pro Pro Arg
50                  55                  60

Arg Leu Arg Leu Arg Leu Ala Pro Pro Arg Ile Thr Ala Ala Val Thr
65                  70                  75                  80

Gly Gly Pro Arg Arg Pro Arg Arg Ala Pro Pro Leu Glu Cys
            85                  90                  95

Ala Gly Gly Ser Ser Ser Ser Leu Arg Arg Pro Arg Glu Glu Glu
            100                 105                 110

Glu Glu Glu Glu Glu Glu Arg Ser Ser Thr Ala His Ala Gly Val Ser
            115                 120                 125

Leu Val Gly Glu Asn Lys Val Leu Gln Met Ser Ser Ile Val Pro Lys
130                 135                 140

Ala Ser Asn Ile Phe Trp His Asp Cys Ala Val Gly Gln Ala Asp Arg
145                 150                 155                 160

Gln Lys Leu Leu Lys Gln Lys Gly Cys Val Val Trp Ile Thr Gly Leu
            165                 170                 175

Ser Gly Ser Gly Lys Ser Thr Leu Ala Cys Thr Leu Asp Arg Glu Leu
            180                 185                 190

His Thr Arg Gly Lys Leu Ser Tyr Val Leu Asp Gly Asp Asn Leu Arg
            195                 200                 205

His Gly Leu Asn Lys Asp Leu Gly Phe Lys Ala Glu Asp Arg Ala Glu
            210                 215                 220

Asn Ile Arg Arg Val Gly Glu Val Ala Lys Leu Phe Ala Asp Ala Gly

```
                    225                 230                 235                 240

Leu Val Cys Ile Ala Ser Phe Ile Ser Pro Tyr Arg Arg Asp Arg Glu
                245                 250                 255

Ser Cys Arg Ala Leu Leu Ser Asp Gly Ser Phe Ile Glu Val Phe Leu
                260                 265                 270

Asn Met Pro Leu Glu Leu Cys Glu Ser Arg Asp Pro Lys Gly Leu Tyr
                275                 280                 285

Lys Leu Ala Arg Ala Gly Lys Ile Lys Gly Phe Thr Gly Ile Asp Asp
                290                 295                 300

Pro Tyr Glu Ser Pro Leu Asn Ser Glu Ile Glu Ile Lys Glu Val Asp
305                 310                 315                 320

Gly Val Cys Pro Ser Pro Ser Asp Met Ala Gly Gln Val Val Thr Tyr
                325                 330                 335

Leu Glu Glu Lys Gly Phe Leu His Asp
                340                 345

<210> SEQ ID NO 84
<211> LENGTH: 497
<212> TYPE: DNA
<213> ORGANISM: Arabidopsis thaliana
<220> FEATURE:
<221> NAME/KEY: MISC_FEATURE
<223> OTHER INFORMATION: 10044_13489782_L33

<400> SEQUENCE: 84
aagaactcac ctaacacaca aacaaaggaa cttcactttt ttttcccaca ccacatcaca     60
ccatgtttag agccatgagc acaaggaaag tccatggtgg ctacgaaaag ctcggcgatg    120
aagaagcgag actgaagagg gtctctagcg ttccggctag tgtttatggt cattcaagaa    180
acccggttca agaagtgaag aagacaccga cagcgaaacc aaccggtggt tctgttcatc    240
ctttgtttag tttctttgac gttcattttc aaagaaagaa gaagaagacg acgaagaaga    300
agagtttagc aacggcgaaa ccagagtttg ctaggtatat ggagtatgtg agagaaggag    360
gtgtatggga tccgagttct aacgcaccag tgattcatta cagatagatt cgtcaaggaa    420
aatgaataaa agatttgtat atcgtctttt ttttcaaata tataatctat gagaaagcca    480
aacaatcctt gattcgg                                                   497

<210> SEQ ID NO 85
<211> LENGTH: 114
<212> TYPE: PRT
<213> ORGANISM: Arabidopsis thaliana
<220> FEATURE:
<221> NAME/KEY: MISC_FEATURE
<223> OTHER INFORMATION: peptide_10044_13489782_L33

<400> SEQUENCE: 85

Met Phe Arg Ala Met Ser Thr Arg Lys Val His Gly Gly Tyr Glu Lys
1               5                   10                  15

Leu Gly Asp Glu Glu Ala Arg Leu Lys Arg Val Ser Ser Val Pro Ala
                20                  25                  30

Ser Val Tyr Gly His Ser Arg Asn Pro Val Gln Glu Val Lys Lys Thr
            35                  40                  45

Pro Thr Ala Lys Pro Thr Gly Gly Ser Val His Pro Leu Phe Ser Phe
        50                  55                  60

Phe Asp Val His Phe Gln Arg Lys Lys Lys Thr Thr Lys Lys Lys
65                  70                  75                  80

Ser Leu Ala Thr Ala Lys Pro Glu Phe Ala Arg Tyr Met Glu Tyr Val
```

85                  90                  95

Arg Glu Gly Gly Val Trp Asp Pro Ser Ser Asn Ala Pro Val Ile His
                100                 105                 110

Tyr Arg

<210> SEQ ID NO 86
<211> LENGTH: 114
<212> TYPE: PRT
<213> ORGANISM: Arabidopsis thaliana
<220> FEATURE:
<221> NAME/KEY: MISC_FEATURE
<223> OTHER INFORMATION: gi[48]35241

<400> SEQUENCE: 86

Met Phe Arg Ala Met Ser Thr Arg Lys Ile His Gly Gly Tyr Glu Lys
1               5                   10                  15

Leu Gly Asp Glu Glu Ala Arg Leu Lys Arg Val Ser Ser Val Pro Ala
                20                  25                  30

Ser Val Tyr Gly His Ser Arg Asn Pro Val Gln Glu Val Lys Lys Thr
            35                  40                  45

Pro Thr Ala Lys Pro Thr Gly Gly Ser Val His Pro Leu Phe Ser Phe
        50                  55                  60

Phe Asp Val His Phe Gln Arg Lys Lys Asn Thr Ala Lys Lys Lys
65                  70                  75                  80

Ser Leu Ala Thr Ala Lys Pro Glu Phe Ala Arg Tyr Met Glu Tyr Val
                85                  90                  95

Arg Glu Gly Gly Val Trp Asp Pro Ser Ser Asn Ala Pro Val Ile His
                100                 105                 110

Tyr Arg

<210> SEQ ID NO 87
<211> LENGTH: 113
<212> TYPE: PRT
<213> ORGANISM: Brassica napus
<220> FEATURE:
<221> NAME/KEY: MISC_FEATURE
<223> OTHER INFORMATION: CeresClone:1068483

<400> SEQUENCE: 87

Met Phe Arg Ala Met Ser Thr Arg Lys Val His Gly Gly Tyr Glu Lys
1               5                   10                  15

Leu Val Glu Asp Glu Pro Lys Leu Lys Arg Val Thr Ser Val Pro Ala
                20                  25                  30

Ser Val Tyr Gly Asn Ser Arg Asn Pro Val Gln Glu Val Lys Lys
            35                  40                  45

Thr Pro Thr Val Lys Pro Thr Gly Gly Ser Val His Pro Leu Leu Ser
        50                  55                  60

Phe Phe Asp Val Arg Phe Gln Lys Lys Lys Lys Thr Lys Lys Ser
65                  70                  75                  80

Leu Ala Thr Ala Lys Pro Glu Phe Ala Arg Tyr Met Ala Tyr Val Lys
                85                  90                  95

Glu Gly Gly Val Trp Asp Pro Asn Ser Asn Ala Pro Val Ile His Tyr
                100                 105                 110

Arg

<210> SEQ ID NO 88
<211> LENGTH: 118
<212> TYPE: PRT

<213> ORGANISM: Glycine max
<220> FEATURE:
<221> NAME/KEY: MISC_FEATURE
<223> OTHER INFORMATION: CeresClone:584111

<400> SEQUENCE: 88

```
Met Phe Arg Ser Met Thr Thr Arg Arg Gly Tyr Glu Arg Leu Gly Lys
1               5                   10                  15

Glu Ser Ala Thr Thr Ala Leu Leu His Glu Gly Phe Lys Arg Ser Thr
            20                  25                  30

Ser Leu Pro Ser Trp Gly Ser Asn Ser Arg Lys Met Ala Leu Gly
        35                  40                  45

Ser Thr Tyr Gly Glu Ile Asn Leu Lys Arg Asn Pro Thr Lys Lys Gly
    50                  55                  60

Asn Asn Asn Ser Asp Lys Lys Ser His Pro Leu Leu Ser Phe Leu Ala
65                  70                  75                  80

Leu Arg Arg Lys Lys Lys Thr Thr Ala Arg Pro Glu Phe Ala Arg Tyr
                85                  90                  95

Leu Glu Tyr Leu Lys Glu Gly Gly Met Trp Asp Phe Asn Ser Asn Lys
            100                 105                 110

Pro Val Met Tyr Tyr Glu
        115
```

<210> SEQ ID NO 89
<211> LENGTH: 913
<212> TYPE: DNA
<213> ORGANISM: Arabidopsis thaliana
<220> FEATURE:
<221> NAME/KEY: MISC_FEATURE
<223> OTHER INFORMATION: 10987_3769_L34

<400> SEQUENCE: 89

```
aaaaatctgg aacggataaa ataatttgct cggcttcctc agctccaatg gcggcgacga        60
tgatcggaat taacctctcc tgcttcaaat caacatcgtt cttctcaccg gacctcaatt       120
ctctccaatc aaagctctct ctcctatctc tcaaaccctc tccaacacag ccacggaaat       180
caacagtcat ccgtatgggc ggtggtccga gaactttccc cggcggtgta tcaaaatggc       240
aatggaaaag gatgcaagcg aagaaacaga acagcttct caaagcaagg ttatgcagag        300
aacgtcagat ctacgagatg cgaaaacgcg ccgagctaaa agcggcggtg gctgagctag       360
aacgaccatg ggaaccgatt cataaaccac cgaatctatt ctcagtttgt gctgatgagc       420
aagttaaagt actcgcggat cggtttcaga aacctggtgg atttgattta tggactgata       480
gagatggtcc tcaattgttt gagagtgttg atgatttgcc ttctgctagg ttttttccta       540
aaggtgttgt tcatagtgtt aaaccttatg gtagattatc atctagctct gttgttgatg       600
atggtgatga gagtgaggtt aaagatgaag aaattgggaa gaagttacgt ggtcgtaggg       660
tgaggaagag aggtgatgat ggaggtaaga ggaggactga aaatcgtggt aatggtggga       720
gattgagaaa tggagggtct tcttcttctc aggtgtatga tatgactttg cagaatgatg       780
ggagatatga aattggatct taggtatgag ttcttctttg ttgtgtttgg atcattgatg       840
tctctgaaca taatttgtat gtaatctgga atagtttgat tgtgattatg caagttttca       900
gttttaggga agc                                                          913
```

<210> SEQ ID NO 90
<211> LENGTH: 251
<212> TYPE: PRT
<213> ORGANISM: Arabidopsis thaliana
<220> FEATURE:
<221> NAME/KEY: MISC_FEATURE
<223> OTHER INFORMATION: peptide_10987_3769_L34

<400> SEQUENCE: 90

```
Met Ala Ala Thr Met Ile Gly Ile Asn Leu Ser Cys Phe Lys Ser Thr
1               5                   10                  15

Ser Phe Phe Ser Pro Asp Leu Asn Ser Leu Gln Ser Lys Leu Ser Leu
            20                  25                  30

Leu Ser Leu Lys Pro Ser Pro Thr Gln Pro Arg Lys Ser Thr Val Ile
        35                  40                  45

Arg Met Gly Gly Gly Pro Arg Thr Phe Pro Gly Val Ser Lys Trp
50                  55                  60

Gln Trp Lys Arg Met Gln Ala Lys Lys Gln Lys Gln Leu Leu Lys Ala
65                  70                  75                  80

Arg Leu Cys Arg Glu Arg Gln Ile Tyr Glu Met Arg Lys Arg Ala Glu
                85                  90                  95

Leu Lys Ala Ala Val Ala Glu Leu Glu Arg Pro Trp Glu Pro Ile His
            100                 105                 110

Lys Pro Pro Asn Leu Phe Ser Val Cys Ala Asp Glu Gln Val Lys Val
        115                 120                 125

Leu Ala Asp Arg Phe Gln Lys Pro Gly Gly Phe Asp Leu Trp Thr Asp
130                 135                 140

Arg Asp Gly Pro Gln Leu Phe Glu Ser Val Asp Asp Leu Pro Ser Ala
145                 150                 155                 160

Arg Phe Phe Pro Lys Gly Val Val His Ser Val Lys Pro Tyr Gly Arg
                165                 170                 175

Leu Ser Ser Ser Val Val Asp Asp Gly Asp Glu Ser Glu Val Lys
            180                 185                 190

Asp Glu Glu Ile Gly Lys Lys Leu Arg Gly Arg Val Arg Lys Arg
        195                 200                 205

Gly Asp Asp Gly Gly Lys Arg Arg Thr Glu Asn Arg Gly Asn Gly Gly
    210                 215                 220

Arg Leu Arg Asn Gly Gly Ser Ser Ser Ser Gln Val Tyr Asp Met Thr
225                 230                 235                 240

Leu Gln Asn Asp Gly Arg Tyr Glu Ile Gly Ser
                245                 250
```

<210> SEQ ID NO 91
<211> LENGTH: 1252
<212> TYPE: DNA
<213> ORGANISM: Arabidopsis thaliana
<220> FEATURE:
<221> NAME/KEY: MISC_FEATURE
<223> OTHER INFORMATION: cdna13500101_clone17206_L35

<400> SEQUENCE: 91

```
atcattcgtg tactaatttt accttcatag acttaattaa gatacgatca tggcgtcgtt      60
tgtctttgtg atttctcttc ttcttctctc tttttcgtcg gctgttttct ccgatgatgc     120
ttcttttcag aaacttccgg tgcctgacaa gaggtcaggc cctgaatctt cgcctttga     180 ctctaccggc ggattctaca ccggagtctc cggtggtaaa atcctcaagt acgttcctgg     240
gaagggttat gtcgattttg cccagatcac agattcctcg aactcggcat ggtgcaacgg     300
agcattagga accgctttcg ccggaaagtg tggtcgacca gcgggaatag ccttaaacag     360
caaaacaggt gatctctatg tcgccgatgc tccgttgggt cttcacgtta tctctcccgc     420
```

```
aggaggtttg gccacaaagc tggccgacag tgttgacgga aagcctttca agtttcttga      480
cggtcttgat gttgatccca ccaccggcgt cgtctacttc acttccttca gttccaagtt      540
tggaccccgg gaagtgttaa tcgcagtggg attaaaagac gcgagcggaa agctgttcaa      600
atacgaccca gcgaccaaag ccgtgactga gttaatggaa ggtctaagtg gtgctgctgg      660
ttgtgcagtg agctcagatg gttcattcgt gctagttagc gagttcataa agagtaacat      720
caagaaatat tggattaaag ggcccaaagc tggaactatt gaagacttct caagtcttgt      780
ctcgaacccc gacaacatca ggagggtagg ttctaccgga aatttctggg tcgcctctgt      840
cgtgaacaag gttgttatgc ctaccgaccc tagggcggtc aaactagacg ctaatggaaa      900
agtgctccag accatttttcc tcaagaatga gtttgggaat actttgctta gtgaagtcaa      960
cgagttcaac ggccatcttt acatcggaac tcttactgga cctttcgccg gagtcatgaa     1020
actttaaatt ggtatcaact atatggttct ttggtgatta ccatttttga tatcattttg     1080
aaaggtctgt ttacagttat tttaaccata ataatatccc ctcaaatgtc ctgcttgtta     1140
cgtgggtgac acatttgttc ggtgattcct tgaataggct actactactt attgtttcat     1200
attttcgaag agattatctc tagttcttaa ggctttggtt ttctttgttt cc             1252
```

<210> SEQ ID NO 92
<211> LENGTH: 325
<212> TYPE: PRT
<213> ORGANISM: Arabidopsis thaliana
<220> FEATURE:
<221> NAME/KEY: MISC_FEATURE
<223> OTHER INFORMATION: peptide_cdna13500101_clone17206_L35

<400> SEQUENCE: 92

```
Met Ala Ser Phe Val Phe Val Ile Ser Leu Leu Leu Ser Phe Ser
1               5                   10                  15

Ser Ala Val Phe Ser Asp Asp Ala Ser Phe Gln Lys Leu Pro Val Pro
            20                  25                  30

Asp Lys Arg Ser Gly Pro Glu Ser Phe Ala Phe Asp Ser Thr Gly Gly
        35                  40                  45

Phe Tyr Thr Gly Val Ser Gly Gly Lys Ile Leu Lys Tyr Val Pro Gly
    50                  55                  60

Lys Gly Tyr Val Asp Phe Ala Gln Ile Thr Asp Ser Ser Asn Ser Ala
65                  70                  75                  80

Trp Cys Asn Gly Ala Leu Gly Thr Ala Phe Ala Gly Lys Cys Gly Arg
                85                  90                  95

Pro Ala Gly Ile Ala Leu Asn Ser Lys Thr Gly Asp Leu Tyr Val Ala
            100                 105                 110

Asp Ala Pro Leu Gly Leu His Val Ile Ser Pro Ala Gly Gly Leu Ala
        115                 120                 125

Thr Lys Leu Ala Asp Ser Val Asp Gly Lys Pro Phe Lys Phe Leu Asp
    130                 135                 140

Gly Leu Asp Val Asp Pro Thr Thr Gly Val Val Tyr Phe Thr Ser Phe
145                 150                 155                 160

Ser Ser Lys Phe Gly Pro Arg Glu Val Leu Ile Ala Val Gly Leu Lys
                165                 170                 175

Asp Ala Ser Gly Lys Leu Phe Lys Tyr Asp Pro Ala Thr Lys Ala Val
            180                 185                 190

Thr Glu Leu Met Glu Gly Leu Ser Gly Ala Ala Gly Cys Ala Val Ser
        195                 200                 205

Ser Asp Gly Ser Phe Val Leu Val Ser Glu Phe Ile Lys Ser Asn Ile
```

```
        210                 215                 220
Lys Lys Tyr Trp Ile Lys Gly Pro Lys Ala Gly Thr Ile Glu Asp Phe
225                 230                 235                 240

Ser Ser Leu Val Ser Asn Pro Asp Asn Ile Arg Arg Val Gly Ser Thr
                245                 250                 255

Gly Asn Phe Trp Val Ala Ser Val Val Asn Lys Val Val Met Pro Thr
                260                 265                 270

Asp Pro Arg Ala Val Lys Leu Asp Ala Asn Gly Lys Val Leu Gln Thr
                275                 280                 285

Ile Phe Leu Lys Asn Glu Phe Gly Asn Thr Leu Leu Ser Glu Val Asn
                290                 295                 300

Glu Phe Asn Gly His Leu Tyr Ile Gly Thr Leu Thr Gly Pro Phe Ala
305                 310                 315                 320

Gly Val Met Lys Leu
                325

<210> SEQ ID NO 93
<211> LENGTH: 335
<212> TYPE: PRT
<213> ORGANISM: Arabidopsis thaliana
<220> FEATURE:
<221> NAME/KEY: MISC_FEATURE
<223> OTHER INFORMATION: gi[17]104523

<400> SEQUENCE: 93

Met Thr Ser Phe Cys Ser Met Ile Ser Leu Leu Leu Leu Ser Leu
1               5                   10                  15

Ser Ser Ala Val Phe Ser Asp Asp Ala Ser Phe Gln Lys Leu Pro Val
                20                  25                  30

Pro Glu Thr Arg Ser Gly Pro Glu Ala Phe Ala Phe Asp Ser Thr Gly
                35                  40                  45

Lys Gly Phe Tyr Thr Gly Val Ser Gly Gly Lys Ile Leu Lys Tyr Leu
                50                  55                  60

Pro Glu Thr Gly Tyr Val Asp Phe Ala Gln Ile Thr Glu Ser Ser Asn
65                  70                  75                  80

Ser Ser Trp Cys Asp Gly Thr Ile Gly Thr Ala Leu Ala Gly Arg Cys
                85                  90                  95

Gly Arg Pro Ala Gly Ile Ala Phe Asn Glu Lys Thr Gly Asp Leu Tyr
                100                 105                 110

Val Ala Asp Ala Pro Leu Gly Leu His Val Ile Ser Pro Ala Gly Gly
                115                 120                 125

Leu Ala Thr Lys Ile Thr Asp Ser Val Asp Gly Lys Pro Phe Lys Phe
                130                 135                 140

Leu Asp Gly Leu Asp Val Asp Pro Thr Thr Gly Val Val Tyr Phe Thr
145                 150                 155                 160

Ser Phe Ser Ser Arg Phe Ser Pro Ile Gln Val Leu Ile Ala Leu Gly
                165                 170                 175

Leu Lys Asp Ala Thr Gly Lys Leu Tyr Lys Tyr Asp Pro Ser Thr Lys
                180                 185                 190

Val Val Thr Val Leu Met Glu Gly Leu Ser Gly Ser Ala Gly Cys Ala
                195                 200                 205

Val Ser Ser Asp Gly Ser Phe Val Leu Val Ser Gln Phe Thr Lys Ser
                210                 215                 220

Asn Ile Lys Arg Tyr Trp Ile Lys Gly Pro Lys Ala Gly Ser Ser Glu
225                 230                 235                 240
```

Asp Phe Thr Asn Ser Val Ser Asn Pro Asp Asn Ile Lys Arg Ile Gly
            245                 250                 255

Ser Thr Gly Asn Phe Trp Val Ala Ser Val Val Asn Lys Ile Ile Val
            260                 265                 270

Pro Thr Asn Pro Ser Ala Val Lys Val Asn Ser Asn Gly Glu Val Leu
            275                 280                 285

Gln Thr Ile Pro Leu Lys Asp Lys Phe Gly Asp Thr Leu Leu Ser Glu
            290                 295                 300

Val Asn Glu Phe Glu Gly Asn Leu Tyr Ile Thr Leu Thr Gly Pro
305                 310                 315                 320

Phe Ala Gly Ile Leu Lys Leu Glu Lys Gly Ser Cys Pro Ala Thr
            325                 330                 335

<210> SEQ ID NO 94
<211> LENGTH: 335
<212> TYPE: PRT
<213> ORGANISM: Arabidopsis thaliana
<220> FEATURE:
<221> NAME/KEY: MISC_FEATURE
<223> OTHER INFORMATION: gi[17]54985

<400> SEQUENCE: 94

Met Thr Ser Phe Cys Ser Met Ile Ser Leu Leu Leu Leu Ser Leu
1               5                   10                  15

Ser Ser Pro Val Phe Ser Asp Asp Ala Ser Phe Gln Lys Leu Pro Val
            20                  25                  30

Pro Glu Thr Arg Ser Gly Pro Glu Ala Phe Ala Phe Asp Ser Thr Gly
            35                  40                  45

Lys Gly Phe Tyr Thr Gly Val Ser Gly Gly Lys Ile Leu Lys Tyr Leu
50                  55                  60

Pro Glu Thr Gly Tyr Val Asp Phe Ala Gln Ile Thr Glu Ser Ser Asn
65                  70                  75                  80

Ser Ser Trp Cys Asp Gly Thr Ile Gly Thr Ala Leu Ala Gly Arg Cys
            85                  90                  95

Gly Arg Pro Ala Gly Ile Ala Phe Asn Glu Lys Thr Gly Asp Leu Tyr
            100                 105                 110

Val Ala Asp Ala Pro Leu Gly Leu His Val Ile Ser Pro Ala Gly Gly
            115                 120                 125

Leu Ala Thr Lys Ile Thr Asp Ser Val Asp Gly Lys Pro Phe Lys Phe
            130                 135                 140

Leu Asp Gly Leu Asp Val Asp Pro Thr Thr Gly Val Val Tyr Phe Thr
145                 150                 155                 160

Ser Phe Ser Ser Arg Phe Ser Pro Ile Gln Val Leu Ile Ala Leu Gly
            165                 170                 175

Leu Lys Asp Ala Thr Gly Lys Leu Tyr Lys Tyr Asp Pro Ser Thr Lys
            180                 185                 190

Val Val Thr Val Leu Met Glu Gly Leu Ser Gly Ser Ala Gly Cys Ala
            195                 200                 205

Val Ser Ser Asp Gly Ser Phe Val Leu Val Ser Gln Phe Thr Lys Ser
            210                 215                 220

Asn Ile Lys Arg Tyr Trp Ile Lys Gly Pro Lys Ala Gly Ser Ser Glu
225                 230                 235                 240

Asp Phe Thr Asn Ser Val Ser Asn Pro Asp Asn Ile Lys Arg Ile Gly
            245                 250                 255

Ser Thr Gly Asn Phe Trp Val Ala Ser Val Val Asn Lys Ile Ile Val
            260                 265                 270

```
Pro Thr Asn Pro Ser Ala Val Lys Val Asn Ser Asn Gly Glu Val Leu
            275                 280                 285

Gln Thr Ile Pro Leu Lys Asp Lys Phe Gly Asp Thr Leu Leu Ser Glu
            290                 295                 300

Val Asn Glu Phe Glu Gly Asn Leu Tyr Ile Gly Thr Leu Thr Gly Pro
305                 310                 315                 320

Phe Ala Gly Ile Leu Lys Ile Glu Lys Gly Ser Cys Pro Ala Thr
                325                 330                 335

<210> SEQ ID NO 95
<211> LENGTH: 338
<212> TYPE: PRT
<213> ORGANISM: Arabidopsis thaliana
<220> FEATURE:
<221> NAME/KEY: MISC_FEATURE
<223> OTHER INFORMATION: CeresClone:124660
<220> FEATURE:
<221> NAME/KEY: misc_feature
<222> LOCATION: (102)..(102)
<223> OTHER INFORMATION: Xaa can be any naturally occurring amino acid

<400> SEQUENCE: 95

Met Thr Ser Phe Cys Ser Met Ile Ser Leu Leu Leu Leu Leu Leu Leu
1               5                   10                  15

Leu Ser Leu Ser Ser Ala Val Ile Ser Asp Asp Ala Ser Phe Gln Lys
            20                  25                  30

Leu Pro Val Pro Glu Thr Arg Ser Gly Pro Glu Ala Phe Ala Phe Asp
            35                  40                  45

Ser Thr Gly Lys Gly Phe Tyr Thr Gly Val Ser Gly Lys Ile Leu
50                  55                  60

Lys Tyr Leu Pro Glu Thr Gly Tyr Val Asp Phe Ala Gln Ile Thr Glu
65                  70                  75                  80

Ser Ser Asn Ser Ser Trp Cys Asp Gly Thr Ile Gly Thr Ala Leu Ala
                85                  90                  95

Gly Arg Cys Gly Arg Xaa Ala Gly Ile Ala Phe Asn Glu Lys Thr Gly
            100                 105                 110

Asp Leu Tyr Val Ala Asp Ala Pro Leu Gly Leu His Val Ile Ser Pro
            115                 120                 125

Ala Gly Gly Leu Ala Thr Lys Ile Thr Asp Ser Val Asp Gly Lys Pro
            130                 135                 140

Phe Lys Phe Leu Asp Gly Leu Asp Val Asp Pro Thr Thr Gly Val Val
145                 150                 155                 160

Tyr Phe Thr Ser Phe Ser Ser Arg Phe Ser Pro Ile Gln Val Leu Ile
                165                 170                 175

Ala Leu Gly Leu Lys Asp Ala Thr Gly Lys Leu Tyr Lys Tyr Asp Pro
            180                 185                 190

Ser Thr Lys Val Val Thr Val Leu Met Glu Gly Leu Ser Gly Ser Ala
            195                 200                 205

Gly Cys Ala Val Ser Ser Asp Gly Ser Phe Val Leu Val Ser Gln Phe
            210                 215                 220

Thr Lys Ser Asn Ile Lys Arg Tyr Trp Ile Lys Gly Pro Lys Ala Gly
225                 230                 235                 240

Ser Ser Glu Asp Phe Thr Asn Ser Val Ser Asn Pro Asp Asn Ile Lys
                245                 250                 255

Arg Ile Gly Ser Thr Gly Asn Phe Trp Val Ala Ser Val Val Asn Lys
            260                 265                 270
```

```
Ile Ile Val Pro Thr Asn Pro Ser Ala Val Lys Val Asn Ser Asn Gly
            275                 280                 285

Glu Val Leu Gln Thr Ile Pro Leu Lys Asp Lys Phe Gly Asp Thr Leu
    290                 295                 300

Leu Ser Glu Val Asn Glu Phe Glu Gly Asn Leu Tyr Ile Gly Thr Leu
305                 310                 315                 320

Thr Gly Pro Phe Ala Gly Ile Leu Lys Leu Glu Lys Gly Ser Cys Pro
                325                 330                 335

Ala Thr

<210> SEQ ID NO 96
<211> LENGTH: 344
<212> TYPE: PRT
<213> ORGANISM: Rauvolfia serpentina
<220> FEATURE:
<221> NAME/KEY: MISC_FEATURE
<223> OTHER INFORMATION: gi[62]903513

<400> SEQUENCE: 96

Met Ala Lys Leu Ser Asp Ser Gln Thr Met Ala Leu Phe Thr Val Phe
1               5                   10                  15

Leu Leu Phe Leu Ser Ser Ser Leu Ala Leu Ser Ser Pro Ile Leu Lys
            20                  25                  30

Glu Ile Leu Ile Glu Ala Pro Ser Tyr Ala Pro Asn Ser Phe Thr Phe
        35                  40                  45

Asp Ser Thr Asn Lys Gly Phe Tyr Thr Ser Val Gln Asp Gly Arg Val
    50                  55                  60

Ile Lys Tyr Glu Gly Pro Asn Ser Gly Phe Val Asp Phe Ala Tyr Ala
65                  70                  75                  80

Ser Pro Tyr Trp Asn Lys Ala Phe Cys Glu Asn Ser Thr Asp Ala Glu
                85                  90                  95

Lys Arg Pro Leu Cys Gly Arg Thr Tyr Asp Ile Ser Tyr Asn Leu Gln
            100                 105                 110

Asn Asn Gln Leu Tyr Ile Val Asp Cys Tyr Tyr His Leu Ser Val Val
        115                 120                 125

Gly Ser Glu Gly Gly His Ala Thr Gln Leu Ala Thr Ser Val Asp Gly
    130                 135                 140

Val Pro Phe Lys Trp Leu Tyr Ala Val Thr Val Asp Gln Arg Thr Gly
145                 150                 155                 160

Ile Val Tyr Phe Thr Asp Val Ser Thr Leu Tyr Asp Asp Arg Gly Val
                165                 170                 175

Gln Gln Ile Met Asp Thr Ser Asp Lys Thr Gly Arg Leu Ile Lys Tyr
            180                 185                 190

Asp Pro Ser Thr Lys Glu Thr Thr Leu Leu Leu Lys Glu Leu His Val
        195                 200                 205

Pro Gly Gly Ala Glu Val Ser Ala Asp Ser Ser Phe Val Leu Val Ala
    210                 215                 220

Glu Phe Leu Ser His Gln Ile Val Lys Tyr Trp Leu Glu Gly Pro Lys
225                 230                 235                 240

Lys Gly Thr Ala Glu Val Leu Val Lys Ile Pro Asn Pro Gly Asn Ile
                245                 250                 255

Lys Arg Asn Ala Asp Gly His Phe Trp Val Ser Ser Ser Glu Glu Leu
            260                 265                 270

Asp Gly Asn Met His Gly Arg Val Asp Pro Lys Gly Ile Lys Phe Asp
        275                 280                 285
```

```
Glu Phe Gly Asn Ile Leu Glu Val Ile Pro Leu Pro Pro Pro Phe Ala
    290                 295                 300
Gly Glu His Phe Glu Gln Ile Gln Glu His Asp Gly Leu Leu Tyr Ile
305                 310                 315                 320
Gly Thr Leu Phe His Gly Ser Val Gly Ile Leu Val Tyr Asp Lys Lys
                325                 330                 335
Gly Asn Ser Phe Val Ser Ser His
            340
```

```
<210> SEQ ID NO 97
<211> LENGTH: 1150
<212> TYPE: DNA
<213> ORGANISM: Arabidopsis thaliana
<220> FEATURE:
<221> NAME/KEY: MISC_FEATURE
<223> OTHER INFORMATION: clone104691_L45

<400> SEQUENCE: 97
```

| | | | | |
|---|---|---|---|---|
| acgactacaa | agtacaagaa | agtctcattt | gagaataatt | gagcgataaa | gaaacggtat | 60 |
| gacgtcgttt | tgctccatga | tttctcttct | tcttcttctc | tctctttcat | cggcggtttt | 120 |
| ctccgatgac | gcttctttcc | agaaacttcc | ggtgccggaa | actaggtcag | gtcccgaagc | 180 |
| tttcgctttt | gattccaccg | gtaaagggtt | ctataccggt | gtctccggtg | gtaaaatcct | 240 |
| caagtacctc | cccgagacgg | gttatgttga | ctttgcccag | atcactgaat | cctcgaactc | 300 |
| ttcatggtgc | gatggtacta | ttggaacggc | tttagccgga | cgctgtggtc | gaccagcagg | 360 |
| aatagcattc | aacgagaaaa | caggtgatct | ttacgtcgcc | gatgctccgt | tgggtcttca | 420 |
| cgttatttct | cccgccggtg | gtttggctac | gaagatcacc | gacagtgttg | acggaaagcc | 480 |
| tttcaagtttt | cttgacggtc | ttgacgttga | tcccactact | ggtgtcgtct | acttcacttc | 540 |
| cttcagctca | cgcttctccc | caatccaagt | gttgattgca | ttggggttaa | aggacgcgac | 600 |
| cggaaagctc | tacaaatacg | acccatcgac | caaagtcgtg | actgtactga | tggaagggct | 660 |
| aagtggttca | gccgggtgtg | cagtgagctc | agatggttcg | tttgtgctgg | ttagtcagtt | 720 |
| cacaaaaagt | aacatcaaga | ggtattggat | caagggaccc | aaagctggtt | cttctgaaga | 780 |
| cttcaccaac | tcagtctcaa | accctgacaa | tatcaaaaga | attggctcta | ctggaaactt | 840 |
| ttgggtcgct | tcagtggtga | acaagatcat | cgtacctacg | aacccatcag | cagtcaaagt | 900 |
| taactctaat | ggtgaagttc | ttcaaacaat | tcctctcaaa | gataaatttg | gagacactct | 960 |
| gctcagcgaa | gtcaacgaat | tcgagggcaa | tttatatata | ggaactctca | ccggaccatt | 1020 |
| tgctggaatt | cttaagctcg | aaaagggttc | ttgtcctgcc | acttagatct | cttatttgaa | 1080 |
| tgcatccgat | gtgttacaat | aatatatata | tatgagcttt | ttatttattt | ctgaataaaa | 1140 |
| taaccactta | | | | | 1150 |

```
<210> SEQ ID NO 98
<211> LENGTH: 335
<212> TYPE: PRT
<213> ORGANISM: Arabidopsis thaliana
<220> FEATURE:
<221> NAME/KEY: MISC_FEATURE
<223> OTHER INFORMATION: peptide_clone104691_L45

<400> SEQUENCE: 98
```

```
Met Thr Ser Phe Cys Ser Met Ile Ser Leu Leu Leu Leu Ser Leu
1               5                   10                  15
Ser Ser Ala Val Phe Ser Asp Asp Ala Ser Phe Gln Lys Leu Pro Val
            20                  25                  30
```

-continued

```
Pro Glu Thr Arg Ser Gly Pro Glu Ala Phe Ala Phe Asp Ser Thr Gly
         35                  40                  45

Lys Gly Phe Tyr Thr Gly Val Ser Gly Gly Lys Ile Leu Lys Tyr Leu
     50                  55                  60

Pro Glu Thr Gly Tyr Val Asp Phe Ala Gln Ile Thr Glu Ser Ser Asn
 65                  70                  75                  80

Ser Ser Trp Cys Asp Gly Thr Ile Gly Thr Ala Leu Ala Gly Arg Cys
                 85                  90                  95

Gly Arg Pro Ala Gly Ile Ala Phe Asn Glu Lys Thr Gly Asp Leu Tyr
                100                 105                 110

Val Ala Asp Ala Pro Leu Gly Leu His Val Ile Ser Pro Ala Gly Gly
            115                 120                 125

Leu Ala Thr Lys Ile Thr Asp Ser Val Asp Gly Lys Pro Phe Lys Phe
        130                 135                 140

Leu Asp Gly Leu Asp Val Asp Pro Thr Thr Gly Val Val Tyr Phe Thr
145                 150                 155                 160

Ser Phe Ser Ser Arg Phe Ser Pro Ile Gln Val Leu Ile Ala Leu Gly
                165                 170                 175

Leu Lys Asp Ala Thr Gly Lys Leu Tyr Lys Tyr Asp Pro Ser Thr Lys
            180                 185                 190

Val Val Thr Val Leu Met Glu Gly Leu Ser Gly Ser Ala Gly Cys Ala
        195                 200                 205

Val Ser Ser Asp Gly Ser Phe Val Leu Val Ser Gln Phe Thr Lys Ser
    210                 215                 220

Asn Ile Lys Arg Tyr Trp Ile Lys Gly Pro Lys Ala Gly Ser Ser Glu
225                 230                 235                 240

Asp Phe Thr Asn Ser Val Ser Asn Pro Asp Asn Ile Lys Arg Ile Gly
                245                 250                 255

Ser Thr Gly Asn Phe Trp Val Ala Ser Val Val Asn Lys Ile Ile Val
            260                 265                 270

Pro Thr Asn Pro Ser Ala Val Lys Val Asn Ser Asn Gly Glu Val Leu
        275                 280                 285

Gln Thr Ile Pro Leu Lys Asp Lys Phe Gly Asp Thr Leu Leu Ser Glu
    290                 295                 300

Val Asn Glu Phe Glu Gly Asn Leu Tyr Ile Gly Thr Leu Thr Gly Pro
305                 310                 315                 320

Phe Ala Gly Ile Leu Lys Leu Glu Lys Gly Ser Cys Pro Ala Thr
                325                 330                 335
```

<210> SEQ ID NO 99
<211> LENGTH: 325
<212> TYPE: PRT
<213> ORGANISM: Arabidopsis thaliana
<220> FEATURE:
<221> NAME/KEY: MISC_FEATURE
<223> OTHER INFORMATION: CeresClone:17206

<400> SEQUENCE: 99

```
Met Ala Ser Phe Val Phe Val Ile Ser Leu Leu Leu Leu Ser Phe Ser
 1               5                  10                  15

Ser Ala Val Phe Ser Asp Asp Ala Ser Phe Gln Lys Leu Pro Val Pro
             20                  25                  30

Asp Lys Arg Ser Gly Pro Glu Ser Phe Ala Phe Asp Ser Thr Gly Gly
         35                  40                  45

Phe Tyr Thr Gly Val Ser Gly Gly Lys Ile Leu Lys Tyr Val Pro Gly
```

```
                    50                  55                  60
Lys Gly Tyr Val Asp Phe Ala Gln Ile Thr Asp Ser Ser Asn Ser Ala
 65                  70                  75                  80

Trp Cys Asn Gly Ala Leu Gly Thr Ala Phe Ala Gly Lys Cys Gly Arg
                 85                  90                  95

Pro Ala Gly Ile Ala Leu Asn Ser Lys Thr Gly Asp Leu Tyr Val Ala
            100                 105                 110

Asp Ala Pro Leu Gly Leu His Val Ile Ser Pro Ala Gly Gly Leu Ala
            115                 120                 125

Thr Lys Leu Ala Asp Ser Val Asp Gly Lys Pro Phe Lys Phe Leu Asp
            130                 135                 140

Gly Leu Asp Val Asp Pro Thr Thr Gly Val Val Tyr Phe Thr Ser Phe
145                 150                 155                 160

Ser Ser Lys Phe Gly Pro Arg Glu Val Leu Ile Ala Val Gly Leu Lys
                165                 170                 175

Asp Ala Ser Gly Lys Leu Phe Lys Tyr Asp Pro Ala Thr Lys Ala Val
            180                 185                 190

Thr Glu Leu Met Glu Gly Leu Ser Gly Ala Ala Gly Cys Ala Val Ser
            195                 200                 205

Ser Asp Gly Ser Phe Val Leu Val Ser Glu Phe Ile Lys Ser Asn Ile
            210                 215                 220

Lys Lys Tyr Trp Ile Lys Gly Pro Lys Ala Gly Thr Ile Glu Asp Phe
225                 230                 235                 240

Ser Ser Leu Val Ser Asn Pro Asp Asn Ile Arg Arg Val Gly Ser Thr
                245                 250                 255

Gly Asn Phe Trp Val Ala Ser Val Val Asn Lys Val Val Met Pro Thr
            260                 265                 270

Asp Pro Arg Ala Val Lys Leu Asp Ala Asn Gly Lys Val Leu Gln Thr
            275                 280                 285

Ile Phe Leu Lys Asn Glu Phe Gly Asn Thr Leu Leu Ser Glu Val Asn
            290                 295                 300

Glu Phe Asn Gly His Leu Tyr Ile Gly Thr Leu Thr Gly Pro Phe Ala
305                 310                 315                 320

Gly Val Met Lys Leu
                325

<210> SEQ ID NO 100
<211> LENGTH: 325
<212> TYPE: PRT
<213> ORGANISM: Arabidopsis thaliana
<220> FEATURE:
<221> NAME/KEY: MISC_FEATURE
<223> OTHER INFORMATION: gi[30]984544

<400> SEQUENCE: 100

Met Ala Ser Phe Val Phe Val Ile Ser Leu Leu Leu Ser Phe Ser
 1               5                  10                  15

Ser Ala Val Phe Ser Asp Asp Ala Ser Phe Gln Lys Leu Pro Val Pro
                 20                  25                  30

Asp Lys Arg Ser Gly Pro Glu Ser Phe Ala Phe Asp Ser Thr Gly Gly
             35                  40                  45

Phe Tyr Thr Gly Val Ser Gly Gly Lys Ile Leu Lys Tyr Val Pro Gly
         50                  55                  60

Lys Gly Tyr Val Asp Phe Ala Gln Ile Thr Asp Ser Ser Asn Ser Ala
 65                  70                  75                  80
```

Trp Cys Asn Gly Ala Leu Gly Thr Ala Phe Ala Gly Lys Cys Gly Arg
            85                  90                  95

Pro Ala Gly Ile Ala Leu Asn Ser Lys Thr Gly Asp Leu Tyr Val Ala
            100                 105                 110

Asp Ala Pro Leu Gly Leu His Val Ile Ser Pro Ala Gly Gly Leu Ala
            115                 120                 125

Thr Lys Leu Ala Asp Ser Val Asp Gly Lys Pro Phe Lys Phe Leu Asp
            130                 135                 140

Gly Leu Asp Val Asp Pro Thr Thr Gly Val Val Tyr Phe Thr Ser Phe
145                 150                 155                 160

Ser Ser Lys Phe Gly Pro Arg Glu Val Leu Ile Ala Val Gly Leu Lys
            165                 170                 175

Asp Ala Ser Gly Lys Leu Phe Lys Tyr Asp Pro Ala Thr Lys Ala Val
            180                 185                 190

Thr Glu Leu Met Glu Gly Leu Ser Gly Ala Ala Gly Cys Ala Val Ser
            195                 200                 205

Ser Asp Gly Ser Phe Val Leu Val Ser Glu Phe Ile Lys Ser Asn Ile
            210                 215                 220

Lys Lys Tyr Trp Ile Lys Gly Pro Lys Ala Gly Thr Ile Glu Asp Phe
225                 230                 235                 240

Ser Ser Leu Val Ser Asn Pro Asp Asn Ile Arg Arg Val Gly Ser Thr
            245                 250                 255

Gly Asn Phe Trp Val Ala Ser Val Val Asn Lys Val Val Met Pro Thr
            260                 265                 270

Asp Pro Arg Ala Val Lys Leu Asp Ala Asn Gly Lys Val Leu Gln Thr
            275                 280                 285

Ile Phe Leu Lys Asn Glu Phe Gly Asn Thr Leu Leu Ser Glu Val Asn
            290                 295                 300

Glu Phe Asn Gly His Leu Tyr Ile Gly Thr Leu Thr Gly Pro Phe Ala
305                 310                 315                 320

Gly Val Met Lys Leu
            325

<210> SEQ ID NO 101
<211> LENGTH: 328
<212> TYPE: PRT
<213> ORGANISM: Arabidopsis thaliana
<220> FEATURE:
<221> NAME/KEY: MISC_FEATURE
<223> OTHER INFORMATION: gi[30]698979

<400> SEQUENCE: 101

Met Arg Ser Phe Val Ser Leu Ile Ser Leu Leu Leu Leu Ser Phe
1                   5                   10                  15

Ser Ser Ser Val Leu Ser Thr Lys Lys Ser Ser Phe Gln Lys Leu Pro
            20                  25                  30

Val Pro Gly Asn Arg Thr Gly Pro Glu Ala Phe Ala Phe Asp Ser Thr
            35                  40                  45

Gly Lys Gly Phe Tyr Thr Gly Val Thr Gly Gly Lys Ile Leu Lys Tyr
            50                  55                  60

Leu Pro Lys Lys Gly Tyr Val Asp Phe Ala Gln Ile Thr Asn Ser Ser
65                  70                  75                  80

Lys Ser Ser Leu Cys Asp Gly Ala Leu Gly Thr Thr Asn Val Glu Lys
            85                  90                  95

Cys Gly Arg Pro Ala Gly Ile Ala Phe Asn Thr Lys Thr Gly Asp Leu
            100                 105                 110

Tyr Val Ala Asp Ala Leu Gly Leu His Val Ile Pro Arg Arg Gly
            115                 120                 125

Gly Leu Ala Lys Lys Ile Ala Asp Ser Val Gly Gly Lys Pro Phe Leu
    130                 135                 140

Phe Leu Asp Gly Leu Asp Val Asp Pro Thr Thr Gly Val Val Tyr Phe
145                 150                 155                 160

Thr Ser Phe Ser Ser Thr Phe Gly Pro Arg Asp Val Leu Lys Ala Val
                165                 170                 175

Ala Thr Lys Asp Ser Thr Gly Lys Phe Phe Lys Tyr Asp Pro Ser Lys
            180                 185                 190

Lys Val Val Thr Val Leu Met Glu Gly Leu Ser Gly Ser Ala Gly Cys
            195                 200                 205

Ala Val Ser Ser Asp Gly Ser Phe Val Leu Val Gly Gln Phe Thr Lys
            210                 215                 220

Ser Asn Ile Lys Arg Tyr Trp Ile Lys Gly Ser Lys Ala Gly Thr Ser
225                 230                 235                 240

Glu Asp Phe Thr Asn Ser Val Ser Asn Pro Asp Asn Ile Lys Arg Ile
                245                 250                 255

Gly Ser Thr Gly Asn Phe Trp Val Ala Ser Val Val Asn Ser Ala Thr
            260                 265                 270

Gly Pro Thr Asn Pro Ser Ala Val Lys Val Ser Ser Ala Gly Lys Val
            275                 280                 285

Leu Gln Thr Ile Pro Leu Lys Asp Lys Phe Gly Asp Thr Leu Val Ser
            290                 295                 300

Glu Val Asn Glu Tyr Lys Gly Gln Leu Tyr Ile Gly Ala Leu Phe Gly
305                 310                 315                 320

Pro Phe Ala Gly Ile Leu Lys Leu
                325

<210> SEQ ID NO 102
<211> LENGTH: 329
<212> TYPE: PRT
<213> ORGANISM: Arabidopsis thaliana
<220> FEATURE:
<221> NAME/KEY: MISC_FEATURE
<223> OTHER INFORMATION: gi[12]325143

<400> SEQUENCE: 102

Met Met Arg Ser Phe Val Ser Leu Ile Ser Leu Leu Leu Leu Leu Ser
1               5                   10                  15

Phe Ser Ser Ser Val Leu Ser Thr Lys Lys Ser Ser Phe Gln Lys Leu
            20                  25                  30

Pro Val Pro Gly Asn Arg Thr Gly Pro Glu Ala Phe Ala Phe Asp Ser
            35                  40                  45

Thr Gly Lys Gly Phe Tyr Thr Gly Val Thr Gly Lys Ile Leu Lys
    50                  55                  60

Tyr Leu Pro Lys Lys Gly Tyr Val Asp Phe Ala Gln Ile Thr Asn Ser
65                  70                  75                  80

Ser Lys Ser Ser Leu Cys Asp Gly Ala Leu Gly Thr Thr Asn Val Glu
                85                  90                  95

Lys Cys Gly Arg Pro Ala Gly Ile Ala Phe Asn Thr Lys Thr Gly Asp
            100                 105                 110

Leu Tyr Val Ala Asp Ala Ala Leu Gly Leu His Val Ile Pro Arg Arg
            115                 120                 125

Gly Gly Leu Ala Lys Lys Ile Ala Asp Ser Val Gly Gly Lys Pro Phe

```
                130             135             140
Leu Phe Leu Asp Gly Leu Asp Val Asp Pro Thr Thr Gly Val Val Tyr
145                 150                 155                 160

Phe Thr Ser Phe Ser Ser Thr Phe Gly Pro Arg Asp Val Leu Lys Ala
                165                 170                 175

Val Ala Thr Lys Asp Ser Thr Gly Lys Phe Phe Lys Tyr Asp Pro Ser
                180                 185                 190

Lys Lys Val Val Thr Val Leu Met Glu Gly Leu Ser Gly Ser Ala Gly
                195                 200                 205

Cys Ala Val Ser Ser Asp Gly Ser Phe Val Leu Val Gly Gln Phe Thr
                210                 215                 220

Lys Ser Asn Ile Lys Arg Tyr Trp Ile Lys Gly Ser Lys Ala Gly Thr
225                 230                 235                 240

Ser Glu Asp Phe Thr Asn Ser Val Ser Asn Pro Asp Asn Ile Lys Arg
                245                 250                 255

Ile Gly Ser Thr Gly Asn Phe Trp Val Ala Ser Val Val Asn Ser Ala
                260                 265                 270

Thr Gly Pro Thr Asn Pro Ser Ala Val Lys Val Ser Ala Gly Lys
                275                 280                 285

Val Leu Gln Thr Ile Pro Leu Lys Asp Lys Phe Gly Asp Thr Leu Val
                290                 295                 300

Ser Glu Val Asn Glu Tyr Lys Gly Gln Leu Tyr Ile Gly Ala Leu Phe
305                 310                 315                 320

Gly Pro Phe Ala Gly Ile Leu Lys Leu
                325

<210> SEQ ID NO 103
<211> LENGTH: 347
<212> TYPE: PRT
<213> ORGANISM: Glycine max
<220> FEATURE:
<221> NAME/KEY: MISC_FEATURE
<223> OTHER INFORMATION: CeresClone:621848

<400> SEQUENCE: 103

Met Lys Leu Ser Thr Leu Phe Leu Phe Leu Phe His Leu Ala His Ala
1               5                   10                  15

Ala Leu Ser Asp Glu Ala Thr Phe Ile Arg Asp Gly Leu Lys Ser Tyr
                20                  25                  30

Ser Gln Leu Asp Leu Pro His Ser Val Phe Gly Ser Glu Ser Val Ala
                35                  40                  45

Phe Asp Cys His Gly Lys Gly Pro Tyr Val Gly Val Ser Asp Gly Arg
            50                  55                  60

Ile Leu Lys Trp His Glu Thr Lys Arg Glu Trp Ile Asp Phe Ala Val
65                  70                  75                  80

Thr Ser Pro His Arg Asn Lys Lys Leu Cys Asp Gly Leu Thr Asn Asp
                85                  90                  95

Lys Met Glu Ser Met Cys Gly Arg Pro Leu Gly Leu Lys Phe Asn Thr
                100                 105                 110

Leu Thr Cys Glu Leu Tyr Ile Ala Asp Ala Tyr Phe Gly Leu Leu Val
                115                 120                 125

Val Gly Pro Gly Gly Gly Val Ala Lys Gln Leu Ala Thr Ser Ala Glu
                130                 135                 140

Gly Val Pro Phe Arg Phe Thr Asn Ala Leu Asp Ile Asp Thr Lys Thr
145                 150                 155                 160
```

-continued

```
Gly Glu Val Tyr Phe Thr Asp Ser Ser Ile Met Phe Gln Arg Arg Val
            165                 170                 175

Tyr Ile Ser Ile Ile Leu Ser Gly Asp Arg Thr Gly Arg Leu Leu Lys
        180                 185                 190

Tyr Val Pro Ser Thr Gln Ser Val His Val Leu Val Lys Gly Leu Ala
        195                 200                 205

Phe Pro Asn Gly Val Ala Leu Ser Lys Asp Asn Ser Phe Ile Ile Val
    210                 215                 220

Ala Glu Ser Thr Thr Phe Lys Ile Leu Lys Ile Gln Val Arg Asp Ser
225                 230                 235                 240

Lys Thr Asn Asn Asn Ile Glu Pro Phe Ala Gln Val Pro Arg Ser
                245                 250                 255

Pro Asp Asn Ile Lys Arg Asn Ala Lys Gly Glu Phe Trp Val Ala Leu
            260                 265                 270

Asn Ser Gly Arg Gly Leu Ile Gln Lys Leu Glu Asn Glu Ile Glu Thr
                275                 280                 285

Thr Leu Pro Trp Asn Ala Asp Pro Val Ala Ile Lys Phe Asp Glu Lys
        290                 295                 300

Gly Arg Ala Ile Glu Val Leu Asp Gly Glu Tyr Gly Arg Gln Leu Asp
305                 310                 315                 320

Ser Val Ser Glu Val Glu Glu His Gly Ser Leu Trp Ile Gly Ser
                325                 330                 335

Ala Val Gln Pro Tyr Ile Gly Leu Ile Lys Ala
            340                 345
```

<210> SEQ ID NO 104
<211> LENGTH: 347
<212> TYPE: PRT
<213> ORGANISM: Catharanthus roseus
<220> FEATURE:
<221> NAME/KEY: MISC_FEATURE
<223> OTHER INFORMATION: gi[18]222

<400> SEQUENCE: 104

```
Met Met Ala Val Phe Phe Met Phe Phe Leu Leu Leu Ser Ser Ser
1               5                   10                  15

Ser Ser Ser Ser Ser Ser Ser Pro Ile Leu Lys Lys Ile Phe Ile Glu
                20                  25                  30

Ser Pro Ser Tyr Ala Pro Asn Ala Phe Thr Phe Asp Ser Thr Asp Lys
        35                  40                  45

Gly Phe Tyr Thr Ser Val Gln Asp Gly Arg Val Ile Lys Tyr Glu Gly
    50                  55                  60

Pro Asn Ser Gly Phe Thr Asp Phe Ala Tyr Ala Ser Pro Phe Trp Asn
65                  70                  75                  80

Lys Ala Phe Cys Glu Asn Ser Thr Asp Pro Glu Lys Arg Pro Leu Cys
                85                  90                  95

Gly Arg Thr Tyr Asp Ile Ser Tyr Asp Tyr Lys Asn Ser Gln Met Tyr
            100                 105                 110

Ile Val Asp Gly His Tyr His Leu Cys Val Val Gly Lys Glu Gly Gly
        115                 120                 125

Tyr Ala Thr Gln Leu Ala Thr Ser Val Gln Gly Val Pro Phe Lys Trp
    130                 135                 140

Leu Tyr Ala Val Thr Val Asp Gln Arg Thr Gly Ile Val Tyr Phe Thr
145                 150                 155                 160

Asp Val Ser Ser Ile His Asp Asp Ser Pro Glu Gly Val Glu Glu Ile
                165                 170                 175
```

```
Met Asn Thr Ser Asp Arg Thr Gly Arg Leu Met Lys Tyr Asp Pro Ser
            180                 185                 190

Thr Lys Glu Thr Thr Leu Leu Lys Glu Leu His Val Pro Gly Gly
        195                 200                 205

Ala Glu Ile Ser Ala Asp Gly Ser Phe Val Val Ala Glu Phe Leu
210                 215                 220

Ser Asn Arg Ile Val Lys Tyr Trp Leu Glu Gly Pro Lys Lys Gly Ser
225                 230                 235                 240

Ala Glu Phe Leu Val Thr Ile Pro Asn Pro Gly Asn Ile Lys Arg Asn
                245                 250                 255

Ser Asp Gly His Phe Trp Val Ser Ser Glu Glu Leu Asp Gly Gly
            260                 265                 270

Gln His Gly Ser Val Val Ser Arg Gly Ile Lys Phe Asp Gly Phe Gly
            275                 280                 285

Asn Ile Leu Gln Val Ile Pro Leu Pro Pro Tyr Glu Gly Glu His
            290                 295                 300

Phe Glu Gln Ile Gln Glu His Asp Gly Leu Leu Tyr Ile Gly Ser Leu
305                 310                 315                 320

Ser His Ser Ser Val Gly Ile Leu Val Tyr Asp Asp His Asp Asn Lys
                325                 330                 335

Gly Asn Ser Tyr Val Ser Gln Leu Val Ile Asn
            340                 345

<210> SEQ ID NO 105
<211> LENGTH: 352
<212> TYPE: PRT
<213> ORGANISM: Catharanthus roseus
<220> FEATURE:
<221> NAME/KEY: MISC_FEATURE
<223> OTHER INFORMATION: gi[18]220

<400> SEQUENCE: 105

Met Ala Asn Phe Ser Glu Ser Lys Ser Met Met Ala Val Phe Phe Met
1               5                   10                  15

Phe Phe Leu Leu Leu Leu Ser Ser Ser Ser Ser Ser Ser Ser Ser Ser
                20                  25                  30

Pro Ile Leu Lys Lys Ile Phe Ile Glu Ser Pro Ser Tyr Ala Pro Asn
            35                  40                  45

Ala Phe Thr Phe Asp Ser Thr Asp Lys Gly Phe Tyr Thr Ser Val Gln
50                  55                  60

Asp Gly Arg Val Ile Lys Tyr Glu Gly Pro Asn Ser Gly Phe Thr Asp
65                  70                  75                  80

Phe Ala Tyr Ala Ser Pro Phe Trp Asn Lys Ala Phe Cys Glu Asn Ser
                85                  90                  95

Thr Asp Pro Glu Lys Arg Pro Leu Cys Gly Arg Thr Tyr Asp Ile Ser
            100                 105                 110

Tyr Asp Tyr Lys Asn Ser Gln Met Tyr Ile Val Asp Gly His Tyr His
        115                 120                 125

Leu Cys Val Val Gly Lys Glu Gly Gly Tyr Ala Thr Gln Leu Ala Thr
130                 135                 140

Ser Val Gln Gly Val Pro Phe Lys Trp Leu Tyr Ala Val Thr Val Asp
145                 150                 155                 160

Gln Arg Thr Gly Ile Val Tyr Phe Thr Asp Val Ser Ser Ile His Asp
                165                 170                 175

Asp Ser Pro Glu Gly Val Glu Glu Ile Met Asn Thr Ser Asp Arg Thr
```

```
                        180                 185                 190
Gly Arg Leu Met Lys Tyr Asp Pro Ser Thr Lys Glu Thr Thr Leu Leu
                195                 200                 205

Leu Lys Glu Leu His Val Pro Gly Gly Ala Glu Ile Ser Ala Asp Gly
            210                 215                 220

Ser Phe Val Val Val Ala Glu Phe Leu Ser Asn Arg Ile Val Lys Tyr
225                 230                 235                 240

Trp Leu Glu Gly Pro Lys Lys Gly Ser Ala Glu Phe Leu Val Thr Ile
                245                 250                 255

Pro Asn Pro Gly Asn Ile Lys Arg Asn Ser Asp Gly His Phe Trp Val
                260                 265                 270

Ser Ser Ser Glu Glu Leu Asp Gly Gln His Gly Arg Val Val Ser
            275                 280                 285

Arg Gly Ile Lys Phe Asp Gly Phe Gly Asn Ile Leu Gln Val Ile Pro
            290                 295                 300

Leu Pro Pro Pro Tyr Glu Gly Glu His Phe Glu Gln Ile Gln Glu His
305                 310                 315                 320

Asp Gly Leu Leu Tyr Ile Gly Ser Leu Phe His Ser Ser Val Gly Ile
                325                 330                 335

Leu Val Tyr Asp Asp His Asp Asn Lys Gly Asn Ser Tyr Val Ser Ser
                340                 345                 350

<210> SEQ ID NO 106
<211> LENGTH: 343
<212> TYPE: PRT
<213> ORGANISM: Zea mays
<220> FEATURE:
<221> NAME/KEY: MISC_FEATURE
<223> OTHER INFORMATION: CeresClone:316544

<400> SEQUENCE: 106

Met Ala Ala Ala Ala Thr Arg Ser Leu His Ser Phe Leu Ala Leu Leu
1               5                   10                  15

Leu Leu Leu Ala Ala Ala Ala Ala Ala Ala Leu Ser Tyr Glu Thr
                20                  25                  30

Lys Ser Ile Asp Pro Gly Leu Val Val Met Thr Leu Pro Glu Pro Val
            35                  40                  45

Ser Gly Pro Glu Ser Leu Ala Phe Asp Gly Arg Gly Gly Pro Tyr
        50                  55                  60

Ser Gly Val Ser Asp Gly Arg Val Leu Arg Trp Gln Gly Pro Leu Arg
65                  70                  75                  80

Gly Trp Thr Glu Phe Ala Tyr Asn Ser Lys His Arg Ser Val Ala Leu
                85                  90                  95

Cys Ala Pro Asp Lys Lys Leu Val Pro Glu Ser Leu Cys Gly Arg
                100                 105                 110

Pro Leu Gly Leu Gln Phe His Arg Gln Ser Gly Asp Leu Tyr Val Ala
            115                 120                 125

Asp Ala Tyr Leu Gly Leu Leu Arg Val Ala Ala Arg Gly Gly Leu Ala
            130                 135                 140

Gln Val Val Ala Thr Glu Ala Ala Gly Gly Pro Phe Asn Phe Leu Asn
145                 150                 155                 160

Gly Leu Asp Val Asp Gln Arg Thr Gly Asp Val Tyr Phe Thr Asp Ser
                165                 170                 175

Ser Ala Thr Tyr Arg Arg Ser Asp Tyr Leu Leu Val Val Ala Met Gly
                180                 185                 190
```

```
Asp Glu Thr Gly Arg Leu Leu Arg Tyr Glu Arg Arg Thr Gly Arg Val
        195                 200                 205

Gly Val Leu Gln Ala Gly Leu Ser Tyr Pro Asn Gly Val Ala Val Ser
    210                 215                 220

Ala Asp Gly Thr His Val Val Ala His Thr Ala Leu Cys Glu Leu
225                 230                 235                 240

Arg Arg Tyr Trp Ile Arg Gly Ala Arg Ala Gly Thr Ser Asp Thr Phe
                245                 250                 255

Ala Glu Leu Pro Gly Tyr Pro Asp Asn Leu Arg Ala Asp Gly Arg Gly
                260                 265                 270

Gly Tyr Trp Val Ala Leu Ser Ser Gly Val Ala Ala Asp Glu Ala Ala
            275                 280                 285

Ala Ala Pro Thr Val Ala Val Arg Val Ser Arg Asp Gly Asn Val Thr
    290                 295                 300

Glu Ala Leu Asp Gly Phe Ser Phe Val Ser Val Ser Glu Val Ala Gln
305                 310                 315                 320

Arg Gly Gly Ala Leu Trp Val Gly Ser Val Asp Thr Pro Tyr Ala Gly
                325                 330                 335

Gln Leu Lys Arg Arg Ala Ser
                340
```

<210> SEQ ID NO 107
<211> LENGTH: 364
<212> TYPE: PRT
<213> ORGANISM: Oryza sativa subsp. japonica
<220> FEATURE:
<221> NAME/KEY: MISC_FEATURE
<223> OTHER INFORMATION: gi[50]899872

<400> SEQUENCE: 107

```
Met Arg Lys Gly Ala Ala Gly Met Ala Cys Thr Cys Ser Ala Ala Ala
1               5                   10                  15

Ala Ala Ser Ala Leu Val Lys Leu Leu Val Leu Val Ala Ala Val Ala
            20                  25                  30

Ala Thr Thr Ser Ala Gly Gly Gly Asp Glu Pro Thr Tyr Glu Thr Lys
        35                  40                  45

Ser Ile Asp Pro Ser Leu Ala Val Met Thr Leu Pro Ala Pro Val Thr
50                  55                  60

Gly Pro Glu Ser Leu Ala Phe Asp Gly Arg Gly Asp Gly Pro Tyr Thr
65                  70                  75                  80

Gly Gly Ser Asp Gly Arg Ile Leu Arg Trp Arg Gly Arg Leu Gly
                85                  90                  95

Trp Thr Glu Phe Ala Tyr Asn Ser Arg His Lys Ser Val Gly Val Cys
                100                 105                 110

Ser Pro Glu Lys Lys Leu Val Val Pro Glu Ser Val Cys Gly Arg Pro
            115                 120                 125

Leu Gly Leu Gln Phe His His Ala Ser Gly Asp Leu Tyr Val Ala Asp
                130                 135                 140

Ala Tyr Leu Gly Leu Leu Arg Val Pro Ala Arg Gly Gly Leu Ala Glu
145                 150                 155                 160

Val Val Ala Thr Glu Ala Ala Gly Val Pro Phe Asn Phe Leu Asn Gly
                165                 170                 175

Leu Asp Val Asp Gln Arg Thr Gly Asp Val Tyr Phe Thr Asp Ser Ser
                180                 185                 190

Thr Thr Tyr Arg Arg Ser Gln Tyr Leu Leu Val Val Ala Met Gly Asp
                195                 200                 205
```

```
Glu Thr Gly Arg Leu Leu Arg Tyr Asp Ala Arg Arg Arg Val Thr
    210                 215                 220
Val Leu His Ser Gly Leu Pro Tyr Pro Asn Gly Val Ala Val Ser Asp
225                 230                 235                 240
Asp Gly Thr His Val Val Ala His Thr Gly Leu Cys Glu Leu Arg
                245                 250                 255
Arg Tyr Trp Leu Arg Gly Pro Arg Ala Gly Lys Ser Glu Thr Phe Ala
                260                 265                 270
Glu Val Pro Gly Tyr Pro Asp Asn Val Arg Arg Asp Gly Asp Gly Gly
                275                 280                 285
Tyr Trp Val Ala Leu Ser Arg Gly Ala Asp Asn Asp Val Ala Pro
    290                 295                 300
Thr Val Ala Val Arg Val Thr Ala Ala Gly Lys Lys Lys Gly Gly
305                 310                 315                 320
Ala Ala Val Val Ala Glu Ala Leu Ala Gly Phe Ser Phe Val Thr Val
                325                 330                 335
Ser Glu Val Ala Glu Gln Asn Gly Thr Leu Trp Ile Gly Ser Val Asp
                340                 345                 350
Thr Pro Tyr Ala Gly Ala Ala Val Arg Gly Arg Arg
                355                 360

<210> SEQ ID NO 108
<211> LENGTH: 351
<212> TYPE: PRT
<213> ORGANISM: Ophiorrhiza pumila
<220> FEATURE:
<221> NAME/KEY: MISC_FEATURE
<223> OTHER INFORMATION: gi[13]928598

<400> SEQUENCE: 108

Met His Ser Ser Glu Ala Met Val Val Ser Ile Leu Cys Ala Leu Phe
1               5                   10                  15
Leu Ser Ser Leu Ser Leu Val Ser Ser Pro Glu Phe Phe Glu Phe
                20                  25                  30
Ile Glu Ala Pro Ser Tyr Gly Pro Asn Ala Tyr Ala Phe Asp Ser Asp
                35                  40                  45
Gly Glu Leu Tyr Ala Ser Val Glu Asp Gly Arg Ile Ile Lys Tyr Asp
    50                  55                  60
Lys Pro Ser Asn Lys Phe Leu Thr His Ala Val Ala Ser Pro Ile Trp
65                  70                  75                  80
Asn Asn Ala Leu Cys Glu Asn Asn Thr Asn Gln Asp Leu Lys Pro Leu
                85                  90                  95
Cys Gly Arg Val Tyr Asp Phe Gly Phe His Tyr Glu Thr Gln Arg Leu
                100                 105                 110
Tyr Ile Ala Asp Cys Tyr Phe Gly Leu Gly Phe Val Gly Pro Asp Gly
                115                 120                 125
Gly His Ala Ile Gln Leu Ala Thr Ser Gly Asp Gly Val Glu Phe Lys
    130                 135                 140
Trp Leu Tyr Ala Leu Ala Ile Asp Gln Gln Ala Gly Phe Val Tyr Val
145                 150                 155                 160
Thr Asp Val Ser Thr Lys Tyr Asp Asp Arg Gly Val Gln Asp Ile Ile
                165                 170                 175
Arg Ile Asn Asp Thr Thr Gly Arg Leu Ile Lys Tyr Asp Pro Ser Thr
                180                 185                 190
Glu Glu Val Thr Val Leu Met Lys Gly Leu Asn Ile Pro Gly Gly Thr
```

```
                195                 200                 205
Glu Val Ser Lys Asp Gly Ser Phe Val Leu Val Gly Glu Phe Ala Ser
210                 215                 220

His Arg Ile Leu Lys Tyr Trp Leu Lys Gly Pro Lys Ala Asn Thr Ser
225                 230                 235                 240

Glu Phe Leu Leu Lys Val Arg Gly Pro Gly Asn Ile Lys Arg Thr Lys
                245                 250                 255

Asp Gly Asp Phe Trp Val Ala Ser Ser Asp Asn Asn Gly Ile Thr Val
                260                 265                 270

Thr Pro Arg Gly Ile Arg Phe Asp Glu Phe Gly Asn Ile Leu Glu Val
                275                 280                 285

Val Ala Ile Pro Leu Pro Tyr Lys Gly Glu His Ile Glu Gln Val Gln
290                 295                 300

Glu His Asp Gly Ala Leu Phe Val Gly Ser Leu Phe His Glu Phe Val
305                 310                 315                 320

Gly Ile Leu His Asn Tyr Lys Ser Ser Val Asp His His Gln Glu Lys
                325                 330                 335

Asn Ser Gly Gly Leu Asn Ala Ser Phe Lys Glu Phe Ser Ser Phe
                340                 345                 350

<210> SEQ ID NO 109
<211> LENGTH: 342
<212> TYPE: PRT
<213> ORGANISM: Rauvolfia mannii
<220> FEATURE:
<221> NAME/KEY: MISC_FEATURE
<223> OTHER INFORMATION: gi[21]097

<400> SEQUENCE: 109

Lys Leu Ser Asp Ser Gln Thr Met Ala Leu Phe Thr Val Phe Leu Leu
1               5                   10                  15

Phe Leu Ser Ser Ser Leu Ala Leu Ser Ser Pro Ile Leu Lys Glu Ile
                20                  25                  30

Leu Ile Glu Ala Pro Ser Tyr Ala Pro Asn Ser Phe Thr Phe Asp Ser
                35                  40                  45

Thr Asn Lys Gly Phe Tyr Thr Ser Val Gln Asp Gly Arg Val Ile Lys
50                  55                  60

Tyr Glu Gly Pro Asn Ser Gly Phe Val Asp Phe Ala Tyr Ala Ser Pro
65                  70                  75                  80

Tyr Trp Asn Lys Ala Phe Cys Glu Asn Ser Thr Asp Ala Glu Lys Arg
                85                  90                  95

Pro Leu Cys Gly Arg Thr Tyr Asp Ile Ser Tyr Asn Leu Gln Asn Asn
                100                 105                 110

Gln Leu Tyr Ile Val Asp Cys Tyr Tyr His Leu Ser Val Val Gly Ser
                115                 120                 125

Glu Gly Gly His Ala Thr Gln Leu Ala Thr Ser Val Asp Gly Val Pro
130                 135                 140

Phe Lys Trp Leu Tyr Ala Val Thr Val Asp Gln Arg Thr Gly Ile Val
145                 150                 155                 160

Tyr Phe Thr Asp Val Ser Thr Leu Tyr Asp Asp Arg Gly Val Gln Gln
                165                 170                 175

Ile Met Asp Thr Ser Asp Lys Thr Gly Arg Leu Ile Lys Tyr Asp Pro
                180                 185                 190

Ser Thr Lys Glu Thr Thr Leu Leu Leu Lys Glu Leu His Val Pro Gly
                195                 200                 205
```

Gly Ala Glu Val Ser Ala Asp Ser Ser Phe Val Leu Val Ala Glu Phe
210                 215                 220

Leu Ser His Gln Ile Val Lys Tyr Trp Leu Glu Gly Pro Lys Lys Gly
225                 230                 235                 240

Thr Ala Glu Val Leu Val Lys Ile Pro Asn Pro Gly Asn Ile Lys Arg
            245                 250                 255

Asn Ala Asp Gly His Phe Trp Val Ser Ser Glu Glu Leu Asp Gly
            260                 265                 270

Asn Met His Gly Arg Val Asp Pro Lys Gly Ile Lys Phe Asp Glu Phe
            275                 280                 285

Gly Asn Ile Leu Glu Val Ile Pro Leu Pro Pro Phe Ala Gly Glu
290                 295                 300

His Phe Glu Gln Ile Gln Glu His Asp Gly Leu Leu Tyr Ile Gly Thr
305                 310                 315                 320

Leu Phe His Gly Ser Val Gly Ile Leu Val Tyr Asp Lys Lys Gly Asn
                325                 330                 335

Ser Phe Val Ser Ser His
            340

<210> SEQ ID NO 110
<211> LENGTH: 1954
<212> TYPE: DNA
<213> ORGANISM: Arabidopsis thaliana
<220> FEATURE:
<221> NAME/KEY: MISC_FEATURE
<223> OTHER INFORMATION: PROMOTER: 326 REPORT: 56

<400> SEQUENCE: 110
gtgggtaaaa gtatccttct ttgtgcattt ggtattttta agcatgtaat aagaaaaacc       60
aaaatagacg gctggtattt aataaaagga gactaatgta tgtatagtat atgatttgtg      120
tggaatataa taaagttgta aaatatagat gtgaagcgag tatctatctt ttgactttca      180
aaggtgatcg atcgtgttct ttgtgatagt tttggtcgtc ggtctacaag tcaacaacca      240
ccttgaagtt ttcgcgtctc ggtttcctct tcgcatctgg tatccaatag catacatata      300
ccagtgcgga aaatggcgaa gactagtggg cttgaaccat aaggtttggc cccaatacgg      360
attccaaaca acaagcctag cgcagtcttt tgggatgcat aagactaaac tgtcgcagtg      420
atagacgtaa gatatatcga cttgattgga atcgtctaag ctaataagtt taccttgacc      480
gtttatagtt gcgtcaacgt ccttatggag attgatgccc atcaaataaa cctgaaaatc      540
catcaccatg accaccataa actcccttgc tgccgctgct ttggcttgag caaggtgttt      600
ccttgtaaag ctccgatctt tggataaagt gttccacttt ttgcaagtag ctctgacccc      660
tctcagagat gtcaccggaa tcttagacag aacctcctct gccaaatcac ttggaagatc      720
ggacaatgtc atcattttg caggtaattt ctccttcgtt gctgctttgg cttgagcacg      780
gtgcttcttt gtaaagctcc gatctttgga taagagcgga tcggaatcct ctaggaggtg      840
ccagtcccct tgacctattaa tttatagaag gttttagtgt attttgttcc aatttcttct      900
ctaacttaac aaataacaac tgcctcatag tcatgggctt caaattttat cgcttggtgt      960
atttcgttat ttgcaaggcc ttggcccatt tgagcccaa taactaaatc tagccttttc     1020
agaccggaca tgaacttcgc atattggcgt aactgtgcag ttttaccttt ttcggatcag     1080
acaagatcag atttagacca cccaacaata gtcagtcata tttgacaacc taagctagcc     1140
gacactacta aaagcaaac aaaagaagaa ttctatgttg tcatttttacc ggtggcaagt     1200
ggacccttct ataaaagagt aaagagacag cctgtgtgtg tataatctct aattatgttc     1260

```
accgacacaa tcacacaaac ccttctctaa tcacacaact tcttcatgat ttacgacatt    1320
aattatcatt aactctttaa attcacttta catgctcaaa atatctaat ttgcagcatt    1380 aatttgagta ccgataacta ttattataat cgtcgtgatt cgcaatcttc ttcattagat    1440
gctgtcaagt tgtactcgca cgcggtggtc cagtgaagca atccaacgg tttaaaacct    1500 tcttacattt ctagatctaa tctgaaccgt cagatatcta gatctcattg tctgaacaca    1560
gttagatgaa actgggaatg aatctggacg aaattacgat cttacaccaa cccctcgac    1620 gagctcgtat atataaagct tatacgctcc tccttcacct tcgtactact actaccacca    1680
catttcttta gctcaacctt cattactaat ctccttttaa ggtatgttca cttttcttcg    1740
attcatactt tctcaagatt cctgcatttc tgtagaattt gaaccaagtg tcgatttttg    1800
tttgagagaa gtgttgattt atagatctgg ttattgaatc tagattccaa ttttaattg    1860 attcgagttt gttatgtgtg tttatactac ttctcattga tcttgtttga tttctctgct    1920
ctgtattagg tttctttcgt gaatcagatc ggaa                               1954

<210> SEQ ID NO 111
<211> LENGTH: 2016
<212> TYPE: DNA
<213> ORGANISM: Arabidopsis thaliana
<220> FEATURE:
<221> NAME/KEY: MISC_FEATURE
<223> OTHER INFORMATION: PROMOTER: 32449; REPORT: 92

<400> SEQUENCE: 111
gatcggcctt cttcaggtct tctctgtagc tctgttactt ctatcacagt tatcgggtat      60
ttgagaaaaa agagttagct aaaatgaatt tctccatata atcatggttt actacaggtt     120
tacttgattc gcgttagctt tatctgcatc caaagttttt tccatgatgt tatgtcatat     180
gtgataccgt tactatgttt ataactttat acagtctggt tcactggagt ttctgtgatt     240
atgttgagta catactcatt catcctttgg taactctcaa gtttaggttg tttgaattgc     300
ctctgttgtg atacttattg tctattgcat caatcttcta atgcaccacc ctagactatt     360
tgaacaaaga gctgtttcat tcttaaacct ctgtgtctcc ttgctaaatg gtcatgcttt     420
aatgtcttca cctgtctttc tcttctatag atatgtagtc ttgctagata gttagttcta     480
cagctctctt ttgtagtctt gttagagagt tagttgagat attacctctt aaaagtatcc     540
ttgaacgctt tccggttatg accaatttgt tgtagctcct tgtaagtaga acttactggg     600
accagcgaga cagtttatgt gaatgttcat gcttaagtgt cgaacgtatc tatctctact     660
atagctctgt agtcttgtta gacagttagt tttatatctc catttttttg tagtcttgct     720
agttgagata ttacctcttc tcttcaaagt atccttgaac gctcaccggt tatgaaatct     780
ctacactata gctctgtagt cttgctagat agttagttct ttagctctct ttttgtagcc     840
tagttcttta gctctccttt tgtagccttg ctacagagta agatgggata ttacctcctt     900
gaacgctctc cggttatgac caatttgttg tagctccttg taagtagaac ttaggataga     960
gtgagtcaac tttaagaaag aacctagtat gtggcataac cagattgcag gctctgtctc    1020
ggctacagta acgtaactct atagctcttt gttttgttca gaaagaacca gtgattggat    1080
gattcgtcct tagaaactgg acctaacaac agtcattggc tttgaaatca agccacaaca    1140
atgcctatat gaaccgtcca tttcatttat ccgtttcaaa ccagcccatt acatttcgtc    1200
ccattgataa ccaaaagcgg ttcaatcaga ttatgtttta attttaccaa attctttatg    1260
aagtttaaat tatactcaca ttaaaaggat tattggataa tgtaaaaatt ctgaacaatt    1320
```

```
actgattttg gaaaattaac aaatattctt tgaaatagaa gaaaaagcct ttttcctttt    1380
gacaacaaca tataaaatca tactcccatt aaaaagattt taatgtaaaa ttctgaatat    1440
aagatatttt ttacaacaac aaccaaaaat atttattttt ttccttttt acagcaacaa     1500 gaaggaaaaa cttttttttt tgtcaagaaa aggggagatt atgtaaacag ataaaacagg    1560
gaaaataact aaccgaactc tcttaattaa catcttcaaa taaggaaaat tatgatccgc    1620
atatttagga agatcaatgc attaaaacaa cttgcacgtg gaaagagaga ctatacgctc    1680
cacacaagtt gcactaatgg tacctctcac aaaccaatca aaatactgaa taatgccaac    1740
gtgtacaaat tagggtttta cctcacaacc atcgaacatt ctcgaaacat tttaaacagc    1800
ctggcgccat agatctaaac tctcatcgac caattttga ccgtccgatg gaaactctag     1860
cctcaaccca aaactctata taagaaatc ttttccttcg ttattgctta ccaaatacaa     1920
accctagccg ccttattcgt cttcttcgtt ctctagtttt ttcctcagtc tctgttctta    1980
gatcccttgt agtttccaaa tcttccgata aggcct                              2016
```

<210> SEQ ID NO 112
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 1-4

<400> SEQUENCE: 112

Gln Trp Cys Val Ala
1               5

<210> SEQ ID NO 113
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 1-4

<400> SEQUENCE: 113

Glu Gln Thr Thr Asp
1               5

<210> SEQ ID NO 114
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 1-4

<400> SEQUENCE: 114

Glu Leu Gln Ala
1

<210> SEQ ID NO 115
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 1-4

```
<400> SEQUENCE: 115

Asp Cys Ser Lys Ile
1               5

<210> SEQ ID NO 116
<211> LENGTH: 17
<212> TYPE: PRT
<213> ORGANISM: Artificial sequence
<220> FEATURE:
<221> NAME/KEY: misc_feature
<222> LOCATION: (1)..(17)
<223> OTHER INFORMATION: Fragment of consensus sequence of Table 1-4

<400> SEQUENCE: 116

Asn Gln Pro Cys Phe Leu Pro Asn Thr Ile Arg Asp His Ala Ser Tyr
1               5                   10                  15

Ala

<210> SEQ ID NO 117
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 1-4

<400> SEQUENCE: 117

Asn Ser Tyr Tyr Gln Thr
1               5

<210> SEQ ID NO 118
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 1-4

<400> SEQUENCE: 118

Phe Lys Gly Ala
1

<210> SEQ ID NO 119
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 1-4

<400> SEQUENCE: 119

Ile Ile Thr Glu
1

<210> SEQ ID NO 120
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 1-4

<400> SEQUENCE: 120
```

```
Asp Pro Ser His Gly Ser Cys
1               5
```

<210> SEQ ID NO 121
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 2-8

<400> SEQUENCE: 121

```
Met Gln Met Leu Arg
1               5
```

<210> SEQ ID NO 122
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 2-8

<400> SEQUENCE: 122

```
Leu Ser Thr Arg Thr Arg Ser Arg Arg Gly Gly Tyr Glu Arg Val
1               5                   10                  15
```

<210> SEQ ID NO 123
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 2-8

<400> SEQUENCE: 123

```
Ser Asp Asp Ser Thr Phe Ser Leu Leu Gly Ala Lys Leu Arg Arg Ser
1               5                   10                  15

Thr Ser Val Pro Tyr Tyr Ala Pro Ser
            20                  25
```

<210> SEQ ID NO 124
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 2-8

<400> SEQUENCE: 124

```
Ile Arg Leu Gly
1
```

<210> SEQ ID NO 125
<211> LENGTH: 30
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 2-8

<400> SEQUENCE: 125

```
Gly Asp Phe Pro Val Ile Leu Glu Lys Leu Pro Arg Gln Lys Pro Thr
1               5                   10                  15

Lys Thr Val Val Thr Ser Lys Leu Ser His Pro Ile Phe Ser
            20                  25                  30
```

<210> SEQ ID NO 126
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 2-8

<400> SEQUENCE: 126

```
Asp Gly Tyr Arg Arg Arg
1               5
```

<210> SEQ ID NO 127
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 2-8

<400> SEQUENCE: 127

```
Thr Ala Lys Pro Glu Phe Ser Arg Tyr
1               5
```

<210> SEQ ID NO 128
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 2-8

<400> SEQUENCE: 128

```
Glu Tyr Leu Lys Glu
1               5
```

<210> SEQ ID NO 129
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 2-8

<400> SEQUENCE: 129

```
Gly Met Trp Asp Leu Arg Ser Asn Ser Pro Val Ile Tyr Phe Lys
1               5                   10                  15
```

<210> SEQ ID NO 130
<211> LENGTH: 19
<212> TYPE: PRT
<213> ORGANISM: Artificial sequence
<220> FEATURE:
<221> NAME/KEY: misc_feature
<222> LOCATION: (1)..(19)
<223> OTHER INFORMATION: Fragment of consensus sequence of Table 3-9

<400> SEQUENCE: 130

```
Lys Lys His Phe Val Leu Val His Gly Ala Cys His Gly Ala Trp Cys
```

```
1               5                  10                 15
Trp Tyr Lys

<210> SEQ ID NO 131
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 131

Lys Pro Leu Leu Glu Ala
1               5

<210> SEQ ID NO 132
<211> LENGTH: 13
<212> TYPE: PRT
<213> ORGANISM: Artificial sequence
<220> FEATURE:
<221> NAME/KEY: misc_feature
<222> LOCATION: (1)..(13)
<223> OTHER INFORMATION: Fragment of consensus sequence of Table 3-9

<400> SEQUENCE: 132

Gly His Arg Val Thr Ala Leu Asp Leu Ala Ala Ser Gly
1               5                   10

<210> SEQ ID NO 133
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 133

Pro Arg Gln Ile
1

<210> SEQ ID NO 134
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 3-9

<400> SEQUENCE: 134

Tyr Ser Glu Pro Leu Met Glu Leu Met
1               5

<210> SEQ ID NO 135
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 3-9

<400> SEQUENCE: 135

Glu Lys Val Val Leu Val Gly His Ser
1               5
```

```
<210> SEQ ID NO 136
<211> LENGTH: 22
<212> TYPE: PRT
<213> ORGANISM: Artificial sequence
<220> FEATURE:
<221> NAME/KEY: misc_feature
<222> LOCATION: (1)..(22)
<223> OTHER INFORMATION: Fragment of consensus sequence of Table 3-9

<400> SEQUENCE: 136

Gly Gly Leu Asn Ile Ala Leu Ala Met Glu Lys Phe Pro Glu Lys Ile
1               5                   10                  15

Ser Val Ala Val Phe Leu
            20

<210> SEQ ID NO 137
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 137

Met Pro Asp Thr Glu His
1               5

<210> SEQ ID NO 138
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 138

Val Leu Glu Lys
1

<210> SEQ ID NO 139
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 139

Trp Met Asp Thr Glu Phe
1               5

<210> SEQ ID NO 140
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 140

Thr Ser Met Ile
1
```

```
<210> SEQ ID NO 141
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 3-9

<400> SEQUENCE: 141

Leu Tyr Gln Leu Ser Pro
1               5

<210> SEQ ID NO 142
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 3-9

<400> SEQUENCE: 142

Met Leu Val Arg Pro Gly Ser Leu Phe Ile
1               5                   10

<210> SEQ ID NO 143
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 3-9

<400> SEQUENCE: 143

Tyr Gly Ser Val Lys Arg Val Tyr Ile Tyr
1               5                   10

<210> SEQ ID NO 144
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 3-9

<400> SEQUENCE: 144

Phe Gln Arg Trp Met Ile Glu Asn Tyr Pro
1               5                   10

<210> SEQ ID NO 145
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 3-9

<400> SEQUENCE: 145

Glu Ile Glu Gly
1

<210> SEQ ID NO 146
<211> LENGTH: 7
<212> TYPE: PRT
<213> ORGANISM: Artificial sequence
```

```
<220> FEATURE:
<221> NAME/KEY: misc_feature
<222> LOCATION: (1)..(7)
<223> OTHER INFORMATION: Fragment of consensus sequence of Table 3-9

<400> SEQUENCE: 146

Ser Lys Pro Gln Glu Leu Ser
1               5

<210> SEQ ID NO 147
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 147

Phe Ile Gln Cys Leu
1               5

<210> SEQ ID NO 148
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 148

Lys Leu Val Tyr Thr Pro
1               5

<210> SEQ ID NO 149
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 5-8

<400> SEQUENCE: 149

Ser Thr Tyr Gln Asn Leu Arg Phe Leu
1               5

<210> SEQ ID NO 150
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 5-8

<400> SEQUENCE: 150

Thr Pro Lys Pro Leu Val Ile Ile Thr Pro
1               5                   10

<210> SEQ ID NO 151
<211> LENGTH: 16
<212> TYPE: PRT
<213> ORGANISM: Artificial sequence
<220> FEATURE:
<221> NAME/KEY: misc_feature
<222> LOCATION: (1)..(16)
<223> OTHER INFORMATION: Fragment of consensus sequence of Table 5-8
```

```
<400> SEQUENCE: 151

Ser His Ile Gln Ala Ala Val Val Cys Ser Lys Lys His Gly Leu Gln
1               5                   10                  15

<210> SEQ ID NO 152
<211> LENGTH: 16
<212> TYPE: PRT
<213> ORGANISM: Artificial sequence
<220> FEATURE:
<221> NAME/KEY: misc_feature
<222> LOCATION: (1)..(16)
<223> OTHER INFORMATION: Fragment of consensus sequence of Table 5-8

<400> SEQUENCE: 152

Arg Val Arg Ser Gly Gly His Asp Tyr Glu Gly Leu Ser Tyr Val Ser
1               5                   10                  15

<210> SEQ ID NO 153
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 5-8

<400> SEQUENCE: 153

Pro Phe Val Val Val Asp Leu
1               5

<210> SEQ ID NO 154
<211> LENGTH: 17
<212> TYPE: PRT
<213> ORGANISM: Artificial sequence
<220> FEATURE:
<221> NAME/KEY: misc_feature
<222> LOCATION: (1)..(17)
<223> OTHER INFORMATION: Fragment of consensus sequence of Table 5-8

<400> SEQUENCE: 154

Thr Ala Trp Val Gln Ala Gly Ala Thr Leu Gly Glu Leu Tyr Tyr Arg
1               5                   10                  15

Ile

<210> SEQ ID NO 155
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 155

Glu Lys Ser Lys
1

<210> SEQ ID NO 156
<211> LENGTH: 22
<212> TYPE: PRT
<213> ORGANISM: Artificial sequence
<220> FEATURE:
<221> NAME/KEY: misc_feature
<222> LOCATION: (1)..(22)
<223> OTHER INFORMATION: Fragment of consensus sequence of Table 5-8

<400> SEQUENCE: 156
```

```
Gly Phe Pro Ala Gly Val Cys Pro Thr Val Gly Val Gly Gly His Ile
1               5                   10                  15

Ser Gly Gly Gly Tyr Gly
            20
```

<210> SEQ ID NO 157
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 5-8

<400> SEQUENCE: 157

```
Leu Met Arg Lys Tyr Gly Leu Ala Ala Asp Asn Val Ile Asp Ala
1               5                   10                  15
```

<210> SEQ ID NO 158
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 5-8

<400> SEQUENCE: 158

```
Val Asp Asn Gly Lys Leu Leu Asp Arg Lys Ser Met Gly Glu Asp Leu
1               5                   10                  15

Phe Trp Ala Ile Arg Gly Gly Gly Gly
            20                  25
```

<210> SEQ ID NO 159
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 159

```
Ser Phe Gly Val
1
```

<210> SEQ ID NO 160
<211> LENGTH: 17
<212> TYPE: PRT
<213> ORGANISM: Artificial sequence
<220> FEATURE:
<221> NAME/KEY: misc_feature
<222> LOCATION: (1)..(17)
<223> OTHER INFORMATION: Fragment of consensus sequence of Table 5-8

<400> SEQUENCE: 160

```
Leu Ala Trp Lys Ile Lys Leu Val Pro Val Pro Glu Thr Val Thr Val
1               5                   10                  15

Phe
```

<210> SEQ ID NO 161
<211> LENGTH: 6
<212> TYPE: PRT
<213> ORGANISM: Artificial sequence
<220> FEATURE:
<221> NAME/KEY: misc_feature

```
<222> LOCATION: (1)..(6)
<223> OTHER INFORMATION: Fragment of consensus sequence of Table 5-8

<400> SEQUENCE: 161

Arg Thr Leu Glu Gln Asn
1               5

<210> SEQ ID NO 162
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 162

Lys Trp Gln Gln Val Ala
1               5

<210> SEQ ID NO 163
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 163

Thr Val Arg Ala
1

<210> SEQ ID NO 164
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 164

Leu Phe Leu Gly Gly
1               5

<210> SEQ ID NO 165
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 165

Leu Met Asn Lys
1

<210> SEQ ID NO 166
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 5-8

<400> SEQUENCE: 166
```

```
Phe Pro Glu Leu Gly Leu
1               5

<210> SEQ ID NO 167
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 5-8

<400> SEQUENCE: 167

Glu Met Ser Trp Ile Glu Ser Val Leu Tyr Tyr
1               5                   10

<210> SEQ ID NO 168
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 168

Glu Val Leu Leu Asn
1               5

<210> SEQ ID NO 169
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 5-8

<400> SEQUENCE: 169

Lys Ser Asp Tyr Val Lys Glu Pro Ile Pro Lys Ser Gly Leu Glu
1               5                   10                  15

<210> SEQ ID NO 170
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 170

Pro Tyr Gly Gly
1

<210> SEQ ID NO 171
<211> LENGTH: 26
<212> TYPE: PRT
<213> ORGANISM: Artificial sequence
<220> FEATURE:
<221> NAME/KEY: misc_feature
<222> LOCATION: (1)..(26)
<223> OTHER INFORMATION: Fragment of consensus sequence of Table 5-8

<400> SEQUENCE: 171

Glu Ile Ser Glu Ser Ala Ile Pro Phe Pro His Arg Ser Gly Val Leu
1               5                   10                  15
```

Tyr Lys Ile Gln Tyr Val Val Asn Trp Glu
            20                  25

<210> SEQ ID NO 172
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 5-8

<400> SEQUENCE: 172

Gly Asp Glu Ala
1

<210> SEQ ID NO 173
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 5-8

<400> SEQUENCE: 173

Arg His Leu Asn Trp
1               5

<210> SEQ ID NO 174
<211> LENGTH: 26
<212> TYPE: PRT
<213> ORGANISM: Artificial sequence
<220> FEATURE:
<221> NAME/KEY: misc_feature
<222> LOCATION: (1)..(26)
<223> OTHER INFORMATION: Fragment of consensus sequence of Table 5-8

<400> SEQUENCE: 174

Tyr Met Thr Pro Tyr Val Ser Lys Asn Pro Arg Glu Ala Tyr Val Asn
1               5                   10                  15

Tyr Arg Asp Leu Asp Leu Gly Val Asn Ser
            20                  25

<210> SEQ ID NO 175
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 5-8

<400> SEQUENCE: 175

Val Trp Gly Glu Lys Tyr Phe Lys
1               5

<210> SEQ ID NO 176
<211> LENGTH: 13
<212> TYPE: PRT
<213> ORGANISM: Artificial sequence
<220> FEATURE:
<221> NAME/KEY: misc_feature
<222> LOCATION: (1)..(13)
<223> OTHER INFORMATION: Fragment of consensus sequence of Table 5-8

<400> SEQUENCE: 176

Asn Phe Lys Arg Leu Val Val Lys Thr Lys Val Asp Pro

-continued

```
1               5                  10

<210> SEQ ID NO 177
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 5-8

<400> SEQUENCE: 177

Asn Phe Phe Arg Asn Glu Gln Ser Ile Pro
1               5                  10

<210> SEQ ID NO 178
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 178

Met Pro Val Val Gly Met Gly Thr Ala
1               5

<210> SEQ ID NO 179
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 6-8

<400> SEQUENCE: 179

Ala Ile Leu Glu Ala Ile Lys
1               5

<210> SEQ ID NO 180
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 180

Gly Tyr Arg His Phe Asp Thr Ala Ala
1               5

<210> SEQ ID NO 181
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 181

Leu Gly Glu Ala Leu Ala Glu Ala Ile
1               5

<210> SEQ ID NO 182
```

```
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 6-8

<400> SEQUENCE: 182

Asp Leu Phe Val Thr Ser Lys Leu Trp
1               5

<210> SEQ ID NO 183
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 6-8

<400> SEQUENCE: 183

Leu Val Val Pro Ala Leu
1               5

<210> SEQ ID NO 184
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 6-8

<400> SEQUENCE: 184

Lys Ser Leu Lys Asn Leu Gln Leu Asp Tyr Ile Asp Leu Tyr Leu Ile
1               5                   10                  15

His Trp Pro Ile Ser Leu Lys Pro Gly
            20                  25

<210> SEQ ID NO 185
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 6-8

<400> SEQUENCE: 185

Glu Asp Leu Leu Pro
1               5

<210> SEQ ID NO 186
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 186

Lys Gly Val Trp
1

<210> SEQ ID NO 187
<211> LENGTH: 5
```

```
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 6-8

<400> SEQUENCE: 187

Ala Met Glu Glu Cys
1               5

<210> SEQ ID NO 188
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 6-8

<400> SEQUENCE: 188

Lys Leu Gly Leu Ala Lys Ala Ile Gly Val Ser Asn Phe Ser
1               5                   10

<210> SEQ ID NO 189
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 189

Lys Lys Leu Glu
1

<210> SEQ ID NO 190
<211> LENGTH: 18
<212> TYPE: PRT
<213> ORGANISM: Artificial sequence
<220> FEATURE:
<221> NAME/KEY: misc_feature
<222> LOCATION: (1)..(18)
<223> OTHER INFORMATION: Fragment of consensus sequence of Table 6-8

<400> SEQUENCE: 190

Leu Leu Ser Val Ala Thr Ile Pro Pro Ala Val Asn Gln Val Glu Met
1               5                   10                  15

Asn Pro

<210> SEQ ID NO 191
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 6-8

<400> SEQUENCE: 191

Trp Gln Gln Lys Lys Leu Arg Glu Phe Cys Lys
1               5                   10

<210> SEQ ID NO 192
<211> LENGTH: 11
<212> TYPE: PRT
<213> ORGANISM: Artificial sequence
```

```
<220> FEATURE:
<221> NAME/KEY: misc_feature
<222> LOCATION: (1)..(11)
<223> OTHER INFORMATION: Fragment of consensus sequence of Table 6-8

<400> SEQUENCE: 192

Val Thr Ala Tyr Ser Pro Leu Gly Ala Lys Gly
1               5                   10

<210> SEQ ID NO 193
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 6-8

<400> SEQUENCE: 193

Val Leu Lys Glu Ile Ala Glu Ala Lys Gly Lys Thr Val Ala Gln
1               5                   10                  15

<210> SEQ ID NO 194
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 6-8

<400> SEQUENCE: 194

Val Ser Leu Arg Trp Val Tyr Glu Gln Gly Val Thr Leu Ile
1               5                   10

<210> SEQ ID NO 195
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 6-8

<400> SEQUENCE: 195

Lys Glu Arg Met Lys Gln Asn Leu
1               5

<210> SEQ ID NO 196
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 6-8

<400> SEQUENCE: 196

Ile Phe Asp Trp Glu Leu Thr Glu Glu Asp
1               5                   10

<210> SEQ ID NO 197
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8
```

```
<400> SEQUENCE: 197

Gln Ile Pro Gln
1

<210> SEQ ID NO 198
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 198

Arg Arg Leu Ile
1

<210> SEQ ID NO 199
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 6-8

<400> SEQUENCE: 199

Gly Pro Tyr Lys Ser
1               5

<210> SEQ ID NO 200
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 6-8

<400> SEQUENCE: 200

Asp Leu Trp Asp
1

<210> SEQ ID NO 201
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 7-6

<400> SEQUENCE: 201

Val Ser Pro Ala Phe
1               5

<210> SEQ ID NO 202
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 7-6

<400> SEQUENCE: 202

Ala Gly Ser Ser
```

```
<210> SEQ ID NO 203
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 7-6

<400> SEQUENCE: 203

Ser Asp Ser Ser Ile
1               5

<210> SEQ ID NO 204
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 7-6

<400> SEQUENCE: 204

Val Gly Lys Ser Thr Asn Ile
1               5

<210> SEQ ID NO 205
<211> LENGTH: 44
<212> TYPE: PRT
<213> ORGANISM: Artificial sequence
<220> FEATURE:
<221> NAME/KEY: misc_feature
<222> LOCATION: (1)..(44)
<223> OTHER INFORMATION: Fragment of consensus sequence of Table 7-6

<400> SEQUENCE: 205

Trp His Asp Cys Ala Val Ser Lys Ser Asp Arg Gln Glu Leu Leu Lys
1               5                   10                  15

Gln Lys Gly Cys Val Ile Trp Ile Thr Gly Leu Ser Gly Ser Gly Lys
            20                  25                  30

Ser Thr Leu Ala Cys Ala Leu Ser Arg Ala Leu His
        35                  40

<210> SEQ ID NO 206
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 7-6

<400> SEQUENCE: 206

Arg Gly Lys Leu
1

<210> SEQ ID NO 207
<211> LENGTH: 18
<212> TYPE: PRT
<213> ORGANISM: Artificial sequence
<220> FEATURE:
<221> NAME/KEY: misc_feature
<222> LOCATION: (1)..(18)
<223> OTHER INFORMATION: Fragment of consensus sequence of Table 7-6

<400> SEQUENCE: 207
```

```
Tyr Ile Leu Asp Gly Asp Asn Val Arg His Gly Leu Asn Ser Asp Leu
1               5                   10                  15

Ser Phe

<210> SEQ ID NO 208
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 7-6

<400> SEQUENCE: 208

Ala Glu Asp Arg Ala Glu
1               5

<210> SEQ ID NO 209
<211> LENGTH: 16
<212> TYPE: PRT
<213> ORGANISM: Artificial sequence
<220> FEATURE:
<221> NAME/KEY: misc_feature
<222> LOCATION: (1)..(16)
<223> OTHER INFORMATION: Fragment of consensus sequence of Table 7-6

<400> SEQUENCE: 209

Asn Ile Arg Arg Val Gly Glu Val Ala Lys Leu Phe Ala Asp Ala Gly
1               5                   10                  15

<210> SEQ ID NO 210
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 7-6

<400> SEQUENCE: 210

Val Cys Ile Ala Ser Leu Ile Ser Pro Tyr Arg
1               5                   10

<210> SEQ ID NO 211
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 7-6

<400> SEQUENCE: 211

Ala Cys Arg Ala Leu Leu Pro
1               5

<210> SEQ ID NO 212
<211> LENGTH: 25
<212> TYPE: PRT
<213> ORGANISM: Artificial sequence
<220> FEATURE:
<221> NAME/KEY: misc_feature
<222> LOCATION: (1)..(25)
<223> OTHER INFORMATION: Fragment of consensus sequence of Table 7-6

<400> SEQUENCE: 212

Gly Asp Phe Ile Glu Val Phe Met Asp Val Pro Leu Glu Val Cys Glu
```

```
1               5                   10                  15
Ala Arg Asp Pro Lys Gly Leu Tyr Lys
            20                  25

<210> SEQ ID NO 213
<211> LENGTH: 27
<212> TYPE: PRT
<213> ORGANISM: Artificial sequence
<220> FEATURE:
<221> NAME/KEY: misc_feature
<222> LOCATION: (1)..(27)
<223> OTHER INFORMATION: Fragment of consensus sequence of Table 7-6

<400> SEQUENCE: 213

Ala Arg Ala Gly Lys Ile Lys Gly Phe Thr Gly Ile Asp Asp Pro Tyr
1               5                   10                  15

Glu Ala Pro Leu Asp Cys Glu Ile Val Ile Gln
            20                  25

<210> SEQ ID NO 214
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 7-6

<400> SEQUENCE: 214

Met Ala Asp Ile Val Val Ser Tyr Leu Glu
1               5                   10

<210> SEQ ID NO 215
<211> LENGTH: 23
<212> TYPE: PRT
<213> ORGANISM: Artificial sequence
<220> FEATURE:
<221> NAME/KEY: misc_feature
<222> LOCATION: (1)..(23)
<223> OTHER INFORMATION: Fragment of consensus sequence of Table 8-7

<400> SEQUENCE: 215

Met Phe Arg Ala Met Ser Thr Arg Lys Val His Gly Gly Tyr Glu Lys
1               5                   10                  15

Leu Gly Asp Glu Glu Ala Arg
            20

<210> SEQ ID NO 216
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 8-7

<400> SEQUENCE: 216

Leu Lys Arg Val
1

<210> SEQ ID NO 217
<211> LENGTH: 14
<212> TYPE: PRT
<213> ORGANISM: Artificial sequence
<220> FEATURE:
<221> NAME/KEY: misc_feature
<222> LOCATION: (1)..(14)
```

<223> OTHER INFORMATION: Fragment of consensus sequence of Table 8-7

<400> SEQUENCE: 217

Ser Val Pro Ala Ser Val Tyr Gly His Ser Arg Asn Pro Val
1               5                   10

<210> SEQ ID NO 218
<211> LENGTH: 15
<212> TYPE: PRT
<213> ORGANISM: Artificial sequence
<220> FEATURE:
<221> NAME/KEY: misc_feature
<222> LOCATION: (1)..(15)
<223> OTHER INFORMATION: Fragment of consensus sequence of Table 8-7

<400> SEQUENCE: 218

Gln Glu Val Lys Lys Thr Pro Thr Ala Lys Pro Thr Gly Gly Ser
1               5                   10                  15

<210> SEQ ID NO 219
<211> LENGTH: 18
<212> TYPE: PRT
<213> ORGANISM: Artificial sequence
<220> FEATURE:
<221> NAME/KEY: misc_feature
<222> LOCATION: (1)..(18)
<223> OTHER INFORMATION: Fragment of consensus sequence of Table 8-7

<400> SEQUENCE: 219

Val His Pro Leu Ser Phe Phe Asp Val His Phe Gln Arg Lys Lys Lys
1               5                   10                  15

Lys Thr

<210> SEQ ID NO 220
<211> LENGTH: 19
<212> TYPE: PRT
<213> ORGANISM: Artificial sequence
<220> FEATURE:
<221> NAME/KEY: misc_feature
<222> LOCATION: (1)..(19)
<223> OTHER INFORMATION: Fragment of consensus sequence of Table 8-7

<400> SEQUENCE: 220

Lys Lys Lys Ser Leu Ala Thr Ala Lys Pro Glu Phe Ala Arg Tyr Met
1               5                   10                  15

Glu Tyr Val

<210> SEQ ID NO 221
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 8-7

<400> SEQUENCE: 221

Glu Gly Gly Val Trp Asp Pro
1               5

<210> SEQ ID NO 222
<211> LENGTH: 9
<212> TYPE: PRT
<213> ORGANISM: Artificial sequence
<220> FEATURE:
<221> NAME/KEY: misc_feature
<222> LOCATION: (1)..(9)

<223> OTHER INFORMATION: Fragment of consensus sequence of Table 8-7

<400> SEQUENCE: 222

Ser Asn Ala Pro Val Ile His Tyr Arg
1               5

<210> SEQ ID NO 223
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 10-6

<400> SEQUENCE: 223

Leu Leu Leu Leu Leu Ser Ala Ser Ser Ala Val
1               5                   10

<210> SEQ ID NO 224
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 10-6

<400> SEQUENCE: 224

Asp Pro Ser Phe Gln Lys
1               5

<210> SEQ ID NO 225
<211> LENGTH: 27
<212> TYPE: PRT
<213> ORGANISM: Artificial sequence
<220> FEATURE:
<221> NAME/KEY: misc_feature
<222> LOCATION: (1)..(27)
<223> OTHER INFORMATION: Fragment of consensus sequence of Table 10-6

<400> SEQUENCE: 225

Ser Gly Pro Glu Ala Phe Ala Phe Asp Ser Thr Gly Lys Gly Phe Tyr
1               5                   10                  15

Thr Gly Val Ser Asp Gly Arg Ile Leu Lys Tyr
            20                  25

<210> SEQ ID NO 226
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 10-6

<400> SEQUENCE: 226

Val Asp Phe Ala
1

<210> SEQ ID NO 227
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 10-6

```
<400> SEQUENCE: 227

Leu Cys Gly Arg Pro
1               5

<210> SEQ ID NO 228
<211> LENGTH: 19
<212> TYPE: PRT
<213> ORGANISM: Artificial sequence
<220> FEATURE:
<221> NAME/KEY: misc_feature
<222> LOCATION: (1)..(19)
<223> OTHER INFORMATION: Fragment of consensus sequence of Table 10-6

<400> SEQUENCE: 228

Gly Ile Ala Phe Asn Lys Thr Gly Asp Leu Tyr Val Ala Asp Ala Tyr
1               5                   10                  15

Leu Gly Leu

<210> SEQ ID NO 229
<211> LENGTH: 35
<212> TYPE: PRT
<213> ORGANISM: Artificial sequence
<220> FEATURE:
<221> NAME/KEY: misc_feature
<222> LOCATION: (1)..(35)
<223> OTHER INFORMATION: Fragment of consensus sequence of Table 10-6

<400> SEQUENCE: 229

Gly Gly Leu Ala Thr Gln Leu Ala Thr Ser Val Asp Gly Val Pro Phe
1               5                   10                  15

Lys Trp Leu Asp Gly Leu Asp Val Asp Gln Arg Thr Gly Val Val Tyr
            20                  25                  30

Phe Thr Asp
        35

<210> SEQ ID NO 230
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 10-6

<400> SEQUENCE: 230

Val Leu Ile Val
1

<210> SEQ ID NO 231
<211> LENGTH: 12
<212> TYPE: PRT
<213> ORGANISM: Artificial sequence
<220> FEATURE:
<221> NAME/KEY: misc_feature
<222> LOCATION: (1)..(12)
<223> OTHER INFORMATION: Fragment of consensus sequence of Table 10-6

<400> SEQUENCE: 231

Thr Gly Arg Leu Leu Lys Tyr Asp Pro Ser Thr Lys
1               5                   10

<210> SEQ ID NO 232
<211> LENGTH: 8
<212> TYPE: PRT
<213> ORGANISM: Artificial sequence
```

```
<220> FEATURE:
<221> NAME/KEY: misc_feature
<222> LOCATION: (1)..(8)
<223> OTHER INFORMATION: Fragment of consensus sequence of Table 10-6

<400> SEQUENCE: 232

Val Thr Val Leu Met Lys Gly Leu
1               5

<210> SEQ ID NO 233
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 10-6

<400> SEQUENCE: 233

Asp Gly Ser Phe Val Leu Val Ala Glu Phe
1               5                   10

<210> SEQ ID NO 234
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 10-6

<400> SEQUENCE: 234

Ile Lys Lys Tyr Trp
1               5

<210> SEQ ID NO 235
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 10-6

<400> SEQUENCE: 235

Lys Gly Pro Lys Ala Gly Ser Ser
1               5

<210> SEQ ID NO 236
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 10-6

<400> SEQUENCE: 236

Asn Pro Asp Asn Ile Lys Arg
1               5

<210> SEQ ID NO 237
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 10-6
```

```
<400> SEQUENCE: 237

Gly Asn Phe Trp Val Ala Ser Ser
1               5

<210> SEQ ID NO 238
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 10-6

<400> SEQUENCE: 238

Leu Ser Glu Val
1

<210> SEQ ID NO 239
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 10-6

<400> SEQUENCE: 239

Leu Tyr Ile Gly Thr Leu
1               5

<210> SEQ ID NO 240
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 10-6

<400> SEQUENCE: 240

Pro Phe Ala Gly Ile Leu
1               5

<210> SEQ ID NO 241
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 11-6

<400> SEQUENCE: 241

Ala Leu Val Ser Leu Leu Leu Leu Ser
1               5                   10

<210> SEQ ID NO 242
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 11-6

<400> SEQUENCE: 242

Pro Ser Phe Gln Lys Leu
```

```
<210> SEQ ID NO 243
<211> LENGTH: 27
<212> TYPE: PRT
<213> ORGANISM: Artificial sequence
<220> FEATURE:
<221> NAME/KEY: misc_feature
<222> LOCATION: (1)..(27)
<223> OTHER INFORMATION: Fragment of consensus sequence of Table 11-6

<400> SEQUENCE: 243

Ser Gly Pro Glu Ser Phe Ala Phe Asp Ser Thr Gly Lys Gly Phe Tyr
1               5                   10                  15

Thr Gly Val Ser Asp Gly Arg Ile Leu Lys Tyr
            20                  25

<210> SEQ ID NO 244
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 11-6

<400> SEQUENCE: 244

Val Asp Phe Ala
1

<210> SEQ ID NO 245
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 11-6

<400> SEQUENCE: 245

Leu Cys Gly Arg Pro
1               5

<210> SEQ ID NO 246
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 11-6

<400> SEQUENCE: 246

Gly Ile Ser Phe Asn
1               5

<210> SEQ ID NO 247
<211> LENGTH: 14
<212> TYPE: PRT
<213> ORGANISM: Artificial sequence
<220> FEATURE:
<221> NAME/KEY: misc_feature
<222> LOCATION: (1)..(14)
<223> OTHER INFORMATION: Fragment of consensus sequence of Table 11-6

<400> SEQUENCE: 247

Lys Thr Gly Asp Leu Tyr Val Ala Asp Ala Tyr Leu Gly Leu
1               5                   10
```

```
<210> SEQ ID NO 248
<211> LENGTH: 11
<212> TYPE: PRT
<213> ORGANISM: Artificial sequence
<220> FEATURE:
<221> NAME/KEY: misc_feature
<222> LOCATION: (1)..(11)
<223> OTHER INFORMATION: Fragment of consensus sequence of Table 11-6

<400> SEQUENCE: 248

Gly Gly Leu Ala Thr Gln Leu Ala Thr Ser Val
1               5                   10

<210> SEQ ID NO 249
<211> LENGTH: 23
<212> TYPE: PRT
<213> ORGANISM: Artificial sequence
<220> FEATURE:
<221> NAME/KEY: misc_feature
<222> LOCATION: (1)..(23)
<223> OTHER INFORMATION: Fragment of consensus sequence of Table 11-6

<400> SEQUENCE: 249

Gly Val Pro Phe Lys Trp Leu Asp Gly Leu Asp Val Asp Gln Arg Thr
1               5                   10                  15

Gly Val Val Tyr Phe Thr Asp
            20

<210> SEQ ID NO 250
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 11-6

<400> SEQUENCE: 250

Thr Gly Arg Leu
1

<210> SEQ ID NO 251
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 11-6

<400> SEQUENCE: 251

Lys Tyr Asp Pro Ser Thr Lys
1               5

<210> SEQ ID NO 252
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 252

Val Thr Val Leu Met Lys Gly Leu
1               5
```

```
<210> SEQ ID NO 253
<211> LENGTH: 10
<212> TYPE: PRT
<213> ORGANISM: Artificial sequence
<220> FEATURE:
<221> NAME/KEY: misc_feature
<222> LOCATION: (1)..(10)
<223> OTHER INFORMATION: Fragment of consensus sequence of Table 11-6

<400> SEQUENCE: 253

Asp Gly Ser Phe Val Leu Val Ala Glu Phe
1               5                   10

<210> SEQ ID NO 254
<211> LENGTH: 5
<212> TYPE: PRT
<213> ORGANISM: Artificial sequence
<220> FEATURE:
<221> NAME/KEY: misc_feature
<222> LOCATION: (1)..(5)
<223> OTHER INFORMATION: Fragment of consensus sequence of Table 11-6

<400> SEQUENCE: 254

Ile Lys Lys Tyr Trp
1               5

<210> SEQ ID NO 255
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 255

Lys Gly Pro Lys Ala Gly Thr Ser
1               5

<210> SEQ ID NO 256
<211> LENGTH: 9
<212> TYPE: PRT
<213> ORGANISM: Artificial sequence
<220> FEATURE:
<221> NAME/KEY: misc_feature
<222> LOCATION: (1)..(9)
<223> OTHER INFORMATION: Fragment of consensus sequence of Table 11-6

<400> SEQUENCE: 256

Asn Pro Asp Asn Ile Lys Arg Asn Gly
1               5

<210> SEQ ID NO 257
<211> LENGTH: 8
<212> TYPE: PRT
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 257

Gly Asn Phe Trp Val Ala Ser Ser
1               5

<210> SEQ ID NO 258
<211> LENGTH: 8
<212> TYPE: PRT
```

```
<213> ORGANISM: Artificial sequence
<220> FEATURE:
<221> NAME/KEY: misc_feature
<222> LOCATION: (1)..(8)
<223> OTHER INFORMATION: Fragment of consensus sequence of Table 11-6

<400> SEQUENCE: 258

Asp Pro Arg Ala Val Lys Val Asp
1               5

<210> SEQ ID NO 259
<211> LENGTH: 7
<212> TYPE: PRT
<213> ORGANISM: Artificial sequence
<220> FEATURE:
<221> NAME/KEY: misc_feature
<222> LOCATION: (1)..(7)
<223> OTHER INFORMATION: Fragment of consensus sequence of Table 11-6

<400> SEQUENCE: 259

Val Leu Gln Val Ile Pro Leu
1               5

<210> SEQ ID NO 260
<211> LENGTH: 4
<212> TYPE: PRT
<213> ORGANISM: Artificial sequence
<220> FEATURE:
<221> NAME/KEY: misc_feature
<222> LOCATION: (1)..(4)
<223> OTHER INFORMATION: Fragment of consensus sequence of Table 11-6

<400> SEQUENCE: 260

Ile Ser Glu Val
1

<210> SEQ ID NO 261
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 11-6

<400> SEQUENCE: 261

Leu Tyr Ile Gly Ser Leu
1               5

<210> SEQ ID NO 262
<211> LENGTH: 6
<212> TYPE: PRT
<213> ORGANISM: Artificial sequence
<220> FEATURE:
<221> NAME/KEY: misc_feature
<222> LOCATION: (1)..(6)
<223> OTHER INFORMATION: Fragment of consensus sequence of Table 11-6

<400> SEQUENCE: 262

Pro Phe Ala Gly Ile Leu
1               5
```

NUCLEOTIDE SEQUENCES AND POLYPEPTIDES ENCODED THEREBY USEFUL FOR MODIFYING PLANT CHARACTERISTICS

This application is a divisional of application Ser. No. 15/953,264, filed on Apr. 13, 2018 (pending), which application is a continuation of application Ser. No. 14/565,186, filed on Dec. 9, 2014 (now U.S. Pat. No. 9,957,521), which is a divisional of application Ser. No. 13/184,361 filed on Jul. 15, 2011 (now U.S. Pat. No. 8,962,921), which claims priority to application Ser. No. 11/140,450 filed on May 27, 2005 (now U.S. Pat. No. 8,022,273), which claims priority under 35 U.S.C. § 119(e) of U.S. Provisional Application No. 60/575,253 filed on May 27, 2004. The entirety of each of the above-mentioned patent applications is hereby incorporated by reference.

This application is a divisional of application Ser. No. 13/184,361 filed on Jul. 15, 2011, which claims priority to application Ser. No. 11/140,450 filed on May 27, 2005, which claims priority under 35 U.S.C. § 119(e) of U.S. Provisional Application No. 60/575,253 filed on May 27, 2004. The entirety of each of the above-mentioned patent applications is hereby incorporated by reference.

FIELD OF THE INVENTION

The present invention relates to isolated polynucleotides, polypeptides encoded thereby, and the use of those sequences for making transgenic plants with modulated water use efficiency.

BACKGROUND OF THE INVENTION

Plants are constantly exposed to a variety of biotic (e.g., pathogen infection and insect herbivory) and abiotic (e.g., high or low temperature, drought, flood, anaerobic conditions and salinity) stresses. To survive these challenges, plants have developed elaborate mechanisms to perceive external signals and to manifest adaptive responses with proper physiological and morphological changes (Bohnert et al., 1995). Plants exposed to heat and/or low water or drought conditions typically have low yields of plant material, seeds, fruit and other edible products. Some countries of the world consistently have very low rainfall and therefore have problems growing sufficient food crops for their population. Yet it has been observed that some plants survive and thrive in low water environments. It would, therefore, be of great interest and importance to be able to identify genes that confer improved water efficiency characteristics to thereby enable one to create transformed plants (such as crop plants) with modulated water efficiency characteristics to, thereby, better survive high and/or low heat, high and/or low water, and drought or flood conditions. Exogenous application to plants of high concentrations of PEG and mannitol are known to produce osmotic stress resulting in the retardation of growth and vigor and are used to assess drought responses. Exogenous application of ABA stimulates drought-responses in plants and can, therefore, be an important screen to identify genes that confer improved water efficiency.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. (Zhang et al. (2004) *Plant Physiol.* 135:615). There is a need for generally applicable processes that improve forest or agricultural plant growth potential. Therefore, the present invention relates to a process for increasing the abiotic stress tolerance and consequently the growth potential in plants, characterized by expression of recombinant DNA molecules stably integrated into the plant genome.

SUMMARY OF THE INVENTION

The present invention, therefore, relates to isolated polynucleotides, polypeptides encoded thereby, and the use of those sequences for making transgenic plants with modulated water use efficiency.

The present invention also relates to processes for increasing the growth potential in plants under abnormal water conditions, recombinant nucleic acid molecules and polypeptides used for these processes and their uses, as well as to plants themselves.

Unless otherwise defined, all technical and scientific terms used herein have the same meaning as commonly understood by one of ordinary skill in the art to which this invention belongs.

DETAILED DESCRIPTION OF THE INVENTION

1. Definitions

The following terms are utilized throughout this application:

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Drought: Plant species vary in their capacity to tolerate drought conditions. For each species, optimal growth can be achieved if a certain level of water is always available. Other factors such as temperature and soil conditions have a significant impact on the availability of water to the plant. "Drought" can be defined as the set of environmental conditions under which a plant will begin to suffer the effects of water deprivation, such as decreased photosynthesis, loss of turgor (wilting) and decreased stomatal conductance. This drought condition results in a significant reduction in yield. Water deprivation may be caused by lack of rainfall or limited irrigation. Alternatively, water deficit may also be caused by high temperatures, low humidity, saline soils, freezing temperatures or water-logged soils that damage roots and limit water uptake to the shoot. Since plant species vary in their capacity to tolerate water deficit, the precise environmental conditions that cause drought stress can not be generalized. However, drought tolerant plants produce higher biomass and yield than plants that are not drought tolerant. Differences in physical appearance, recovery and yield can be quantified and statistically analyzed using well known measurement and analysis methods.

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology*, 13; 486 (1995)), biolistic methods (Armaleo et al., *Current Genetics* 17; 97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Flood: Plant species vary in their capacity to tolerate flooding. Some plants, such as rice, are cultivated in water while plants such as corn do not tolerate flooding. "Flood," as referred to within, is the state of water saturation at which soils become hypoxic or anoxic, thus limiting respiration in the root. Reduced respiration damages roots and can limit the permeability of roots to water, resulting in decreased leaf water potential and wilting. Since plant species vary in their capacity to tolerate flooding, the precise environmental conditions that cause flood stress can not be generalized. However, flood tolerant plants are characterized by their ability to retain their normal appearance or recover quickly from flood. Such flood tolerant plants produce higher biomass and yield than plants that are not flood tolerant. Differences in physical appearance, recovery and yield can be quantified and statistically analyzed using well known measurement and analysis methods.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical and within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily to the same degree. Typically, comparable proteins give the same characteristics where the quantitative measurement due to one of the comparables is at least 20% of the other; more typically, between 30 to 40%; even more typically, between 50-60%; even more typically, 70 to 80%; even more typically between 90 to 100%.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

High Temperature: Plant species vary in their capacity to tolerate high temperatures. Very few plant species can survive temperatures higher than 45° C. The effects of high temperatures on plants, however, can begin at lower temperatures depending on the species and other environmental conditions such as humidity and soil moisture. "High temperature" can be defined as the temperature at which a given plant species will be adversely affected as evidenced by symptoms such as decreased photosynthesis. Since plant species vary in their capacity to tolerate high temperature, the precise environmental conditions that cause high temperature stress can not be generalized. However, high temperature tolerant plants are characterized by their ability to retain their normal appearance or recover quickly from high temperature conditions. Such high temperature tolerant plants produce higher biomass and yield than plants that are not high temperature tolerant. Differences in physical appearance, recovery and yield can be quantified and statistically analyzed using well know measurement and analysis methods.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light.

Low Temperature: Plant species vary in their capacity to tolerate low temperatures. Chilling-sensitive plant species, including may agronomically important species, can be injured by cold, above-freezing temperatures. At temperatures below the freezing-point of water most plant species will be damaged. Thus, "low temperature" can be defined as the temperature at which a given plant species will be adversely affected as evidenced by symptoms such as decreased photosynthesis and membrane damage (measured by electrolyte leakage). Since plant species vary in their capacity to tolerate low temperature, the precise environmental conditions that cause low temperature stress can not be generalized. However, low temperature tolerant plants are characterized by their ability to retain their normal appearance or recover quickly from low temperature conditions. Such low temperature tolerant plants produce higher biomass and yield than plants that are not low temperature tolerant. Differences in physical appearance, recovery and yield can be quantified and statistically analyzed using well known measurement and analysis methods.

Plant seeds vary considerably in their ability to germinate under low temperature conditions. Seeds of most plant species will not germinate at temperatures less than 10° C. Once seeds have imbibed water they become very susceptible to disease, water and chemical damage. Seeds that are tolerant to low temperature stress during germination can survive for relatively long periods under which the temperature is too low to germinate. Since plant species vary in their capacity to tolerate low temperature during germination, the precise environmental conditions that cause low temperature stress during germination can not be generalized. However, plants that tolerate low temperature during germination are characterized by their ability to remain viable or recover quickly from low temperature conditions. Such low temperature tolerant plants produce, germinate, become established, grow more quickly and ultimately produce more biomass and yield than plants that are not low temperature tolerant. Differences in germination rate, appearance, recovery and yield can be quantified and statistically analyzed using well known measurement and analysis methods.

Masterpool: The "master pools" discussed in these experiments are a pool of seeds from five different transgenic plants transformed with the same exogenous gene.

Misexpression: The terra "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2444 (1988), by computerized implementations of these algorithms (GAP, BES FIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for. *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A. "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

Specific Promoter: In the context of the current invention, "specific promoters" refers to promoters that have a high preference for being active in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30(2):321-9.); RCc2 and RCc3, promoters that direct root-specific gene transcription in rice (Xu et al., *Plant Mol. Biol.* 27:237 (1995) and TobRB27, a root-specific promoter from tobacco (Yamamoto et al. (1991) *Plant Cell* 3:371).

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \text{ (G+C)})-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log\{[Na^+]/(1+0.7[Na^+])\}+0.41(\% \text{ G+C})-500/L0.63(\% \text{ formamide}) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$ medium or moderate stringency is 26-29° C. below $T_m$, and low stringency is 45-48° C. below $T_m$.

Superpool: As used in the context of the current invention, a "superpool" refers to a mixture of seed from 100 different "master pools". Thus, the superpool contains an equal amount of seed from 500 different events, but only represents 100 transgenic plants with a distinct exogenous nucleotide sequence transformed into them, because the master pools are of 5 different events with the same exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a plant.

2. Important Characteristics of the Polynucleotides and Polypeptides of the Invention The polynucleotides and polypeptides of the present invention are of interest because when they are misexpressed (i.e. when expressed at a non-natural location or in an increased or decreased amount) they produce plants with modified water use efficiency. "Water use efficiency" is a term that includes various responses to environmental conditions that affect the amount of water available to the plant. For example, under high heat conditions water is rapidly evaporated from both the soil and from the plant itself, resulting in a decrease of available water for maintaining or initiating physiological processes. Likewise, water availability is limited during cold or drought conditions or when there is low water content in the soil. Interestingly, flood conditions also affect the amount of water available to the plant because it damages the roots and thus limits the plant's ability to transport water to the shoot. As used herein, modulating water use efficiency is intended to encompass all of these situations as well as other environmental situations that affect the plant's ability to use and/or maintain water effectively (e.g. osmotic stress, salinity, etc.).

The polynucleotides and polypeptides of the invention, as discussed below and as evidenced by the results of various experiments, are useful for modulating water use efficiency. These traits can be used to exploit or maximize plant products for agricultural, ornamental or forestry purposes in different environment conditions of water supply. Modulating the expression of the nucleotides and polypeptides of the present invention leads to transgenic plants that will require less water and result in better yield in high heat and/or drought conditions, or that have increased tolerance levels for an excess of water and result in better yield in wet conditions. Both categories of transgenic plants lead to reduced costs for the farmer and better yield in their respective environmental conditions.

3. The Polynucleotides and Polypeptides of the Invention

The polynucleotides of the invention, and the proteins expressed thereby, are set forth in the Sequence Listing. Some of these sequences are functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity and generally share at least one biochemical and/or phenotypic activity. For example, biochemical functionally comparable proteins are proteins that act on the same reactant to give the same product.

Another class of functionally comparable proteins is phenotypic functionally comparable proteins. The members of this class regulate the same physical characteristic, such as increased drought tolerance. Proteins can be considered phenotypic functionally comparable proteins even if the proteins give rise to the same physical characteristic, but to a different degree.

The polypeptides of the invention also include those comprising the consensus sequences described in Tables 1-4, 2-8, 3-9, 5-8, 6-8, 7-6, 8-7, 10-6 and 11-6. A consensus sequence defines the important conserved amino acids and/or domains within a polypeptide. Thus, all those sequences that conform to the consensus sequence are suitable for the same purpose. Polypeptides comprised of a sequence within and defined by one of the consensus sequences can be utilized for the purposes of the invention namely to make transgenic plants with improved water use efficiency, including improved tolerance to heat or high or low water conditions.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct can be made using standard recombinant DNA techniques (Sambrook et al. 1989) and can be introduced to the species of interest by Agrobacterium-mediated transformation or by other means of transformation as referenced below.

The vector backbone can be any of those, typical in the art such as plasmids, viruses, artificial chromosomes, BACs, YACs and PACs and vectors of the sort described by
(a) BAC: Shizuya et al., Proc. Natl. Acad. Sci. USA 89: 8794-8797 (1992); Hamilton et al., Proc. Natl. Acad. Sri. USA 93: 9975-9979 (1996);
(b) YAC: Burke et al., Science 236:806-812 (1987);
(c) PAC: Sternberg N. et al., Proc Natl Acad Sci USA. January; 87(1):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol Biol 170: 827-842 (1983); or Insertion vector, e.g., Huynh et al., in: Glover N M (ed) DNA Cloning: A practical Approach, Vol. 1 Oxford: IRL Press (1985); T-DNA gene fusion vectors: Walden et al., Mol Cell Biol 1: 175-194 (1990); and
(g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as p326 or CaMV35S. Alternatively, the plant promoter directs transcription of a sequence of the invention in a specific tissue manner (tissue-specific promoter) or is otherwise under more precise environmental control (inducible promoter). Various plant promoters, including constitutive, tissue-specific and inducible, are known to those skilled in the art and can be utilized in the present invention. Typically, preferred promoters to use in the present invention are those that are induced by heat or low water conditions Such as the RD29a promoter (Kasuga et al., Plant Cell Physiol. 45:346 (2004) and Yamaguchi-Shinozaki and Shinozaki, Mol Gen Genet. 236: 331 (1993)) or other. DRE-containing (dehydration-responsive elements) promoters (Liu et al, Cell 10: 1391 (1998)). Another preferred embodiment of the present invention is the use of root specific promoters such as those present in the AtXTH17, AtXH118, AtXTH19 and AtXTH20 genes of Arabidopsis (Vissenberg et al. (2005) Plant Cell Physiol 46:192) or guard cell specific promoters such as TGG1 or KST1 (Husebye et al. (2002) Plant Physiol 128:1180; Plesch et al. (2001) Plant J 28:455).

Alternatively, misexpression can be accomplished using a two component system, whereby the first component comprises a transgenic plant comprising a transcriptional activator operatively linked to a promoter and the second component comprises a transgenic plant comprising a sequence of the invention operatively linked to the target binding sequence/region of the transcriptional activator. The two transgenic plants are crossed and the sequence of the invention is expressed in their progeny. In another alternative, the misexpression can be accomplished by transforming the sequences of the two component system into one transgenic plant line.

Any promoter that functions in plants can be used in the first component, such as those discussed above. Suitable transcriptional activator polypeptides include, but are not limited to, those encoding HAP1 and GAL4. The binding sequence recognized and targeted by the selected transcriptional activator protein (e.g. a UAS element) is used in the second component.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al., Ann. Rev. Genet. 22:421 (1988); and Christou, Euphytica, v. 85, n. 1-3:13-27, (1995).

Processes for the transformation and regeneration of monocotyledonous and dicotyledonous plants are known to the person skilled in the art. For the introduction of DNA into a plant host cell a variety of techniques is available. These techniques include transformation of plant cells by injection (e.g. Newell, 2000), microinjection (e.g. Griesbach (1987) Plant Sci. 50 69-77), electroporation of DNA (e.g. Fromm et al. (1985) Proc. Natl Acad USA 82:5824 and Wan and Lemaux, Plant Physiol. 104 (1994), 37-48), PEG (e.g. Paszkowski et al. (1984) EMBO J. 3:2717), use of bioiistics (e.g. Klein et al. (1987) Nature 327:773), fusion of cells or protoplasts (Willmitzer, L., 1993 Transgenic plants. In: Biotechnology, A Multi-Volume Comprehensive Treatise (H. J. Rehm, G. Reed, A. Pühier, P. Stadler, eds., Vol. 2, 627-659, VCH Weinheim-New York-Basel-Cambridge), via T-DNA using Agrobacterium tumefaciens (e.g. Fraley et al. (Crit. Rev. Plant. Sci. 4, 1-46 and Fromm et al., Biotechnology 8 (1990), 833-844) or Agrobacterium rhizogenes (e.g. Cho et al. (2000) Planta 210:195-204) or other bacterial hosts (e.g. Brootghaerts et al. (2005) Nature 433:629-633), as well as further possibilities.

In addition, a number of non-stable transformation methods well known to those skilled in the art may be desirable for the present invention. Such methods include, but are not limited to, transient expression (e.g. Lincoln et al. (1998) Plant Mol. Biol. Rep. 16:1-4) and viral transfection (e.g. Lacomme et al. (2001) In "Genetically Engineered Viruses" (C. J. A. Ring and E. D. Blair, Eds). Pp. 59-99, BIOS Scientific Publishers, Ltd. Oxford, UK).

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to heat and/or low water conditions, without reduction in fertility, on essentially any plant.

The nucleotide sequences according to the invention encode appropriate proteins from any organism, in particular from plants, fungi, bacteria or animals.

The process according to the invention can be applied to any plant, preferably higher plants, pertaining to the classes of Arigiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidals, Eucomiales, Leitneriales, Myricales, Fagales, Casuarinales, Calyophyllales, Batales, Polygonales, Plumbaginales, Dilleniales, Theaks, Malvaks, Urticales, Lecythidales, Violales, Salicaks, Capparales, Ericaks, Diapensales, Ebenaks, Primulaks, Rosales, Fabaks, Podostemales, Halorogaks, Myrtaks, Cornaks, Proteales, Santaks, Rafflesiales, Celastrales, Euphorbiales, Rhamnales, Sapindales, Juglandales, Geraniales, Polygalales, Umbellales, Gentianales, Polemoniales, Lamiaies, Plantaginales, Scrophulariales, Campanulaks, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadaks and Gnetales.

The method of the invention is preferably used with plants that are interesting for agriculture, horticulture, biomass for bioconversion and/or forestry. Examples are tobacco, oilseed rape, sugar beet, potato, tomato, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

Homologs Encompassed by the Invention

Sequences of the invention include proteins comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid and amino acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

It is understood that certain amino acids may be substituted for other amino acids in a protein or peptide structure (and the nucleic acid sequence that codes for it) without appreciable change or loss of its biological utility or activity. The amino acid changes may be achieved by changing the codons of the nucleic acid sequence.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs (see below). Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

In a further aspect of the present invention, nucleic acid molecules of the present invention can comprise sequences that differ from those encoding a protein or fragment thereof selected from the group consisting of the sequences present in the Sequence Listing due to the fact that the different nucleic acid sequence encodes a protein having one or more conservative amino acid changes.

In another aspect, biologically functional equivalents of the proteins or fragments thereof of the present invention can have about 10 or fewer conservative amino acid changes, more preferably about 7 or fewer conservative amino acid changes, and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

5. Experiments Confirming the Usefulness of the Polynucleotides and Polypeptides of the Invention 5.1 Procedures The nucleotide sequences of the invention were identified by use of a variety of screens for modified water conditions, including heat and/or low water conditions. These screens are recognized by those skilled in the art to be predictive of nucleotide sequences that provide plants with improved water use efficiency including improved tolerance to heat and/or low water conditions because they emulate the different environmental conditions that can result from increased heat and/or low water conditions. These screens generally fall into two categories (1) soil screens and (2) in vitro screens.

Soil screens have the advantage of assaying the response of the entire plant to particular conditions, such as drought or high heat. On the other hand, in vitro screens have the advantage of relying on defined media and so allow more defined manipulation of growth conditions. "Surrogate" in vitro screens use particular chemicals to alter the water available to the plant by manipulating the concentrations and/or components of the growth media. For example, the ability of the plant to maintain the water concentration within its cells, which can occur during times of low water in the soil, can be tested by growing plants on high sucrose media. Such a screen thus allows one to separate the effects of water loss from roots from, for example, the water loss from leaves during high heat conditions. Each of the screens used is described in more detail below.

In general, the screens used to identify the polynucleotides and polypeptides of the invention were conducted using superpools of *Arabidopsis* $T_2$ transformed plants. The $T_1$ plants were transformed with a Ti plasmid containing a particular SEQ ID NO in the sense orientation relative to a constitutive promoter and harboring the plant-selectable marker gene phosphinothricin acetyltransferase (PAT), which confers herbicide resistance to transformed plants. For surrogate screens, seed from multiple superpools (1,200 $T_2$ seeds from each superpool) were tested. $T_3$ seed were collected from the resistant plants and retested on all other surrogate screens. The results of the screens conducted for each SEQ ID NO can be found in the Examples below.

5.1. Mannitol

Screens for mannitol resistant seedlings are surrogate screens for drought (see Quesada et al., Genetic analysis of salt-tolerant mutants in *Arabidopsis thaliana*. Genetics. 2000 154:421-36).

Seeds are sterilized in 30% household bleach for 5 minutes and then washed with double distilled deionized water three times. Sterilized seed is stored in the dark at 4° C. for a minimum of 3 days before use.

Manitol media is prepared by mixing 375 ml sterile 1 mM mannitol with 375 ml sterile 1×MS. Approximately 1200 seeds are evenly spaced per PEG plate before incubating at 22° C. for 14 days.

Putative mannitol-resistant seedlings are transferred to MS with 3% sucrose for recovery. Approximately one week later, resistant seedlings are transferred to soil and sprayed with Finale. Finale resistant plants are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested on 375 mM mannitol media.

5.1.2. Polyethylene Glycol (PEG)

Screens for PEG resistant seedlings are surrogate screens for drought (see van der Week et al., Growth of *Arabidopsis thaliana* seedlings under water deficit studied by control of water potential in nutrient-agar media. *J Exp Bot*. 2000 51(350):1555-62).

Seeds are sterilized in 30% household bleach for 5 minutes and then washed with double distilled deionized water three times. Sterilized seed is stored in the dark at 4° C. for a minimum of 3 days before use.

18% PEG media is prepared by mixing 360 ml of hot sterile 50% PEG with 400 ml of hot sterile 0.5×MS media. Approximately 1200 seeds are evenly spaced per PEG plate heave incubating at 22° C. for 14 days.

Putative PEG-resistant seedlings are transferred to MS with 0.01% Finale. One week later, resistant seedlings are transferred to soil. Three days later the seedlings are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested using 20% PEG media.

5.1.3. Soil Drought

Soil drought screens identify plants with enhanced tolerance to drought and enhanced recovery after drought.

Seeds are planted in holed flats containing Zonolite vermiculite that are placed in no-holed flats. Flats are watered with 3 L of Hoagland's solution and covered with a plastic dome before being placed at at 4° C. After 4 days, the flats are moved to the Greenhouse (22° C.) and grown 2 weeks, with 1.5 L Hoagland's solution being added every 4 days, or when top of vermiculite is dry. The final application of Hoagland's solution is 4 days prior to the end of the 2 weeks. After 2 weeks, 1 L Hoagland's solution is added to the no-holed flat. After 10 days plants are wilted but still green.

Green, turgid plants are transplanted to 4" square pots containing 60% sunshine mix #5 and 40% thermo-o-rock vermiculite, with Osmocote (1 tbsp/8 L) and Marathon (1 tbsp/8 L). The soil is moistened and the pots sub-irrigated with water. They are grown under a plastic dome for one day, then the plastic dome is removed for the remaining growth period.

To assess plants for enhanced recovery after drought the green wilted plants remaining in the flats are sub-irrigated with 2.5 L Hoagland's solution and cover with cleared with a plastic dome. The following day, the dome is removed and green survivors transplanted to 4" square pots containing 60% sunshine mix #5, 40% Therm-o-rock vermiculite, Osmocote (1 tbsp/8 L) and marathon (1 tbsp/8 L), The soil is moistened and the pots sub-irrigated with water. They are grown under a plastic dome for one day, then the plastic dome is removed for the remaining growth period.

DNA from a leaf from each plant is transferred to FTA paper via pressure and an aliquot of the DNA containing paper used in PCR reactions using the following cycling conditions 94° C. for 10 min, five cycles of 94° C. for 30 sec, 60° C. for 30 sec, 72° C. for 3 min, five cycles of 94° C. for 30 sec, 60° C. for 30 sec, 72° C. for 3 min, 30 cycles of 94° C. for 30 sec, 53° C. for 30 sec, 72° C. for 3 min, 72° C. for 7 min and 4° C. hold. Aliquots of the reaction product are analyzed on a 1% agarose gel stained with ethidium bromide.

$T_3$ Seed from those plants containing the expected PCR product are collected and retested using 50 seeds from each line.

5.1.4. Heat

High heat screens identify plants with enhanced tolerance to heat and enhanced recovery after heat.

Seeds are sterilized in 30% household bleach for 5 minutes and then washed with double distilled deionized water three times, Sterilized seed is stored in the dark at 4° C. for a minimum of 3 days before use.

MS media, pH 5.7 is prepared. Approximately 12 seeds are evenly spaced per MS plate before incubating in the vertical position at 22° C. for 14 days. Under these conditions, the plates are exposed to 12,030 LUX from above and 3,190 LUX from the bottom.

On day 15 the plates are transferred to a 22° C. oven, which increased temperature in 5° C. increments to 45° C. The duration of treatment at 45° C. was based on complete and homogenous wilting of 100 wild-type seedlings (~10 plates). After exposure to 45° C., seedlings were placed in the horizontal position at 23° C. for recovery, Where they remained for 4-11 days. Heat recovery was assessed based on vigor and greenness and continued growth after treatment.

Leaves of control and non-resistant plants become wilted and yellowed after only 2 days, completely bleaching after an additional 4 days. All wild type (WS) and non-heat resistant plants die by day 6.

DNA is isolated from each plant and used in PCR reactions using the following cycling conditions 95° C. for 30 sec, five cycles of 51° C. for 30 sec, 72° C. tier 1.15 min, 95° C. fir 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested.

To differentiate between natural acquired thermo tolerance of recovered $T_3$ events, seeds were sterilized and stratified in parallel to wildtype seed that was never heat treated and wild-type controls previously heat treated with the $T_2$ events. 15 day old seedlings were heat shocked in the dark at 45° C. for 5 hours, as described above. Duration of treatment at 45° C. was based on complete and homogenous wilting of pre-heat treated wild-type seed and un-pretreated wild-type controls. After exposure to 45° C., seedlings were returned to the permissive temperature of 23° C. for recovery where they remained for another 7 days. Thermo tolerance was assessed based on prolonged greenness and continued growth after treatment.

5.1.5 Heat (Soil)

Seeds are sown in pots containing soil of the following composition: 60% autoclaved Sunshine Mix #5, 40% vermiculite with 2.5 Tbsp Osmocote and 2.5 Tbsp 1% granular Marathon per 25 L of soil. After sowing, pots are covered with plastic propagation domes and seed is placed at 4° C. in the dark for at least 3 days. Pots are then returned to the greenhouse (long day light conditions of 16 hours), covered with 55% shade cloth and provided a normal watering regime.

After 7 days, seedlings were transferred to a 36° C. growth chamber under continuous light and allowed to grow until harvest. Plants were watered minimally so as to allow for some drying of the top soil similar to that in heat-induced drought conditions in the field.

Plants are sprayed with a mixture of 3 ml Finale in 48 oz of water. Spraying is repeated every 3-4 days until only transformants remain. The remaining transformants were weeded to a maximum of 5 evenly spaced transformants per pot.

$T_3$ seed was recovered and tested for thermotolerance and recovery as described above.

5.6 High Sucrose

Screens for germination and growth on limited nutrients and 9% sucrose are surrogate screens for the altered carbon/nitrogen balance frequently associated with drought (see Laby et al., The *Arabidopsis* sugar-insensitive mutants sis4 and sis5 are defective in abscisic acid synthesis and response. *Plant Journal* 23: 587-596).

Seeds are sterilized in 30% household bleach for 5 minutes and then washed with double distilled deionized water three times. Sterilized seed is stored in the dark at 4° C. for a minimum of 3 days before use.

MS media containing 9% sucrose is prepared. Approximately 1200 seeds are evenly spaced per MS-sucrose plate before incubating at 22° C. for 9 days.

Putative sucrose-resistant green seedlings are transferred to MS plates. After one week of recovery, resistant the seedlings are genotyped as described below.

DNA from a leaf from each plant is transferred to FTA paper via pressure and an aliquot of the DNA containing paper used in PCR reactions using the following cycling conditions 94° C. for 10 min, five cycles of 94° C. for 30 sec, 60° C. for 30 sec, 72° C. for 3 min, five cycles of 94° C. for 30 sec, 60° C. for 30 see, 72° C. for 3 min, 30 cycles of 94° C. for 30 see, 53° C. for 30 sec, 72° C. for 3 min, 72° C. for 7 min and 4° C. hold. Aliquots of the reaction product are analyzed on a 1% agarose gel stained with ethidium bromide.

$T_3$ Seed from those plants containing the expected PCR product are collected and retested using 9% sucrose MS media.

5.1.7. ABA

Screens for ARA resistant seedlings are surrogate screens for drought.

Seeds are sterilized in 30% household bleach for 5 minutes and then washed with double distilled deionized water three times. Sterilized seed is stored in the dark at 4° C. for a minimum of 3 days before use.

MS media containing 1.5 µM ABA is prepared. Approximately 1200 seeds are evenly spaced per PEG plate before incubating at 22° C. for 14 days.

Putative ABA-resistant seedlings are transferred to MS with 0.01% Finale. One week later, resistant seedlings are transferred to soil. Three days later the seedlings are genotyped as described below.

DNA is isolated from each plant and used in PCR reactions using the following cycling conditions 95° C. for 30 sec, five cycles of 51° C. for 30 sec, 72° C. for 1.15 min, 95° C. for 30 sec, 25 cycles of 48° C. for 30 sec, 72° C. for 1.15 min, 72° C. for 7 min and 4° C. hold. Aliquots of the reaction product are analyzed on a 1.2% agarose gel stained with ethidium bromide.

$T_3$ Seed from those plants containing the expected PCR product are collected and retested using 1.5 µM ABA MS media.

5.1.8. Procedure for Identifying Functional Homologs and Consensus Sequences

The isolated sequence of the invention was compared to the sequences present in the various gene banks. Pairwise comparisons were conducted and those sequences having the highest percent identity to the query sequence identified as functional homologs.

A multi-pairwise alignment was generated using the amino acid query sequence and the amino acid sequence of the functional homologs. This allowed identification of the conserved regions or domains of the polypeptide. Using the conserved regions as a guide, a consensus sequence was generated. This consensus sequence indicates the critical amino acid residues and those can be either substituted and/or deleted without impacting the biological function of the protein.

5.2 Results

The results of the above experiments are set forth below wherein each individual example relates to all of the experimental results for a particular polynucleotide/polypeptide of the invention.

Example 1—Ceres cDNA 12331850

Clone 11830, Ceres cDNA 12331850, encodes a full-length glycosyl hydrolase family 17 protein, which has similarity to elicitor inducible chitinase Nt-SubE76 GI:11071974 from (*Nicotiana tabacum* (C-terminal homology only) and β-1,3-glucanase.

Ectopic expression of Ceres cDNA 12331850 under the control of the CaMV35S or 32449 promoter induces the following phenotypes:

Germination on high concentrations of polyethylene glycol (PEG), mannitol, and abscissic acid (ABA).

Continued growth on high concentration of PEG, mannitol, and ABA.

Generation and Phenotypic Evaluation of $T_1$ Lines Containing 35S::cDNA 12331850.

Wild-type *Arabidopsis* Wassilewskija (WS) plants were transformed with a Ti plasmid containing cDNA 12331850 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12331850 was identified in resistant plants from each of the three surrogate drought screens, the five individual $T_2$ events containing this cDNA (ME01297) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Results:

Qualitative Analysis of 13 Superpools on PEG, Mannitol, and ABA

Resistant candidates were selected based on increased size compared to the largest wild-type control. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 1-1).

TABLE 1-1

Number of Basta$^R$ seedlings identified on several screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12331850 on PEG, Mannitol, and ABA Screens.

Seedlings that survived transfer to soil and which were Basta$^R$-resistant were subjected to PCR and sequencing. At least one resistant plant in each of the three screens contained 35S::cDNA 12331850 (ME01297) making this a good candidate for further testing. $T_2$ seeds from the 5 independent transformants that contain this clone and that were used in the pooling process were tested for Basta$^R$ resistance and for stress tolerance in the 3 surrogate drought screens.

To identify two independent events of 35S::cDNA 12331850 showing PEG, mannitol and ABA resistance, 36 seedlings from each of five events, ME01297-01, 02, 03, 04, and 05 were screened as previously described. Simultaneously, Basta$^R$ segregation was assessed to identify events containing a single insert segregating in a 3:1 (R:S) ratio as calculated by a chi-square test (Table 1-2). All of the events segregated for a single functional insert.

TABLE 1-2

Basta segregation for ME01297 individual events

| Event | Resistant | Sensitive | Total | Probability of Chi-test* |
|---|---|---|---|---|
| ME01297-01 | 22 | 14 | 36 | 0.05429 |
| ME01297-02 | 26 | 10 | 36 | 0.70031 |
| ME01297-03 | 25 | 11 | 36 | 0.44142 |
| ME01297-04 | 22 | 14 | 36 | 0.05429 |
| ME01297-05 | 24 | 12 | 36 | 0.24821 |

*Chi-test to determine whether actual ratio of resistant to sensitive differs from the expected 3:1 ratio.

Events ME01297-02 and 03 were chosen as the two events because they had the strongest and most consistent resistance to PEG, mannitol and ABA Resistance was observed for ME01297-01, 04, and 05 although not in expected ratios in all three screens (data not shown). The controls were sown the same day and on the same plate as the individual events. The transgenic control in each of these plates is a segregant, from this ME line or another ME line being tested, that failed to show resistance to the particular stress. The PEG, mannitol and ABA (Table 1-3) segregation ratios observed for ME01297-02 and 03 are consistent with the presence of a single insert, similar to what we observed for Basta resistance (Table 1-1).

On 18% PEG, the resistant seedlings from these two events show some root growth and they are green with new leaves emerging. The mannitol resistant seedlings also showed more root and shoot growth than the sensitive This gene is annotated as a glycosyl hydrolase family 17, which has similarity to elicitor inducible chitinase Nt-SubE76 G1:11071974 from *Nicotiana tabacum* (C-terminal homology only). TIGR also notes that the protein contains similarity to beta-1,3-glucanase.

Table 1-4 provides the results of the consensus sequence (SEQ ID NOs: 112-120) analysis based on Ceres cDNA 12331850.

TABLE 1-4

```
                                      /tmp/88911.aln

Lead·clone11830     MSTFLIRILL  PLLLILAMTLP  RRSEAESE--  -----QWCIA  DEQTPDDELQ   43
CeresClone:1058242  MATFMLKLVL  PLLFLFMIPP   KTAYAEFE--  -----QWCVA  DEQTTESELQ   43
CeresClone:1602924  MTIVTTPHFI  TVLEFFLLIS   GGIFGHAKAQ  APGQGTWCVA  KPATSDEDLQ   50
gi|129465664        MRGTAGVPDQ  PVPTPTPSVP   TSSSPVPKPP  TQGNKKWCVP  KAEATDAQLQ   50

Consensus           M-TF-----L  P--LF-FM--P  --S-AE----  --G--QWCVA  -EQTTD-ELQ   50

Lead·clone11830     AALDWACGKG  GADCSKMQQE   NQPCFLPNTI  RDHASFAFNS  YYQTYKNKGG   93
CeresClone:1058242  AALDWACGKG  GADCSKIQV-   NQPCYLPNTL  KDHSAYAFNS  YYQKFKHSGG   92
CeresClone:1602924  NNINYACTY-  -VDQRIIRP-   GSVCFEPQKL  VNRASVAMNL  YYQTNGRNMW   97
gi|29465664         SNIDYVQSQS  GMDQGPIQA-   NGACFNPNTV  RAHASYAMNS  WYQSKGRNDF   99

Consensus           A--D--AC-KG  G-DCSKIQ--  NQPCFLPNTI  RDHASYA-NS  YYQT---NG-   100

Lead·clone11830     SCYFKGAAMI  TELDPSHGSC   DYEYNP                              119
CeresClone:1058242  SCYFRGAAIT  TEVDPSHGSC   HYDFIP                              118
CeresClone:1602924  NCDFKGSGII  AVTDPSYGDC   KYSYKQ                              123
gi|29465664         DCDESGTGAL  TSSDPSNGSC   --SFLS                              123

Consensus           SC-FKGA-II  TE-DPSHGSC   -Y----P                             126
``` seedlings. The ABA resistant seedlings showed a slight increase in growth. The phenotype of the resistant seedlings is unique to each of the screens.

TABLE 1-3

Segregation of Resistance to PEG, mannitol and ABA in ME01297-02 and ME01297-03 Progeny.

| | PEG | | | mannitol | | | ABA | | |
|---|---|---|---|---|---|---|---|---|---|
| | R | S | Probability of Chi-test | R | S | Probability of Chi-test | R | S | Probability of Chi-test |
| ME01297-02 | 49 | 23 | 0.174 | 47 | 25 | 0.057 | 50 | 22 | 0.276 |
| ME01297-03 | 58 | 14 | 0.276 | 51 | 21 | 0.414 | 56 | 16 | 0.586 |
| Expected (3:1 segregation) | 54 | 18 | | 54 | 18 | | 54 | 18 | |

Qualitative and Quantitative Analysis of Progeny of T$_2$ Plants Isolated on High Concentrations of PEG, Mannitol, and ABA Screens.

Progeny from T$_2$ plants that were recovered from the three screens and which contained cDNA 12331850 (SP1-A1, SP1-P1, and SP1-M18) were analyzed and also found to be resistant to PEG mannitol and ABA indicating that resistance is transmitted to the next generation. Taken together, 1) the isolation of resistant seedlings containing cDNA 12331850 from all three screens, 2) the inheritance of this resistance in a subsequent generation, and 3) the fact that the progeny from two or more events from the original transformation also segregated for resistance to the stresses, provide strong evidence that cDNA 12331850 when overexpressed can provide tolerance to osmotic stress.

Example 2—Ceres cDNA 12334963

Clone 35743, Ceres cDNA 12334963, encodes a full-length putative hypothetical protein. Ectopic expression of Ceres cDNA 12334963 under the control of the 35S promoter induces the following phenotypes:

Germination on high concentrations of polyethylene glycol (PEG), mannitol, and abscissic acid (ABA).

Continued growth on high PEG, mannitol, and ABA.

Generation and Phenotypic Evaluation of T$_1$ Lines Containing 35S::cDNA 12334963.

Wild-type *Arabidopsis* Wassilewskija (WS) plants were transformed with a Ti plasmid containing cDNA 12334963 in the sense orientation relative to the CaMV35S constitutive promoter. The T$_i$ plasmid vector used for this construct, CRS338, contains PAT and confers herbicide resistance to transformed plants. Ten independently transformed events were selected and evaluated for their qualitative phenotype in the T$_1$ generation. No positive or negative phenotypes were observed in the T$_1$ plants.

Screens of Superpools on High PEG, Mannitol, and ABA as Surrogate Screens for Drought Tolerance.

Seeds from 13 superpools (1,200 T$_2$ seeds from each superpool) from the CaMV35S or 32449 over-expression lines were tested on 3 drought surrogate screens (high concentrations of PEG, mannitol and ABA) as described above. T$_3$ seeds were collected from the resistant plants and analyzed for resistance on all three surrogate drought screens.

Once cDNA 12334963 was identified in resistant plants from each of the three surrogate drought screens, the five individual T$_2$ events containing this cDNA (ME01467) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Results:

Qualitative Analysis of 13 Superpools on PEG, Mannitol, and ABA.

Resistant candidates were selected based on increased size when compared to the largest wild-type control seedlings. All three screens resulted in a decrease in germination for both wildtype and superpools compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the T$_3$ generation. All recovered candidates showed signs of vigorous re-growth on soil, although the development was slightly delayed as compared to unstressed plants, presumably because of the transient exposure to stress. The plants transferred to soil were sprayed with Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 2-1).

TABLE 2-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12334963 on PEG, Mannitol, and ABA Seedlings that survived transfer to soil and which were Basta$^R$-resistant were subjected to PCR and sequencing. At least one resistant plant in each of the three osmotic screens contained 35S::cDNA 12334963 (ME01467) making this a good candidate for further testing. T$_2$ seeds from the 5 independent transformants that contain this clone and that were used in the pooling process were tested for Basta$^R$ resistance and for stress tolerance in the 3 surrogate drought screens.

To identify two independent events of 35S::cDNA 12334963 showing PEG, mannitol and ABA resistance, 36 seedlings from each of five events, ME01467-01, 02, 03, 04, and 05 were screened as previously described. Simultaneously, Basta segregation was assessed to identify events containing a single insert segregating in a 3:1 (R:S) ratio as calculated by a Chi-square test (Table 2-2). All of the lines segregated for a single functional insert.

TABLE 2-2

Basta$^R$ segregation for ME01467 individual events

| Event | Resistant | Sensitive | Total | Probability of Chi-test* |
|---|---|---|---|---|
| ME01467-01 | 28 | 8 | 36 | 0.70031 |
| ME01467-02 | 29 | 7 | 36 | 0.44142 |
| ME01467-03 | 24 | 12 | 36 | 0.24821 |
| ME01467-04 | 28 | 8 | 36 | 0.70031 |
| ME01467-05 | 27 | 9 | 36 | 1 |

*Chi-test to determine whether actual ratio of resistant to sensitive differs from the expected 3:1 ratio.

Events ME01467-03 and 05 were chosen as the two events because had the strongest and most consistent resistance to PEG, mannitol and ABA. Resistance was observed for ME01467-01, 02, and 04, although not in expected ratios in all three screens (data not shown). The controls were sown the same day and in the same plate as the individual events. The transgenic control in each of these plates is a segregant, from this ME line or another ME line being tested, that failed to show resistance to the particular osmotic stress. The PEG (Tables 2-3 and 2-4), mannitol (Tables 2-5 and 2-6) and ABA (Tables 2-7 and 2-8) segregation ratios observed for ME01467-03 and 05 are consistent with the presence of a single insert as demonstrated by Chi-Square. This result is similar to the observation for Basta$^R$ resistance (Table 2-2).

On 18% PEG, the resistant seedlings from these two events showed some root growth hut they were also green with emergence of new leaves at day 14. The mannitol-resistant seedlings showed more root and shoot growth than the PEG resistant seedlings. The resistant seedlings on ABA show the least amount of growth, and very little root growth relative to the mannitol and PEG screens. The phenotype

TABLE 2-3

Chi-square analysis assuming a 3:1 (R:S) ratio for progeny of ME01467-03 containing 35S::cDNA 12334963 on PEG.

| Event | Observed | Expected | $\chi^2$ | Probability of Chi-Test |
|---|---|---|---|---|
| PEG Resistant | 24 | 24 | 0 | 1.0 |
| PEG Sensitive | 8 | 8 | 0 | |
| | 32 | 32 | 0 | | of the resistant seedlings is unique on each of the screens.

TABLE 2-4

Chi-square analysis assuming a 3:1 (R:S) ratio for progeny of ME01467-05 containing 35S::cDNA 12334963 on PEG.

| Event | Observed | Expected | $\chi^2$ | Probability of Chi-Test |
|---|---|---|---|---|
| PEG Resistant | 26 | 27 | 0.037 | 0.7 |
| PEG Sensitive | 10 | 9 | 0.111 | |
| | 36 | 36 | 0.148 | |

TABLE 2-5

Chi-square analysis assuming a 3:1 (R:S) ratio for progeny of ME01467-03 containing 35S::cDNA 12334963 on mannitol.

| Event | Observed | Expected | $\chi^2$ | Probability of Chi-Test |
|---|---|---|---|---|
| Mannitol Resistant | 29 | 27 | 0.148 | 0.4 |

TABLE 2-5-continued

Chi-square analysis assuming a 3:1 (R:S) ratio for progeny of ME01467-03 containing 35S::cDNA 12334963 on mannitol.

| Event | Observed | Expected | $\chi^2$ | Probability of Chi-Test |
|---|---|---|---|---|
| Mannitol Sensitive | 7 | 9 | 0.444 | |
| | 36 | 36 | 0.592 | |

TABLE 2-6

Chi-square analysis assuming a 3:1 (R:S) ratio for progeny of ME01467-05 containing 35S::cDNA 12334963 on mannitol.

| Event | Observed | Expected | $\chi^2$ | Probability of Chi-Test |
|---|---|---|---|---|
| Mannitol Resistant | 18 | 27 | 3 | 0.0005 |
| Mannitol Sensitive | 18 | 9 | 9 | |
| | 36 | 36 | 12 | |

TABLE 2-7

Chi-square analysis assuming a 3:1 (R:S) ratio for progeny of ME01467-03 containing 35S::cDNA 12334963 on ABA.

| Event | Observed | Expected | $\chi^2$ | Probability of Chi-Test |
|---|---|---|---|---|
| ABA Resistant | 25 | 26.25 | 0.0595 | 0.626 |
| ABA Sensitive | 10 | 8.75 | 0.179 | |
| | 35 | 35 | 0.239 | |

TABLE 2-8

Chi-square analysis assuming a 3:1 (R:S) ratio for progeny of ME01467-05 containing 35S::cDNA 12334963 on ABA.

| Event | Observed | Expmed | $\chi^2$ | Probability of Chi-Test |
|---|---|---|---|---|
| ABA Resistant | 22 | 27 | 0.926 | 0.054 |
| ABA Sensitive | 14 | 9 | 2.78 | |
| | 36 | 36 | 3.706 | |

Qualitative and Quantitative Analysis of Progeny of T$_2$ Plants Isolated on PEG, Mannitol and ABA Progeny of the T$_2$ plants that were recovered from the three screens and which contained cDNA 12334963 (SP1-A12, SP1-P9, and SP1-M4) were analyzed and found to be resistant to PEG, mannitol and ABA, indicating that resistance is transmitted to the next generation.

Taken together, 1) the isolation of resistant seedlings containing cDNA 12334963 from all three surrogate screens for drought, 2) the inheritance of this resistance in the next generation, and 3) the fact that the progeny from two or more events from the original transformation also segregated for resistance to these osmotic stresses, provides strong evidence that cDNA 12334963, when over-expressed, can provide tolerance to drought, freezing and other osmotic stresses.

Table 2-8 provides the results of the consensus sequence (SEQ NOs: 121-129) analysis based on Ceres cDNA 12334963.

TABLE 2-8

/tmp/Lead·clone35743.aln

```
CeresaClone:584111  --MERSMTTR  R-----GYER  LGKESATIAL  LHEGFKRSTS  LPSWGSNSSR   43
Lead·clone35743     MQMLRNLSTR  TRSRRGGYER  V-SDDSTFSL  LGAKLRRSTS  VPYYAPS---   46
gi|38603980         MQMLRNLSTR  TRSRRGGYER  V-SDDSTFSL  LGAKLRRSTS  VPYYAPS---   46
CeresClone:963524   MQMLRSFSTR  TRSRRGGYER  V-IDDSTFSL  LGAKLRRSTS  VPYYAPS---   46

Consensus           MQMLR-LSTR  TRSRRGGYER  V-SDDSTFSL  LGAKLRRSTS  VPYYAPS---   50

CeresClone:584111   KMALGSTYGE  TNLKRNPLKK  GNNN--SDRK  SHPLLSFIAL  ---RKKKKTT   88
Lead·clone35743     -IRLG-GDFP  VILEKLPRQK  PTKTVVTSKL  SHPIFSLFDG  YRRRSKKKAT   94
gi|38603980         -IRLG-GDFP  VILEKLPRQK  PTKTVVTSKL  SHPIFSLFDG  YRRHNKKKAT   94
CeresClone:963524   -IKLGAGGVP  TILEELPRQK  SKKVKPTSKF  SHPIFSFLYG  ---KKKKSTT   92

Consensus           -IRLC-GDFP  VILEKLPRQK  PTKTVVTSKL  SHPIFS--DG  YRRR-KKK-T  100

CeresClone:584111   ARPEFARYLE  YLKEGGMWDF  NSNKPVMYYE                           118
Lead·clone35743     AKPEFSRYHE  YLKESGMWDL  RSNSPVIYFK                           124
gi|38603980         AKPEFSRYHE  YLKESGMWDL  RSNSPVIYFK                           124
CeresClone:963524   RKPEFSRYLE  YLKEGGMWDA  RTNTPV----                           118

Consensus           AKPEFSRY-E  YLKE-GMWDL  RSNSPVIYFK                           130
```

Example 3—Ceres cDNA 12333678

Clone 26006, Ceres cDNA 12333678, encodes a full-length glycosyl hydrolase. Ectopic expression of Ceres cDNA 12333678 under the control of the CaMV35S promoter induces the following phenotypes:

Germination on high concentrations of polyethylene glycol (PEG), mannitol and abscissic acid (ABA).

Continued growth on high PEG, mannitol and ABA.

Generation and Phenotypic Evaluation of T$_1$ Lines Containing 35S::cDNA 12333678, Wild-type *Arabidopsis* Wassilewskija (WS) plants were transformed with a Ti plasmid containing cDNA 12333678 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol and ABA) as described above. $T_3$ seeds were collected from the resistant plants and analyzed for resistance on all three surrogate drought screens.

Once cDNA 12333678 was identified in resistant plants from each of the three surrogate drought screens, the five individual $T_2$ events containing this cDNA (ME01334) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the $18^{th}$ plant isolated from a mannitol screen of Superpool 1.

Results:

Qualitative Analysis of 13 Superpools on PEG, Mannitol and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed compared to unstressed plants, presumably because of the transient exposure to stress. The plants transferred to soil were sprayed with B Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 3-1).

TABLE 3-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |

TABLE 3-1-continued

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12333678 on PEG, Mannitol and ABA Seedlings that survived transfer to soil and which were Basta$^R$-resistant were subjected to PCR and sequencing. At least one resistant plant in each of the three osmotic screens contained 35S::cDNA 12333678 (ME01.334). $T_2$ seeds from the 5 independent transformants that contain this clone and that were used in the pooling process were tested for Basta$^R$ resistance and for stress tolerance in the 3 surrogate drought screens.

To identify two independent events of 35S::cDNA 12333678 showing PEG, mannitol, and ABA resistance, 36 seedlings from each of four events, ME01334-01, 02, 03, and 04 were screened as previously described. Simultaneously, Basta$^R$ segregation was assessed to identify events containing a single insert segregating in a 3:1 (R:S) ratio as calculated by a Chi-square test (Table 3-2). All of the events tested segregated for a single functional insert.

TABLE 3-2

Basta$^R$ segregation for ME01334 individual events

| Event | Resistant | Sensitive | Total | Probability of Chi-test* |
|---|---|---|---|---|
| ME01334-01 | 28 | 8 | 36 | 0.70031 |
| ME01334-02 | 22 | 14 | 36 | 0.05429 |
| ME01334-03 | 31 | 5 | 36 | 0.12366 |
| ME01334-04 | 24 | 12 | 36 | 0.24821 |
| ME01334-5 | | | Insufficient seeds to test | |

*Chi-test to determine whether actual ratio of resistant to sensitive differs from the expected 3:1 ratio.

Events ME01334-01 and 04 were chosen as the two events because they had the strongest and most consistent resistance to PEG, mannitol and ABA. Resistance was observed for ME01334-02 and 03 although not in expected ratios in all three screens (data not shown). The controls were sown the same day and in the same plate as the individual events. The transgenic control in each of these plates is a segregant, from this ME line or another ME line being tested, that failed to show resistance to the particular stress. The PEG (Tables 3-3 and 3-4), mannitol (Tables 3-5 and 3-6) and ABA (Tables 3-7 and 3-8) segregation ratios observed for ME01334-01 and 01 are consistent with the presence of a single insert as demonstrated by Chi-Square. This is similar to that observed for Basta$^R$ resistance (Table 3-2).

On 18% PEG, the resistant seedlings from these two events show some root growth but they are also green with new leaves emerging at day 14. The mannitol-resistant seedlings showed more root and shoot growth than the PEG resistant seedlings. The resistant seedlings on ABA show the least amount of growth, and very little root growth relative to the mannitol and PEG screens. The phenotype of the resistant seedlings is unique on each of the screens.

TABLE 3-3

Chi-square analysis assuming a 3:1 (R:S) ratio for progeny of ME01334-01 containing 35S::cDNA 12333678 on PEG.

| Event | Observed | Expected | $\chi^2$ | Probability of Chi-Test |
|---|---|---|---|---|
| PEG Resistant | 26 | 26.25 | 0.002 | 0.922 |
| PEG Sensitive | 9 | 8.75 | 0.007 | |
| | 35 | 35 | 0.009 | |

TABLE 3-4

Chi-square analysis assuming a 3:1 (R:S) ratio for progeny of ME01334-04 containing 35S::cDNA 12333678 on PEG.

| Event | Observed | Expected | $\chi^2$ | Probability of Chi-Test |
|---|---|---|---|---|
| PEG Resistant | 27 | 27 | 0 | 1.0 |
| PEG Sensitive | 9 | 9 | 0 | |
| | 36 | 36 | 0 | |

TABLE 3-5

Chi-square analysis assuming a 3:1 (R:S) ratio for progeny of ME01334-01 containing 35S::cDNA 12333678 on mannitol.

| Event | Observed | Expected | $\chi^2$ | Probability of Chi-Test |
|---|---|---|---|---|
| Mannitol Resistant | 14 | 23.25 | 3.68 | 0.0001 |
| Mannitol Sensitive | 17 | 7.75 | 11.04 | |
| | 31 | 31 | 14.72 | |

TABLE 3-6

Chi-square analysis assuming a 3:1 (R:S) ratio for progeny of ME01334-04 containing 35S::cDNA 12333678 on mannitol.

| Event | Observed | Expected | $\chi^2$ | Probability of Chi-Test |
|---|---|---|---|---|
| Mannitol Resistant | 16 | 22.5 | 1.88 | 0.006 |
| Mannitol Sensitive | 14 | 7.5 | 5.63 | |
| | 30 | 30 | 7.51 | |

TABLE 3-7

Chi-square analysis assuming a 3:1 (R:S) ratio for progeny of ME01334-01 containing 35S::cDNA 12333678 on ABA.

| Event | Observed | Expected | $\chi^2$ | Probability of Chi-Test |
|---|---|---|---|---|
| ABA Resistant | 24 | 24 | 0 | 1.0 |
| ABA Sensitive | 8 | 8 | 0 | |
| | 32 | 32 | 0 | |

TABLE 3-8

Chi-square analysis assuming a 3:1 (R:S) ratio for progeny of ME01334-04 containing 35S::cDNA 12333678 on ABA.

| Event | Observed | Expected | $\chi^2$ | Probability of Chi-Test |
|---|---|---|---|---|
| ABA Resistant | 19 | 25.5 | 1.657 | 0.01 |
| ABA Sensitive | 15 | 8.5 | 4.97 | |
| | 34 | 34 | 6.627 | |

Qualitative and Quantitative Analysis of Progeny of $T_2$ Plants Isolated on PEG, Mannitol and ABA Progeny from $T_2$ plants that were recovered from the three screens and contained cDNA 12333678 (SP1-A2, SP1-P3, and SP1-M19) were analyzed and also found to be resistant to PEG, mannitol and ABA indicating that resistance is transmitted to the next generation. Taken together, 1) the isolation of resistant seedlings containing cDNA 12333678 from all three surrogate screens for drought, 2) the inheritance of this resistance in the next generation, and 3) the fact that the progeny from two or more events from the original transformation also segregated for resistance to these osmotic stresses, provides strong evidence that cDNA. 12333678 when over-expressed provides tolerance to osmotic stress.

This gene is annotated as an alpha/beta hydrolase, a probable acetone-cyanohydrin lyase. Acetone-cyanohydrin lyase is involved in the catabolism of cyanogenic glycosides.

Table 3-9 provides the results of the consensus sequence (SEQ ID NOs: 130-146) analysis based on Ceres cDNA 12333678.

TABLE 3-9

```
/tmp/Lead·clone26006.aln gi|15866583        MGGDGGAEQP VIHFVHVHGA SHGAWCWYKL TSLLETAGPK ITSVDLTGAG  50
gi|2780225         --------MA VVDFVLIHTI CHGAWIWYKL KPVLEAAGHK VTALDLAASG  42
gi|50513520        --------MA FAHFVLIHTI CHGAWIWHKL KPLLEALGHK VTALDLAASG  42
gi|6435646         --------MA FAHFVLIHTI CHGAWIWHKL KPLLEALGHK VTALDLAASG  42
gi|57899620        ---MEGSSSS SKHFILVHGL CHGAWCWYKV VTMLRSEGHR VTALDLAASG  47
CeresClone:936068  ----MEGSSS GKHFILIHGL CHGAWCWYKL VPMLRAAGHR VTALDMAASG  46
gi|34907176        ---MEISSSS KKHFILVHGL CHGAWCWYRV VAALRAAGHR ATALDMAASG  47
gi|56393011        -MEKSMSPFV KKHFVLVHTA FHGAWCWYKI VALMRSSGHN VTALDLKASG  49
gi|41814856        -----MEKGD KNHFVLVHGA CHGAWCWYKV VTILRSEGHK VSVLDMAASG  45
gi|56392765        -----MEKGN KNHFVLVHGA CHGAWCWYKV VTILRSEGHK VSVLDMAASG  45
CeresClone:644331  -MEACAGQAS SAHIVLVHGA LGGWSWFKV ATRLRSAGHR VSTPDLAASG  49
gi|53830670        -------MEV MKHFVTLHGV GHGAWYYKL KPRIEAAGHK CTAVNLAASG  43
Lead·clone26006    ----MSEEKR KQHFVLVHGA CHGAWCWYKV KPLLEALGHR VTALDLAASG  46
CeresClone:1010900 ----MSEEKR KQHFVLVHGS CHGAWCWYKV KPLLEAVGHR VTAVDLAASG  46
gi|20196998        ----MSEEKR KQHFVLVHGS CHGAWCWYKV KPLLEAVGHR VTAVDLAASG  46
gi|27754457        -MHSAANAKQ QKHFVLHGG CLGAWIWYKL KPLLESAGHK VTAVDLSAAG  46
gi|6651393         --MEEVVGME EKHFVLVHGV NHGAWCWYKL KARLVAGGHR VTAVDLAASG  49
gi|14279437        -------MKE GKHFVLHGA CHGWSWYKL KPLLEAAGHK VTALDLAASG  48
gi|40549303                                                                43

Consensus          ---------- KKHFVLVHGA CHGAWCWYK- KPLLEA-GHR VTALDLAASG  50 gi|15866583        IS-VTDSNIV LESDQYNRPL FSLLSDLPP- SHKVILVGHS IGGGSVTDAL  98
gi|2780225         VD-PRQIEQI NSFDEYSEPL LTFMESLPQ- GEKVILVGES CGGLNIAIAA  90
gi|50513520        VD-PRQIEEI GSFDEYSEPL LTFLEALPP- GEKVILVGES CGGLNIAIAA  90
gi|6435646         VD-PRQIEEI GSFDEYSEPL LTFLEALPP- GEKVILVGES CGGLNIAIAA  90
gi|57899620        VH-PARVDEV HSFEEYSQPL LDAVAEAPA- GERLILVGHS FGGLSIALAM  95
CeresClone:936068  AH-PARMDEV PSFEDYSWPL LDAVAAAPA- GERLVLVGHS LGGLNIALAM  94
gi|34907176        AH-PARVDEV GTFEEYSRPL LDAVAAAAAP GERLVLVGHS HGGLSVALAM  96
gi|56393011        IN-PKQALQI PNFSDYLSPL MBFMASLPA- NEKIILVGHA LGGLAISKAM  97
gi|41814856        IN-PKHVDDL NSMADYNEPL MBFMNSLPQ- LERVVLVGHS MGGINISLAM  93
gi|56392765        IN-PKHVEDL NSMADYNEPL MBFMNSLPQ- QERVVLVGHS MGGINISLAM  93
CeresClone:644331  VD-PRPLREV PTFRDYTKPL LDLLESLPS- GEKVVLVGHS LGGVNVALAC  97
gi|53830670        IN-BKKLEEV RSSIDYAAPL LEVLDSVPE- NEKVILVGHS GGGMTAAVGM  97
Lead·clone26006    IDITRSITDI SIICEQYSEPL MQLMTSLPN- DEKVVLVGHS FGGLSLALAM  91
CeresClone:1010900 IDITRSITDI PIICEQYSEPL TKLLTSLPN- DEKVVLVGHS FGGLNLAIAM  95
gi|20196998        IDITRSITDI PIICEQYSEPL TKLLTSLPN- DEKVVLVGHS FGGLNLAIAM  95
gi|27754457        IN-PRRLDEI HTFRDYSEPL MEVMASIPP- DEKVVLLGHS FGGMSLGLAM  95
gi|6651393         IN-MKRIEDV HTFHAYSEPL MEVLASLPA- BEKVVLVGHS LGGVTLALAG  97
gi|14279437        TD-LRKIEEL RILYDYTIPL MELMSLSA- DEKVILVGHS LGGMNLGLAM  96
gi|40549303                                                                91

Consensus          I--PRQI-EI --FE-YSEPL MELM-SLP-- -EKVVLVGHS -GGLNIALAM 100 gi|15866583        CRFLDKISMA IYLAASMVKP GSVPSPHVSD MHADAREEN- IW---EYTYG 144
gi|2780225         DKYPEKIAAA VFQNSLLPDT KHKPSYVVDK LMEVFPD--- -WKDTEYFEF 136
gi|50513520        DKYCEKIAAA VFHNSMLPDT EHCPSYVVDK LMEVFPD--- -WKDTIYFTY 136
gi|6435646         DYKCEKIAAA VFHNSMLPDT EHCPSYVVDK LMEVFPD--- -WKDTIYFTY 136
gi|57899620        ERFPEKIAVA VFVAAAVPCV GKR--ILPEL IREKAPKDM- -LLDSKMIPI 141
CeresClone:936068  ERFPRKVAAA VFLAACMPCV GREMGATIEE IMRRIKPDF- -FMDMKRMVL 142
gi|34907176        ERFPDKVAAA VFVAAAMPCV GKHMGVPTEE FMRRTAPEG- LLMDCEMVAI 145
gi|56393011        ELFPEKISVA VFLSGLMPGP NIDAITVCTK AGSAVLG--- -QLDNCVTYE 143
gi|41814856        EKFPQKIVVA VFVTAFMPGP DLNLVALSQQ YNQQVES--- -HMDTEFVYN 139
gi|56392765        EKFPHKIAVA VFVSASMPGP DLNLVAMIQQ YSQQVET--- -PMDTEFVYN 139
CeresClone:644331  ELFPEKIAAA VAFRAFMPDH RSPPSYVEEE BVEGRTLD-- -WMDTEFKPQ 144
gi|53830670        EKFPNKISLA VFLNAIMPDT ENRPSYVEEE YTAKTPPEA- -WKDQFSAY 139
Lead·clone26006    EKFPEKISVA VFLTAFMPDT EHSPSFVDKN FGSNMPQEA- -WMGTEFPY 143
CeresClone:1010900 EKFPEKISVA VFLTAFMPDT EHSPSFVDKN FGSNMPQEA- -WMGTEFPY 143
gi|20196998        EKFPKKISVA VFLTAFMPDT EHSPSFVDKN FGSNMPQEA- -WMGTEFPY 143
gi|27754457        ELYPEKISVA VFMSAMMPDP NHSLTYPPEK YNEKCPADM- -MLDSQFSTY 143
gi|6651393         DKFPHKISVA VFVTAFMPDT THRPSFVLEQ YSEKMGKEDD SWLDTQFSQC 145
gi|14279437        EKYPQKIYAA VFLAAFMPDS VHNSSFVLEQ YNRTEAEN- -WLDTQFLPY 146
gi|40549303                                                               139

Consensus          EKFPEKISVA VFL-A-MPDT EH-PS-VLEK -----P-E-- -WMDTEF--Y 150
```

TABLE 3-9-continued

/tmp/Lead·clone26006.aln

```
gi|15866583        EG-IDKPPTG VIMKQEFLRQ YYYSQSPLED VSLATKLLRP APMRAFQDLD 193
gi|2780225         SNSNGETITG MVLGLKLMRE NLYDICPPED YELAKMLTRR GSLFQSI-LA 185
gi|50513520        TK-DGKEITG LKLGFTLLRE NLYILCGPEE YELAKMLTRK GSLFQNI-LA 184
gi|6435646         TK-DGKEITG LKLGFTLLRE NLYILCGPEE YELAKMLTRK GSLFQNI-LA 184
gi|57899620        NN-KQGPGTA ILLGPNFLAE KGYPLSPAED LTLAKLLVRP TSQFVDDPTM 190
CeresClone:936068  NT-SQGPRPA LVFGPKILAA KLYDRSSGED QTLAIMLVRP GCQFLDDPTM 191
gi|34907176        NN-SQGSGVA INLGPTFLAQ KYYQQSPAED LALAKMLVRP GNQFMDDPVM 194
gi|56393011        NG-PTNPPTT LIAGPKFLAT NVYHLSPIED LALATALVRP LYLYLAEDIS 192
gi|41814856        NG-QDKAPTS LVLGPEVLAT NFYQLSPPED LTLATYLVRP VPLFDESILL 188
gi|56392765        NG-LDKGPTS VVLGPKVLAT IYYQFSPPED LTLATYLVRP VPLFDRSVLL 188
CeresClone:644331  DP-EGKLPTS MLFGPLVTRA KFFQLCSPED LTLGRSLMRV NSMFVDD-LR 192
gi|53830670        G---DPPITS LVCGPEFISS TLYHLSPIED HALGKILVRP GSLFIED-LL 185
Lead·clone26006    G--SDNSGLS VFFSTDFMKH RLYQLSPVED LELGLLLKRP SSLFINE-LS 190
CeresClone:1010900 G--SDNSGLS MFFSPDFMKL GLYQLSPVED LELGLLLMRP GSLFIND-LS 190
gi|20196998        G--SDNSGLS MFFSPDFMKL GLYQLSPVED LELGLLLMRP GSLFIND-LS 190
gi|27754457        G--SDNSGLS MFFSPDFMKL GLYQLSPVED LELGLLLMRP GSLFIND-LS 190
gi|6651393         GN-PENPGMS MILGPQFMAL KMFQNCSVED LELAKMLTRP GSLFFQD-LA 190
gi|14279437        DA-SNPSHIS MLFGREFLTI KIYQLCPPED LELAKMLVRP GSMFIDN-LS 193
gi|40549303        GS-PEEPLTS MFFGPKFLAH KLYQLCSPED LALASSLVRP SSLFMED-LS 194

Consensus          --------TS MI-GP-FL-- -LYQLSP-ED L-LA-MLVRP GSLFI-D-LS 200 gi|15866583        KSPP---NPE VEKMPRVYIK TGKDNLFSSV -RQDLLVKNW PPSQFYVLEE 239
gi|2780225         QREK-FTEKG YGSIKKIYVW TGDDKIFLPE -FQLWQIENY KRDLMPRVMG 233
gi|50513520        KRPF-FTKEG YGSIKKIYVW TDQDEIFLPE -FQLWQIENY KPDKVYKVEG 232
gi|6435646         KRPF-FTKEG YGSIKKIYVW TDQDEIFLPE -FQLWQIENY KPDKVYKVEG 232
gi|57899620        KDDRLLISAN YSGVKRVQLM AMEDDL--KE -VHRYMITLS PGVEVEEIAG 237
CeresClone:936068  KDEALLTEAK YGSVKKVYVI AMADASNSEE -MQRWMVDMS PGTBAEEIAG 240
gi|34907176        KDESLLINGN YGSVKKVYVI AKADSSSTEE -MQRWMVAMS PGTDVEEIAG 243
gi|56393011        KEVV-LSSKR YGSVKRVFIV ATENDALKKE -FLKLMIEKN PPDEVKEIEG 240
gi|41814856        ANTT-LSKEK YGSVHRVYVV CDKDNVLKEQ QFQKWLINNN PPDEVQIIHN 237
gi|56392765        TNTT-LSKEK YGSVHRVYVV CDKDRVLKEE QFQRWLIKNN PPNEVQMIHD 237
CeresClone:644331  LQPP-HTEAR YGSVRKAYVV FKDDHAIVEQ -FQRMWVHNY PVDEVMEIDG 240
gi|53830670        KAEK-FTEEG FGSVPRVYVI AAEDKIIPPE -FQRWMIENN PVKEVKEIKG 233
Lead·clone26006    KMEN-FSEKG YGSVPRAYIV CKEDNIISED -HQRWMIHNY PANLVIEMBE 238
CeresClone:1010900 KMKN-FSDEG YGSVPRVFIV CKEDKAIPEE -RQRWMIDNF PVNLVMEMBE 238
gi|20196998        KMKN-FSDEG YGSVPRVFIV CKEDKAIPEE -RQRWMIDNF PVNLVMEMBE 238
gi|27754457        KMKN-FSDEG YGSVPRVFIV CKEDKAIPEE -RQRWMIDNF PVNLVMEMBE 238
gi|6651393         KAKK-FSTER YGSVKRAYIF CNEDKSFPVE -FQKWFVESV GADKVKEIKE 238
gi|14279437        KESK-FSDEG YGSVKRVYLV CEEDIGLPKQ -FQHWMIQNY PVNEVMEIKG 241
gi|40549303        KAKY-FTDER FGSVKRVYIV CTEDKGIPEE -FQRWQIDNI GVTEAIEIKG 242

Consensus          K----F--E- YGSVKRVYIV --ED--I-EE -FQRWMIENY P--EV-EIEG 250 gi|15866583        SDHSAFFSVP TTLFVYLLRA VSFLHK         265
gi|2780225         GDHKLQLTKT NEIAGILQKV ADIYA-         258
gi|50513520        GDHLLQLTKT KEIAEILQEV ADIYN-         257
gi|6435646         GDHKLQLTKT KEIAEILQEV ADIYN-         257
gi|57899620        ADHAVMCSRP RELSDLLAKI GSKYD-         262
CeresClone:936068  ADHMAMCSKP RELCDVLLRI ADKYE-         265
gi|34907176        ADHAVMNSKP RELCDILIKI ANKYE-         268
gi|56393011        SDHVIMMSKP QQLFTILLSI ANKYK-         265
gi|41814856        ADHMVMFSKP RDLSSCLVMI SQKYY-         262
gi|56392765        AGHMVMFSKP RELCSCLVMI SQKYH-         262
CeresClone:644331  ADHMALLSTP TELARCLADI AVKYAA         266
gi|53830670        ADHMPVFSKP DELSQOLLDI AKKHA-         258
Lead·clone26006    TDHMPMFCKP QVLSDHLLAI ADNFS-         263
CeresClone:1010900 TDHMPMFCKP QQLSDYFLKI ADKFV-         263
gi|20196998        TDHMPMFCKP QQLSDYFLKI ADKFV-         263
gi|27754457        TDHMPMFCKP QQLSDYFLKI ADKFV-         263
gi|6651393         ADHMGMLSQP REVCKCLLDI SDS---         263
gi|14279437        GDHMAMLSDP QKLCDCLSQI SLKYA-         264
gi|40549303        ADHMAMLQEP QKLCASLLEI AHKYN-         267

Consensus          -DHM-M-SKP QELS--LL-I A-KY--         276
```

23/05/05 plur = 9.500000-collision-box-noboxcol colbyconsensus

Example 4—Ceres cDNA 12384873

Clone 34419, Ceres cDNA 12384873, encodes a full-length strictosidine synthase. Ectopic expression of Ceres cDNA 12384873 under the control of the CaMV35S promoter induces the following phenotypes:

Germination on high concentrations of polyethylene glycol (PEG), mannitol, and abscissic acid (ABA).
Continued growth on high PEG, mannitol, and ABA.

Generation and Phenotypic Evaluation of $T_1$ Lines Containing 35S::cDNA 12384873

Wild-type *Arabidopsis* Wassilewskija. (WS) plants were transformed with a $T_i$ plasmid containing cDNA 12384873 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12384873 was identified in resistant plants from each of the three surrogate drought screens, the five individual $T_2$ events containing this cDNA (ME01490) were screened on high PEG, mannitol and ABA to identify events with the resistance phenotype.

Superpools (SP) are referred to as SP1, SP2 and so on. The letter following the hyphen refers to the screen (P=PEG, M mannitol and A=ABA) and the number following the letter refers to a number assigned to each plant obtained from that screen on that superpool. For example, SP1-M18 is the 18$^{th}$ plant isolated from a mannitol screen of Superpool 1.

Qualitative Analysis of 13 Superpools on PEG, Mannitol, and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta$^R$ to eliminate any false-positives, or any lines where the Basta$^R$ marker was suppressed. All of the Basta$^R$-resistant candidates flowered and set seed. Resistant seedlings were recovered from Superpools 1, 7 and 11 on all screens (Table 4-1).

TABLE 4-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

Qualitative and Quantitative Analysis of 5 Independent Events Representing 35S::cDNA 12384873 on PEG, Mannitol and ABA Seedlings that survived transfer to soil and which were Basta$^R$-resistant were subjected to PCR and sequencing. At least one resistant plant in each of the three osmotic screens contained 35S::cDNA 12384873 (ME01490 g. $T_2$ seeds from the 5 independent transformants that contain this clone and that were used in the pooling process were tested for Basta$^R$ resistance and for stress tolerance in the 3 surrogate drought screens.

To identify two independent events of 35S::cDNA 12384873 showing PEG, mannitol and ABA resistance, 36 seedlings from each of five events, ME01490-01, 02, 03, 04, and 05 were screened as previously described. Simultaneously, Basta$^R$ segregation was assessed to identify events containing a single insert segregating in a 3:1 (R:S) ratio as calculated by a Chi-square test (Table 4-2). Three of the events segregated for a single functional insert (-01, -02 and -04). For the other two events one segregated for two independent inserts (-03) and one segregated for a deficiency of Basta$^R$ seedlings (-05).

TABLE 4-2

Basta$^R$ segregation for ME01490 individual events

| Event | Resistant | Sensitive | Total | Probability of Chi-test* |
|---|---|---|---|---|
| ME01490-01* | 24 | 12 | 36 | 0.24821 |
| ME01490-02* | 26 | 10 | 36 | 0.70031 |
| ME01490-03 | 35 | 1 | 36 | 0.00208** |
| ME01490-04 | 28 | 8 | 36 | 0.70031 |
| ME01490-05 | 21 | 15 | 36 | 0.02092** |

*Chi-test to determine whether actual ratio of resistant to sensitive differs from the expected 3:1 ratio.
**Significantly different than a 3:1 (R:S) ratio Events ME01490-01 and -02 were chosen as the two events because they had the strongest and most consistent resistance to PEG, mannitol and ABA. Resistance was observed for ME01490-03, -04, and -05 although not in expected ratios in all three screens (data not shown). The controls were sown the same day and in the same plate as the individual lines. The transgenic control in each of these plates is a segregant, from this ME line or another ME line being tested, that failed to show resistance to the particular stress. The PEG (Tables 4-3 and 4-4), mannitol (Tables 4-5 and 4-6) and ABA (Tables 4-7 and 4-8) segregation ratios observed for ME01490-01 and -02 are consistent with the presence of single insert, as demonstrated by Chi-square. This result is similar to that observed for Basta$^R$ resistance (Table 4-2).

TABLE 4-3

Chi-square analysis assuming a 3:1 (R:S) ratio for progeny of ME01490-01 containing 35S::cDNA 12384873 on PEG.

| Event | Observed | Expected | $\chi^2$ | Probability of Chi-Test |
|---|---|---|---|---|
| PEG Resistant | 29 | 27 | 0.148 | 0.441 |
| PEG Sensitive | 7 | 9 | 0.444 | |
| | 36 | 36 | 0.592 | |

TABLE 4-4

Chi-square analysis assuming a 3:1 (R:S) ratio for progeny
of ME01490-02 containing 35S::cDNA 12384873 on PEG.

| Event | Observed | Expected | $\chi^2$ | Probability of Chi-Test |
|---|---|---|---|---|
| PEG Resistant | 24 | 24.75 | 0.0227 | 0.763 |
| PEG Sensitive | 9 | 8.25 | 0.068 | |
| | 33 | 33 | 0.0907 | |

TABLE 4-5

Chi-square analysis assuming a 3:1 (R:S) ratio for progeny
of ME01490-01 containing 35S::cDNA 12384873 on mannitol.

| Event | Observed | Expected | $\chi^2$ | Probability of Chi-Test |
|---|---|---|---|---|
| Mannitol Resistant | 22 | 26.25 | 0.688 | 0.097 |
| Mannitol Sensitive | 13 | 8.75 | 2.06 | |
| | 35 | 35 | 2.748 | |

TABLE 4-6

Chi-square analysis assuming a 3:1 (R:S) ratio for progeny
of ME01490-02 containing 35S::cDNA 12384873 on mannitol.

| Event | Observed | Expected | $\chi^2$ | Probability of Chi-Test |
|---|---|---|---|---|
| Mannitol Resistant | 20 | 23.25 | 0.454 | 0.178 |
| Mannitol Sensitive | 11 | 7.75 | 1.363 | |
| | 31 | 31 | 1.817 | |

TABLE 4-7

Chi-square analysis assuming a 3:1 (R:S) ratio for progeny
of ME01490-01 containing 35S::cDNA 12384873 on ABA.

| Event | Observed | Expected | $\chi^2$ | Probability of Chi-Test |
|---|---|---|---|---|
| ABA Resistant | 28 | 27 | 0.037 | 0.7 |
| ABA Sensitive | 8 | 9 | 0.148 | |
| | 36 | 36 | 1.85 | |

TABLE 4-8

Chi-square analysis assuming a 3:1 (R:S) ratio for progeny
of ME01490-02 containing 35S::cDNA 12384873 on ABA.

| Event | Observed | Expected | $\chi^2$ | Probability of Chi-Test |
|---|---|---|---|---|
| ABA Resistant | 23 | 27 | 0.593 | 0.124 |
| ABA Sensitive | 13 | 9 | 1.78 | |
| | 36 | 36 | 2.373 | |

Qualitative and Quantitative Analysis of Progeny of $T_2$ Plants Isolated on PEG, Mannitol and ABA Progeny of the $T_2$ plants that were recovered from the three screens and contained cDNA 12384873 (SP1-A18, SP1-P14, SP1-M5, SP1-M6 and SP1-M7) were analyzed and also found to be resistant to PEG, mannitol and ABA indicating that resistance is transmitted to the next generation. Taken together, 1) the isolation of resistant seedlings containing cDNA 12384873 from all three surrogate screens for drought, 2) the inheritance of this resistance in the next generation, and 3) the fact that the progeny from two or more events from the original transformation also segregated for resistance to these osmotic stresses, provides strong evidence that cDNA 12384873 When over-expressed can provide tolerance to osmotic stress.

Clone 34419 encodes the first 29 amino acids of a strictosidine synthase protein, and then a frame shift results in a novel stretch of 63 amino acids on the 3' end of the protein.

Example 5—Ceres cDNA 12659859

Ceres cDNA 12659859 encodes a. FAD-linked oxidoreductase family, a probable berberine bridge enzyme from *Arabidopsis thaliana*. Ectopic expression of Ceres cDNA 12659859 under the control of the CaMV35S promoter induces the following phenotypes:

Germination on high concentrations of polyethylene glycol (PEG), mannitol and abscissic acid (ABA).

Continued growth on high concentration of PEG, mannitol and ABA.

Generation and Phenotypic Evaluation of $T_1$ Lines Containing 35S::cDNA 12659859.

Wild-type *Arabidopsis* Wassilewskija (WS) plants were transformed with a Ti plasmid containing cDNA 12659859 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12659859 was identified in resistant plants from each of the three surrogate drought screens, the five individual $T_2$ events containing this cDNA (SR01010) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A ABA) and the number following the letter refers to a number assigned to each plant obtained from that screen on that superpool. For example, SP1-M18 is the 18$^{th}$ plant isolated from a mannitol screen of Superpool 1.

Qualitative and Quantitative Analysis of 2 Independent Events Representing 35S::cDNA 12659859 (SIMON) on PEG, Mannitol and ABA To identify two independent events of 35S::cDNA 12659859 showing PEG, mannitol, and ABA resistance, 36 seedlings from each of three events, SR01010-01, 02, and 03 were screened as previously described. Basta$^R$ segregation was assessed to identify lines containing a single insert segregating in a 3:1 (R:S) ratio as calculated by a Chi-square test (Table 5-1). Two of three $T_2$ generation events (01 and 03) segregated for a single insert although the segregation ratio for -01 is also not different than a 15:1 (R:S) ratio.

TABLE 5-1

Basta$^R$ segregation for SR01010 individual events

| Event | Resistant | Sensitive | Total | Probability of Chi-test* |
|---|---|---|---|---|
| SR01010-01 | 32 | 4 | 36 | 0.05429 |
| SR01010-02 | 32 | 3 | 35 | 0.0248** |
| SR01010-03 | 24 | 12 | 36 | 0.24821 |
| SR01010-01-1 | 27 | 9 | 36 | 1 |
| SR01010-03-1 | 20 | 13 | 33 | 0.05619 |

*Chi-test to determine whether actual ratio of resistant to sensitive differs from the expected 3:1 ratio.
**Significantly different than a 3:1 (R:S) ratio Lines SR0101-01 and -03 were chosen as the two events because they had a strong and consistent resistance to PEG, mannitol and ABA. Resistance was observed for SR01010-02 although not in expected ratios in all three screens (data not shown) The controls were sown the same day and in the same plate as the individual lines. The PEG (Tables 5-2 and 5-3), mannitol (Tables 5-4 and 5-5) and ABA (Tables 5-6 and 5-7) segregation ratios observed for SR01010-01 and -03 are consistent with the presence of single insert as demonstrated by chi-square, similar to what we observed for Basta$^R$ resistance (Table 5-1).

The progeny from one resistant $T_2$ plant from each of these two events was tested in the $T_3$ generation in the same manner. Resistance to PEG, mannitol and ABA was also observed in the $T_3$ generation. Taken together, the segregation of resistant seedlings containing cDNA. 12659859 from two events on all three drought surrogate screens and the inheritance of this resistance in a subsequent generation, provide strong evidence that cDNA 12659859 when overexpressed can provide tolerance to drought.

TABLE 5-2

Chi-square analysis assuming a 3:1 (R:S) ratio for progeny of SR01010-01T$_2$ containing 35S::cDNA 12659859 on PEG.

| Event | Observed | Expected | $\chi^2$ | Probability |
|---|---|---|---|---|
| PEG Resistant | 31 | 26.25 | .860 | .064 |
| PEG Sensitive | 4 | 8.75 | 2.579 | |
| | 35 | 35 | 3.438 | |

TABLE 5-3

Chi-square analysis assuming a 3:1 (R:S) ratio for progeny of SR01010-03 T$_2$ containing 35S::cDNA 12659859 on PEG.

| Event | Observed | Expected | $\chi^2$ | Probability |
|---|---|---|---|---|
| PEG Resistant | 28 | 27 | .037 | .700 |
| PEG Sensitive | 8 | 9 | .111 | |
| | 36 | 36 | .148 | |

TABLE 5-4

Chi-square analysis assuming a 3:1 (R:S) ratio for progeny of SR01010-01T$_2$ containing 35S::cDNA 12659859 on mannitol.

| Event | Observed | Expected | $\chi^2$ | Probability |
|---|---|---|---|---|
| Mannitol Resistant | 25 | 27 | .148 | .441 |
| Mannitol Sensitive | 11 | 9 | .444 | |
| | 36 | 36 | .593 | |

TABLE 5-5

Chi-square analysis assuming a 3:1 (R:S) ratio for progeny of SR01010-3 T$_2$ containing 35S::cDNA 12659859 on mannitol.

| Event | Observed | Expected | $\chi^2$ | Probability |
|---|---|---|---|---|
| Mannitol Resistant | 21 | 20.25 | .028 | .739 |
| Mannitol Sensitive | 6 | 6.75 | .083 | |
| | 27 | 27 | .111 | |

TABLE 5-6

Chi-square analysis assuming a 3:1 (R:S) ratio for progeny of SR01010-01T$_2$ containing 35S::cDNA 12659859 on ABA.

| Event | Observed | Expected | $\chi^2$ | Probability |
|---|---|---|---|---|
| ABA Resistant | 30 | 27 | .333 | .248 |
| ABA Sensitive | 6 | 9 | 1 | |
| | 36 | 36 | 1.333 | |

TABLE 5-7

Chi-square analysis assuming a 3:1 (R:S) ratio for progeny of SR01010-03 T$_2$ containing 35S::cDNA 12659859 on ABA.

| Event | Observed | Expected | $\chi^2$ | Probability |
|---|---|---|---|---|
| ABA Resistant | 27 | 27 | 0 | 1.0 |
| ABA Sensitive | 9 | 9 | 0 | |
| | 36 | 36 | 0 | |

Table 5-8 provides the results of the consensus sequence (SEQ ID NOs: 147-177) analysis based on Ceres eDNA 12659859.

TABLE 5-8

/tmp/Lead•cDNA12659859.aln

```
gi|20563190        ----MNNSRS VFLLVLALSF CVSFGALSSI FDV--TSTSE DFITCLQSNS  44
gi|41393750        ----MARSRA FAFALLTCAV AASCHLVALSA PPPYAKQVER DFLTCLTKDI  46
gi|53792953        ----MSTTPI AASRRLVLIL CTLAISCSSG IAGFAAGDDD AFIRCLAAAA  46
gi|26005814        ---MNCSAFS FWFVCKIIPF FLSFHIQTSI ANP-----RE NFLKCFSKHI  42
Lead•cDNA12659859  ---MGISKPL LLFSILVLYF SLYTITPTSS LAS---LQD QFINCVQRNT  43
CeresClone: 522974 NTRESRNQRT MKSLRSILAT FVVLLSISLT ISL---PIEE AFNHCLTQHS  47
gi|18652400        ---MANITSS FNMQTSILTL LLLLLSTQSS ATS--RSITD RFIQCLHDRA  45
gi|18652398        ----MAILMS FNFKSYLFPL LLVLLSTHSS ATS--TSIID RFTQCLNNRA  44
gi|13161397        ---MKIT---- --LSCYYTFA TVIALLFSFT PSS--ADTHE NFLQCLYSYP  39
CeresClone: 561310 ---TEIREII VNMELSYCAV FLILLIPISR ADA--TSVEK QFKECLLIQL  45

Consensus          ---------S ------IL-L -L--LS-SSS --S----VE --FIQCL-S--  50 gi|20563190        N-NVTTISQL VFTPAN--TS YIPIWQAAAD PIRFNKSYIP KPSVIVTPTD  91
gi|41393750        P------PRQ LYAKSS--PA YASVWSSTVR NIKFLSDKTV KPLMIITPIN  88
gi|53792953        V------PPRL VHTPGS--AS YAPTLMSSIR NLRFVTPGTP RPLAIVAAAE  89
gi|26005814        P-NNVANPKL VYTQHD--QL TMSILNSTIQ NLRFISDTTP KPLVIVTPSN  89
Lead•cDNA12659859  H-VYFPLEKT FFAPTKNVSM FSQVELSTAQ NLRFLKKSMP KPGFIFSPIH  92
CeresClone: 522974 Q-TPNQFPSS IYTMTN--GS FIISILESTAQ NLRYLLPSVP KPDFIFTPLD  94
gi|18652400        D-PSFPITGE VYTPGN--SS FPTVLQNMYR NLRFNETTTP KPFLIITAEH  92
gi|18652398        D-PSFPLSGQ LYTPDN--SS FPSVLQAMYR NLRFNESTTP KPILIITALH  91
gi|13161397        H-NINSISSV LYTQTN--SS YFSVLDATMQ NLRF-SDSR KPLVIVTPQV  84
CeresClone: 561310 DGNSEHIEKI TFTSSS--IL YPQWWDSLAQ NPRWVNISSR KPLMILTPFH  93

Consensus          ---S--I-KL VYTP-N--SS Y-SVL-STVQ NLRFL---TP KPLVIITP--  100 gi|20563190        ETQIQILALLC AKKHGYBFRI RDGGHDFEGN SYIA-NA--P FVMLDLVNMR  138
gi|41393750        ASHIQAAVVC GRRHGMRIRV RSGGHDYEGL SYRS-EKPEP BAVVDMNKMR  137
gi|53792953        AGHAQAAVRC GRRHGVRVRA RSGGHDYEGL SYLSLDRRER FAVLDLAALR  139
gi|26005814        NSHIQAIILG SKKVGLQIRT RSGGHDYEGL SYIS-QV--T FVVVDLRNMH  136
Lead•cDNA12659859  ESHVQASIIC SKKLRMHLRV RSGGHDYEGL SYVS-QIDKP FILMDLSKMR  141
CeresClone: 522974 DSQVQAAVVC AKKLGIHMRV RSGGHDYEGL SYVS-LIEKP FMILDLAKLR  143
gi|18652400        VSHIQAAVVC GKONRLLLKT RSGGHDYEGL SYLT-NTNQP FFIVDMFNLR  141
gi|18652398        PSHIQAAVVC AKIHRLLMKT RSGGHDYEGL SYVT-NSNQP FFVVDMFNLR  140
gi|13161397        VSHIQAFIIKC SQRHGLQIRT RSGGHDYEGL SYVA-RV--P FVILDLLNER  131
CeresClone: 561310 ESPIQAAILC SKELKLQLRV RSGGHDYEGL SYLS-DV--P FVMVDLININ  140

Consensus          -SHIQAAVVC SKKHGLQ-RV RSGGHDYEGL SYVS--V--P FVVVDL-N-R  150 gi|20563190        AIEINVENRT ALVQGGALLG ELYYITSQKT DTLYFPAGIW AGVGVSGFLS  188
gi|41393750        AVSIDGKAAL AWVDSGAQLG DLYYGIAKAS PKLGFVAGVC TTIGVGGHFS  187
gi|53792953        DMRVDADRAE AWVGSGATLG ELYYAVGAAS RTLAFPAGVC PTVGVGGHIS  189
gi|26005814        SIKIDVHSQT AWVEAGATLG EVYYWINEKN ENLSFPGGYC PTVGVGGHFS  186
Lead•cDNA12659859  QVNINIQDNS AWVQSGATVG ELYYRIAEKS KVHGFPAGLC SSLGIGGHIT  191
CeresClone: 522974 AVNVDIARNT AWIQAGATIG EVYYRISEKS AVHGFPAGLC TTLGIGGHIT  193
gi|18652400        SINVDIBQET AWVQAGATLG EVYYRIAEKS NKHGFPAGVC PTVGVGGHFS  191
gi|18652398        SINVSIEDET AWVQAGATLG EVYYRIAEKS NSHAFPAGVC PTVGVGGHFS  190
gi|13161397        BIKVDVENRT AWVQVGATLG ELYYTISQAS RTLGFPAGVC YSVGAGGHIS  181
CeresClone: 561310 SIBINLADET AWVQAGASIG ELYYKISKAS KVHGFPAGTC PSVGIGGHIS  190

Consensus          SI--DVE--T AWVQAGATLG ELYYRI-EKS K--GFPAGVC PTVGVGGHIS  200 gi|20563190        GGGYGNLLRK YGLGADNVLD IRFMDVNGNI LDRKSMGEDL FWALRGGGAS  238
gi|41393750        GGGFGMLLRK YGTIAADNVID AKVVDAQGRL LDRKAMGEDH FWAIRGGGGE  237
gi|53792953        GGGFGTLMRR YGLAADNVLD AVLVDADGRL LNRITMGEGL FWAIRGGGGE  239
gi|26005814        GGGYGALMRN YGLAADNIID AHLVNVDGKV LDRKSMGEDL FWAIRGGGGE  236
Lead•cDNA12659859  GGAYGSMMRK YGLAADNVLD AKIVDANGKL LDRAAMGEDL FWAIRGGAGG  241
CeresClone: 522974 GGAYGSMMRK YGLAADNVLD ARIVDANGKL LDRKAMGEDL FWAIRGGGGG  243
gi|18652400        GGGYGNLMRK YGLSVDNIVD AQIIDVNGKL LDRKSMGEDL FWAITGGGGV  241
gi|18652398        GGGYGNLMGK YGLSVDNIVD AQLIDVNGKL LNRKSMGEDL FWAITGGGGA  240
gi|13161397        GGYGFLMLRK HGLAADNVVD AFIIDANGKI HDRKSMGEDV FWAIRGGGDA  231
CeresClone: 561310 GGGQGLLMRK HGLAADNVVD AYLIDANGKI HDRKSMGEDV FWAIRGGDAS  240

Consensus          GGGYG-LMRK TGLAADNVID A--VD-NGKL LDRKSMGEDL FWAIRGGGG-  250
```

TABLE 5-8-continued

/tmp/Lead•cDNA12659859.aln

```
gi|20563190          SFGIVLQWKL NLVPVPERVT LFSVSYTLEQ G-ATDIFHKY QMVLPKEDRD  287
gi|41393750          SFGIVASWQV KLLPVPPKVT VFQVHKGIKE G-AIDLVTKW QIVAPALPDD  286
gi|53792953          SFGVVLSWKL RLVRVPETVT VFTIRRPRNQ S-ATDLIIKW QEISPSLPRD  288
gi|26005814          NFGIIAAWKI KLVAVPSKST IFSVKKNMEI HGLVKLFNKW QNIAYKMDKD  286
Lead•cDNA12659859    SFGIILAWKI KLVPVPKTVT VFTIVKTLQQ DVGNKIISKW QRVADKLVEE  291
CeresClone: 522974   SFGVILWWKI KLVPVPQTVT VFTVITKTLEQ G-GSKLLHRW QVAPHIDEN   292
gi|18652400          SFGVVLAYKI KLVRVPEVVT VFTIERRBEQ N-LSTIAERW VQVADKLDRD  290
gi|18652398          SFGVVVAYKI KLVRVPTTVT VFNVQRTSEQ N-LSTIAHRW IQVADKLDND  289
gi|13161397          SFGVIVSWKI KLVPVPSTVT VFNVERILEE N-ATEIIEKW QLVANKLDER  280
CeresClone: 561310   SFGVILAWKI KLVRVPPIVT GENVPRTREE G-VTDLIHRW QYIAHDLHED  289

Consensus            SFGV-LAWKI KLVPVPETVT VF-V-RTLEQ N-----I-KW QQVA-KLD-D  300 gi|20563190          LLIRVQLNTE YIGNTTQK-- -TVRILFHGI MQGNIDTLLP LLNQSFPELN  334
gi|41393750          LMIRIMAM-- ---------- -GQGAMFEAL YLGTCKDLVL LMTARFPELG  323
gi|53792953          VILRVVVQ-- ---------- -SQHAQFBSL FLGRCRRLAR LMRARFPELG  325
gi|26005814          LVLMTHFITK NITDNHGKNK TTVHGYFSSI FHGGVDSLVD LMNKSFPELG  336
Lead•cDNA12659859    LFIRVLFN-- VAGTGGNK-- -TVTTSYNAL FLGGKGTLMN VMKKSFPELG  336
CeresClone: 522974   LFIRVIIQ-P GNGTIVPGKR -TVTTSYNAL FLGGANRLLQ VMKHGFPELG  339
gi|18652400          LFLRMTFS-V INDTINGGK- -TVRAIFPTL YLGNSRNLVT LLNKDFPELG  336
gi|18652398          LFLRMTFN-V INNTNGEK-- -TIRGLFPTL YLGNSTALVA LLNKDFPELG  335
gi|13161397          IFLRMDLA-R ANSSQHGKL- -ALQANFVAM HQGGMEELIP LMQKNFPELG  327
CeresClone: 561310   LVIRVIAQ-- ISGHDKSK-- -KFRATFNSI FLGGVDRLIP LMNESFPELG  334

Consensus            L--RVV---- -------K-- -TVRA-FN-L FLGG-D-LV- LMNK-FPELG  350 gi|20563190          VTREMCQEVR MVQTLLEFSG FNI----STP TSVLAN-RSA IPKLSFKGKS  379
gi|41393750          MNATHCKEMT WIESVPYIPM GPK----GIV RD-LLN-RTS NIKAFGKYKS  367
gi|53792953          MLQSDCEEIT WIQSTVYFAF YSS----SKP LELLLD-RGT EPDRYFKAKS  370
gi|26005814          IKKIDCKEFS WIDTIIFYSG VVNFNTANFK KEILLD-RSA GKKTAFSIKL  385
Lead•cDNA12659859    LTFKDCIEMS WLESIAYISG FPT----HTP TNVLLQGKSP FPKVSFKAKS  382
CeresClone: 522974   LIRKDCVEIS WIESVLYIAG YPD----GTA PEVLLQ-GKS TTKAYFKAKS  384
gi|18652400          LQESDCTEMS WVESVLYYTG FPS----GTP TTALLS-RTP QRLNPFKIKS  381
gi|18652398          VEISDCIEMS WIESVLFYTN FPI----GTP TTALLS-RTP QRLNPFKIKS  380
gi|13161397          LKRKDCTEIS WIGSAVFING ALIGSSGHEA PEVLLN-RTQ IRSGKYKGXS  376
CeresClone: 561310   LQAKDCTEMS WIQSVMFIAG YNI----EDP LELLLN-RTT MFKRSFKAKS  379

Consensus            L---DC-EMS WIESVLYY-G FP------TP -EVLLN-RT- --K--FK-KS  400 gi|20563190          DYVRIPIPRS GLRKLWRKMF ENDNSQT-LF MYTFGGKMEE YSDTAIPYPH  428
gi|41393750          DYVLEPIPKS DWEKLFTWLV KPGAGV--MI MDPYGGGIAS VPESATPFPR  415
gi|53792953          DYVQEPIPRH AWESTMPWLE BHDAGL--LI LDPYGGEMAR VSPAAIPFPR  418
gi|26005814          DYVKKPIPET AMVKILEKLY EEDVGAGMYV LYPYGGIMEE ISESAIPFPH  435
Lead•cDNA12659859    DFVKTPIPES GLQGIFKKLL KEDIPL--MI WNPYGGMMAK IPESQIPFPH  430
CeresClone: 522974   DFVREVITEK SLNALWKIFL QDDGPL--MI WNPYGGKMSR IAESATPFPH  432
gi|18652400          DYVQNPISKR QFEFIFERMK ELENQM--LA FNPYGGRMSE ISEFAKPFPH  429
gi|18652398          DYVKNTISKQ GFESIFERMK ELENQM--LA FNPYGGRMSE ISEFAKPFPH  428
gi|13161397          DYVRKPIPVD GLRGLWRWLN DDKVQYSQLQ FAPYGGKMDN ISESEIPFAH  426
CeresClone: 561310   DFFKEPVPKS GLEGAWKLLL EEEIAF--LI MEPYGGRMNE ISESEIPFPH  427

Consensus            DYVKEPIPKS GLE-IW-KL- E-D--M--LI --PYGG-M-E ISESAIPFPH  450 gi|20563190          RAGVLYQVFK RVDFMDQPSD KTLISLRRLA WLRSFDKTLE PYVTSNPREA  478
gi|41393750          RSGVLFNIQY VVYWFGEGAA AL-----PTO WIRDIYDFMT PYVSKNPRQA  460
gi|53792953          RKGNLYNLQY YSFWHEHGAE TL---ERHLS WVRGLYGEME PYVSKNPRTG  465
gi|26005814          RAGIMYELWY TASWEKQEDN -----EKHIN WVRSVYNFIT PYVSQNPRLA  480
Lead•cDNA12659859    RKGVLFKVQY VISWLD-SDK RP---SRHIN WIRDLYSYMT PYVSSNPREA  476
CeresClone: 522974   RKGVLYKIQH VTGWLD-GEK SM---AKHMN WMRKFYFYMA PYVSKYPRET  476
gi|18652400          RSGNIAKIQY EVNWEDLSDE AE---NRYLN TIRLMYDYMT PFVSKNPREA  476
gi|18652398          RSGNIAKIQY EVNWDELGVE AA---NRYLN FIRVMYDYMT PFVSKNPREA  475
gi|13161397          RSGYIFHIHY VVVWQEEGDE AT---QRHVN WIRRLYKYME PYVSNSPRAA  473
CeresClone: 561310   RKGNLYNLQY LVNWEVNSDE AS---RHLQ WAKMVYKYMT PYVSKSPRAA  474

Consensus            RSGVLYKIQY VVNWE--GDE A-----RHLN W-R-LY-YMT PYVSKNPREA  500
```

TABLE 5-8-continued

/tmp/Lead•cDNA12659859.aln

```
gi|20563190          YMNYNDLDLG FDS-----AA YEEASEWGER YWKRENFKKL IRIKAKVDPE  523
gi|41393750          YVNYRDLDLG VNQVVGNVST YASGKVWGEK YFKG-NPERL ARIKGKIDPE  509
gi|53792953          YVNYRDMDLG RNEIEGNVTS YTKGKVWGEK YFRG-NPERL AAVKAMVDPD  514
gi|26005814          YLNYRDLDLG KIN-HASPNN YTQARIWGEK YFGK-NFNRL VKVKTKVDPN  528
Lead•cDNA12659859    YVNYRDLDLG RNI-KDVKTC IKQAQVWGAN YFKN-NFNRL MMIKAKVDPE  524
CeresClone: 522974   YVNYRDLDIG MNQ-KN-NTS LLKASSWGYR YFKG-NFNRL VKVKTKVDPS  525
gi|18652400          FLNYRDLDIG INS-HG-RNA YTEGMVYGHK YFKETNYKRL VSVKTKVDPD  524
gi|18652398          FLNYRDLDIG VNS-HG-KNA YGEGMVYGHK YFKETNYKRL TMVKTRVDPS  523
gi|13161397          YVNYRDLDIG VNK-NG-YTS YHQASIWGLK YFSN-NFKRL ATVKTKVDPH  520
CeresClone: 561310   YFNYKDLDLG KNK-LD-STS YSEASVWGKK YFKG-NFRRL AQIKTKFDPL  521

Consensus            YVNYRDLDLG VNS--G--TS Y-EA-VWGEK YFK--NFKRL V-VKTKVDP-  550 gi|20563190          NFFRHPQSIP VES--RPLSD M                                 542
gi|41393750          DYFRNEQSIP PLL------- -                                 522
gi|53792953          DFFRNEQSIP PLPAAKGWSS I                                 535
gi|26005814          NFFRNEQSIP PLP--PHHH- -                                 545
Lead•cDNA12659859    NFFRNEQSIP PM-------- -                                 536
CeresClone: 522974   NFFRNEQSIP LLP--TGKKE -                                 543
gi|18652400          NFFRNEQSIP TLS--S---- -                                 538
gi|18652398          NFFRNEQSIP TLS--SSWK- -                                 540
gi|13161397          NFFRNEQSIP TLS--KE--- -                                 535
CeresClone: 561310   NFFRNEQSIP LLN--SHHS- -                                 538

Consensus            NFFRNEQSIP -LS------- -                                 571
```

23/05/05 plur = 5.000000-collision-box-noboxcol colbyconsensus

Example 6—Ceres cDNA 12723147

Ceres cDNA 12723147 encodes an *Arabidopsis* putative aldo/keto reductase. Ectopic expression of Ceres cDNA 12723147 under the control of the CaMV35S promoter induces the following phenotypes:

Germination on high concentrations of polyethylene glycol (PEG), mannitol and abscissic acid (ABA).

Continued growth on high concentration of PEG, mannitol and ABA.

Generation and Phenotypic Evaluation of $T_1$ Lines Containing 35S::cDNA 12723147.

Wild-type *Arabidopsis* Wassilewskija (WS) plants were transformed with a Ti plasmid containing cDNA 12723147 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 12723147 was identified in resistant plants from each of the three surrogate drought screens, the five individual $T_2$ events containing this cDNA (SR01013) were screened on high PEG, mannitol and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the $18^{th}$ plant isolated from a mannitol screen of Superpool 1.

Qualitative and Quantitative Analysis Of Independent Events Representing 35S::cDNA 12659859 (SR01010) on PEG, Mannitol and ABA To identify two independent events of 35S::cDNA 12659859 showing PEG, mannitol, and ABA resistance, 36 seedlings from each of two events, SR01013-01 and -02 were screened as previously described. Basta$^R$ segregation was assessed to verify that the lines contained a single insert segregating in a 3:1 (R:S) ratio as calculated by a chi-square test (Table 6-1). Both lines (01 and 02) segregated for a single insert in the $T_2$ generation (Table 1)

TABLE 6-1

Basta$^R$ segregation for SR01013 individual events

| Event | Resistant | Sensitive | Total | Probability of Chi-test* |
|---|---|---|---|---|
| SR01013-01 | 30 | 5 | 35 | 0.14323 |
| SR01013-02 | 30 | 6 | 36 | 0.24821 |
| SR01013-01-3 | 34 | 1 | 36 | 0.00248** |
| SR01013-02-2 | 32 | 0 | 32 | 0.00109** |

*Chi-test to determine whether actual ratio of resistant to sensitive differs from the expected 3:1 ratio.
**Significantly different than a 3:1 (R:S) ratio Lines SR01013-01 and -02 were chosen as the two events because they had a strong and consistent resistance to PEG, mannitol and ABA. The controls were sown the same day and in the same plate as the individual lines. The PEG (Tables 6-2 and 6-3), mannitol (Tables 6-4 and 6-5) and ABA (Tables 6-6 and 6-7) segregation ratios observed for SR01013-01 and -02 are consistent with the presence of single insert as demonstrated by chi-square, similar to what we observed for Basta$^R$ resistance (Table 6-1).

The progeny from one resistant $T_2$ plant from each of these two events were tested in the same manner as the $T_2$. Resistance to PEG, mannitol and ABA was also observed in the $T_3$ generation. Taken together, the segregation of resistant seedlings containing cDNA 12723147 from two events on all three drought surrogate screens and the inheritance of this resistance in a subsequent generation, provide strong evidence that cDNA 12723147 when over-expressed can provide tolerance to drought.

TABLE 6-2

Chi-square analysis assuming a 3:1 (R:S) ratio for progeny of SR01013-01$T_2$ containing 35S::cDNA 12723147 on PEG.

| Event | Observed | Expected | $\chi^2$ | Probability of Chi-Test |
|---|---|---|---|---|
| PEG Resistant | 22 | 27 | 0.926 | 0.054 |
| PEG Sensitive | 14 | 9 | 2.778 | |
| | 36 | 36 | 3.704 | |

TABLE 6-3

Chi-square analysis assuming a 3:1 (R:S) ratio for progeny of SR01013-02 $T_2$ containing 35S::cDNA 12723147 on PEG.

| Event | Observed | Expected | $\chi^2$ | Probability of Chi-Test |
|---|---|---|---|---|
| PEG Resistant | 26 | 27 | 0.037 | .700 |
| PEG Sensitive | 10 | 9 | .111 | |
| | 36 | 36 | .148 | |

TABLE 6-4

Chi-square analysis assuming a 3:1 (R:S) ratio for progeny of SR01013-01 $T_2$ containing 35S::cDNA 12723147 on mannitol.

| Event | Observed | Expected | $\chi^2$ | Probability of Chi-Test |
|---|---|---|---|---|
| Mannitol Resistant | 28 | 27 | .037 | .700 |
| Mannitol Sensitive | 8 | 9 | .111 | |
| | 36 | 36 | .148 | |

TABLE 6-5

Chi-square analysis assuming a 3:1 (R:S) ratio for progeny of SR01013-02 $T_2$ containing 35S::cDNA 12723147 on mannitol.

| Event | Observed | Expected | $\chi^2$ | Probability of Chi-Test |
|---|---|---|---|---|
| Mannitol Resistant | 18 | 27 | 3 | .0005 |
| Mannitol Sensitive | 18 | 9 | 9 | |
| | 36 | 36 | 12 | |

TABLE 6-6

Chi-square analysis assuming a 3:1 (R:S) ratio for progeny of SR01013-02 $T_2$ containing 35S::cDNA 12723147 on ABA.

| Event | Observed | Expected | $\chi^2$ | Probability |
|---|---|---|---|---|
| ABA Resistant | 13 | 24 | 5.042 | 7.098 |
| ABA Sensitive | 19 | 8 | 15.125 | |
| | 32 | 32 | 20.167 | |

TABLE 6-7

Chi-square analysis assuming a 3:1 (R:S) ratio for progeny of SR01013-02 $T_2$ containing 35S::cDNA 12723147 on ABA.

| Event | Observed | Expected | $\chi^2$ | Probability |
|---|---|---|---|---|
| ABA Resistant | 13 | 24 | 5.042 | 7.098 |
| ABA Sensitive | 19 | 8 | 15.125 | |
| | 32 | 32 | 20.167 | |

Table 6-8 provides the results of the consensus sequence (SEQ. ID NOs: 178-200) analysis based on Ceres cDNA 12723147.

TABLE 6-8

```
/tmp/Lead•cDNA.aln gi|543632              MASAKAMMGQ ERQDHFVL-- --KSGHAIPA VGLGTWRAGS DTAHSVQIAI  46
gi|1155213             -MASAKAMGQ GEQDRFVL-- --KSGHAIPA VGLGTWRAGS DTAHSVQIAI  45
gi|728592              MASAKATMGQ GEQDHFVL-- --KSGHAMPA VGLGTWRAGS DTAHSVRIAI  46
gi|13160397            --------MA EEIRFFKL-- --NTGAKIPS VGLGTWQS-- -SPGDAAQAV  35
gi|13160399            --------MA EEIRFFBL-- --NTGAKIPS VGLGTWQS-- -SPGDAAQAV  35
gi|2792295             ---------M AKVPSVTLSS CGDDIQTMPV IGMGTSSYPR ADPETAKAAI  41
gi|50380153            ---------M AKVPSVTLSS CGDDIQTMPV IGMGTSSYPR ADPETAKAAI  41
CeresClone: 290117     ---MASAGTT AVVPEVALRS G-NARTAMPM VGMGTASF-P LVHEAVKDAV  45
gi|50900438            --------MA VVVPEAVLRH --GDARPMPA VGMGVAEY-P STPERTRDAV  39
gi|50900440            --------M AAVPEVALRH --GAGRPMPA VGVGTADSAA TSPETKRGAV  39
gi|53988164            ------MTA TQIPEVVLES S-NGRRIMPV LGFGTASN-N LQPEVLIEAV  41
gi|18728               ------MAAA IEIPTIVFPN S-SAQQRMPV VGMGSAPD-F TCKKDTKEAI  42
gi|20147510            ------MAA IEIPTIVFPN S-FAQHRVPV VEMGSAPD-F TCKKDTKEAI  41
gi|1514979             ----MAAAA IEIPTKVLPN S-TCELRVPV IGMGSAPD-F TCKKDTKEAI  43
gi|1514981             ------MAAA IEIPTKVLPN S-TCELRVPV IGMGSAPD-F TCKKDTKEAI  42
gi|537298              ------MGS VEIPTKVLTN T-SSQLKMPV VGMGSAPD-F TCKKDTKDAI  41
```

TABLE 6-8-continued

/tmp/Lead•cDNA.aln

```
gi|563538              -------MDS VEIPTKVLTN T-SSQLKMPV VGMGSAPD-F TCKKDTKDAI   41
gi|563540              -------MGS VEIPTKVLTN T-SSQLKMPV VGMGSAPD-F TCKKDTKDAI   41
gi|563536              -------MGS VEIPTKVLTN T-SSQLKMPV VGMGSAPD-F TCKKDTKDAI   41
gi|537296              -------MGS VEIPTKVLTN T-SSQLKMPV VGMGSAPD-F TCKKDTKDAI   41
CeresClone: 473625     -------MEA KKIPEVLL-- -NSGKKMPV  IGLGTASIPL PSHEALTSIL   39
gi|2792155             -------MAE KKIPEVLL-- --NSGKKMPV IGMGTSVESR PSNDVLASIF   39
CeresClone: 474019     -------MAG KKIPDVLL-- --NSGKKMPV IGMGTSVENR PSNETLASIY   39
Lead•cDNA              -------MSL TTVPTLAIRS GPSGHHSMPV LGFGTAASPL PEPTMLKETV   43
gi|15218958            -------MSA LTFPIG---- --SVHHLMPV LALGTAASPP PEPIVLKRTV   37
gi|5080825             -----MVASG HEVVTLTFPI G-SVHHLMPV LALGTAASPP PEPIVLKRTV   44
gi|31429855            --------M  ATIPEVPAS- --ELIQTMPR VGMGTAAFPF TSSEDTTAAM   38
gi|31429856            -------MAM ATIPEVPAS- --ALLPTMPR IGMGTAAFPF TSSEETTAAL   40
gi|50920555            -------MSD GGAGAK---- --GAGFGMPR VGMGTAVQ-G PRPEPIRRAV   36
CeresClone: 1074583    -------MGA GD-------- --KTAAGMPR IGMGTAVQ-G PKPDPIRRAV   32
CeresClone: 677995     -------MGA GD-------- --KTAAGMPR IGMGTAVQ-G PKPDPIRRAV   32
gi|6478216             -------MEI GGVPVVTI-- --SSGRCMPI LGMGTAENNL QGSERVKLAI   39
gi|40781601            -------MA  FTIPEVPLS- --SGGRKMPV LGLGTAADPP VDPETVRKAV   39

Consensus              -------M-- -EIP--VL-- --SS---MPV VGMGTA---- ---E--K-AI   50 gi|543632              IEA---GYRH VDTAAEYGVE KEVGKGLKAA MEAGI--DRK DLFVTSKLWC   91
gi|1155213             IEA---GYRH VDTAAQYGIE KEVDKGLKAA MEAGI--DRK DLFVTSKIWR   90
gi|728592              IEA---GYRH VDTAAEYGVE KEVGKGLKAA MEAGI--DRK DLFVTSKIWC   91
gi|13160397            EVAIKCGYRH IDGARLYENE KEIGVVLKKL FDDGVV-KRE DLFITSKLWS   84
gi|13160399            EVAIKCGYRH IDGARLYENE KEIGVVLKKL FDDGVV-KRE DLFITSKLWS   84
gi|2792295             LEAIRAGYRH FDTAAAYGSE KDLGEAIAEA LRLQLIKSRD ELFITTKLWA   91
gi|50380153            LEAIRAGYRH FDTAAAYGSE KDLGEAIAEA LRLQLIKSRD ELFITTKLWA   91
CeresClone: 290117     LSAIEVGFRH FDTASMYGTE KPLGDAVAEA LRRGTLRSRE DLFVTSKLWC   95
gi|50900438            LAALEAGFRH FDTASLYRTE APLGEAIAEA TRRGLLASRE EAFVTTKLWC   89
gi|50900440            LAALEVGFRH FDTAALYGTE APLGEAIAEA TRRGLVASRE EVFVTTKLWC   89
gi|53988164            LEAIKLGYRH FDTASIYGSE QILGVAIAQA LKLGLVASRD ELFITSKLWC   91
gi|18728               IEAVKQGYRH FDTAAAYGSE QALGEALKEA IHLGLV-SRQ DLFVTSKLWV   91
gi|20147510            IEAVKQGYRH FDTAAAYGSE QALGEALKEA VDLGLV-SRQ DLFVTSKLWV   90
gi|1514979             IEAIKQGYRH FDTAAAYGSE TALGEALKEA RDLGLV-TRE DLFVTSKLWV   92
gi|1514981             IEAIKQGYRH FDTAAAYGSE TALGEALKEA RDLGLV-TRE DLFVTSKLWV   91
gi|537298              IEAIKQGYRH FDTAAAYGSE QALGEALKEA IHLGLV-TRE ELFVTSKLWV   90 gi|563538              IEAIKQGYRH FDTAAAYGSE QALGEALKEA IHLGLV-TRE ELFVTSKLWV   90
gi|563540              IEAIKQGYRH FDTAAAYGSE QALGEALKEA IHLGLV-TRD ELFVTSKLWV   90
gi|563536              IEAIKQGYRH FDTAAAYGSE QALGEALKEA IHLGLV-TRD ELFVTSKLWV   90
gi|537296              IEAIKQGYRH FDTAAAYGSE QALGEALKEA IHLGLV-TRD ELFVTSKLWV   90
CeresClone: 473625     IDAFEVGYRH FDTASLYESE ESLGKAVAKA LELGLINSRE ELFITSKLWS   89
gi|2792155             VDAIQVGYRH FDSASVYGTE EAIGMAVSKA IEQGLIKSRD EVFITSKPWN   89
CeresClone: 474019     VEAIEVGYRH FDTAVYGTE  EAIGLAVSKA IDKGLIKSRD EVFITSKPWN   89
Lead•cDNA              IEAIKLGYRH FDTSPRYQTE EPIGEALAEA VSLGLVRSRS EFFVTTKLWC   93
gi|15218958            LEAIKLGYRH FDTSPRYQTE EPLGEALAEA VSLGLIQSRS ELFVTSKLWC   87
gi|5080825             LEAIKLGYRH FDTSPRYQTE EPLGEALAEA VSLGLIQSRS ELFVTSKLWC   94
gi|31429855            LRAIBLGYRH FDTARIYATE GCVGEAVAEA VRRGLIASRA DVFVTSKLWC   88
gi|31429856            LRAIBLGYRH FDTARLYATE GCVSEAVAEA VRRGLVASRA DVFVTSKLWC   90
gi|50920555            LKAIEAGYRH FDTAAHYETE APIGEAAAEA VRSGAIASRA DLFITSKLWC   86
CeresClone: 1074583    LRAIEVGYRH FDTAAHYETE APIGEAAAEA VRSGAVASRD DLFITSKLWC   82
CeresClone: 677995     LRAIEVGYRH FDTAAHYETE APIGEAAAEA VRSGAVASRD DLFITSKLWC   82
gi|6478216             LKAIEVGYRH FDTAFVYQTE GSLGEVAAEA LQNGLIKSRD ELFITSKLWC   89
gi|40781601            TEALKLGYRH FDTAALYNSE QPLGDAIAEA LGEGLIKSRD ELFITSKLWC   89

Consensus              LEAIK-GYRH FDTAA-YG-E Q-LGEALAEA I--GLV-SR- DLFVTSKLW-  100 gi|543632              TDLVPDRVRP ALEKTLKDLQ LDYDLYLIH  WPFRLKDG-- AHKPEAGEV   139
gi|1155213             TNLAPERARP ALENTLKDLQ LDYIDLYLIH WPFRLKDG-- AHQPBAGEV   138
gi|728592              TNLAPERVRP ALENTLKDLQ LDYIDLYHIH WPFRLKDG-- AHMPBAGEV   139
gi|13160397            TDHAPEDVPV ALDKTLEDLQ LDYIDLYLIH WPVRLKKG-- -SVGLDPENF  131
gi|13160399            TDHAPEDVPV ALDKTLEDLQ LDYIDLYLIH WPVRLKKG-- -SVGLDPENF  131
gi|2792295             SFAEKDLVLP SIKASLSNLQ VEYIDMYIIH WPFKLGKE-V RTMPVERDLV  140
gi|50380153            SFAEKDLVLP SIKASLSNLQ VEYIDMYIIH WPFKLGKE-V RTMPVERDLV  140
CeresClone: 290117     SQNHPDLVLP SLRETLKNLQ MEYVDLYLIH WPVCLKPG-P PELPTRKENA  144
gi|50900438            TQCHPDLVLP SLRESLRNLQ MEYVDLYLIH LPISVKPG-P MVFPVKKEDV  138
gi|50900440            TQCHPGLVLP SLRESLRNLQ MEYVDLYLVH WPISVKPG-P PMLPVKREDA  138
gi|53988164            NDGHPNLVIP ALKKSLQNLE LEYLDLYLIH WPISAKPG-K LSHALEEKDQ  140
gi|18728               TENHPHLVLP ALRKSLKILQ LEYLDLYLIH WPLSSQPG-K FSFPIBVEDL  140
gi|20147510            TDNHPHLVVS ALRKSLKILQ LEYLDLYLIH WPLSSQPG-K FSFPIBVEDL  139
gi|1514979             TENHPHLVVP ALRKSLEILQ LEYLDLYLIH WPLSSQPG-K FSFPIQAEDL  141
gi|1514981             TENHPHLVVP ALRKSLEILQ LEYLDLYLIH WPLSSQPG-K FSFPIQAEDL  140
gi|537298              TENHPHLVIP ALQKSLKILQ LDYLDLYLIH WPLSSQPG-K FSFPIDVADL  139
```

TABLE 6-8-continued

/tmp/Lead•cDNA.aln

```
gi|563538           TENHPHLVIP ALQKSLKILQ LDYLDLYLIH WPLSSQPG-K FSFPIDVADL 139
gi|563540           TENHPHLVIP ALQKSLKILQ LDYLDLYLIH WPLSSQPG-K FTFPIDVADL 139
gi|563536           TENHPHLVIP ALQKSLKILQ LDYLDLYLIH WPLSSQPG-K FSFPIDVADL 139
gi|537296           TENHPHLVIP ALQKSLKILQ LDYLDLYLIH WPLSSQPG-K FSFPIDVADL 139
CeresClone: 473625  TDAHPDLVVP ALKTSLQKLG LEYVDLYLIH WPVRLKPEAK GYHNILKENV 139
gi|2792155          TDAHPDLIVP ALKITLKKLG MEYVDLYLIH WPVRLRHDLE NPVIFSKEDL 139
CeresClone: 474019  TDAHRDLIVP ALKITLKKLG TEYVDLYLIH WPVRLRHDLE NPTVFTKEDV 139
Lead•cDNA           ADAHGGLVVP AIKRSLKNLQ LDYLDLYIIH WPVSSKPG-K YKFPIDEDDF 142
gi|15218958         ADAHGGLVVP AIQRSLETLK LDYLDLYLIH WPVSSKPG-K YKFPIBEDDF 136
gi|5080825          ADAHGGLVVP AIQRSLETLK LDYLDLYLIH WPVSSKPG-K YKFPIBEDDF 143
gi|31429855         SDLHAGRVVP AARETLRNLG MDYVDLLLVH WPVSLTPG-N YDFPFPKEVI 137
gi|31429856         SDLHAGRVVP AARETLRNLG MDYVDLLLVH WPATVAPG-S YDFPFPKEEM 139
gi|50920555         SDAHRDRVLP ALRQTLWNLG MEYVDLYLVH WPVSMKPG-R YKAPFTADDF 135
CeresClone: 1074583 SDAHRDRVVP ALRQTLRNLG MEYVDLYLVH WPVSMKPG-R FKAPFTAEDF 131
CeresClone: 677995  SDAHRDRVVP ALRQTLRNLG MEYVDLYLVH WPVSMKPG-R FKAPFTAEDF 131
gi|6478216          ADAYPDHVLP ALQNSLRNLK LEYLDLYLIH WPVSLKPG-K FMHPIPKDEI 138
gi|40781601         SDAHRENVEP ALQKTLKNLK LEYIDMYLIH WPVSSKPG-N MEYPIKKEDF 138

Consensus           TD-HP-LVVP AL-KSLKNLQ LDYIDLYLIH WPISLKPG-K F--PIE-EDL 150 gi|543632           LE-FDMEGVW KEMENLVKDG LVKDIGVCNY TVTKLNRLLQ SAKIAPAVCQ 188
gi|1155213          LE-FDMEGVW KEMEKLVKDG LVKDIDVCNF TVTKLNRLLR SANIPPAVCQ 187
gi|728592           LE-FDMEGVW KEMENLVKDG LVKDIGVCNY TVTKLNRLLR SAKIPPAVCQ 188
gi|13160397         IP-TDIPGTW KAMBALYDSG KARAIGVSNF TLKKLSDLLD VARIPPAVNQ 180
gi|13160399         VP-TDIPGTW KAMBALYDSG KARAIGVSNF TLKKLSDLLD VARIPPAVNQ 180
gi|2792295          QP-LDIKSVW EAMEECKKLG LARGIGVSNF TSSMLEELLS FAEIPPAVNQ 189
gi|50380153         QP-LDIKSVW EAMEECKKLG LARGIGVSNF TSSMLEELLS FAEIPPAVNQ 189
CeresClone: 290117  VP-LDLAGVW RAMEECQRLG LAKAIGVSNF TTIRHLDGVLA VATVPPAVNQ 193
gi|50900438         VP-FDFGGVW RAMEECHRLG LAKAIGVSNF TTKHIDKLLA VATILPAVNQ 187
gi|50900440         VP-FDFEGVW RAMEECHRLG LAKAIGVSNF TTKHLDKLLA VATIPPAVNQ 187
gi|53988164         MP-MDFKGVW ADMEEAQRLG LITKSIGISNF STKKTQNLLS FATIPPSVNQ 189
gi|18728            LP-FDVKGVW ESMEECQKLG LITKAIGVSNF SVKKLQNLLS VATIRPVVDQ 189
gi|20147510         LP-FDVKGVW EAMQECQKLG LITKAIGVSNF SVKKLQNLLS VATIRPVVNQ 188
gi|1514979          LP-FDVKGVW ESMEESLKLG LITKAIGVSNF SVKKLQNLLS VATIRPAVNQ 190
gi|1514981          LP-FDVKGVW ESMEESLKLG LITKAIGVSNF SVKKLQNLLS VATIRPAVNQ 189
gi|537298           LP-FDVKGVW ESMEESLKLG LITKAIGVSNF SVKKLENLLS VATVLPAVNQ 188 gi|563538           LP-FDVKGVW ESMEESLKLG LITKAIGVSNF SVKKLENLLS VATVLPAVNQ 188
gi|563540           LP-FDVKGVW ESMEESLKLG LITKAIGVSNF SVKKLENLLS VATVLPAVNQ 188
gi|563536           LP-FDVKGVW ESMEESLKLG LITKAIGVSNF SVKKLENLLS VATVLPAVNQ 188
gi|537296           LP-FDVKGVW ESMEESLKLG LITKAIGVSNF SVKKLENLLS VATVLPAVNQ 188
CeresClone: 473625  LPSFDMKGIW EAMEECYRLG IAKSIGVSNF GIKKLSQLLE NATIPPAVNQ 188
gi|2792155          LP-FDIEGTW KAMEECYRLG IAKSIGICNY GTKKLTKLLE IATIPPAVNQ 188
CeresClone: 474019  LP-FDIEGIW KAMEECYRLG IAKSIGICNY GIKKLTKLLE IATIPPAVNQ 188
Lead•cDNA           MP-MDFEVVW SEMEECQRLG LAKCIGVSNF SCKKLQHILS IATIPPSVNQ 191
gi|15218958         LP-MDYETVW SEMEECQRLG VAKCIGVSNF SCKKLQHILS IAKIPPSVNQ 185
gi|5080825          LP-MDYETVW SEMEECQRLG VAKCIGVSNF SCKKLQHILS IAKIPPSVNQ 192
gi|31429855         LPSFDMEGVW RGMEECHRLG LARAIGVSNF SAKKLEQLLS LAAVRPAVNQ 187
gi|31429856         APAFDMEGVW RGMEECHRLG LARAIGVSNF SAKKLEQLLS FAVMREAANQ 189
gi|50920555         VP-FDMRAVW EAMEECHRLG LAKAIGVCNF SCKKLDILLS FATIPPAVNQ 184
CeresClone: 1074583 VP-FDMRAVW EAMEECHRLG LAKAVANF SCKKLEILLS FATIPPTVNQ 180
CeresClone: 677995  VP-FDMRAVW EAMEECHRLG LAKAVANF SCKKLEILLS FATIPPIVNQ 180
gi|6478216          FP-IDYKSVW AAMEKQMLG LITKSIGVSNF SCKKLHYLMA TANIPPAVNQ 187
gi|40781601         LQ-MDYKSVW EAMEECQKLG LITKAIGVSNF SCKKLSDVLA NAKVPPAVNQ 187

Consensus           LP-FD-KGVW -AMEEC-KLG LAKAIGVSNF S-KKLE-LLS VATIPPAVNQ 200 gi|543632           MEMHPGWKND KILBACKKHG THATAYSPLC SS------E KNLAHDPVVE 231
gi|1155213          MEMHPGWKND KIFBACKKHG IHVTAYSPLG SS------E KNLVHDPVVE 230
gi|728592           MEMHPGWKND KIFBACKKHG IHITAYSPLG SS------E KNLAHDPVVE 231
gi|13160397         VGCHPSCAQT KLRAFCKSKG VHLSGYSPLG SPGTPW--K HDVLENPILV 228
gi|13160399         VGCHPSCAQT KLRAFCKSKG IHLSGYSPLG SPGTPW--K HDVLENPILV 228
gi|2792295          LEMNPAWQLK KLRDFCKAKG IHVTAYSPLG AARIKWG--D DRVLGSDIIE 237
gi|50380153         LEMNPAWQLK KLRDFCKAKG IHVTAYSPLG AARIKWG--D DRVLGSDIIE 237
CeresClone: 290117  VELNPAWQQR TLRAYCADRG IHVAAYSPLG --GQNWDGQG SAVLDSEVLA 241
gi|50900438         VEMNPTWQQR TVREYCDAKG IRVTAYSPLG --GQNWGGSA NYVMESSVLT 235
gi|50900440         VEMNPVWQQR TVREYCAAKG IRVAAYSPLG --GQNWIGEG NYVMESPVLA 235
gi|53988164         VEMSPFWQQK KLRDFCKASG IVVTAFSPLG AIGTSWG--T NHVLESKVLN 237
gi|18728            VEMNLAWQQK KLREFCKENG IIVTAFSPL- RKGASRG--P NEVMENDVLK 236
gi|20147510         VEMNLAWQQK KLREFCKENG IVITAFSPL- RKGASRG--P NEVMENDVLK 235
gi|1514979          VEMNLAWQQK KLREFCNANG IVLTAFSPL- RKGASRG--P NEVMENDMLK 236
gi|1514981          VEMNLAWQQK KLREFCNANG IVLTAFSPL- RKGASRG--P NEVMENDMLK 236
gi|537298           VEMNLAWQQK KLREFCNANG IVLTAFSPL- RKGASRG--P NEVMENDMLK 235
```

TABLE 6-8-continued

/tmp/Lead•cDNA.aln

```
gi|563538              VEMNLAWQQK KLREFCNANG IVLTAFSPL- RKGASRG--P NEVMENDMLK 235
gi|563540              VEMNLAWQQK KLREFCNAHG IVLTAFSPL- RKGASRG--P NEVMENDMLK 235
gi|563536              VEMNLAWQQK KLREFCNAHG IVLTAFSPL- RKGASRG--P NEVMENDMLK 235
gi|537296              VEMNLAWQQK KLREFCNAHG IVLTAFSPV- RKGASRG--P NEVMENDMLK 235
CeresClone: 473625     VEMSPTWQQG KLKEFCKQKG IHVSAWSPLG AYKSAQG--T NAVMESPILK 237
gi|2792155             VEMNPSWQQG NLREFCKQKG IHVSAWSPLG AYKIFWG--S GAVMENQILQ 236
CeresClone: 474019     VEMNPSWQQG KLREFCKQKG IHVSAWSALG AYKIFWG--S GAVMENPILQ 236
Lead•cDNA              VEMSPIWQQR KLRELCRSND IVVTAYSVLG SRGAFWG--T PKIMESDVLK 239
gi|15218958            VEMSPVWQQR KLRELCKSKG IVVTAYSVLG SRGAFWG--T HKIMESDVLK 233
gi|5080825             VEMSPVWQQR KLRELCKSKG IVVTAYSVLG SRGAFWG--T HKIMESDVLQ 240
gi|31429855            VEVNPMWQQR TLREVCRREG VQLCGYSPLG AKGTPWG--S AAVMDSGVLQ 235
gi|31429856            VEVNPMWQQR TLREVCRREG VQLCGYSPLG AKGTPWG--S AAVMDSGVLH 237
gi|50920555            VEVNPVWQQR KLRELCREKG VQICAYSPLG ASGTHWG--S DSVMASAVLR 232
CeresClone: 1074583    VEVNPVWQQR KLREFCRGKG IQLCAYSPLG AKGTHWG--S DAVMDAGVLQ 228
CeresClone: 677995     VEVNPVWQQR KLREFCRGKG IQLCTYSPLG AKGTHWG--S DAVMDAGVLQ 228
gi|6478216             VEMNPIWQQQ KLRDYCKITNN IMVTAYSPLG AKGTHWG--S SGVMDSEVLN 235
gi|40781601            VEVNPCWQQK QLTEFCKSNG ILVMAYAALG AVGTFYG--T NRVMGSEVLN 235

Consensus              VEMNP-WQQK KLREFCK-KG I-VTAYSPLG AKG--WG--- N-VME--VLK 250 gi|543632              KVANKLNKTP GQ---VLIKW ALQRGTIVIP KSSKDERIKE NIQVFGWEIP 278
gi|1155213             KVANKLNKTP GQ---VLIKW ALQRGTSVIP KSSKDERIKE NIQAFGWEIP 277
gi|728592              KVANKLNKTP GQ---VLIKW ALQRGTSVIP KSSKDERIKE NIQVFGWEIP 278
gi|13160397            DVAEKLGKTP AQ---VAIRW GLQMGHSVLP KSVHESRIKE NIDVFSWCIP 275
gi|13160399            DVAEKLGKTP AQ---VALRW GLQMGHSVLP KSVHESRIKE NIDVFSWCIP 275
gi|2792295             EIAQAKGKST AQ---ISLRW VYEQGVSIVT KSYNKERMRQ NLDIFDFCLT 284
gi|50380153            EIAQAKGKST AQ---ISLRW VYEQGVSIVT KSYNKERMRQ NLDIFDFCLT 284
CeresClone: 290117     AIAKARGKTV AQ---VALRW IHEQGVTCIV KSYSKERLRQ NLGIFDWELT 288
gi|50900438            EIARARGKSI AQ---VSLRW IYEQGVTPIA KSYRKERLKE NLEIFDWELT 282
gi|50900440            DIARARGKSI AQ---IHEQGVTPIP KSYNKERLKE NLEIFDWELT 282
gi|53988164            EIAEAHGKTV AQ---VCIRW VYQGATLAV KSYNKERLKQ NVQVFDWELT 284
gi|18728               EIADAHGKSI AQ---VSLRW LYEQGVTFVP KSYDKERMNQ NLHIFDWALT 283
gi|20147510            EIADAHGKSI AQ---VSLRW LYEQGVTFVP KSYDKERMNQ NLQIFDWALT 282
gi|1514979             GIAEAHGKSI AQ---VSLRW LYEQGVTFVA KSYDKERMNQ NLQIFDWELT 284
gi|1514981             GIAEAHGKSI AQ---VSLRW LYEQGVTFVA KSYDKERMNQ NLQIFDWELT 283
gi|537298              EIADAHGKSV AQ---ISLRW LYEQGVTFVP KSYDKERMNQ NLCIFDWSLT 282 gi|563538              EIADAHGKSV AQ---ISLRW LYEQGVTFVP KSYDKERMNQ NLCIFDWSLT 282
gi|563540              EIADAHGKSV AQ---ISLRW LYEQGVTFVP KSYDKERMNQ NLRIFDWSLT 282
gi|563536              EIADAHGKSV AQ---ISLRW LYEQGVTFVP KSYDKERMNQ NLRIFDWSLT 282
gi|537296              EIADAHGKSV AQ---ISLRW LYEQGVTFVP KSYDKERMNQ NLRIFDWSLT 282
CeresClone: 473625     EIACEROKSM AQ---IALRW IYEQGAIAIV KSFNKERMKQ NLDIFDWELS 284
gi|2792155             DIALAKGKTI AQ---VALRW VYQQGSSAMA KSFNKERMKQ NLEIFDFELS 283
CeresClone: 474019     DIAKAKGKTI AQ---VALRW VYQQGSSAMA KSTNSERMKQ XLDIFDFMLS 283
Lead•cDNA              EIAEAKEKTV AQ---VSMRW AYEEGVSMVV KSFTKERLEE NLKIFDWELT 286
gi|15218958            EIAEAKGKTV AQ---VSMRW AYEEGVSMVV KSFRKDRLEE NLKIFDWSLT 280
gi|5080825             EIAEAKGKTV AQ---VSMRW AYEEGVSMVV KSFRKDRLEE NLKIFDWELT 287
gi|31429855            EIAGAKGKTL AQ---ICLRW LYEQGDVLLV KTYNEKRMKE NLDIFNWELT 282
gi|31429856            DIAQTKGKTL AQ---ICLRW MYEQGDVLLV KTYNENRMKE NLDIFDWELT 284
gi|50920555            DIAQSKGKTV AQARHVCLRW VYEQGDCLIV KSFDEARMRE NLDIVGWELT 282
CeresClone: 1074583    EIAASRGKSV AQ---VCLRW VYEQGDCLIV KSFDEARMRE NLDVDGWELT 275
CeresClone: 677995     EIAASRGKSV AQ---VCLRW VYEQGDCLIV KSFDEARMRE NLDVDGWELT 275
gi|6478216             QISQVRGKSV AQ---VSLRW VYEQGASLLV KSFNEERMKE NLKIFDWELS 282
gi|40781601            EIARIRGNTV AQ---VCLRW AYEQGIGGLV KSFNKERMEQ NLQIFNWTLS 282

Consensus              EIAEAKGKTV AQ---VSLRW VYEQGVTLI- KSY-KERMKQ NL-IFDWELT 300 gi|543632              EEDFQVLC-S IKDEKRVLTG EELFVNKTHG PYKS-ASEVW DNEN--- 320
gi|1155213             EDDFQVLC-S IKDEKRVLTG EELFVNKTHG PYKS-ASEVW DHEN--- 319
gi|728592              EEDFKVLC-S IKDEKRVLTG EELFVNKTHG PYRS-ARDVW DHEN--- 320
gi|13160397            DDLFAKFS-E IEQVSPGKPE FPVH--PEIS QYKT-VEEMW DGGI--- 315
gi|13160399            DVLFAKFS-E IEQVSPGKPE FPVH--PEIS QYKT-VEEMW DGGI--- 315
gi|2792295             EELEKMS-H LPQ-RKGVT- --FA--SILG PHDI-VLEV- DEEL--- 319
gi|50380153            EELEKMS-H LPQ-RKGVT- --FA--SILG PHDI-VLKV- DEEL--- 319
CeresClone: 290117     DEERLKIS-Q IPQ-RKVVQT SSLF--SQEG EPTA-VDPA ELNILEE 329
gi|50900438            DEDRLKIS-Q IPQ-RKRVTA ASLF--SPDG EFIS--VDLP DIEIVEE 323
gi|50900440            KEDRLKIS-Q KKIVTA ARMF--SPDG EFAS--VDLS DMEIVEE 323
gi|53988164            EEDLEKIN-Q IPQ-RKMMPR EELV--TATG PYKS-LDDLW DGEY--- 323
gi|18728               EQDHHKIS-Q ISQ-SRLIS- ---------G PTKPGLADLW DDQI--- 315
gi|20147510            QEDHHKIS-Q ISQ-SRLIS- ---------G PTKPQLSDLW DDEI--- 314
gi|1514979             TEDHQKID-Q IKQ-NRLIP- ---------G PTKPQLNDLW DDEI--- 316
gi|1514981             TEDHQKID-Q IKQ-NRLIP- ---------G PTKPQLNDLW DDEI--- 315
gi|537298              KEDHEKID-Q IKQ-NRLIP- ---------G PTKPGLNDLY DD----- 312
```

TABLE 6-8-continued

/tmp/Lead•cDNA.aln

```
gi|563538              KEDHEKID-Q IKQ-NRLIP- --------G PIKPGLNDLY DD-----    312
gi|563540              KEDHEKID-Q IKQ-NRLIP- --------G PIKPGLNDLY DD-----    312
gi|563536              KEDHEKIA-Q IKQ-NRLIP- --------G PIKPGLNDLY DD-----    312
gi|537296              KEDHEKIA-Q IKQ-NRLIP- --------G PIKPGLNDLY DD-----    312
CeresClone: 473625     QEESQKFS-Q IPQ-RRMYRG ITFV--SENG PYKT-LEELW D-----    320
gi|2792155             EEELEKIK-Q IPQ-RRQYTG DMWL--SENG SQKT-LEELW DGDV---    322
CeresClone: 474019     EEDLERIS-Q VPQ-RRQYTG DIWL--SENG SQKT-LEELW DGDV---    322
Lead•cDNA              EDETQRISTE IPQ-FRNVHG EVYT--SKKG PIKS-VAEMW DGEI---    326
gi|15218958            EEEKQRISTE ISQ-SRIVDG EVYI--SEKG PIKS-VIEMW DGEI---    320
gi|5080825             EEEKQRISTE ISQ-SRIVDG EVYI--SEKG PIKS-VIEMW DGEI---    327
gi|31429855            DEERERIS-Q LPQ-LRGLPG LEFI--SDHG PYKS-VEDLW DGDV---    321
gi|31429856            EEERDKIS-K LPQ-QRGLTG MQFV--CDNG PYKC-VEDLW DGA----    322
gi|50920555            EEERQRIA-G IPQ-RKINRA LRFV--SDHG PYKS-LDDLW DGEI---    321
CeresClone: 1074583    EEEHRRIA-E IPQ-RKINLG KRYV--SEHG PYKS-LEELW DGEI---    314
CeresClone: 677995     EEEHRRIA-E IPQ-RKINLG KRYV--SEHG PYKS-LEELW DGEI---    314
gi|6478216             PEDLKNIS-E LPQ-RRVSTG DPFV--SING PYKS-VEELW DDEV---    321
gi|40781601            DDESKKIS-E IPQ-GRACLG TDYT--SVHG PYKT-IEELW DGEF---    321

Consensus              EED--KIS-Q IPQ-RRLI-- ------S--G PYKS-L-DLW D-EI---    347
```

23/05/05 plur = 16.500000-collision-box-noboxcol colbyconsensus

Example 7—Ceres eDNA 13488750

Clone 125039, Ceres cDNA 13488750, encodes a full-length putative adenylylsulfate (APS) kinase from *Arabidopsis thaliana*. Ectopic expression of Ceres cDNA 13488750 under the control of the CaMV35S promoter induces the following phenotypes:

Continued growth under high heat conditions.

Generation and Phenotypic Evaluation of $T_1$ Lines Containing 35S::cDNA 13488750.

Wild-type *Arabidopsis* Wassilewskija (WS) plants were transformed with a Ti plasmid containing cDNA 13488750 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No negative phenotypes were observed in the $T_1$ plants although three of the T1 lines produced a small rosette (ME02526-01, 02 and 05). $T_2$ and $T_3$ lines of events ME02526-01 and ME02526-05 did not show the small rosette phenotype.

Screens of Masterpools for Heat Tolerance Via Heat Shock In Vitro.

Seeds from 100 masterpools from the CaMV35S or 32449 over-expression lines were tested for heat tolerance in vitro as described above.

Once cDNA 13488750 was identified in tolerant plants from the screen, five individual. $T_2$ events containing this eDNA (ME02526) were screened on soil as described above to identify events with the resistance phenotype.

Qualitative Analysis of the $T_2$ Masterpool of cDNA 13488750 Plants Heat Shocked on Plates Visual phenotyping of the masterpool containing cDNA 13488750 (ME02526) on agar or soil showed no visible alterations in phenotype (data not shown). After heat-shock at 15 days of age, the ME02526 masterpool showed greater heat recovery as compared to the wild-type control and other transgenic masterpools. Assessment was a measure of "greenness" as well as continued growth at 23° C. after heat shock at 45° C. for between 5 and 8 hours Immediately after the heat shock stress, the extent of stress-induced damage in the control and ME02526 masterpool appeared comparable. The leaves and cotyledons were wilted and droopy although still green. However, after 4 days of recovery, 2 of 10 plants in the ME02526 masterpool had completely recovered and were growing again. Other seedlings showed some recovery as measured by greenness compared to the wild-type control.

Qualitative and Quantitative Analysis of Individual $T_2$ Events of eDNA 13488750 Under Continual Heat Treatment on Soil Five independent events of ME02526 were tested on soil as described above. Two of the events (ME02526-04 and -05) showed heat resistance after continual growth at 36° C. Heat resistance was noted as decreased chlorosis compared to wild-type. Segregation frequencies of the transgene under test suggest that these two events contain a single insert, as calculated by a chi-square test (Tables 7-1, 7-2 and 7-3). Ten and 11 plants from events 04 and 05, respectively, showed continued vigor and decreased chlorosis after continuous heat treatment compared to wild-type controls.

TABLE 7-1

Chi-square analysis assuming a 3:1 (R:S) ratio for progeny of ME02526-04 and -05 containing 35S::cDNA 1.34887.50 on Finale.

| Event | Observed | Expected | $\chi^2$ | Probability of Chi-Test |
|---|---|---|---|---|
| ME02526-04 Finale Resistant | 29 | 27 | 0.593 | 0.44 |
| ME02526-04 Finale Sensitive | 7 | 9 | | |
| | 36 | 36 | | |
| ME02526-05 Finale Resistant | 27 | 27 | 0 | 1 |
| ME02526-05 Finale Sensitive | 9 | 9 | | |
| | 36 | 36 | | |

TABLE 7-2

Chi-square analysis assuming a 3:1 (R:S) ratio for progeny of ME02526-04 containing 35S::cDNA 13488750 for thermo tolerance (continual growth at 36° C. on soil).

| Event | Observed | Expected | $\chi^2$ | Probability of Chi-Test |
|---|---|---|---|---|
| Heat Tolerant | 10 | 11.25 | 0.556 | 0.456 |
| Heat Sensitive | 5 | 3.75 | | |
| | 15 | 15 | | |

TABLE 7-3

Chi-square analysis assuming a 3:1 (R:S) ratio for progeny of ME02526-05 containing 35S::cDNA 13488750 for thermo tolerance (continual growth at 36° C. on soil).

| Event | Observed | Expected | $\chi^2$ | Probability of Chi-Test |
|---|---|---|---|---|
| Heat Tolerant | 11 | 11.25 | 0.022 | 0.881 |
| Heat Sensitive | 4 | 3.75 | | |
| | 15 | 15 | | |

TABLE 7-4

Chi-square analysis assuming a 3:1 (R:S) ratio for progeny of ME02526-04 containing 35S::cDNA 13488750 for thermo tolerance (continual growth at 36° C.

| Event | Observed | Expected | $\chi^2$ | Probability of Chi-Test |
|---|---|---|---|---|
| Heat Tolerant | 14 | 14.25 | 0.017 | 0.89 |
| Heal Sensitive | 5 | 4.75 | | |
| | 19 | 19 | | |

TABLE 7-5

Chi-square analysis assuming a 3:1 (R:S) ratio for progeny of ME02526-05 containing 35S::cDNA 13488750 for thermo tolerance (continual growth at 36° C.

| Event | Observed | Expected | $\chi^2$ | Probability of Chi-Test |
|---|---|---|---|---|
| Heat Tolerant | 15 | 14.25 | 0.157 | 0.69 |
| Heat Sensitive | 4 | 4.75 | | |
| | 19 | 19 | | |

The plants that survive the heat treatment show premature bolting and reduced fecundity but much less so than the control plants. Control and ME02526 plants bolt after only 4 days of exposure to 36° C. (11-day old plants), but were more vigorous and less chlorotic than the controls and the height and branch number was comparable to those of wild-type (data not shown). Heat-tolerant lines all showed seed abortion and reduced fecundity (data not shown). Seed abortion and reduced silique size was also prevalent in all wild-type controls (data not shown). Events 04 and 05, which had a thermo tolerant phenotype in the T$_2$ generation, were evaluated in greater detail in the T$_3$ generation for heat resistance and fecundity after prolonged heat stress on MS plates.

Qualitative and Quantitative Analysis of Individual T$_3$ Events Under 36° C. Heat Treatment on Plates Seeds from five individuals of the T$_3$ generation for ME02526-04 and -05 lines and controls were sterilized, stratified and germinated for 7 days at 23° C. prior to exposure to 36° C. heat stress. The events were evaluated for heat resistance to prolonged heat stress.

The thermo tolerant phenotype became apparent after 15 days of 36° C. treatment. T$_3$ progeny from ME02526-04 (Table 7-4) and ME02526-05 (Table 7-5) were found to segregate in the expected 3:1 ratio for the thermo tolerant phenotype.

Qualitative Analysis of Individual T$_3$ Events Heat Shocked on Plates for Differentiation of Natural Acquired Thermotolerance Plants acquire thermotolerance to lethal high temperatures such as 45° C. if previously exposed to moderately high temperature or if the temperature is raised gradually to an otherwise lethal temperature (Vierling, 1991). To ascertain whether the thermotolerance observed in the T$_3$ generation is due to some naturally acquired thermotolerance imparted by heat exposure of the T$_2$ parent plant (ME2526-04 and 05), thermotolerance was assessed by comparing pre-heat treated wild-type and transgenic controls and unheated wild-type controls. T$_3$ events of ME02526-04 and 05 were heat shocked for 4 hours as described above. ME02526-04 and -05 were able to stay greener longer than both pre-heat treated controls and un-heat treated controls. However, both ME02526 lines and all controls (wild-type and transgenic) failed to elongate and thrive after heat treatment at 45° C. and eventually all died. Un-heat treated wild-type control became chlorotic faster (1-day after treatment) than pre-heat treated wildtype control and pre-heat treated transgenic control suggesting that there is some natural acquired thermotolerance that occurs that is not correlated with the over-expression of 35S::cDNA 13488750. Even with exposure to this lethal temperature, ME02526 was greener after 7 days than controls, indicating that ME02526 has a thermotolerance phenotype that is unrelated to the natural mechanisms of acquired thermotolerance.

Table 7-6 provides the results of the consensus sequence (SEQ ID NOs: 201-214) analysis based on Ceres cDNA 13488750.

TABLE 7-6

```
/tmp/Lead•clone125039.aln gi|3329471          ---------- ---------- ---------- ---------- ----MLRAIA    6
CeresClone: 300011  ---------- ---------- -MLARAPPPR PCSSG-VCIA RAHPRAAAVA   28
gi|50938537         MEASLPFHHH HPAASSTAAH HAARLTPPPP PRDPR-ATAR WPPAAAPVR    49
gi|2832300          ---------- ---------- ---MIGSVKR PVVSC-VLPE FDFTESTGLG   26
Lead•clone125039    ---------- ---------- --MDVAAMAR CVGRCMVSPA FGESESHRLS   28
gi|9757873          ---------- ---------- -------MAR CVGRCMVSPA FGESESHRLS   23

Consensus           ---------- ---------- -------M-R PV--C-VSPA F--SES--I-   50 gi|3329471          QR-------- ---------- ---------- -----ARGS- --------AL   14
CeresClone: 300011  AR-------- ---------- ----PGTTR  TLTTVAAAA- ---------   44
gi|50938537         SRS-----PA NLGLPPHPPR RLRLRLAPPR ITAAVTGGPR RPRRRAPPEL   94
gi|2832300          KKSSSVKLPV NFGAFGSGGG EVKLGFLAPI KATEGSKTS- --------SF   67
Lead•clone125039    ER-------- ---------- --RFLKLSSS TNSDPAGSK- --------SL   49
gi|9757873          ER-------- ---------- --RFLKLSSS TNSDPAGSK- --------SL   44

Consensus           ER-------- ---------- --R---LSS- T--D-AGSS- --------SL  100 gi|3329471          QCA------- ---------- APGTEWASCV RGSSGF---- ---IAYDVGE   40
CeresClone: 300011  ---------- ---------- AEAASNGSAA AAVAGISSSS SALVTSIVGK   74
gi|50938537         ECAGGSSSSL RRPREEEEEE EEEERSSTAH AGVSLVGENK VLQMSSIVPK  144
gi|2832300          QVNGKVDNFR HLQPS----- DCNSNSDSSL NNCNGFPGKK IL-QTTFIVGN  111
Lead•clone125039    KLRGKIHRRM SYF------- RPIMAKDESI SSRSGE---- ---TKQINGK   85
gi|9757873          KLRGKIHRRM SYF------- RPIMAKDESI SSRSGE---- ---TKQINGK   80

Consensus           -L-GKI---M ---------- -P---SDSSI -S-SG----- ---T-SIVGK  150 gi|3329471          STNIKWHETM VSRGDKERLL NQRGCVLWFT GLSGSGKSTV ACILEHALNA   90
CeresClone: 300011  STNILWHECA IGQKERQGLL NQKGCVVWIT GLSGSGKSTL ACALSRELHG  124
gi|50938537         ASNIEWHDCA VGQADRQKLL KQKGCVVWIT GLSGSGKSTL ACTLDRELHT  194
gi|2832300          STNILWHKCA VEKSERQEPL QQRGCVIWIT GLSGSGKSTL ACALSRGLHA  161
Lead•clone125039    QKNIVWHDCP VTKSDRQELI KHKGCVIWIT GLSGSGKSSL ACALSRALHN  135
gi|9757873          QKNIVWHDCP VTKSDRQELI KQKGCVIWIT GLSGSGKSSL ACALSRALHN  130

Consensus           STNI-WHDCA VSKSDRQELL KQKGCVIWIT GLSGSGKSTL ACALSRALH-  200 gi|3329471          RGKMTALLDG DNVRHGLNSN LTFIAEDRLE HPPHRRSEQA LQRRWRPPLR  140
CeresClone: 300011  RGHLTYVLDG DNLRHGLNRD LSPGAEDRAE ---NIRRVGE VAKLFADAGL  171
gi|50938537         RGKLSYVLDG DNLRHGLNKD LGFKAEDRAE ---NIRRVGE VAKLFADAGL  241
gi|2832300          KGKLTYILDG DNVRHGLNSD LSFKAEDRAE ---NIRRIGE VAKLFADAGV  208
Lead•clone125039    RGKLSYILDG DNVRHGLNSD LSFEADDRAE ---NIRRVGE VAKLFADSGI  182
gi|9757873          RGKLSYILDG DNVRHGLNSD LSFEADDRAE ---NIRRVGE VAKLFADSGI  177

Consensus           RGKL-YILDG DNVRHGLNSD LSF-AEDRAE ---NIRRVGE VAKLFADAG-  250 gi|3329471          ELHLRPIAPT RPVRERC--- --AGDFVECY MKIPIELCEQ RDPKGLYKKA  185
CeresClone: 300011  VCIASLISPY RSDRSACRDL LPKHSFIEVF LDVPLQVCEA RDPKGLYKLA  221
gi|50938537         VCIASFISPY RRDRESCRAL LSDGSFIEVF LNMPLELCES RDPKGLYKLA  291
gi|2832300          ICIASLISPY RKPPDACRSL LPEGDFIEVF MDVPLKVCEA RDPKGLYKLA  258
Lead•clone125039    ICIASLISPY RIERAACRAL LPQGDFIEVF MDVPLHVCEA RDPKGLYKRA  232
gi|9757873          ICIASLISPY RIERAACRAL LPQGDFIEVF MDVPLHVCEA RDPKGLYKRA  227

Consensus           VCIASLISPY R--R-ACRAL LP-GDFIEVF MDVPLEVCEA RDPKGLYK-A  300 gi|3329471          RAGLMKGFTG IDDPYEEPLE PELIITVREE GSDMNSP--- ----------  222
CeresClone: 300011  RAGKIKGFTG IDDPYEPPSD CEIVIQCK-- VGDCPSP--- ----------  256
gi|50938537         RAGKIKGFTG IDDPYESPLN SEIEIKEV-- DGVCPSP--- ----------  326
gi|2832300          RAGKIKGFTG IDDPYEPPLK SEIVLHQK-- LGMCDSP--- ----------  293
Lead•clone125039    RAGKIKGFTG VDDPYEAPLD CEIVIQNSRD KGLSSSSSSS SSPSSSSSSL  282
gi|9757873          RAGKIKGFTG VDDPYEAPLD CEVHISN-- FSSSSSL--- ----------  262

Consensus           RAGKIKGFTG IDDPYEAPLD CEIVIQ-K-- -G-C-SP--- ----------  350
```

TABLE 7-6-continued

/tmp/Lead•clone125039.aln

```
gi|3329471          EAMAKQIFDY LBAKFGLKGP AVASSGGSCA RVARWGGHGR RRGRQRLAW    271
CeresClone: 300011  ESMAGHVVSY LEINGFLQD- ---------- ---------- ---------    275
gi|50938537         SDMAGQVVTY LEEKGFLHD- ---------- ---------- ---------    345
gi|2832300          CDLADIVISY LEENGYLKA- ---------- ---------- ---------    312
Lead•clone125039    CEMADIVVSY LDQNGYLKKH STKSRDCM-- ---------- ---------    310
gi|9757873          CEMADIVVSY LDQNGYLKKH STKSRNCM-- ---------- ---------    290

Consensus           C-MADIVVSY LE-NG-LK-- S---S----- ---------- ----------   399
```

23/05/05 plur = 3.000000-collision-box-noboxcol colbyconsensus

Example 8—Ceres eDNA 13489782

Clone 10044, Ceres cDNA 13489782, encodes a full-length putative 114-amino acid hypothetical protein from *Arabidopsis thaliana*. Ectopic expression of Ceres cDNA 13489782 under the control of the 32449 promoter induces the following phenotypes:

Germination on high concentrations of polyethylene glycol (PEG) and abscissic acid (ABA) and Continued growth on high concentrations of PEG and ABA.

Generation and Phenotypic Evaluation of $T_1$ Lines Containing 32449::cDNA 13489782

Wild-type *Arabidopsis* Wassilewskija (WS) plants were transformed with a Ti plasmid containing cDNA 13489782 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13489782 was identified in resistant plants from each of the three surrogate drought screens, the five individual $T_2$ events containing this cDNA (ME00446) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Qualitative Analysis of Superpools on PEG, Mannitol, and ABA.

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta to eliminate any false-positives, or any lines where the Basta$^R$ marker was suppressed. All of the Basta-resistant candidates flowered and set seed. Resistant seedlings were recovered from Superpools 1, 7 and 11 on all screens (Table 8-1).

TABLE 8-1

Number of stress-tolerant and Basta$^R$ seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

We obtained sequence from 3, 3, and 13 plants that were both Basta$^R$ and resistant to PEG, mannitol or ABA, respectively. For each of the three surrogate drought screens, one or more plants contained the 32449::clone 10044 (ME00446). The probability of finding a plant containing this cDNA at random in all three screens is 0.03×0.03×0.03.

Qualitative and Quantitative Analysis of 6 Independent Events Representing 32449::cDNA 13489782 on PEG, Mannitol and ABA To identify independent events of 32449::cDNA 13489782 showing PEG, mannitol and ABA resistance, 36 seedlings from each of six events, ME00446-01, 02, 03, 04, 05 and 06 were screened as previously described. Simultaneously, Basta$^R$ segregation was assessed to identify lines containing a single insert segregating in a 3:1 (R:S) ratio as calculated by a Chi-square test (Table 8-2). All of the lines segregated for a single functional insert.

TABLE 8-2

Basta$^R$ segregation for 6 events of ME00446

| ME Line | Assessment | Did Not Germinate | Resistant | Sensitive | Total | Probability of Chi-test |
|---|---|---|---|---|---|---|
| 00446-01 | Oct. 30, 2003 | 1 | 28 | 7 | 35 | 0.49452 |
| 00446-02 | Oct. 30, 2003 | 0 | 28 | 8 | 36 | 0.70031 |
| 00446-03 | Oct. 30, 2003 | 1 | 28 | 7 | 35 | 0.49452 |
| 00446-04 | Oct. 30, 2003 | 1 | 27 | 8 | 35 | 0.7697 |
| 00446-05 | Oct. 30, 2003 | 2 | 24 | 10 | 34 | 0.55245 |
| 00446-06 | Oct. 30, 2003 | 0 | 25 | 11 | 36 | 0.44142 |

*Chi-test to determine whether actual ratio of resistant to sensitive differs from the expected 3:1 ratio.

Events ME00446-02 and 04 were chosen as the two events for further analysis because they had the strongest and most consistent resistance to PEG and ABA. None of the lines showed mannitol resistance at 375 mM concentration. The controls were sown the same day and in the same plate as the individual lines. The PEG (Tables 8-3 and 8-4) and ABA (Tables 8-5 and 8-6) segregation ratios observed for ME00446-02 and -04 are consistent with the presence of single insert as demonstrated by the Chi-Square test. This is similar to that observed for Basta resistance (Table 8-2).

Despite the fact that this line was isolated from all three screens, it was subsequently concluded that it could not be considered mannitol resistant. This is likely due to an overly stringent mannitol concentration. In a superpool screen setting, the seedlings are more densely grown than in an individual line setting. This means that in a superpool screen, there is a lower effective concentration of mannitol. When putative tolerant plant from a superpool is tested as an individual line, the effective concentration it is grown on is actually higher. In the case of ME00446, this difference was enough to invalidate it as mannitol tolerant. In fact, a resistant plant to mannitol was isolated from superpool 11 that corresponds to clone 10044.

TABLE 8-3

Chi-square analysis assuming a 3:1(R:S) ratio for progeny of ME00446-02 containing 32449::clone 10044 on PEG.

| Event | Observed | Expected | $\chi^2$ | Probability of $\chi^2$ |
|---|---|---|---|---|
| PEG Resistant | 30 | 26.95 | 0.3452 | 0.2557 |
| PEG Sensitive | 5 | 7.7 | 0.9468 | |
| Total | 35 | 35 | 1.292 | |

TABLE 8-4

Chi-square analysis assuming a 3:1(R:S) ratio for progeny of ME00446-04 containing 32449::clone 10044 on PEG.

| Event | Observed | Expected | $\chi^2$ | Probability of $\chi^2$ |
|---|---|---|---|---|
| PEG Resistant | 26 | 27.77 | 0.113 | 0.482 |
| PEG Sensitive | 10 | 8.23 | 0.3813 | |
| Total | 36 | 36 | 0.4943 | |

TABLE 8-5

Chi-square analysis assuming a 3:1(R:S) ratio for progeny of ME00446-02 containing 32449::clone 10044 on ABA.

| Event | Observed | Expected | $\chi^2$ | Probability of $\chi^2$ |
|---|---|---|---|---|
| ABA Resistant | 31 | 27 | 0.5926 | 0.1237 |
| ABA Sensitive | 5 | 9 | 1.778 | |
| Total | 36 | 36 | 2.370 | |

TABLE 8-6

Chi-square analysis assuming a 3:1(R:S) ratio for progeny of ME00446-04 containing 32449::clone 10044 on ABA.

| Event | Observed | Expected | $\chi^2$ | Probability of $\chi^2$ |
|---|---|---|---|---|
| ABA Resistant | 31 | 27 | 0.5926 | 0.1237 |
| ABA Sensitive | 5 | 9 | 1.778 | |
| Total | 36 | 36 | 2.370 | |

Qualitative and Quantitative Analysis of Progeny of $T_2$ Plants Isolated on PEG, Mannitol and ABA Progeny from $T_2$ plants that were recovered from the three screens and containing clone 10044 (SP11-M13 and SP11-P5) were found to be resistant to PEG and ABA. Taken together, 1) the isolation of resistant seedlings containing clone 10044 from all three surrogate screens for drought, 2) the inheritance of this resistance in the next generation, and 3) the fact that the progeny from two or more events from the original transformation also segregated for resistance to these osmotic stresses, provide strong evidence that clone 10044 when over-expressed provides resistance to osmotic and dehydration stress.

Table 8-7 provides the results of the consensus sequence (SEQ ID NOs: 215-222) analysis based on Ceres cDNA 13489782.

TABLE 8-7

```
/tmp/Lead•clone10044.aln

CeresClone: 584111    MFRSMTTRR-  --GYERLGKE  SATTALLHEG  FKRSTSLPSW  GSNSSRKMAL   47
CeresCl3ne: 1068483   MFRAMSTRKV  HGGYEKLVED  EPK-------  LKRVTSVPAS  VYGNSRNPV-   42
Lead•clone10044       MFRAMSTRKV  HGGYEKLGDE  EAR-------  LKRVSSVPAS  VYGHSRNPV-   42
gi|4835241            MFRAMSTRKI  HGGYEKLGDE  EAR-------  LKRVSSVPAS  VYGHSRNPV-   42

Consensus             MFRAMSTRKV  HGGYEKLGDE  EAR-------  LKRV-SVPAS  VYGHSRNPV-   50

CeresClone: 584111    GSTYGEINLK  RNPTKKGNNN  SDKKSHPLLS  FLAL---RRK  KKT-------   87
CeresCl3ne: 1068483   -----QEEVK  KTPTVKPTGG  S---VHPLLS  FFDVRFQRKK  KKT--KKSLA   82
Lead•clone10044       ------QEVK  KTPTAKPTGG  S---VHPLFS  FFDVHFQRKK  KKTIKKKSLA   83
gi|4835241            ------QEVK  KTPTAKPTGG  S---VHPLFS  FFDVHFQRKK  KNTAKKKSLA   83

Consensus             ------QEVK  KTPTAKPTGG  S---VHPL-S  FFDVHFQRKK  KKT-KKKSLA  100

CeresClone: 584111    TARPEFARYL  EYLKEGGMWD  PNSNKPVMYY  E                       118
CeresCl3ne: 1068483   TAKPEFARYM  AYVKEGGVWD  PNSNAPVIHY  R                       113
Lead•clone10044       TAKPEFARYM  EYVREGGVWD  PSSNAPVIHY  R                       114
gi|4835241            TAKPEFARYM  EYVREGGVWD  PSSNAPVIHY  R                       114

Consensus             TAKPEFARYM  EYV-EGGVWD  P-SNAPVIHY  R                       131
```

23/05/05 plur = 2.000000-collision-box-noboxcol colbyconsensus

Example 9—Ceres cDNA 13486759

Clone 10987, corresponding Ceres cDNA 13486759, encodes an *Arabidopsis* 251-amino acid expressed protein. Ectopic expression of clone 10987 under the control of the CaMV35S promoter induces the following phenotypes:

Germination on high concentrations of polyethylene glycol (PEG), mannitol, and abscissic acid (ABA), and Continued growth on high concentrations of PEG, mannitol, and ABA.

Generation and Phenotypic Evaluation of $T_1$ Lines Containing 35S::cDNA 13486759

Wild-type *Arabidopsis* Wassilewskija (WS) plants were transformed with a Ti plasmid containing cDNA 13486759 in the sense orientation relative to the CaMV35S constitutive promoter. The $T_i$ plasmid vector used for this construct, CRS338, contains RAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol and ABA as Surrogate Screens for Drought Tolerance Seeds from 13 superpools (1,200 $T_2$ seeds from each superpool) from the CaMV35S or 32449 aver-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13486759 was identified in resistant plants from each of the three surrogate drought screens, the five individual $T_2$ events containing this eDNA (ME03316) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18th plant isolated from a mannitol screen of Superpool 1.

Qualitative Analysis of 13 Superpools on PEG, Mannitol and ABA

Resistant candidates were selected based on increased size when compared to the largest wild-type control seedlings. All three screens resulted in a decrease in germination for both wildtype and superpools as compared to seeds on control media. Wild-type seeds that germinated on any of the screens were small and never developed any first leaves even after 40 days. To ensure that even slightly tolerant individuals were not omitted, seedlings that showed any growth and greening whatsoever were recovered and transferred to soil for assessment in the $T_3$ generation. All recovered candidates showed signs of vigorous re-growth on soil, although the development was slightly delayed as compared to unstressed plants, presumably because of the transient exposure to stress. The plants transferred to soil were sprayed with Basta to eliminate any false-positives, or any lines where the Basta[R] marker was suppressed. All of the Basta-resistant candidates flowered and set seed. Resistant seedlings were recovered from Superpools 1, 7 and 11 on all screens (Table 9-1).

TABLE 9-1

Number of stress-tolerant and Basta[R] seedlings identified on drought surrogate screens.

| Superpool | Promoter | 18% PEG | 375 mM Mannitol | 1.5 uM ABA |
|---|---|---|---|---|
| SP1 | 35S | 10 | 13 | 11 |
| SP2 | 35S | 0 | 6 | 5 |
| SP3 | 35S | 0 | 2 | 10 |
| SP4 | 35S | 0 | 4 | 0 |
| SP5 | 35S | 0 | 0 | 5 |
| SP6 | 35S | 0 | 0 | 4 |
| SP7 | 35S | 1 | 4 | 8 |
| SP8 | 35S | 0 | 4 | 1 |
| SP9 | 32449 | 0 | 0 | 12 |
| SP10 | 32449 | 0 | 0 | 14 |
| SP11 | 32449 | 15 | 3 | 13 |
| SP12 | 32449 | 3 | 0 | 6 |
| SP13 | 32449 | 0 | 2 | 1 |

We obtained sequence from 3, 3, and 13 plants from Superpool 11 that were both Basta[R]-resistant and resistant to PEG, mannitol or ABA, respectively. For each of the three osmotic screens, one or more plants contained the 35S:: clone 10987 (ME03316), which made it a good candidate for further testing. The probability of finding a plant containing this clone 10987 at random in all three screens is 0.03×0.03.

Qualitative and Quantitative Analysis of 5 Independent Events Representing 35S::cDNA 13486759 on PEG, Mannitol and ABA To identify independent events of 35S::cDNA 13486759 showing PEG, mannitol and ABA resistance, 36 seedlings from each of five events, ME03316-01, -02, -03, -04, and -05 were screened as previously described. Simultaneously, Basta$^R$ segregation was assessed to identify events containing a single insert segregating in a 3:1 (R:S) ratio as calculated by a chi-square test (Table 9-2). All of the events segregated for a single functional insert. ME03316-02 could be segregating for two linked or unlinked inserts but the ratios on the surrogate drought screens indicate it is likely to be a single insert.

TABLE 9-2

Basta$^R$ segregation for 5 individual events

| Event | Resistant | Sensitive | Total | Probability of Chi-test |
|---|---|---|---|---|
| ME03316-01 | 23 | 13 | 36 | 0.12366 |
| ME03316-02 | 32 | 4 | 36 | 0.05429 |
| ME03316-03 | 30 | 6 | 36 | 0.24821 |
| ME03316-04 | 25 | 11 | 36 | 0.44142 |
| ME03316-05 | 29 | 7 | 36 | 0.44142 |

*Chi-test to determine whether actual ratio of resistant to sensitive differs from the expected 3:1 ratio.

Lines ME03316-01 and 02 were chosen as the two events for further analysis because they had the strongest and most consistent resistance to PEG, mannitol and ABA. Resistance was observed for ME03316-03, 04, and 05 although not in expected ratios in all three screens (data not shown). The controls were sown the same day and on the same plate as the individual lines. The PEG (Tables 9-3 and 9-4), mannitol (Tables 9-5 and 9-6) and ABA (Table 9-7) segregation ratios observed are consistent with the presence of a single insert as demonstrated by chi-square. ME03316-02 seedlings on ABA (Table 9-8) appear to be segregating for two inserts which is still consistent with the ratio observed on Basta$^R$. Both events segregate for a deficiency of resistant seedlings on mannitol.

TABLE 9-3

Chi-square analysis assuming a 3:1 (R:S) ratio for progeny of ME03316-01 containing 35S::clone 10987 on PEG.

| Event | Observed | Expected | $\chi^2$ | Probability of Chi-Test |
|---|---|---|---|---|
| PEG Resistant | 22 | 27 | 0.93 | 0.0543 |
| PEG Sensitive | 14 | 9 | 2.78 | |
| Total | 36 | 36 | 3.7 | |

TABLE 9-4

Chi-square analysis assuming a 3:1 (R:S) ratio for progeny of ME03316-02 containing 35S::clone 10987 on PEG.

| Event | Observed | Expected | $\chi^2$ | Probability of Chi-Test |
|---|---|---|---|---|
| PEG Resistant | 23 | 26.25 | 0.4024 | 0.2046 |
| PEG Sensitive | 12 | 8.75 | 1.2071 | |
| Total | 35 | 35 | 1.610 | |

TABLE 9-5

Chi-square analysis assuming a 3:1 (R:S) ratio for progeny of ME03316-01 containing 35S::clone 10987 on Mannitol.

| Event | Observed | Expected | $\chi^2$ | Probability of Chi-Test |
|---|---|---|---|---|
| Mannitol Resistant | 19 | 25.5 | 1.657 | 0.01 |
| Mannitol Sensitive | 15 | 8.5 | 4.971 | |
| Total | 34 | 34 | 6.63 | |

TABLE 9-6

Chi-square analysis assuming a 3:1 (R:S) ratio for progeny of ME03316-02 containing 35S::clone 10987 on Mannitol.

| Event | Observed | Expected | $\chi^2$ | Probability of Chi-Test |
|---|---|---|---|---|
| Mannitol Resistant | 18 | 26.25 | 2.593 | 0.0013 |
| Mannitol Sensitive | 17 | 8.75 | 7.779 | |
| Total | 35 | 35 | 10.371 | |

TABLE 9-7

Chi-square analysis assuming a 3:1 (R:S) ratio for progeny of ME03316-01 containing 35S::clone 10987 on ABA.

| Event | Observed | Expected | $\chi^2$ | Probability of Chi-Test |
|---|---|---|---|---|
| ABA Resistant | 27 | 25.5 | 0.0882 | 0.5525 |
| ABA Sensitive | 7 | 8.5 | 0.2647 | |
| Total | 34 | 34 | 0.3529 | |

TABLE 9-8

Chi-square analysis assuming a 3:1 (R:S) ratio for progeny of ME03316-02 containing 35S::clone 10987 on ABA.

| Event | Observed | Expected | $\chi^2$ | Probability of Chi-Test |
|---|---|---|---|---|
| ABA Resistant | 32 | 24.75 | 2.124 | 0.0036 |
| ABA Sensitive | 1 | 8.25 | 6.371 | |
| Total | 33 | 33 | 8.495 | |

Qualitative and Quantitative Analysis of Progeny of T$_2$ Plants Isolated on PEG, Mannitol and ABA Progeny from T$_2$ plants that were recovered from the three screens and containing clone 10987 (SP11-A15, SP11-A16, SP11-P2, and SP11-M10) were found to be resistant to PEG, mannitol and ABA.

On PEG, the progeny of SP11-M10 segregated for a deficiency of resistant seedlings similar to the deficiency that noted for the T2 seedlings in Tables 9-5 and 9-6. A deficiency of resistant seedlings is also noted for the progeny of SP11P2 on PEG. Taken together, 1) the isolation of resistant seedlings containing clone 10987 from all three surrogate screens for drought, 2) the inheritance of this resistance in the next generation, and 3) the fact that the progeny from two or more events from the original transformation also segregated for resistance to these osmotic stresses, these findings provide strong evidence that clone 10987 when over-expressed can provide tolerance to osmotic stresses.

Example 10—Ceres cDNA 13500101

Clone 17206, corresponding to Ceres cDNA 13500101, encodes a putative strictosidine synthase. Ectopic expression of cDNA 13500101 under the control of the CaMV35S promoter induces the following phenotypes:
Germination on high concentrations of polyethylene glycol (PEG) and mannitol.
Continued growth on high concentrations of PEG and mannitol.
Generation and Phenotypic Evaluation of $T_1$ Lines Containing 35S::cDNA 13500101.

Wild-type *Arabidopsis* Wassilewskija (WS) plants were transformed with a Ti plasmid containing cDNA 13500101 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.
Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13500101 was identified in resistant plants from each of the three surrogate drought screens, the five individual $T_7$ events containing this cDNA (SR01000) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.
Qualitative and Quantitative Analysis of 2 Independent Events Representing 35S::cDNA 13500101 (SR01000) on PEG, Mannitol and ABA
To identify two independent events of 35S::clone 17206 showing PEG, mannitol, and ABA resistance, 36 seedlings from each of three events, SR01000-01, 02 and 03 were screened as previously described. Basta segregation was assessed to verify that the lines contained a single insert segregating in a 3:1 (R:S) ratio as calculated by a chi-square test (Table 1). Two lines (-01 and -02) segregated for a single insert (Table 1).

TABLE 10-1

Basta$^R$ segregation for SR01000 individual events

| Eveiat | Resistant | Sensitive | Total | Probability of Chi-test |
|---|---|---|---|---|
| SR01000-01 | 29 | 7 | 36 | 0.44142 |
| SR01000-02 | 23 | 13 | 36 | 0.12366 |
| SR01000-03 | 35 | 0 | 35 | 0.00064 |
| SR01000-01-01 | 35 | 0 | 35 | 0.00064 |
| SR01000-02-01 | 27 | 9 | 36 | 1 |
| SR01000-03-01 | 36 | 0 | 36 | 0.00053 |

*Chi-test to determine whether actual ratio of resistant to sensitive differs from the expected 3:1 ratio.

Testing of the progeny from the $T_2$ resistant plants on the 3 surrogate drought screens showed that lines SR01.000-01 and 02 had a strong and consistent resistance to PEG, mannitol, but not to ABA. These were chosen as the two events for further analysis. The controls were sown the same day and in the same plate as the individual lines. The PEG (Tables 10-2 and 10-3), and mannitol (Tables 10-4 and 10-5) segregation ratios observed for SR01000-01 and 02 are consistent with the presence a of single insert as demonstrated by chi-square (Table 10-1).

TABLE 10-2

Chi-square analysis assuming a 3:1 (R:S) ratio for progeny of SR01000-01 $T_2$ containing 35S::cDNA 13500101on PEG.

| Event | Observed | Expected | $\chi^2$ | Probability of Chi-Test |
|---|---|---|---|---|
| PEG Resistant | 26 | 26.25 | 0.002 | 0.922 |
| PEG Sensitive | 9 | 8.75 | 0.007 | |
| | 35 | 35 | 0.009 | |

TABLE 10-3

Chi-square analysis assuming a 3:1 (R:S) ratio for progeny of SR01000-02 $T_2$ containing 35S::cDNA 13500101on PEG.

| Event | Observed | Expected | $\chi^2$ | Probability of Chi-Test |
|---|---|---|---|---|
| PEG Resistant | 27 | 24.75 | 0.205 | 0.366 |
| PEG Sensitive | 6 | 8.25 | 0.614 | |
| | 33 | 33 | 0.818 | |

TABLE 10-4

Chi-square analysis assuming a 3:1 (R:S) ratio for progeny of SR01000-01 $T_2$ containing 35S::cDNA 13500101on mannitol.

| Event | Observed | Expected | $\chi^2$ | Probability of Chi-Test |
|---|---|---|---|---|
| Mannitol Resistant | 28 | 27 | 0.037 | 0.700 |
| Mannitol Sensitive | 8 | 9 | 0.111 | |
| | 36 | 36 | 0.148 | |

TABLE 10-5

Chi-square analysis assuming a 3:1 (R:S) ratio for progeny of SR01000-02 T₂ containing 35S::cDNA 13500101on mannitol.

| Event | Observed | Expected | $\chi^2$ | Probability of Chi-Test |
|---|---|---|---|---|
| Mannitol Resistant | 30 | 27 | 0.333 | 0.248 |
| Mannitol Sensitive | 6 | 9 | 1.000 | |
| | 36 | 36 | 1.333 | |

Qualitative and Quantitative Analysis of Progeny of T₂ Plants Isolated on PEG, Mannitol and ABA The progeny from one resistant T₂ plant from each of these two events were tested in the same manner as the T₂. Resistance to PEG and mannitol persisted in the second generation. Taken together, 1) the isolation of resistant seedlings containing clone 17026 from two of the surrogate screens for drought (PEG and mannitol), 2) the inheritance of this resistance in the next generation, and 3) the fact that the progeny from two or more events from the original transformation also segregated for resistance to these osmotic stresses, these findings provide strong evidence that clone 17026 when over-expressed can provide tolerance to osmotic stresses.

Table 10-6 provides the results of the consensus sequence (SEQ ID NOs: 223-240) analysis based on. Ceres cDNA 13500101.

TABLE 10-6

/tmp/Lead•clone17206.aln

```
CeresClone: 621848   ---------- ----MKLSTL FLFLFHLAHA ALSDEAT--- ---F--IRDG    28
gi|50899872          MRKGAAGMAC TCSAAAAASA LVKLLVLVAA VAATISAGGG DEPTYETKSI    50
CeresClone: 316544   ---------M AAAATRSLHS FLALLLLLAA AAAAAAL--- ---SYETKSI    35
Lead•clone17206      ---------- -----MASFV FVISLLLLSF SSAVFSD--- ----------    22
CeresClone: 124660   ---------- -MTSFCSMIS LLLLLLLLSL SSAVISD--- ----------    26
gi|17104523          ---------- ----MTSFCS MISLLLLLSL SSAVFSD--- ----------    23
gi|1754985           ---------- ----MTSFCS MISLLLLLSL SSPVFSD--- ----------    23
gi|13928598          ---------- MHSSEAMVVS ILCALFL--S SLSLVSS--- ----------    25
gi|62903513          --------MA KLSDSCDMAL FTVFLLFLSS SLALS----- ----------    27
gi|18220             ------MANF SBSKSMMAVF FMFFLLLLSS SSSSSSS--- ----------    31
gi|18222             ---------- -----MMAVF FMFFLLLLSS SSSSSSS--- ----------    22

Consensus            ---------- --S---S--S FL-LLLLLSA SSAV-S---- ----------    50

CeresClone: 621848   LKSYSQLDLP HSVFGSESVA FDCHGKGFYV GVSDGRILKW HETKREWIDF    78
gi|50899872          DPSLAVMTLP APVTGPESLA FDGRGDGPYT GGSDGRILRW RGGRLGWTEF   100
CeresClone: 316544   DPGLVVMTLP EPVSGPESLA FDGRGGGPYS GVSDGRVLRW QGPLRGWTEF    85
Lead•clone17206      DASFQKLPVP DKRSGPESFA FDSTGLGFYT GVSGGKILKY V-PGKGYVDF    70
CeresClone: 124660   DASFQKLPVP ETRSGPEAFA FDSTGKGFYT GVSGGKILKY L-PETGYVDF    75
gi|17104523          DASFQKLPVP ETRSGPEAFA FDSTGKGFYT GVSGGKILKY L-PETGYVDF    72
gi|1754985           DASFQKLPVP ETRSGPEAFA FDSTGKGFYT GVSGGKILKY L-PETGYVDF    72
gi|13928598          SPEFFH-FIE APSYGPNAYA FDSDG-ELMA SVEDGRIIKY DKPSNKFLTH    73
gi|62903513          SPILKEILIE APSYAPNSFT FDSTNKGFYT SVQDGRVIKY EGPNSGFVDF    77
gi|18220             SPILKKIFIE SPSYAPNAFT FDSTDKGFYT SVQDGRVIKY EGPNSGFTDF    81
gi|18222             SPILKKIFIE SPSYAPNAFT FDSTDKGFYT SVQDGRVIKY EGPNSGFTDF    72

Consensus            DPSFQKL--P -P-SGPEAFA FDSTGKGFYT GVSDGRILKY --P--G-VDF   100

CeresClone: 621848   AVTSPHRNKK LCDGLTNDKM -ESMCGRPLG DKFNTLTQEL YIADAYFGLL   127
gi|50899872          AYNSRHKSVG VCSPEKKLVV PESVCGRPLP LQFHHASGDL YVADAYLGLL   150
CeresClone: 316544   AYNSKHRSVA LCAPDKKLVV PESLCGRPLG LQFHRQSGDL YVADAYLGLL   135
Lead•clone17206      AQIIDSSNSA WCNGALGTAF -AGKCGRPAG IALNSKTGDL YVADAPLGLH   119
CeresClone: 124660   AQITESSNSS WCDGTIGTAL -AGRCGRXAG IAFNEKTGDL YVADAPLGLH   124
gi|17104523          AQITESSNSS WCDGTIGTAL -AGRCGRPAG IAFNEKTGDL YVADAPLGLH   121
gi|1754985           AQITESSNSS WCDGTIGTAL -AGRCGRPAG IAFNEKTGDL YVADAPLGLH   121
gi|13928598          AVASPIWNNA LCENNTNQDL -KPLCGRVYD FGFHYETQRL YIADCYFGLG   122
gi|62903513          AYASPYWNKA FCENSTDAEK -RPLCGRTYD ISYNLQNNQL YIVDCYYHLS   126
gi|18220             AYASPFWNKA FCENSTDPEK -RPLCGRTYD ISYDYKNSQM YIVDGHYHLC   130
gi|18222             AYASPFWNKA FCENSTDPEK -RPLCGRTYD ISYDYKNSQM YIVDGHYHLC   121

Consensus            A--S---N-A WC-------L ---LCGRP-G IAFN-KTGDL YVADAYLGL-   150
```

TABLE 10-6-continued

/tmp/Lead•clone17206.aln

```
CeresClone: 621848   VVGKGGGVAK QLATSAEGVP FRFLNALDID TKTGEVYFTD SSIMFQ--RR  175
gi|50899872          RVPARGGLAE VVATEAAGVP FNFLNGLDVD QRTGDVYFTD SSTIYR--RS  198
CeresClone: 316544   RVAARGGLAQ VVATEAAGGP FNFLNGLDVD QRTGDVYFTD SSAIYR--RS  183
Lead•clone17206      VISPAGGLAT KLADSVDGKP FKFLDGLDVD PTTGVVYFTS FSSKFG--PR  167
CeresClone: 124660   VISPAGGLAT KITDSVDGKP FKFLDGLDVD PTTGVVYFTS FSSRFS--PI  172
gi|17104523          VISPAGGLAT KITDSVDGKP FKFLDGLDVD PTTGVVYFTS FSSRFS--PI  169
gi|1754985           VISPAGGLAT KITDSVDGKP FKFLDGLDVD PTTGVVYFTS FSSRFS--PI  169
gi|13928598          FVGPDGGHAI QLATSGDGVE FKWLYALAID QQAGEVYMTD VSTKYD--DR  170
gi|62903513          VVGSEGGHAT QLATSVDGVP FKWLYAVTVD QRTGIVYFTD VSTLYD--DR  174
gi|18220             VVGKEGGYAT QLATSVQGVP FKWLYAVTVD QRTGIVYFTD VSSIHDDSPE  180
gi|18222             VVGKEGGYAT QLATSVQGVP FKWLYAVTVD QRTGIVYFTD VSSIHDDSPE  171

Consensus            VV-P-GGLAT QLATSVDGVP FKWLDGLDVD QRTGVVYFTD -SS-----P-  200

CeresClone: 621848   VYTSIILSGD RTGRLLKYMP STQSVHVLVK GLAHPNGVAL SKDNSFIIVA  225
gi|50899872          QYLLVVAMGD ETGRLLRYDA RRRRVTVLHS GLPYPNGVAV SDDGIHVVVA  248
CeresClone: 316544   DYLLVVAMGD ETGRLLRYER RTGRMGVLQA GLSYPNGVAV SADGIHVVVA  233
Lead•clone17206      EVLIAVGLKD ASGKLFKYDP ATKAVTELME GLSGAAGCAV SSDGSFVLVS  217
CeresClone: 124660   QVLIALGLKD ATGKLYKYDP STKVVTVLME GLSGAAGCAV SSDGSFVLVS  222
gi|17104523          QVLIALGLKD ATGKLYKYDP STKVVTVLME GLSGAAGCAV SSDGSFVLVS  219
gi|1754985           QVLIALGLKD ATGKLYKYDP STKVVTVLME GLSGAAGCAV SSDGSFVLVS  219
gi|13928598          GVQDIIRIND TTGRLIKYDP STEEVTVLMK GLNIPGGTEV SKDGSFVLVG  220
gi|62903513          GVQQIMDTSD KTGRLIKYDP STKETTLLLK ELHVPGGAEV SADGSFVLVA  224
gi|18220             GVEEIMNTSD RTGRLMKYDP STKETTLLLK ELHVPGGAEI SADGSPVVVA  230
gi|18222             GVEEIMNTSD RTGRLMKYDP STKETTLLLK ELHVPGGAEI SADGSFVVVA  221

Consensus            -VLIV--L-D -TGRLLKYDP STK-VTVLMK GL--P-G-AV S-DGSFVLVA  250

CeresClone: 621848   ESTTFKILKI QVRDSKINNN NIEPFAQVPR SPDNIKR-NA KGEFWVALNS  274
gi|50899872          HTGLCELRRY WLRGPRAGKS --HTFAEVPG YPDNVRR-DG DGGYWVALSR  295
CeresClone: 316544   HTALCELRRY WIRGARAGTS --DTFAELPG YPDNLRA-DG RGGYWVALSS  280
Lead•clone17206      EFIKSNIKKY WIKGPKAGTI --EDFSSLVS NPDNIRRVGA TGNFWVAS--  263
CeresClone: 124660   QFTKSNIKRY WIKGPKAGSS --EDFTNSVS NPDNIKRIGS TGNFWVAS--  268
gi|17104523          QFTKSNIKRY WIKGPKAGSS --EDFTNSVS NPDNIKRIGS TGNFWVAS--  265
gi|1754985           QFTKSNIKRY WIKGPKAGSS --EDFTNSVS NPDNIKRIGS TGNFWVAS--  265
gi|13928598          EFASHRILKY WIKGPKANTS --E-FLLKVR GPGNIKR-TK DGDFWVAS--  264
gi|62903513          EFLSHQIVKY WLEGPKKGTA --E-VLVKIP NPGNIKR-NA DGHFWVSSSE  270
gi|18220             EFLSNRIVKY WLEGPKKGSA --E-FLVTIP NPGNIKR-NS DGHFWVSSSE  276
gi|18222             EFLSNRIVKY WLEGPKKGSA --E-FLVTIP NPGNIKR-NS DGHFWVSSSE  267

Consensus            EF----IKKY W-KGPKAGSS --E-F---V- NPDNIKR-NS -GNFWVASS-  300

CeresClone: 621848   GRGLIQKLEN ELETTLPWNA DPMAIKFDEK GRATEVLDGE YGRQLDSVSE  324
gi|50899872          G------ADN DDVAPLVAVR VTAAGKKKGG GAAMVAEAL- AGFSFVTVSE  338
CeresClone: 316544   G------VAA DEAAAAP--- -TVAVRVSRD GNVTEAL--- DGFSFVSVSE  317
Lead•clone17206      -------VVN KVVMPTD--- -PRAVKLDAN GKVLQTIFLK NEFGNTLLSE  302
CeresClone: 124660   -------VVN KIIVPTN--- -PSAVKVNSN GEVLQTIPLK DKFGDTLLSE  307
gi|17104523          -------VVN KIIVPTN--- -PSAVKVNSN GEVLQTIPLK DKFGDTLLSE  304
gi|1754985           -------VVN KIIVPTN--- -PSAVKVNSN GEVLQTIPLK DKFGDTLLSE  304
gi|13928598          -------SDN NGIIVTI--- -PRGIRFDEF GNILEVVAIP LPYKGEHIEQ  302
gi|62903513          E------LDG NMHGRVD--- -PKGIKFDEF GNILEVIPLP PPFAGEHFEQ  310
gi|18220             E------LDG GQHGRVV--- -SRGIKFDGF GNILQVIPLP PPYEGEHFEQ  316
gi|18222             E------LDG GQHGSVV--- -SRGIKFDGF GNILQVIPLP PPYEGEHFEQ  307

Consensus            -------VDN -VV--T---- -P-A-K-D-- G-VLQ-IPL- --F----LSE  350

CeresClone: 621848   VEBHEGSLWI GSAVQPYLGL I--------- --KA------ ---------  347
gi|50899872          VAEQNGTLWI GSVDTPYAGA A--------- --VRGRR--- ---------  364
CeresClone: 316544   VAQRGGALWV GSVDTPYAGQ L--------- --KRRAS--- ---------  343
Lead•clone17206      VNEFNGHLYI GTLTGPFAGV M--------- --KL------ ---------  325
CeresClone: 124660   VNEFEGNLYI GTLTGPFAGI L--------- --KLEKGSCP AT-------  338
gi|17104523          VNEFEGNLYI GTLTGPFAGI L--------- --KLEKGSCP AT-------  335
gi|1754985           VNEFEGNLYI GTLTGPFAGI L--------- --KLEKGSCP AT-------  335
gi|13928598          VQEHDGALFV GSLFHEEVGI LHNYKSSVDH HQEKNSGGLN ASFKEFSSF  351
gi|62903513          IQEHDGLLYI GSLFHGSVGI L-----VY-- -DKKGNSFVS SH-------  344
gi|18220             IQEHDGLLYI GSLSHSSVGI L-----VYDD HDNKGNSYVS S--------  352
gi|18222             IQEHDGLLYI GSLSHSSVGI L-----VYDD HDNKGNSYVS QLVIN----  347

Consensus            V-E--G-LYI GTL--PFAGI L--------- --KK------ A-------  399
```

23/05/05 plur = 5.500000-collision-box-noboxcol colbyconsensus

Example 11—Ceres cDNA 13509011 (12357529)

Clone 104691, corresponding to Ceres cDNA 13509011 (12357529), encodes a probable strictosidine synthase enzyme. Ectopic expression of cDNA 1.3509011 under the control of the CaMV35S promoter induces the following phenotypes:

Germination on high concentrations of polyethylene glycol (PEG) and mannitol.
Continued growth on high concentration of PEG and mannitol.

Generation and Phenotypic Evaluation of $T_1$ Lines Containing 35S::cDNA 13509011.

Wild-type *Arabidopsis* Wassilewskija (WS) plants were transformed with a Ti plasmid containing cDNA 12334963 in the sense orientation relative to the CaMV35S constitutive promoter. The $T_i$ plasmid vector used for this construct, CRS338, contains PAT and confers herbicide resistance to transformed plants. Ten independently transformed events were selected and evaluated for their qualitative phenotype in the $T_1$ generation. No positive or negative phenotypes were observed in the $T_1$ plants.

Screens of Superpools on High PEG, Mannitol, and ABA as Surrogate Screens for Drought Tolerance.

Seeds from 13 superpools (1,200 $T_2$ seeds from each superpool) from the CaMV35S or 32449 over-expression lines were tested on 3 drought surrogate screens (high concentrations of PEG, mannitol, and ABA) as described above. $T_3$ seeds were collected from the resistant plants and analyzed for resistance on all three surrogate drought screens.

Once cDNA 13509011 was identified in resistant plants from each of the three surrogate drought screens, the five individual $T_2$ events containing this cDNA (SR01002) were screened on high PEG, mannitol, and ABA to identify events with the resistance phenotype.

Superpools (SP) are referred to as SP1, SP2 and so on. The letter following the hyphen refers to the screen (P=PEG, M=mannitol, and A=ABA) and the number following the letter refers to a number assigned to each plant obtained from that screen on that superpool. For example, SP1-M18 is the 18$^{th}$ plant isolated from a mannitol screen of Superpool 1.

Qualitative and quantitative analysis of 2 independent events representing 35S::clone 104691 (SR01002) on PEG, mannitol and ABA To identify two independent events of 35S::clone 104691 showing PEG, mannitol and ABA resistance, 36 seedlings from each of three events, SR01002-01, 02, and 03 were screened as previously described. Simultaneously, Basta segregation was assessed to identify lines containing a single insert segregating in a 3:1 (R:S) ratio as calculated by a chi-square test (Table 1). Two lines (01 and 03) segregated for a single insert.

TABLE 11-1

Basta segregation for SR01002 individual events

| Event | Resistant | Sensitive | Total | Probability of Chi-test |
|---|---|---|---|---|
| SR01002-01 | 26 | 10 | 36 | 0.70031 |
| SR01002-02 | 23 | 8 | 31 | 0.91741 |
| SR01002-03 | 28 | 8 | 36 | 0.70031 |
| SR01002-01-1 | 36 | 0 | 36 | 0.00053 |
| SR01002-02-1 | 28 | 8 | 36 | 0.70031 |
| SR01002-03-1 | 25 | 11 | 36 | 0.44142 |

*Chi-test to determine whether actual ratio of resistant to sensitive differs from the expected 3:1 ratio.

Testing of the progeny from the resistant $T_2$ plants on the 3 surrogate drought screens showed that lines SR01002-01 and 03 had a strong and consistent resistance to PEG, mannitol, but not to ABA. These were chosen as the two events for further analysis. The controls were sown the same day and in the same plate as the individual lines. The PEG (Tables 11-2 and 11-3), and mannitol (Tables 11-4 and 11-5) segregation ratios observed for SR01002-01 and 03 are consistent with the presence of a single insert as demonstrated by chi-square. This is similar to that observed for Basta resistance (Table 11-1),

TABLE 11-2

Chi-square analysis assuming a 3:1 (R:S) ratio for progeny of SR01002-01 $T_2$ containing 35S::clone 104691 on PEG.

| Event | Observed | Expected | $\chi^2$ | Probability |
|---|---|---|---|---|
| PEG Resistant | 22 | 24.75 | 0.306 | 0.269 |
| PEG Sensitive | 11 | 8.25 | 0.917 | |
| | 33 | 33 | 1.222 | |

TABLE 11-3

Chi-square analysis assuming a 3:1 (R:S) ratio for progeny of SR01002-03 $T_2$ containing 35S::clone 104691 on PEG.

| Event | Observed | Expected | $\chi^2$ | Probability |
|---|---|---|---|---|
| PEG Resistant | 24 | 25.5 | 0.088 | 0.552 |
| PEG Sensitive | 10 | 8.5 | 0.265 | |
| | 34 | 34 | 0.353 | |

TABLE 11-4

Chi-square analysis assuming a 3:1 (R:S) ratio for progeny of SR01002-01 $T_2$ containing 35S::clone 104691 on mannitol.

| Event | Observed | Expected | $\chi^2$ | Probability |
|---|---|---|---|---|
| Mannitol Resistant | 30 | 27 | 0.333 | 0.248 |
| Mannitol Sensitive | 6 | 9 | 1.000 | |
| | 36 | 36 | 1.333 | |

TABLE 11-5

Chi-square analysis assuming a 3:1 (R:S) ratio for progeny of SR01002-03 $T_2$ containing 35S::clone 104691 on mannitol.

| Event | Observed | Expected | $\chi^2$ | Probability |
|---|---|---|---|---|
| Mannitol Resistant | 32 | 27 | 0.926 | 0.054 |
| Mannitol Sensitive | 4 | 9 | 2.78 | |
| | 36 | 36 | 3.70 | |

Qualitative and Quantitative Analysis of Progeny of T₂ Plants Isolated on PEG, Mannitol, and ABA Screens.

The progeny from one resistant T₂ plant from each of these two events was tested in the T3 generation in the same manner. Resistance to PEG and mannitol persisted into the next generation. Taken together, 1) the isolation of resistant seedlings containing clone 104691 from two of the surrogate screens for drought (PEG and mannitol), 2) the inheritance of this resistance in the next generation, and 3) the fact that the progeny from two or more events from the original transformation also segregated for resistance to these surrogate drought conditions, these findings provide strong evidence that clone 104691 when over-expressed can provide tolerance to osmotic stresses.

Table 11-6 provides the results of the consensus sequence (SEQ ID NOs: 241-262) analysis based on Ceres cDNA 13509011 (12357529).

TABLE 11-6

/tmp/Lead•clone104691.aln

```
gi|13928598       ----------  ---MHSSEAM  VVSILCALFL  SSL-------  ---SLVSSS-   26
gi|62903513       ---------M  AKLSDSQTMA  LFTVFLLFLS  SSL-------  ---ALSS---   28
gi|21097          ----------  -KLSDSQTMA  LFTVFLLFLS  SSL-------  ---ALSS---   26
gi|18222          ----------  ------MMAV  FFMPFLLLLS  SSS-------  ---SSSSSS-   23
gi|18220          -------MAN  FSESKSMMAV  FFMPFLLLLS  SSS-------  ---SSSSSS-   32
gi|30698979       ----------  ----MRSFVS  LISLLLLLSF  SSS-------  ---VLSTKK-   25
gi|12325143       ----------  ---MMRSFVS  LISLLLLLSF  SSS-------  ---VLSTKK-   26
Lead•clone104691  ----------  ----MTSFCS  MISLLLLLSL  SSA-------  ---VFSDD--   24
CeresClone: 17206 ----------  -----MASFV  FVISLLLLSF  SSA-------  ---VFSDD--   23
gi|30984544       ----------  -----MASFV  FVISLLLLSF  SSA-------  ---VFSDD--   23
CeresClone: 621848 ---------  -----MKLST  LFLFLFHLAH  AALSDEA---  ---TFIRDGL   29
CeresClone: 316544 --------M  AAAATRSLHS  FLALLLLLAA  AAAAAAL---  ---SYETKSI   35
gi|50899872       MRKGAAGMAC  TCSAAAAASA  LVKLLVLVAA  VAATTSAGGG  DEPTYETKSI   50

Consensus         ----------  ------S--A  LVSLLLLLS-  SSA-------  ---S-SS---   50 gi|13928598       -PHFHEF-IE  APSYGPNAYA  FDSDGE-LYA  SVEDGRIIKY  DKPSNKFLTH   73
gi|62903513       -PILKEILIE  APSYAPNSFT  FDSTNKGFYT  SVQDGRVIKY  EGPNSGFVDF   77
gi|21097          -PILKEILIE  APSYAPNSFT  FDSTNKGFYT  SVQDGRVIKY  EGPNSGFVDF   75
gi|18222          -PILKKIFIE  SPSYAPNAFT  FDSTDKGFYT  SVQDGRVIKY  EGPNSGFTDF   72
gi|18220          -PILKKIFIE  SPSYAPNAFT  FDSTDKGFYT  SVQDGRVIKY  EGPNSGFTDF   81
gi|30698979       -SSFQKLPVP  GNRTGPEAFA  FDSTGKGFYT  GVTGGKILKY  L-PKKGYVDF   73
gi|12325143       -SSFQKLPVP  GNRTGPEAFA  FDSTGKGFYT  GVTGGKILKY  L-PKKGYVDF   74
Lead•clone104691  -ASFQKLPVP  ETRSGPEAFA  FDSTGKGFYT  GVSGGKILKY  L-PETGYVDF   72
CeresClone: 17206 -ASFQKLPVP  DKRSGPESFA  FDSTG-GFYT  GVSGGKILKY  V-PGKGYVDF   70
gi|30984544       -ASFQKLPVP  DKRSGPESFA  FDSTG-GFYT  GVSGGKILKY  V-PGKGYVDF   70
CeresClone: 621848 -KSYSQLDLP  HSVFGSESVA  FDCHGKGPMV  GVSDGRILKW  HETKREWIDF   78
CeresClone: 316544 DPGLVVMTLP  EPVSGPESLA  FDGRGGGPYS  GVSDGRVLRW  QGPLRGWIEF   85
gi|50899872       DPSLAVMTLP  APVTGPESLA  FDGRGDGPYT  GGSDGRILRW  RGGRLGWIEF  100

Consensus         -PSFQKL--P  -P-SGPESFA  FDSTGKGFYT  GVSDGRILKY  --P--G-VDF  100 gi|13928598       AVASPIWNNA  LCENNTNQDL  -KPLCGRVYD  FGFHYETQRL  YIADCYFGLG  122
gi|62903513       AYASPYWNKA  FCENSTDAEK  -RPLCGRTYD  ISYNLQNNQL  YIVDCYYHLS  126
gi|21097          AYASPYWNKA  FCENSTDAEK  -RPLCGRTYD  ISYNLQNNQL  YIVDCYYHLS  124
gi|18222          AYASPFWNKA  FCENSTDPEK  -RPLCGRTYD  ISYDYKNSQM  YIVDGHYHLC  121
gi|18220          AYASPFWNKA  FCENSTDPEK  -RPLCGRTYD  ISYDYKNSQM  YIVDGHYHLC  130
gi|30698979       AQITNSSKSS  LCDGALGTTN  -VEKCGRPAG  IAFNTKTGDL  YVADAALGLH  122
gi|12325143       AQITNSSKSS  LCDGALGTTN  -VEKCGRPAG  IAFNTKTGDL  YVADAALGLH  123
Lead•clone104691  AQITESSNSS  WCDGTIGTAL  -AGRCGRPAG  IAFNEKTGDL  YVADAPLGLH  121
CeresClone: 17206 AQITDSSNSA  WCNGALGTAF  -AGKCGRPAG  IALNSKTGDL  YVADAPLGLH  119
gi|30984544       AQITDSSNSA  WCNGALGTAF  -AGKCGRPAG  IALNSKTGDL  YVADAPLGLH  119
CeresClone: 621848 AVTSPHRNKK  LCDGLTNDKM  -ESMCGRPLG  LKFNTLIQEL  YIADAYFGLL  127
CeresClone: 316544 AYNSKHRSVA  LCAPDKKLVV  PESLCGRPLG  LQFHRQSGDL  YVADAYLGLL  135
gi|50899872       AYNSRHKSVG  VCSPEKKLVV  PESVCGRPLG  LQFHHASGDL  YVADAYLGLL  150

Consensus         A--S---N-A  FC--------  ---LCGRP-G  ISFN-KTGDL  YVADAYLGL-  150 gi|13928598       FVGPDGGHAI  QLATSGDGVE  FKWLYALAID  QQAGEVYMTD  VSTKYD--DR  170
gi|62903513       VVGSEGGHAT  QLATSVDGVP  FKWLYAVIVD  QRTGIVYFTD  VSTLYD--DR  174
gi|21097          VVGSEGGHAT  QLATSVDGVP  FKWLYAVIVD  QRTGIVYFTD  VSTLYD--DR  172
gi|18222          VVGKEGGYAT  QLATSVQGVP  FKWLYAVIVD  QRTGIVYFTD  VSSIHDDSPE  171
gi|18220          VVGKEGGYAT  QLATSVQGVP  FKWLYAVIVD  QRTGIVYFTD  VSSIHDDSPE  180
gi|30698979       VIPRRGGLAK  KIADSVGGKP  HLFLDGLDVD  PTTGVVYFTS  FSSIFG--PR  170
gi|12325143       VIPRRGGLAK  KIADSVGGKP  FLFLDGLDVD  PTTGVVYFTS  FSSIFG--PR  171
Lead•clone104691  VISPAGGLAT  KITDSVDGKP  FKFLDGLDVD  PTTGVVYFTS  FSSRFS--PI  169
CeresClone: 17206 VISPAGGLAT  KLADSVDGKP  FKFLDGLDVD  PTTGVVYFTS  FSSKFG--PR  167
gi|30984544       VISPAGGLAT  KLADSVDGKP  FKFLDGLDVD  PTTGVVYFTS  FSSKFG--PR  167
CeresClone: 621848 VVGPGGGVAK  QLATSAEGVP  FRFINALDID  TKTGEVYFTD  SSIMFQ--RR  175
CeresClone: 316544 RVAARGGLAQ  VVATEAAGGP  FNFLNGLDVD  QRTGDVYFTD  SSAIYR--RS  183
gi|50899872       RVPARGGLAE  VVATEAAGVP  FNFLNGLDVD  QRTGDVYFTD  SSTIYR--RS  198

Consensus         VV---GGLAT  QLATSV-GVP  FKWLDGLDVD  QRTGVVYFTD  -SS-----PR  200
```

TABLE 11-6-continued

/tmp/Lead•clone104691.aln

```
gi|13928598        GVQDIIRIND TTGRLIKYDP STEEVTVLMK GLNIPGGTEV SKDGSFVLVG  220
gi|62903513        GVQQIMDTSD KTGRLIKYDP STKETTLLLK ELHVPGGAEV SADSSFVLVA  224
gi|21097           GVQQIMDTSD KTGRLIKYDP STKETTLLLK ELHVPGGAEV SADSSFVLVA  222
gi|18222           GVEEIMNTSD RTGRLMKYDP STKETTLLLK ELHVPGGAEI SADGSFVVVA  221
gi|18220           GVEEIMNTSD RTGRLMKYDP STKETTLLLK ELHVPGGAEI SADGSFVVVA  230
gi|30698979        DVLKAVATKD STGKFFKYDP SKKVVTVLME GLSGSAGCAV SSDGSFVLVG  220
gi|12325143        DVLKAVATKD STGKFFKYDP SKKVVTVLME GLSGSAGCAV SSDGSFVLVG  221
Lead•clone104691   QVLTALGLKD ATGKLYKYDP STKVVTVLME GLSGSAGCAV SSDGSFVLVS  219
CeresClone: 17206  EVLIAVGLKD ASGKLFKYDP ATKAVTELME GLSGAAGCAV SSDGSFVLVS  217
gi|30984544        EVLIAVGLKD ASGKLFKYDP ATKAVTELME GLSGAAGCAV SSDGSFVLVS  217
CeresClone: 621848 VYISTILSGD RTGRLLKYVP STQSVHVLVK GLAFPNGVAL SKDNSFIIVA  225
CeresClone: 316544 DYLLVVAMGD ETGRLLRYER RIGRMGVLQA GLSMPNGVAV SADGTHVVVA  233
gi|50899872        QMLLVVAMGD ETGRLLRYDA RRRRVTVLHS GLPYPNGVAV SDDGTHVVVA  248

Consensus          -VL-VV-T-D -TGRL-KYDP STK-VTVLMK GL--P-G-AV S-DGSFVLVA  250 gi|13928598        EFASHRILKY WLKGPKANTS ---EFLLKVR GPGNIKRTKD -GDFWVASS-  265
gi|62903513        EFLSHQIVKY WLEGPKKGTA ---EVLVKIP NPGNIKRNAD -GHFWVSSSE  270
gi|21097           EFLSHQIVKY WLEGPKKGTA ---EVLVKIP NPGNIKRNAD -GHFWVSSSE  268
gi|18222           EFLSNRIVKY WLEGPKKGSA ---EFLVTIP NPGNIKRNSD -GHFWVSSSE  267
gi|18220           EFLSNRIVKY WLEGPKKGSA ---EFLVTIP NPGNIKRNSD -GHFWVSSSE  276
gi|30698979        QFTKSNIKRY WIKGSKAGTS --EDFTNSVS NPDNIKRIGS TGNFWVAS--  266
gi|12325143        QFTKSNIKRY WIKGSKAGTS --EDFTNSVS NPDNIKRIGS TGNFWVAS--  267
Lead•clone104691   QFTKSNIKRY WIKGPKAGSS --EDFTNSVS NPDNIKRIGS TGNFWVAS--  265
CeresClone: 17206  EFIKSNIKKY WIKGPKAGTI --EDFSSLVS NPDNIRRVGS TGNFWVAS--  263
gi|30984544        EFIKSNIKKY WIKGPKAGTI --EDFSSLVS NPDNIRRVGS TGNFWVAS--  263
CeresClone: 621848 ESTTFKILKI QVRDSKTNNN NIEPFAQVPR SPDNIKRNAK -GEFWVALNS  274
CeresClone: 316544 HTALQELRRY WIRGARAGTS --DTFAELPG YPDNLRADGR -GGYWVALSS  280
gi|50899872        HTGLQELRRY WLRGPRAGKS --ETFAEVPG YPDNVRRDGD -GGYWVALSR  295

Consensus          EF----IKKY W-KGPKAGTS --E-F---V- NPDNIKRNG- -GNFWVASS-  300 gi|13928598        ---------D NNGITVT--- -PRGIRFDEF GN-----ILE VVATPLPYKG  297
gi|62903513        E--------L DGNMHGR--V DPKGIKFDEF GN-----ILE VIPLPPPFAG  305
gi|21097           ---------L DGNMHGR--V DPKGIKFDEF GN-----ILE VIPLPPPFAG  303
gi|18222           ---------L DGGQHGS--V VSRGIKFDGF GN-----ILQ VIPLPPPYEG  302
gi|18220           E--------L DGGQHGS--V VSRGIKFDGF GN-----ILQ VIPLPPPYEG  311
gi|30698979        ---------V VNSATGP--T NPSAVKVSSA GK-----VLQ TIPLKDKFGD  300
gi|12325143        ---------V VNSATGP--T NPSAVKVSSA GK-----VLQ TIPLKDKFGD  301
Lead•clone104691   ---------V VNKIIVP--T NPSAVKVNSN GK-----VLQ TIPLKDKFGD  299
CeresClone: 17206  ---------V VNKVVMP--T DPRAVKLDAN GK-----VLQ TIFLKNEFGN  297
gi|30984544        ---------V VNKVVMP--T DPRAVKLDAN GK-----VLQ TIFLKNEFGN  297
CeresClone: 621848 GRGLIQKLEN EIETTLPWNA DPVAIKFDEK GR-----AIE VLDGEYGRQL  319
CeresClone: 316544 G------VAA DEAAAAP--- -TVAVRVSRD GN-----VTE ALD---GFSF  312
gi|50899872        G--------A DNDDVAP--- -TVAVRVTAA GKKKGGGAAV MAEALAGFSF  333

Consensus          ---------V DN----P--- DPRAVKVD-- GK-----VLQ VIPL---F--  350 gi|13928598        EHIEQVQEHD GALFVGSLFH EEVGIL---- --HNYKSSVD HHQEKNSGGL  341
gi|62903513        EHFEQIQEHD GLLYIGTLFH GSVGILVY-- -DKKGNSFVS SH--------  344
gi|21097           EHFEQIQEHD GLLYIGTLFH GSVGILVY-- -DKKGNSFVS SH--------  342
gi|18222           EHFEQIQEHD GLLYIGSLSH SSVGILVYDD HDNKGNSYVS QLVIN-----  347
gi|18220           EHFEQIQEHD GLLYIGSLFH SSVGILVYDD HDNKGNSYVS S---------  352
gi|30698979        TLVSEVNEYK GQLYIGALFG PFAGIL---- --KL------ ----------  328
gi|12325143        TLVSEVNEYK GQLYIGALFG PFAGIL---- --KL------ ----------  329
Lead•clone104691   TLLSEVNEFE GNLYIGTLTG PFAGIL---- --KLEKGSCP AT--------  335
CeresClone: 17206  TLLSEVNEFN GHLYIGTLTG PFAGVM---- --KL------ ----------  325
gi|30984544        TLLSEVNEFN GHLYIGTLTG PFAGVM---- --KL------ ----------  325
CeresClone: 621848 DSVSEVEEHE GSLWIGSAVQ PYIGLI---- --KA------ ----------  347
CeresClone: 316544 VSVSEVAQRG GALWVGSVDT PYAGQL---- --KRRAS--- ----------  343
gi|50899872        VTVSEVAEQN GTLWIGSVDT PYAGAA---- --VRGRR--- ----------  364

Consensus          --ISEV-E-D G-LYIGSL-- PFAGIL---- --K------- ----------  400
```

TABLE 11-6-continued

/tmp/Lead•clone104691.aln

| gi\|13928598 | NASFKEFSSF | 351 |
| gi\|62903513 | ---------- | 344 |
| gi\|21097 | ---------- | 342 |
| gi\|18222 | ---------- | 347 |
| gi\|18220 | ---------- | 352 |
| gi\|30698979 | ---------- | 328 |
| gi\|12325143 | ---------- | 329 |
| Lead•clone104691 | ---------- | 335 |
| CeresClone: 17206 | ---------- | 325 |
| gi\|30984544 | ---------- | 325 |
| CeresClone: 621848 | ---------- | 347 |
| CeresClone: 316544 | ---------- | 343 |
| gi\|50899872 | ---------- | 364 |
| | | |
| Consensus | ---------- | 410 |

23/05/05 plur = 6.500000-collision-box-noboxcol colbyconsensus

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. A method for producing a plant, the method comprising transforming a plant with a nucleic acid molecule, wherein the nucleic acid molecule comprises:
   a) a first nucleic acid having a regulatory sequence capable of causing transcription in a plant; and
   b) a second nucleic acid encoding a polypeptide, wherein the polypeptide comprises an amino acid sequence that exhibits at least 95% amino acid sequence identity to the amino acid sequence of SEQ ID NO: 31;

wherein said first and second nucleic acids are operably linked, wherein said second nucleic acid is heterologous to said first nucleic acid, and wherein expression of said second nucleic acid in said transformed plant increases drought tolerance, thermotolerance, osmotic stress tolerance, and or water use efficiency as compared to a control plant of the same species lacking said nucleic acid molecule.

2. The method of claim 1, wherein the second nucleic acid sequence comprises a polynucleotide sequence that exhibits at least 90% nucleic acid sequence identity to the polynucleotide sequence of SEQ ID NO: 30.

3. The method of claim 1, wherein the second nucleic acid sequence encodes a polypeptide comprising an amino acid sequence that exhibits at least 97% amino acid sequence identity to the amino acid sequence of SEQ ID NO: 31.

4. The method of claim 1, wherein the second nucleic acid sequence encodes a polypeptide comprising an amino acid sequence that exhibits at least 98% amino acid sequence identity to the amino acid sequence of SEQ ID NO: 31.

5. The method of claim 1, wherein the second nucleic acid sequence encodes a polypeptide comprising an amino acid sequence that exhibits at least 99% amino acid sequence identity to the amino acid sequence of SEQ ID NO: 31.

6. The method of claim 1, wherein the second nucleic acid sequence encodes a polypeptide comprising the amino acid sequence of SEQ ID NO: 31.

7. The method of claim 1, wherein the second nucleic acid sequence comprises a polynucleotide sequence that exhibits at least 95% nucleic acid sequence identity to the polynucleotide sequence of SEQ ID NO: 30.

8. The method of claim 1, wherein the second nucleic acid sequence comprises a polynucleotide sequence that exhibits at least 97% nucleic acid sequence identity to the polynucleotide sequence of SEQ ID NO: 30.

9. The method of claim 1, wherein the second nucleic acid sequence comprises a polynucleotide sequence that exhibits at least 98% nucleic acid sequence identity to the polynucleotide sequence of SEQ ID NO: 30.

10. The method of claim 1, wherein the second nucleic acid sequence comprises a polynucleotide sequence that exhibits at least 99% nucleic acid sequence identity to the polynucleotide sequence of SEQ ID NO: 30.

11. The method of claim 1, wherein the second nucleic acid sequence comprises a polynucleotide sequence that comprises the polynucleotide sequence of SEQ ID NO: 30.

* * * * *